(12) United States Patent
Shin et al.

(10) Patent No.: US 10,937,984 B2
(45) Date of Patent: Mar. 2, 2021

(54) ORGANIC COMPOUND AND LIGHT EMITTING DIODE AND ORGANIC LIGHT EMITTING DIODE DISPLAY DEVICE USING THE SAME

(71) Applicant: LG DISPLAY CO., LTD., Seoul (KR)

(72) Inventors: Ji-Cheol Shin, Seoul (KR); Sung-Hoon Joo, Paju-si (KR); Seon-Keun Yoo, Gunpo-si (KR); Seung-Hee Yoon, Seoul (KR)

(73) Assignee: LG DISPLAY CO., LTD., Seoul (KR)

( * ) Notice: Subject to any disclaimer, the term of this patent is extended or adjusted under 35 U.S.C. 154(b) by 208 days.

(21) Appl. No.: 15/803,227

(22) Filed: Nov. 3, 2017

(65) Prior Publication Data
US 2018/0166647 A1  Jun. 14, 2018

(30) Foreign Application Priority Data

Dec. 12, 2016  (KR) .................. 10-2016-0168918

(51) Int. Cl.
*H01L 51/50* (2006.01)
*H01L 51/00* (2006.01)
(Continued)

(52) U.S. Cl.
CPC ........ *H01L 51/5092* (2013.01); *C07D 401/14* (2013.01); *H01L 27/3209* (2013.01);
(Continued)

(58) Field of Classification Search
None
See application file for complete search history.

(56) References Cited

U.S. PATENT DOCUMENTS

| 2002/0137267 A1* | 9/2002 | Joo ................... H01L 21/02595 |
| | | 438/166 |
| 2003/0170491 A1* | 9/2003 | Liao .................... H01L 51/5036 |
| | | 428/690 |

(Continued)

FOREIGN PATENT DOCUMENTS

| CN | 1438828 A | 8/2003 |
| CN | 103664748 A | 3/2014 |

(Continued)

*Primary Examiner* — Gregory D Clark
(74) *Attorney, Agent, or Firm* — Birch, Stewart, Kolasch & Birch, LLP

(57) ABSTRACT

The present disclosure relates to an organic compound, a light emitting diode and an organic light emitting diode display device using the same. The organic compound is represented by a following chemical formula 1.

Chemical Formula 1

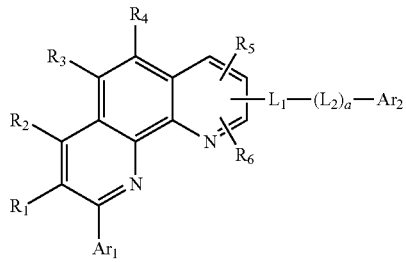

10 Claims, 9 Drawing Sheets

(51) Int. Cl.
*H05B 45/00* (2020.01)
*C07D 401/14* (2006.01)
*H01L 27/32* (2006.01)
*C07D 471/04* (2006.01)
*C09K 11/06* (2006.01)

(52) U.S. Cl.
CPC ...... *H01L 51/0035* (2013.01); *H01L 51/0072* (2013.01); *H01L 51/5072* (2013.01); *H05B 45/60* (2020.01); *C07D 471/04* (2013.01); *C09K 11/06* (2013.01); *H01L 51/0052* (2013.01); *H01L 51/0054* (2013.01); *H01L 51/0058* (2013.01); *H01L 51/0067* (2013.01); *H01L 51/5036* (2013.01)

(56) References Cited

U.S. PATENT DOCUMENTS

2003/0189401 A1* 10/2003 Kido ............... C07C 211/58
313/504
2007/0075312 A1* 4/2007 Chin ............... H01L 27/3209
257/40
2015/0228921 A1 8/2015 Kambe et al.
2015/0303380 A1 10/2015 Kambe et al.
2016/0197289 A1* 7/2016 Sado ............... C07D 487/16
257/40

FOREIGN PATENT DOCUMENTS

| | | | |
|---|---|---|---|
| CN | 104603137 A | 5/2015 | |
| CN | 104871332 A | 8/2015 | |
| CN | 104953037 A | 9/2015 | |
| CN | 105272979 A * | 1/2016 | ............ H01L 51/54 |
| CN | 105272979 A | 1/2016 | |
| CN | 105514287 A | 4/2016 | |
| CN | 106565705 A | 4/2017 | |
| CN | 107556307 A | 1/2018 | |
| EP | 2596621 A1 | 7/2015 | |
| JP | WO2013/145666 A | 10/2013 | |
| KR | 10-2015-0026055 A | 3/2015 | |
| KR | 10-2015-0099750 A | 9/2015 | |
| KR | 10-1914652 B1 | 10/2018 | |
| TW | 201634461 A | 10/2016 | |
| WO | WO 2016/088481 A1 | 6/2016 | |

* cited by examiner

ORGANIC COMPOUND AND LIGHT EMITTING DIODE AND ORGANIC LIGHT EMITTING DIODE DISPLAY DEVICE USING THE SAME

CROSS-REFERENCE TO RELATED APPLICATIONS

This application claims the priority benefit under 35 U.S.C. § 119(a) of Korean Patent Application No. 10-2016-0168918, filed on Dec. 12, 2016, in the Korean Intellectual Property Office, which is incorporated herein by reference in its entirety into the present application.

BACKGROUND

1. Technical Field

The present disclosure relates to an organic compound, and more particularly, to an organic compound where a driving voltage and an emission efficiency are improved and a light emitting diode and an organic light emitting diode display device including the organic compound.

2. Discussion of the Related Art

Requests for a flat panel display having a small space have increased due to demand for display devices. Among various flat panel displays, an organic light emitting diode (OLED) display device, which may be referred to as an organic electroluminescent display (OELD) device, including a light emitting diode (LED) has been the subject of recent research.

The LED is an element where a hole and an electron are injected into an emitting material layer from an anode (a hole injecting electrode) and a cathode (an electron injecting electrode) to constitute an exciton and the emitting material layer emits a light due to transition of the exciton. The LED has an advantage such that an element is formed on a flexible transparent substrate such as plastic. In addition, the LED has a relatively low driving voltage (equal to or lower than 10V), a relatively low power consumption and an excellent color property.

Recently, the LED emitting a white colored light has been applied to various fields such as a thin light source, a light source of a backlight unit for a liquid crystal display (LCD) device and a light source for a full color display device having a color filter layer as well as lighting.

In the white LED, a color purity, a color stability according to variation of current and voltage and a capability of fabrication as well as a high efficiency and a long lifetime have been the subject. The white LED may be classified into a single stack structure and a multiple stack structure. To obtain the white LED having a relatively long lifetime, the LED having a tandem structure where a plurality of emitting units are laminated has been widely used.

For example, the white LED may have the tandem structure where a first emitting part including a blue emitting layer and a second emitting part including a yellow-green emitting layer are vertically laminated. The white LED may emit the white colored light by mixing a light emitted from the blue emitting layer and a light emitted from the yellow-green emitting layer.

In the LED having the tandem structure, a charge generation layer is formed between the first and second emitting parts to increase a current efficiency of each emitting layer and to smoothly distribute charges to each emitting layer. In general, the charge generation layer may have a positive negative (PN) junction structure where an N type charge generation layer and a P type charge generation layer are sequentially formed.

In the charge generation layer of the tandem structure, a charge is generated at an interface between the P type charge generation layer and a hole injecting layer or a hole transporting layer due to an energy level difference between the N type charge generation layer and the P type charge generation layer. As a result, an electron injection property into the N type charge generation layer is deteriorated.

Further, when the N type charge generation layer is doped with a metal, the metal diffuses to the P type charge generation layer and a lifetime of the LED is reduced. Specifically, a material for the charge generation layer has a disadvantage in a thermal stability and an electric stability. When the white LED operates for a relatively long time, the material for the charge generation layer is deteriorated or spoiled. Accordingly, an injection efficiency of an electron generated at the interface between the P type charge generation layer and a hole injecting layer or a hole transporting layer the into the N type charge generation layer is reduced. Since the electron is not injected from the N type charge generation layer into the adjacent electron transporting layer, a property of the LED is deteriorated and a lifetime of the LED is reduced.

SUMMARY

Embodiments relate to an organic compound where an aryl group is connected to a phenanthroline moiety having at least one substituted aromatic ring through at least one linker.

For example, an organic compound of the present disclosure may be represented by a following chemical formula 1.

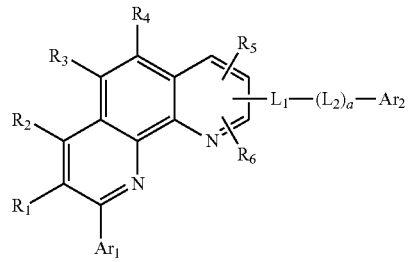

Chemical Formula 1

In the chemical formula 1, each of $R_1$ to $R_6$ is independently one of hydrogen, deuterium, tritium, a non-substituted or substituted alkyl group of C1 to C20, a non-substituted or substituted alkoxy group of C1 to C20, a non-substituted or substituted aryl group of C5 to C60 and a non-substituted or substituted hetero aryl group of C4 to C60; each of $L_1$ and $L_2$ is independently one of a non-substituted or substituted arylene group of C5 to C60 and a non-substituted or substituted hetero arylene group of C5 to C60; a is 0 or 1; and each of $Ar_1$ and $Ar_2$ is independently one of a non-substituted or substituted aryl group of C5 to C60 and a non-substituted or substituted hetero aryl group of C4 to C30.

One or more embodiments relate to a light emitting diode having a tandem structure where the organic compound is applied to a charge generation layer and/or an electron transporting layer and an organic light emitting diode display device.

Advantages and features of the disclosure will be set forth in part in the description, which follows and in part will become apparent to those having ordinary skill in the art upon examination of the following or may be learned from practice of the disclosure. Other advantages and features of the embodiments herein may be realized and attained by the structure particularly pointed out in the written description and claims hereof as well as the appended drawings.

It is to be understood that both the foregoing general description and the following detailed description are explanatory, and are intended to provide further explanation of the embodiments as claimed.

BRIEF DESCRIPTION OF THE DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

DETAILED DESCRIPTION

Figure 1:
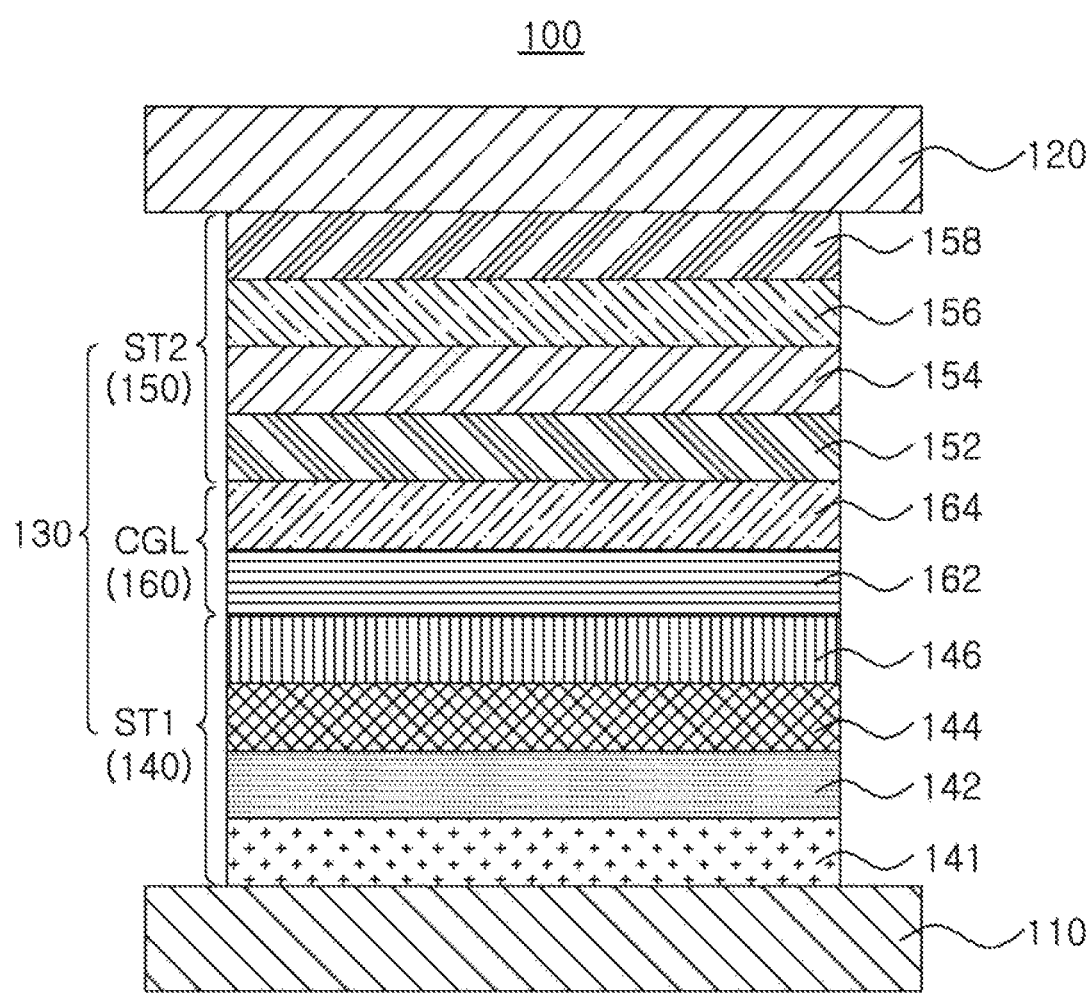
FIG. 1 is a cross-sectional view showing a light emitting diode of a tandem structure having two emitting parts according to a first embodiment of the present disclosure.

Reference will now be made in detail to embodiments of the present disclosure, examples of which are illustrated in the accompanying drawings. In the following description, when a detailed description of well-known functions or configurations related to this document is determined to unnecessarily cloud a gist of an embodiment of the disclosure, the detailed description thereof will be omitted. The progression of processing steps and/or operations described is an example; however, the sequence of steps and/or operations is not limited to that set forth herein and may be changed as is known in the art, with the exception of steps and/or operations necessarily occurring in a certain order. Like reference numerals designate like elements throughout. Names of the respective elements used in the following explanations are selected only for convenience of writing the specification and may be thus different from those used in actual products.

[Organic Compound]

Embodiments relate to an organic compound where an aryl group is connected to a phenanthroline moiety having at least one substituted aromatic ring through at least one linker. For example, an organic compound of the present disclosure may be represented by a following chemical formula 1.

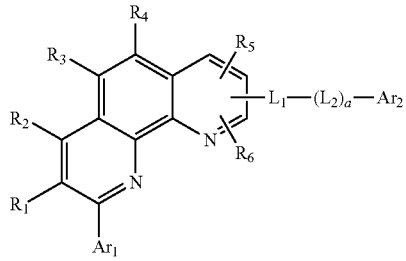

Chemical Formula 1

In the chemical formula 1, each of $R_1$ to $R_6$ is independently one of hydrogen, deuterium, tritium, a non-substituted or substituted alkyl group of C1 to C20, a non-substituted or substituted alkoxy group of C1 to C20, a non-substituted or substituted aryl group of C5 to C60 and a non-substituted or substituted hetero aryl group of C4 to C60; each of $L_1$ and $L_2$ is independently one of a non-substituted or substituted arylene group of C5 to C60 and a non-substituted or substituted hetero arylene group of C5 to C60; a is 0 or 1; and each of $Ar_1$ and $Ar_2$ is independently one of a non-substituted or substituted aryl group of C5 to C60 and a non-substituted or substituted hetero aryl group of C4 to C30.

The term 'non-substituted' preferably means that a hydrogen atom is bonded, and the hydrogen atom includes protium, deuterium and tritium in this case.

A substituent for the word 'substituted' includes one of a non-substituted or substituted with halogen alkyl group of C1 to C20, a non-substituted or substituted with halogen alkoxy group of C1 to C20, halogen, a cyano group, a carboxyl group, a carbonyl group, an amine group, an alkylamine group of C1 to C20, a nitro group, a hydrazyl group, a sulfonyl group, an alkyl silyl group of C1 to C20, an alkoxy silyl group of C1 to C20, a cycloalkyl silyl group of C3 to C30, an aryl silyl group of C5 to C30, a non-substituted or substituted aryl group of C5 to C30 and a hetero aryl group of C4 to C30.

The word 'hetero' in 'a hetero aromatic ring,' 'a hetero cycloalkylene group,' 'a hetero arylene group,' 'a hetero arylalkylene group,' 'a hetero oxyarylene group,' 'a hetero cycloalkyl group,' 'a hetero aryl group,' 'a hetero arylalkyl group,' 'a hetero oxyaryl group' and 'a hetero aryl amine group' means that at least one (e.g., one to five) carbon atoms constituting an aromatic ring or an alicyclic ring is substituted with at least one hetero atom selected from the group including N, O, P, Si, S and a combination thereof.

In the chemical formula 1, the organic compound of the present disclosure includes a phenanthroline moiety. Due to the phenanthroline moiety, transporting property of an electron is improved and diffusion of an alkali metal or an alkali earth metal from an N type charge generation layer to a P type charge generation layer is prevented. Further, the phenanthroline moiety is substituted with an aromatic ring, such as at least one aryl group or a hetero aryl group Ar1. Accordingly, a thermal stability as well as transporting property of an electron is improved in the organic compound according to the present disclosure.

In an exemplary embodiment, each of $R_1$ to $R_6$ may be independently one of hydrogen, deuterium, tritium, a non-substituted or substituted alkyl group of C1 to C20, a non-substituted or substituted alkoxy group of C1 to C20.

In the chemical formula 1, each of $Ar_1$ and $Ar_2$ may be independently one of a non-substituted or substituted aryl group and a non-substituted or substituted hetero aryl group. In an exemplary embodiment, each of $Ar_1$ and $Ar_2$ may include a non-substituted or substituted aromatic ring. For example, each of $Ar_1$ and $Ar_2$ may be independently one of a non-substituted or substituted phenyl, biphenyl, terphenyl, naphthalene, anthracene, indene, indenoindene, heptalenyl, biphenylenyl, indacenyl, phenalenyl, phenanthrenyl, benzophenanthrenyl, dibenzophenanthrenyl, azulenyl, pyrenyl, fluoranthenyl, triphenylenyl, chrysenyl, tetraphenyl,fluoroanthenyl, tetracenyl, pleiadenyl, picenyl, pentaphenyl, pentacenyl, fluorenyl, indenofluorenyl, diazafluorenyl, or a non-fused or fused homo aryl such as spirofluorenyl and/or pyrolyl, pyridinyl, terpyridinyl, phenylpyridinyl, pyrimidinyl,pyridazinyl, triazinyl, tetrazinyl, imidazolyl, pyrazolyl, indolyl, isoindolyl, indazolyl, indolizinyl, pyrolizinyl, carbazolyl, benzocarbazolyl, dibenzocarbazolyl,indolocarbazolyl, indenocarbazolyl, benzofurocarbazolyl, benzothiocarbazolyl, quinolinyl, isoquinolinyl, phthalazinyl, quinoxalinyl, cynolinyl, quinazolinyl, quinozolinyl, quinolizinyl, furyl, benzoquinolinyl, benzoisoquinolinyl, benzoquinazolinyl, benzoquinoxalinyl, acridinyl, phenanthrolinyl, phenanthrenyl, pyrimidinyl, phenanthridinyl, pteridinyl, naphthylridinyl, naphtharidinyl, furanyl, pyranyl, oxazinyl, oxazolyl, oxadiazolyl, triazolyl, dioxinyl, benzofuranyl, dibenzofuranyl, arylthiazolyl, thiopyranyl, xanthenyl, chromenyl, isochromenyl, thioazinyl, thiophenyl,benzothiophenyl, dibenzothiophenyl, carbolinyl, difuropyrazinyl, benzofurodibenzofuranyl, benzothiodibenzofuranyl, or a non-fused or fused hetero aryl such as N-substituted spiro fluorenyl.

For example, each of Ar1 and Ar2 may be independently selected from a group including phenyl, alkylphenyl, biphenyl, alkylbiphenyl, halophenyl, alkoxyphenyl, haloalkoxyphenyl, silylphenyl,naphthyl, alkylnaphthyl, halonaphthyl, cyanonaphthyl, silylnaphthyl, phenylnaphthyl,pyridyl, alkylpyridyl, halopyridyl, cyanopyridyl, alkoxypyridyl, silylpyridyl, phenylpyridyl, pyrimidyl, halopyrimidyl, cyanopyridimyl, alkoxypyrimidyl, phenylpyrimidyl, quinolinyl, isoquinolinyl, phenylquinolinyl, quinoxalinyl, pyrazinyl, quinazolinyl, naphthyridinyl, benzothiophenyl, benzofuranyl, dibenzothiophenyl, arylthiazolyl, dibenzofuranyl, fluorenyl, carbazoyl, imidazolyl, carbolinyl, phenanthrenyl, terphenyl, terpyridinyl, phenylterpyridinyl, triphenylenyl, fluoranthenyl and diazafluorenyl.

In an exemplary embodiment, $Ar_1$ is a homo aryl group such as a substituted or non-substituted phenyl, biphenyl and naphthyl, and $Ar_2$ is a homo aryl group, such as a substituted or non-substituted phenyl, naphthyl, anthracenyl, phenalenyl, phenanthrenyl, pyrenyl, triphenylenyl, chrysenyl, fluoranthenyl, fluorenyl, diphenylfluorenyl and spirofluorenyl, or a hetero aryl group, such as a substituted or non-substitutedpyridyl, pyrazinyl, pyrimidyl, pyridazinyl, triazinyl, quinolinyl, isoquinolinyl, phthalazinyl, quinoxalinyl, cynolinyl, quinazolinyl, quinozolinyl, quinolizinyl and carbazolyl. Although $Ar_2$ of a hetero aryl group may include one or two of an aromatic ring in an exemplary embodiment, the present disclosure is not limited to that set forth herein.

In the chemical formula 1, each of L1 and L2 may be independently selected from a group including a non-substituted or substituted phenylene, biphenylene, terphenylene, tetraphenylene,indenylene, naphthylene, azulenylene, indacenylene, acenaphthylene, fluorenylene, spirofluorenylene, phenalenylene,phenanthrenylene, anthracenylene, fluoranthrenylene, triphenylenylene, pyrenylene, chrysenylene, naphthacenylene, picenylene, perylenylene, pentaphenylene, hexacenylene, pyrrolylene, imidazolylene, pyrazolylene, pyridinylene, pyrazinylene, pyrimidinylene, pyridazinylene, isoindolylene, indolylene, indazolylene, purinylene, quinolinylene, isoquinolinylene, benzoquinolinylene, phthalazinylene, naphthyridinylene, quinoxalinylene, quinazolinylene, benzoi soquinolinylene, benzoquinazolinylene, benzoquinoxalinylene, cinnolinylene, phenanthridinylene, acridinylene, phenanthrolinylene, phenazinylene, benzoxazolylene, benzimidazolylene,furanylene, benzofuranylene, thiophenylene, benzothiophenylene, thiazolylene, isothiazolylene, benzothiazolylene, isoxazolylene, oxazolylene, triazolylene, tetrazolylene, oxadiazolylene, arylthiazolylene, triazinylene, dibenzofuranylene, dibenzothiophenylene, carbazolylene, benzocarbazolylene, dibenzocarbazolylene,indolocarbazolylene, indenocarbazolylene, imidazopyrimidinylene and imidazopyridinylene.

For example, each of L1 and L2 may be independently selected from a group including phenylene, alkylphenylene, cyanophenylene, naphthylene, alkylnaphthylene, biphenylene, alkylbiphenylene, anthracenylene, triphenylene, pyrenylene, benzothiophenylene,benzofuranylene, dibenzothiophenylene, arylthiazolylene, dibenzofuranylene, fluorenylene and triphenylenylene.

Each of L1 and L2 may be one of non-substituted or substituted with alkyl, cyano and halogen phenylene, biphenylene and naphthalene.

The organic compound represented by the chemical formula 1 may include a phenanthroline moiety substituted with at least one aromatic ring. Since the organic compound has a relatively high decomposition temperature or a relatively high glass transition temperature due to the phenanthroline moiety, the organic compound has an excellent thermal stability. As a result, the organic compound may not be deteriorated or spoiled even by a Joule's heat generated from driving of an element. Accordingly, the lifetime of an LED including the organic compound is extended and a driving voltage of the LED including the organic compound is reduced.

Further, since the organic compound represented by the chemical formula 1 includes a phenanthroline moiety having a nitrogen atom of a hybrid orbital of sp² of sufficient electrons, the organic compound has an excellent electron transporting property. As a result, the organic compound may be used for an electron transporting layer to efficiently supply an electron to an emitting material layer. Specifically, a nitrogen atom of a phenanthroline moiety is combined with an alkali metal or an alkali earth metal of a dopant of an N type charge generation layer to form a gap state. As a result, an energy level difference between an N type charge generation layer and a P type charge generation layer is alleviated. Since the injection of an electron into the N type charge generation layer is improved, the electron transporting property from the N type charge generation layer to an adjacent electron transporting layer may be maximized.

In addition, the compound having a nitrogen atom is combined with an alkali metal or an alkali earth metal in an N type charge generation layer to prevent the alkali metal or the alkali earth metal from diffused into a P type charge generation layer. As a result, the reduction of an LED lifetime is prevented.

In an exemplary embodiment, an organic compound represented by the chemical formula 1 may be one of the following compounds:

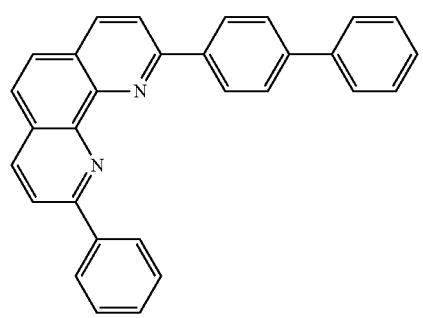

EN-001

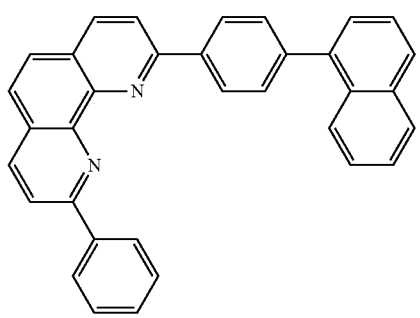

EN-002

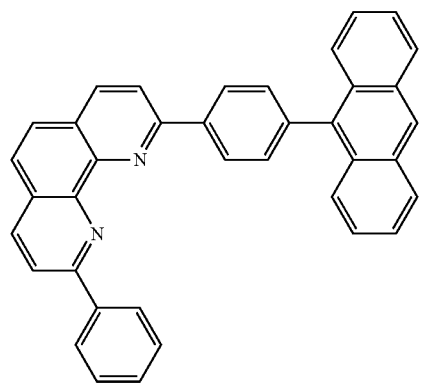

EN-003

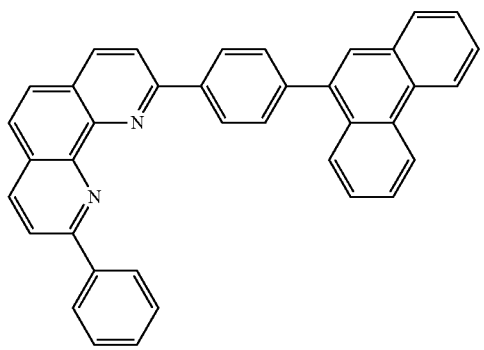

EN-004

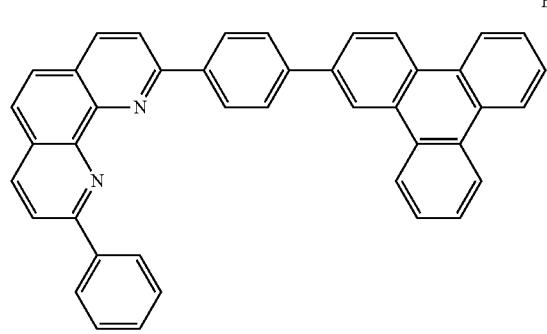

EN-005

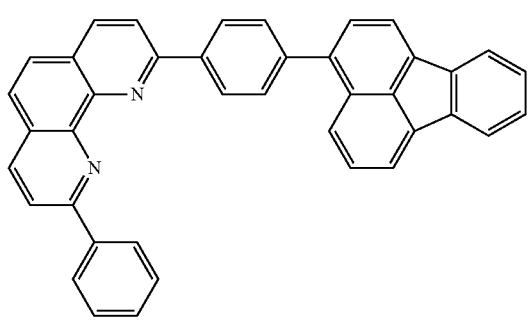

EN-006

-continued
EN-007
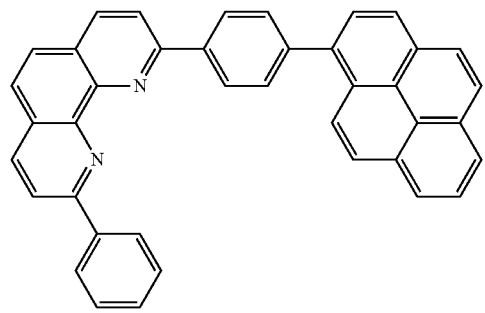
EN-008
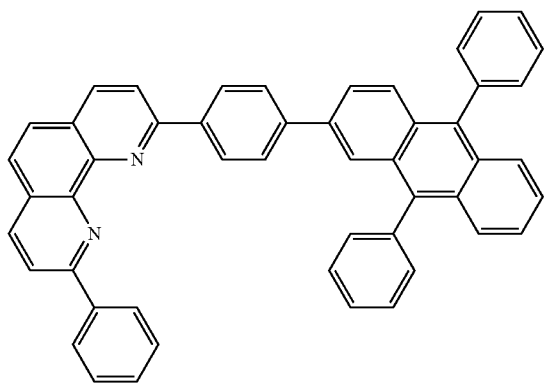
EN-009
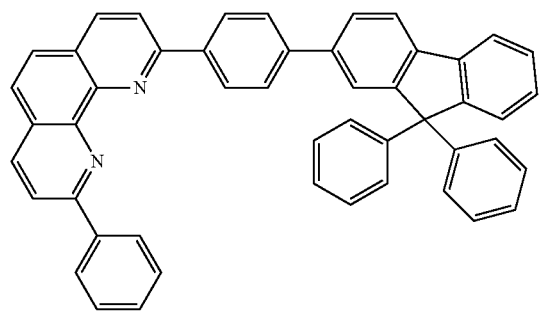
EN-010
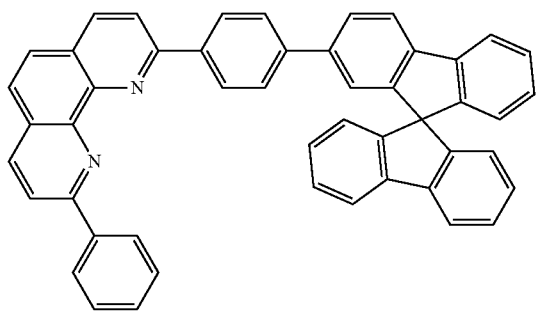
EN-011
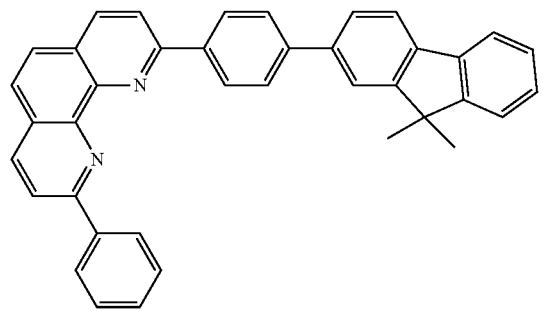
EN-012
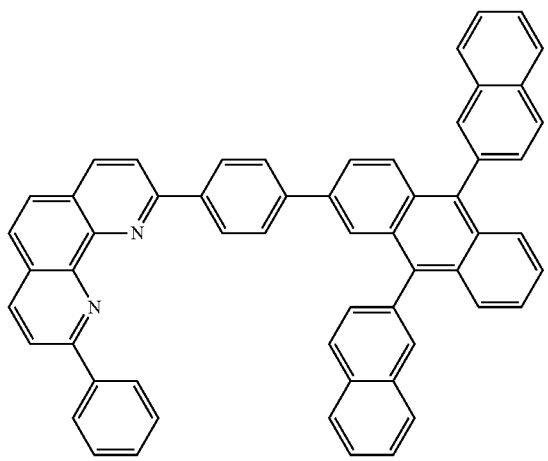
EN-013
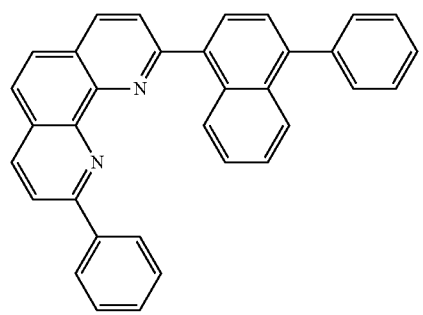
EN-014
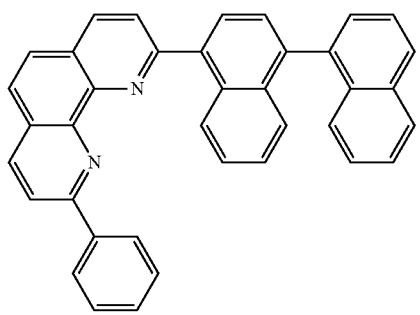

-continued
EN-015
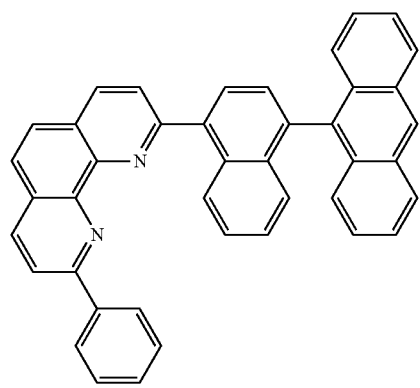
EN-016
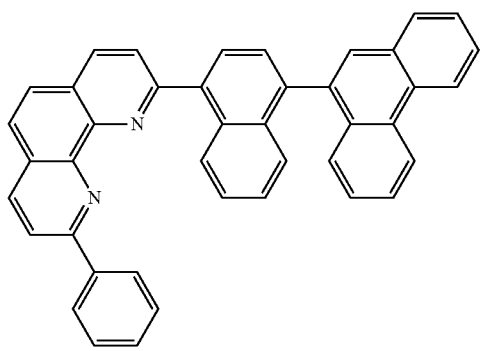
EN-017
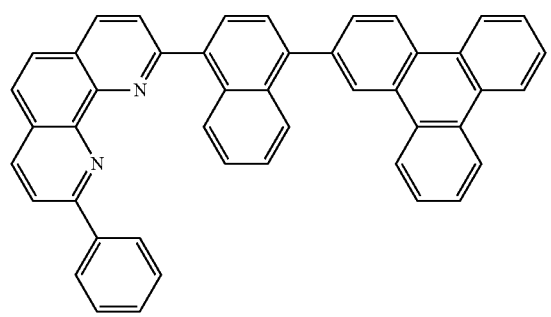
EN-018
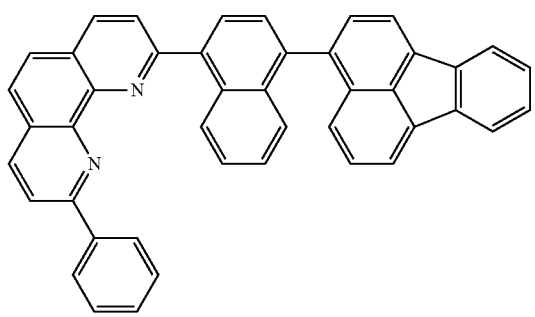
EN-019
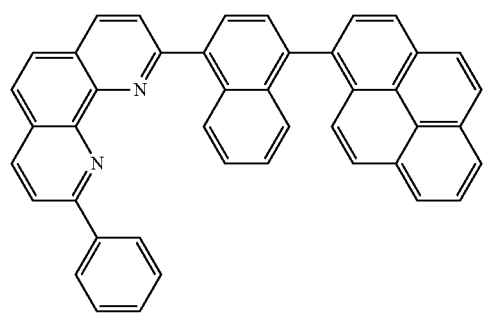
EN-020
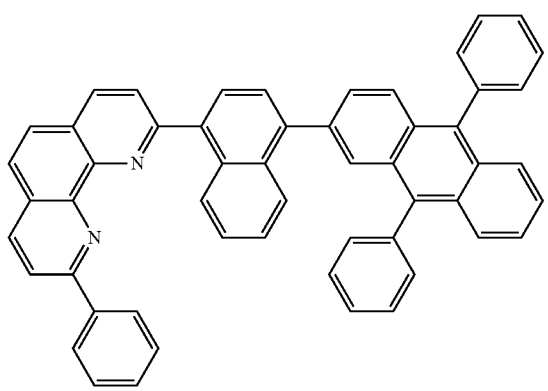
EN-021
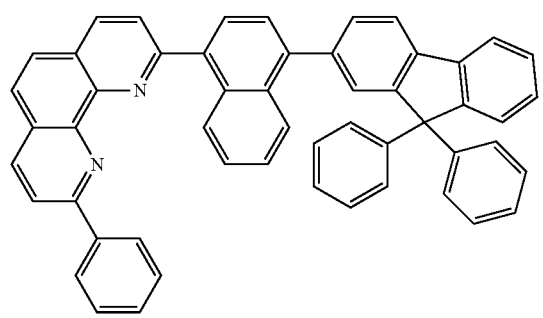
EN-022
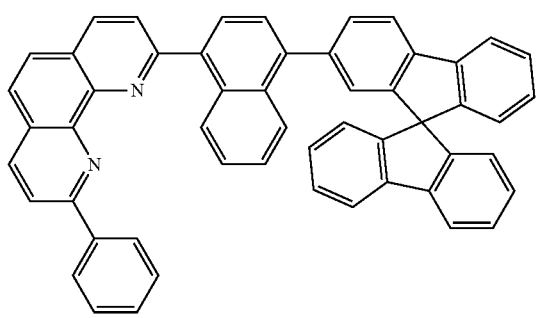

-continued
EN-023
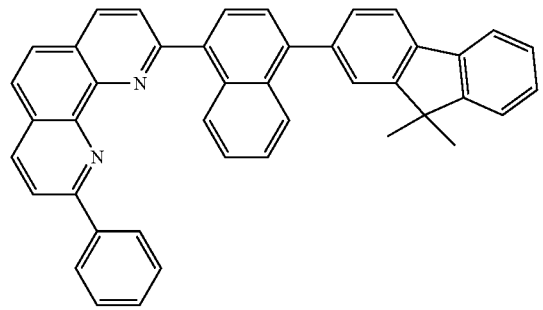
EN-024
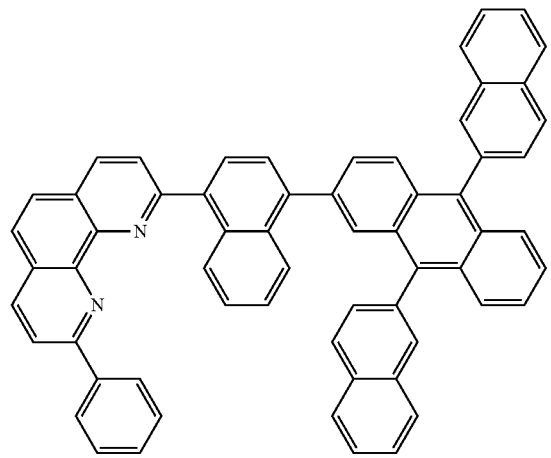
EN-025
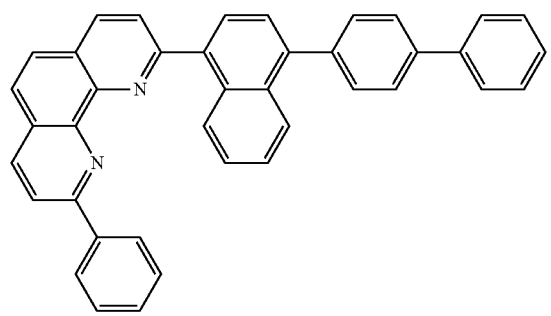
EN-026
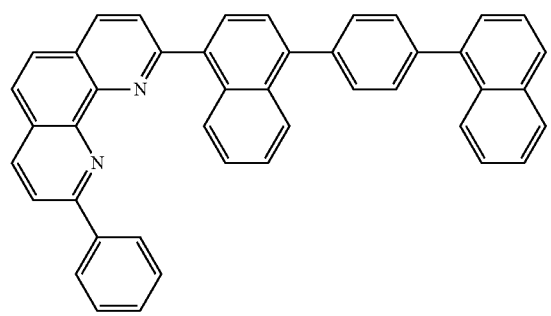
EN-027
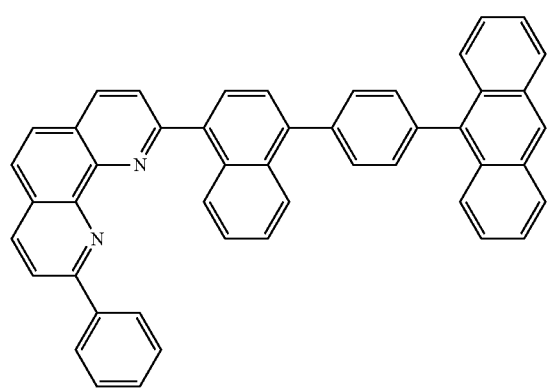
EN-028
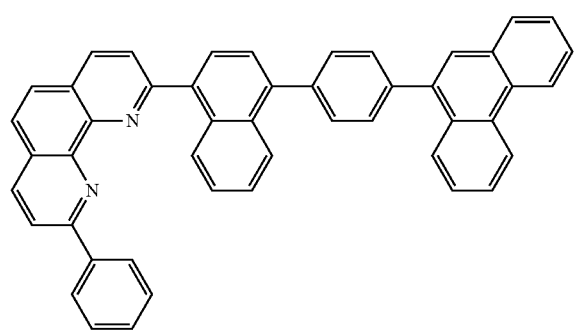
EN-029
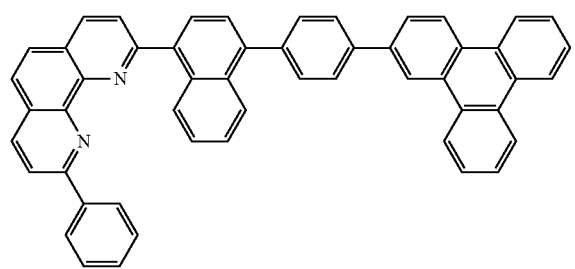
EN-030
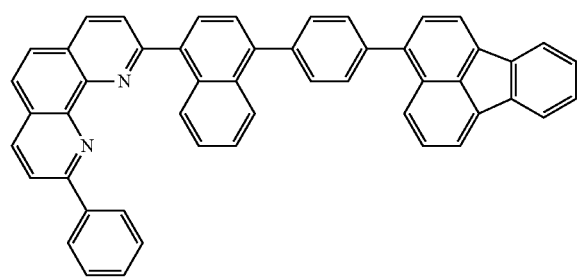

-continued
EN-031
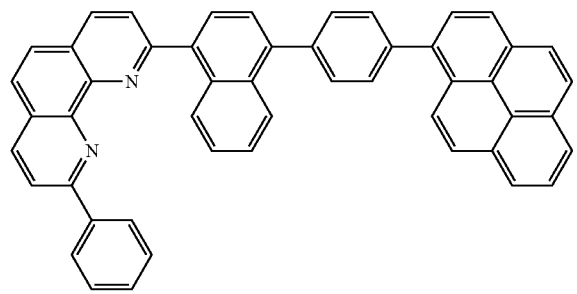
EN-032
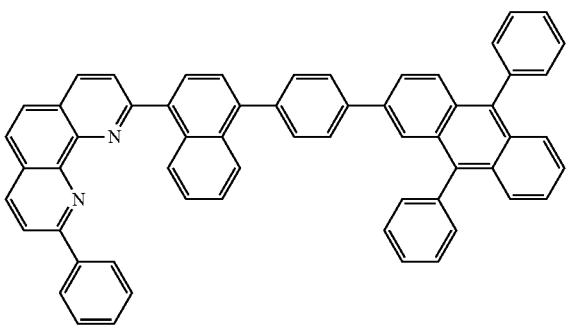
EN-033
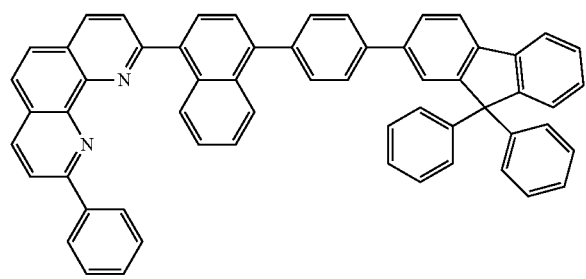
EN-034
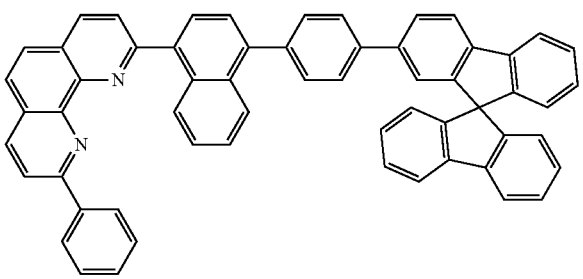
EN-035
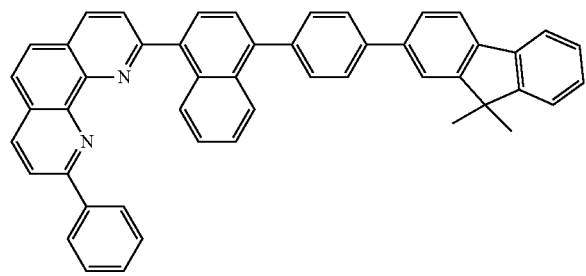
EN-036
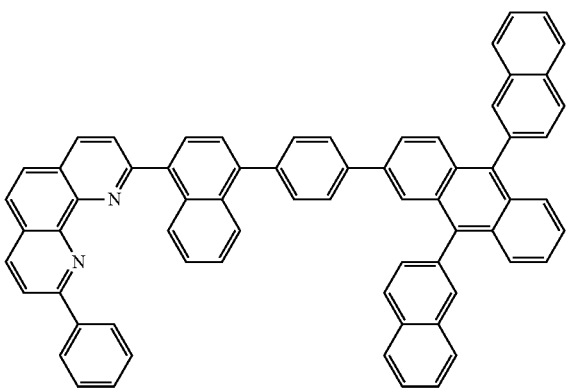
EN-037
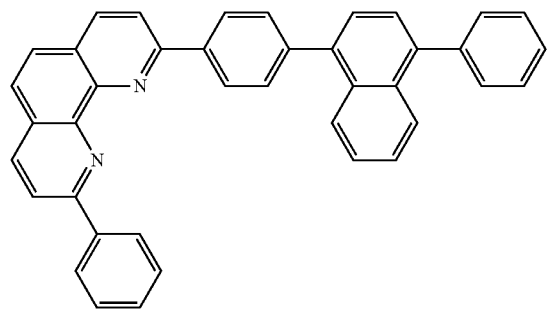
EN-038
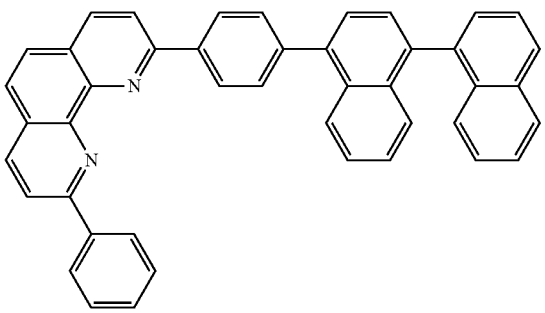

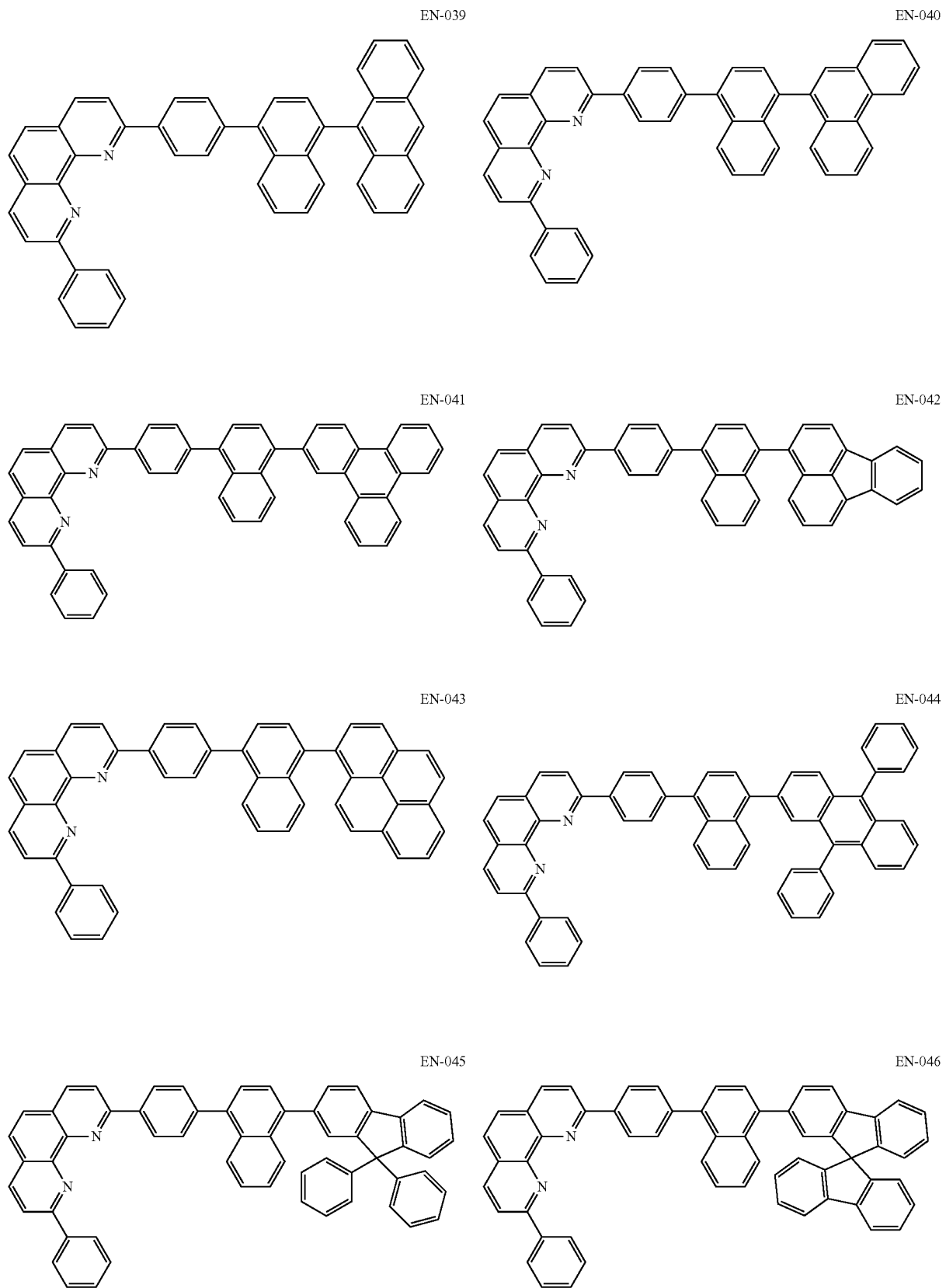

-continued
EN-047
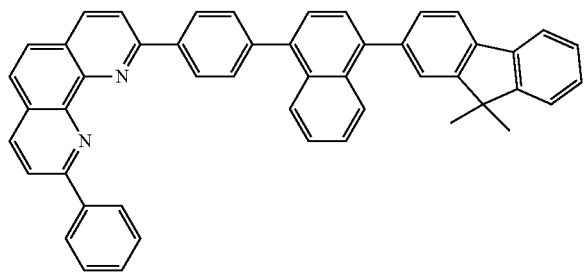
EN-048
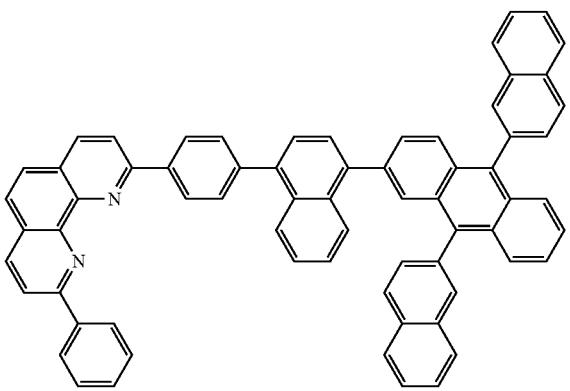
EN-049
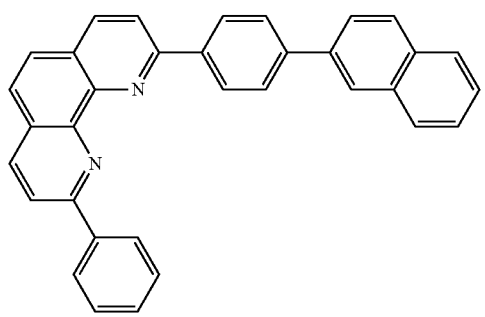
EN-050
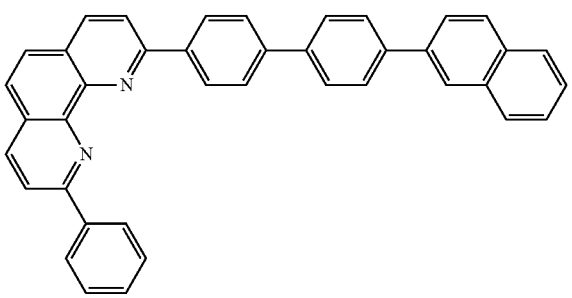
EN-051
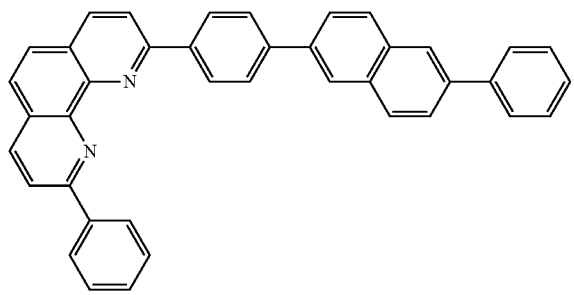
EN-052
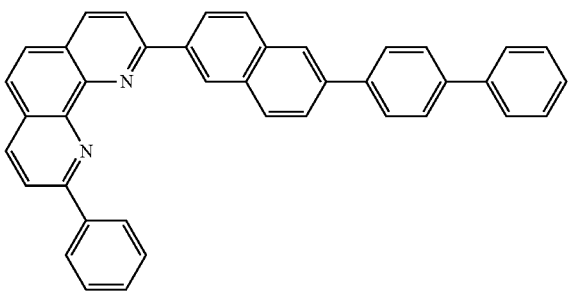
EN-053
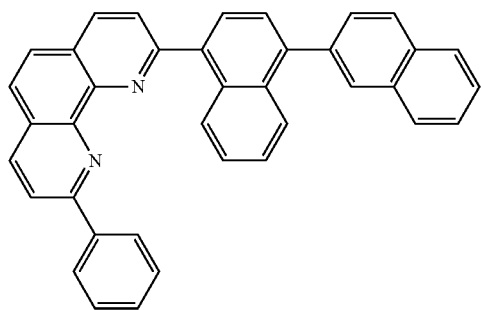
EN-054
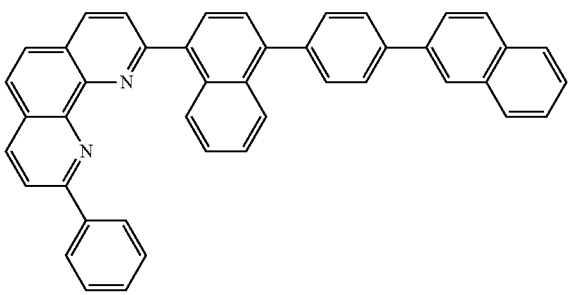

-continued
EN-055
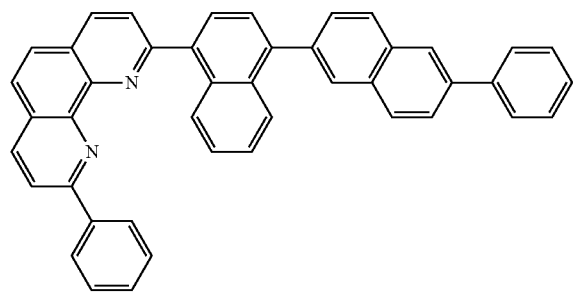
EN-056
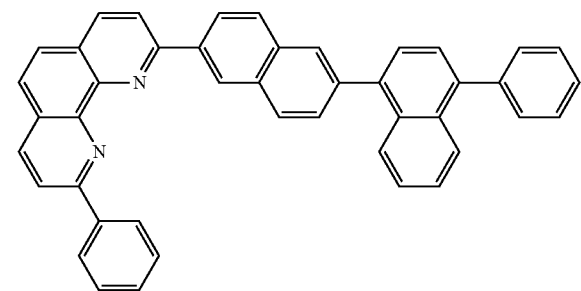
EN-057
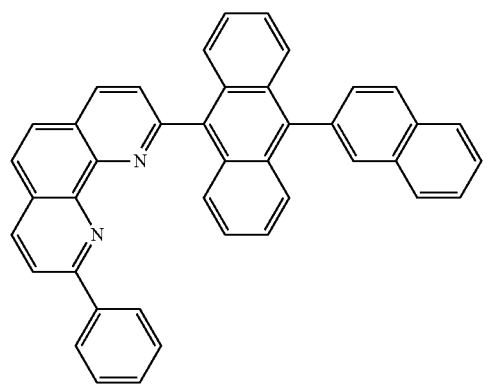
EN-058
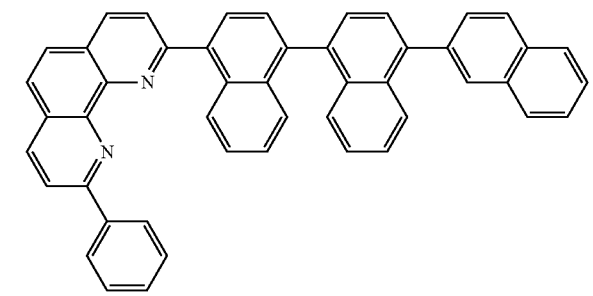
EN-059
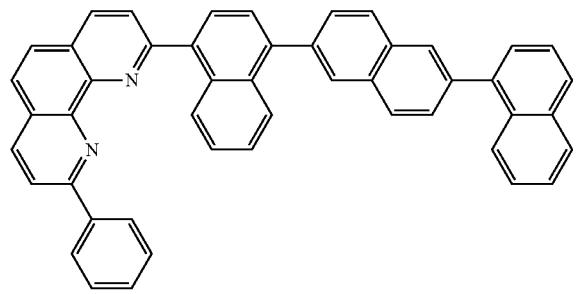
EN-060
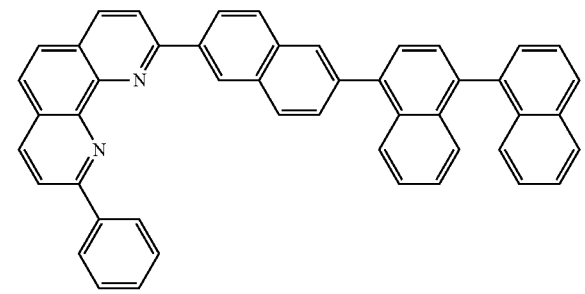
EN-061
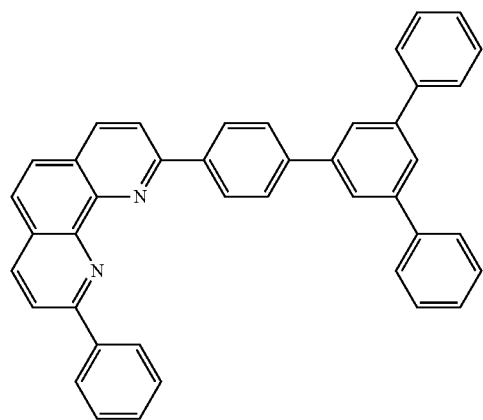
EN-062
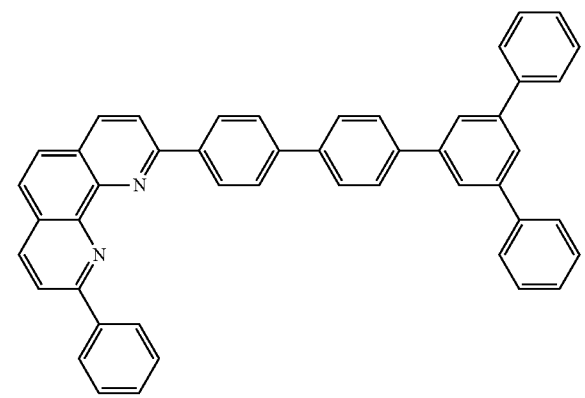

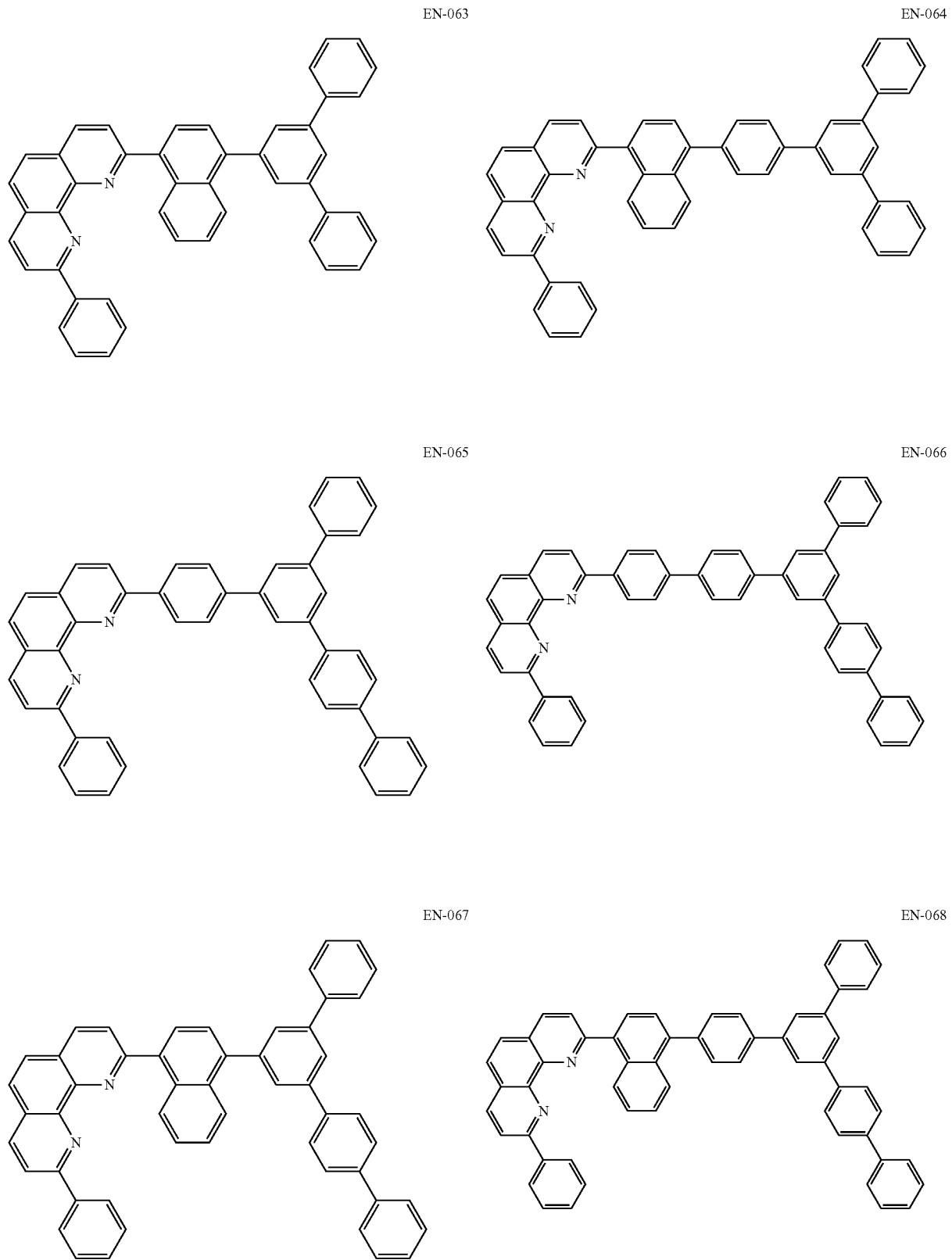

EN-069
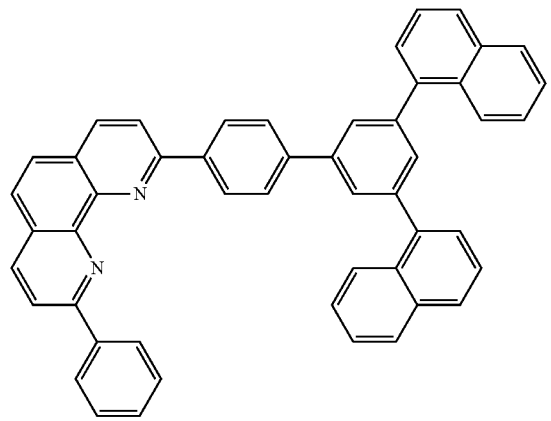
EN-070
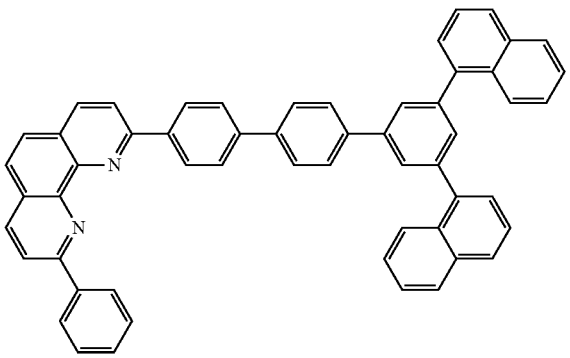
EN-071
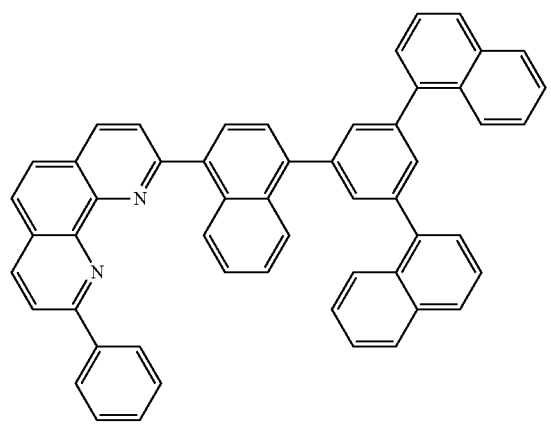
EN-072
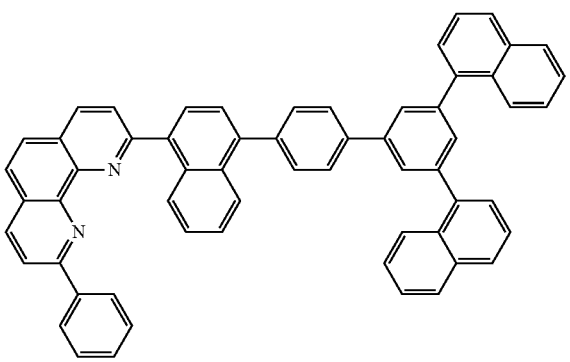
EN-073
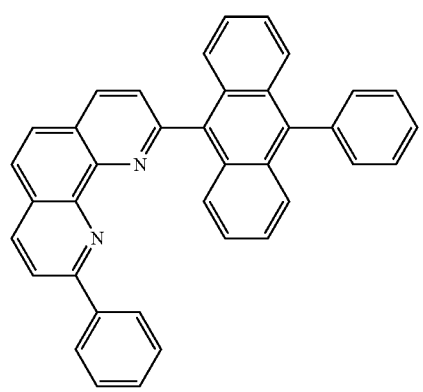
EN-074
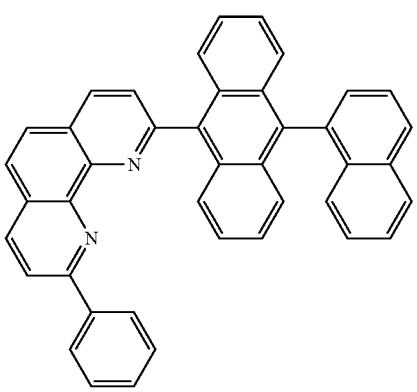
EN-075
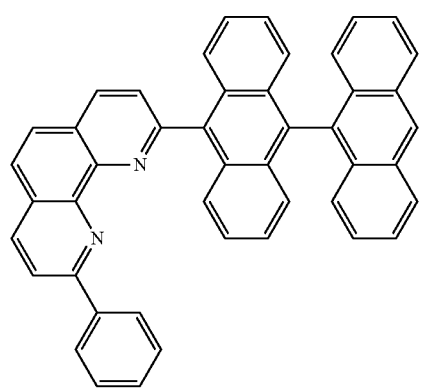
EN-076
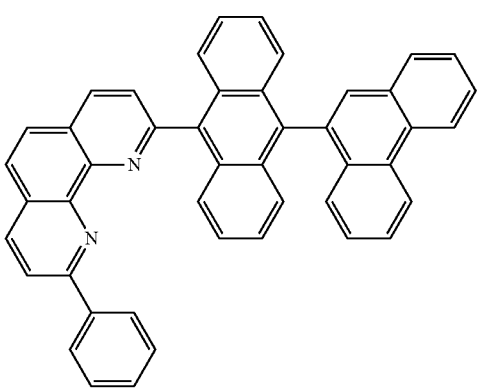

EN-077
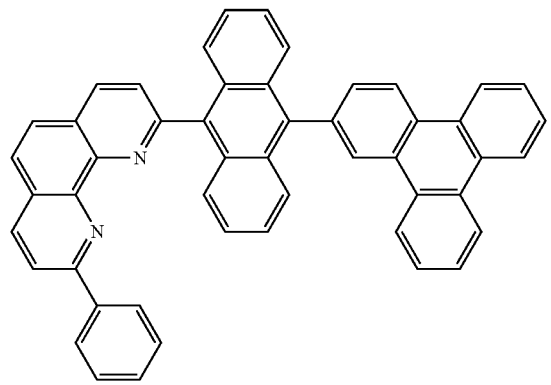
EN-078
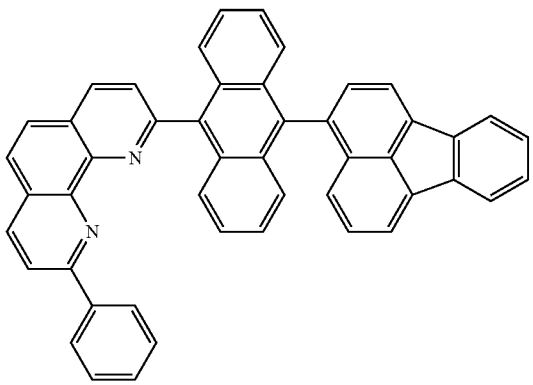
EN-079
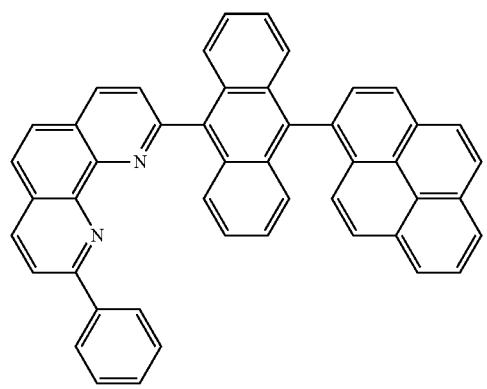
EN-080
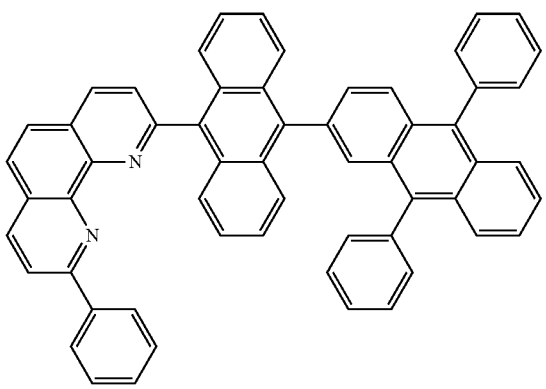
EN-081
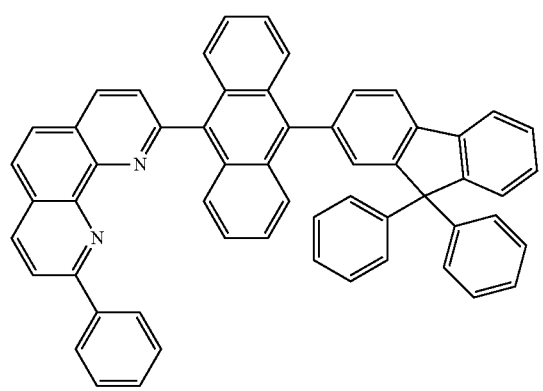
EN-082
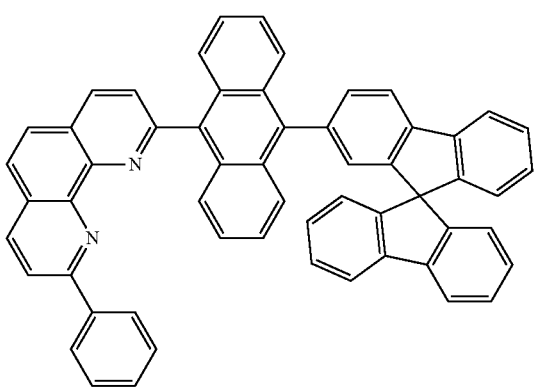

-continued
EN-083
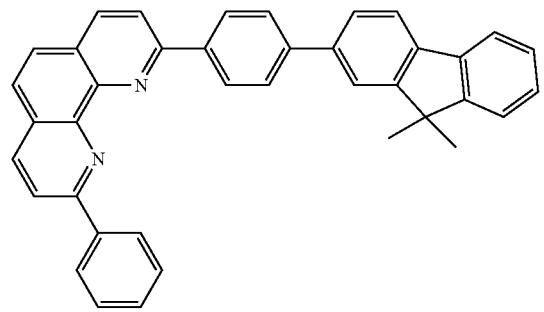
EN-084
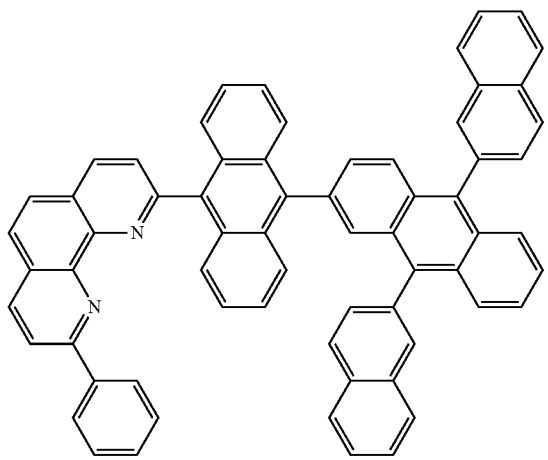
EN-085
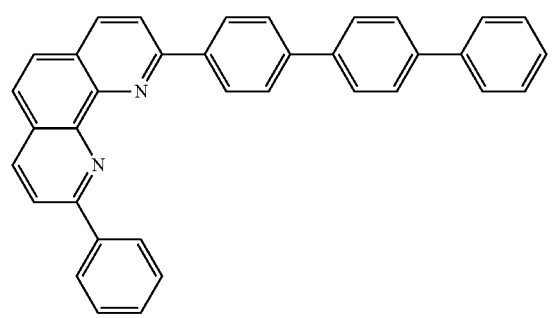
EN-086
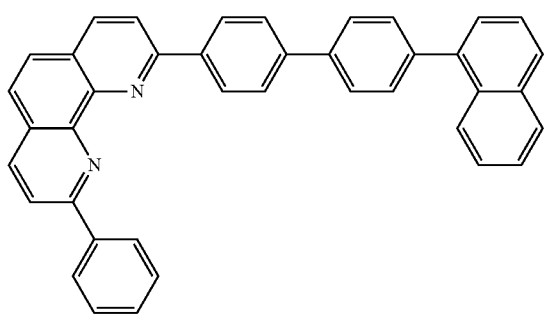
EN-087
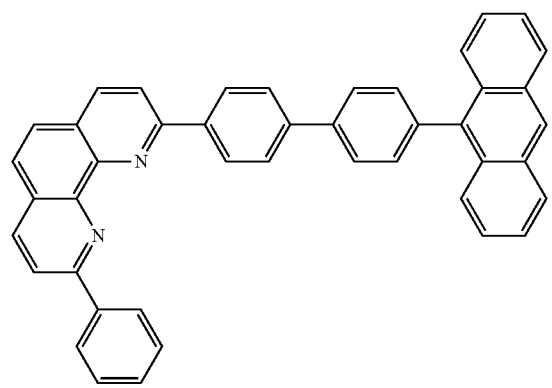
EN-088
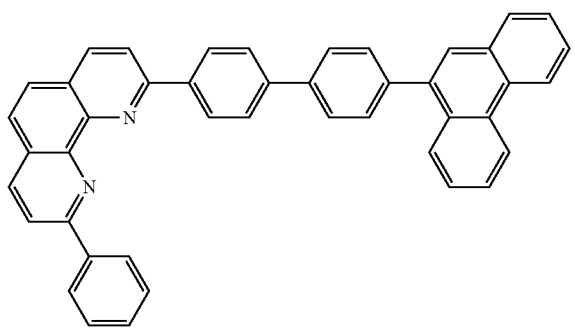
EN-089
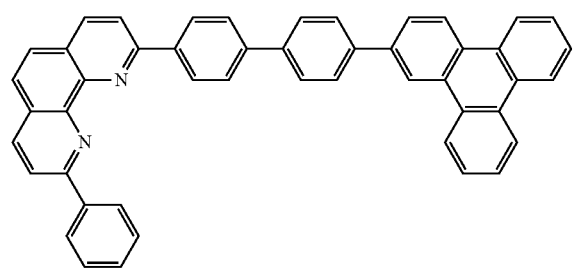
EN-090
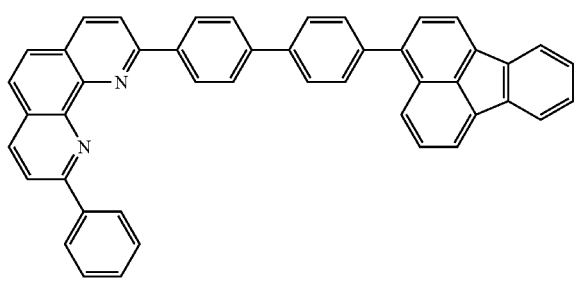

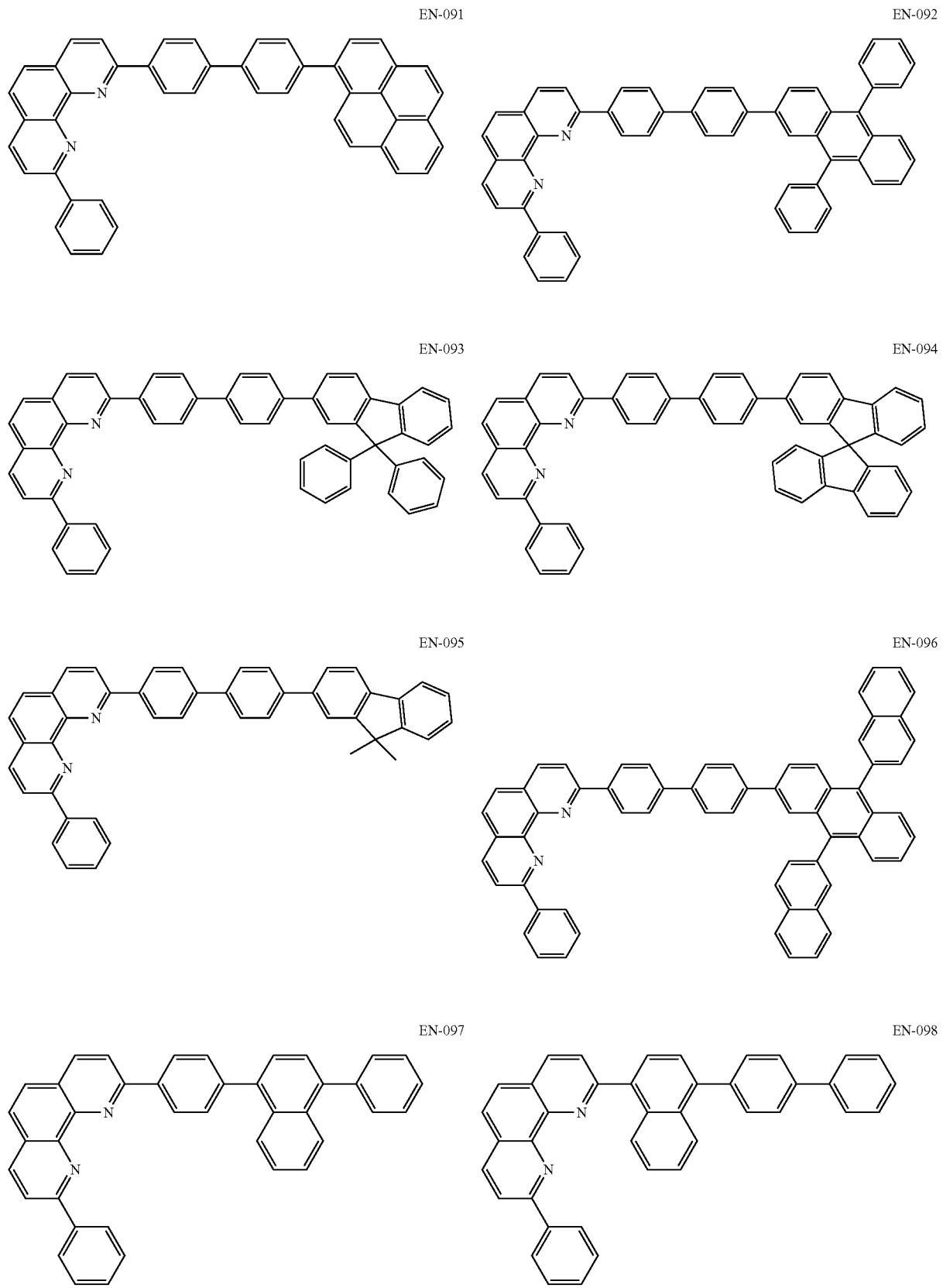

-continued
EN-099
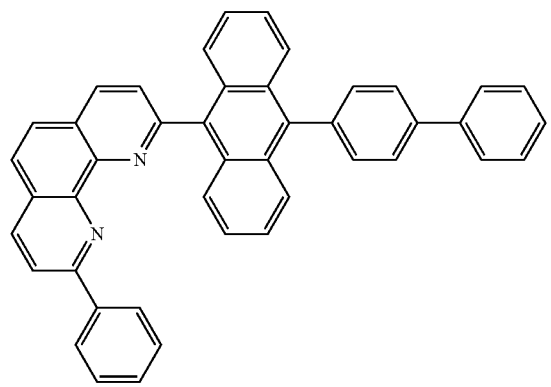
EN-100
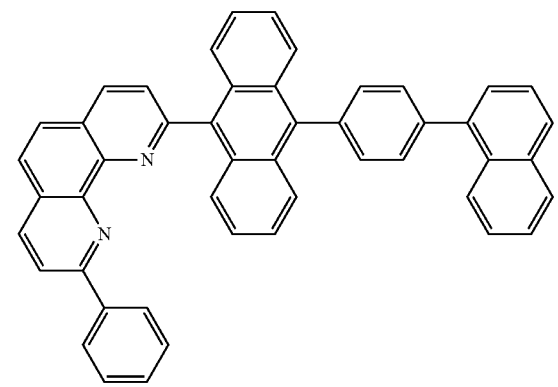
EN-101
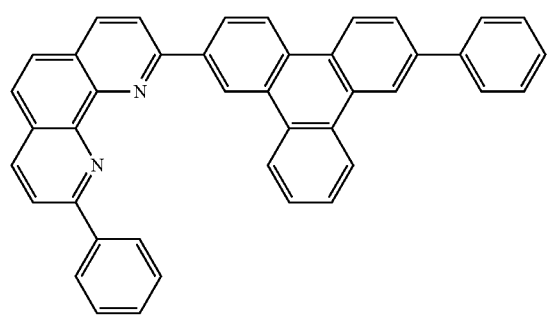
EN-102
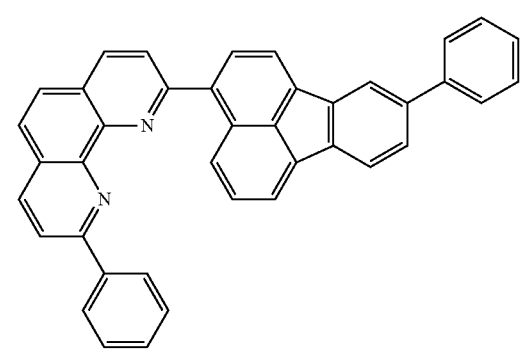
EN-103
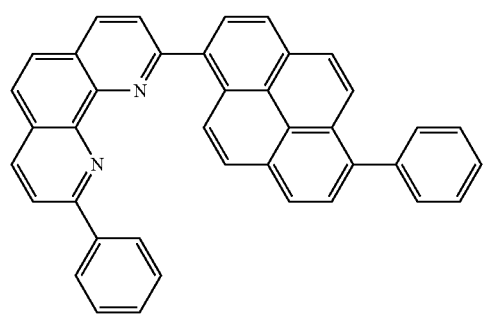
EM-104
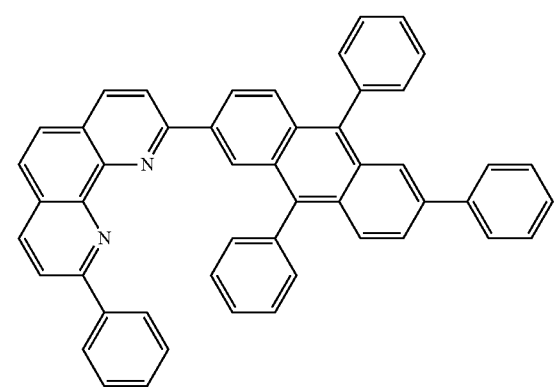
EN-105
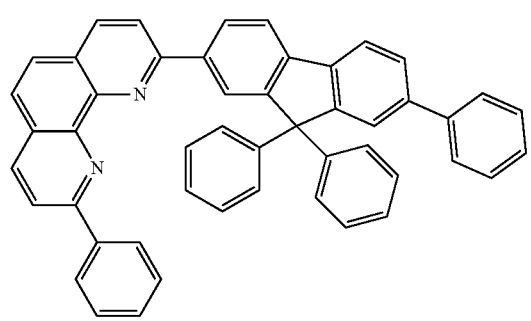
EN-106
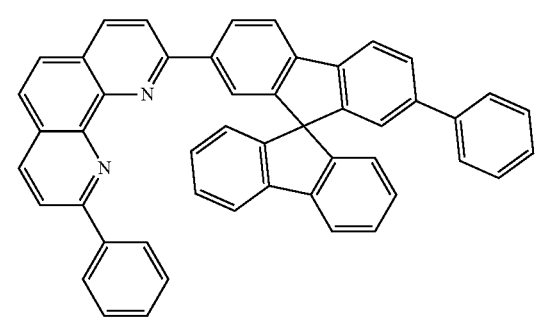

-continued
EN-107
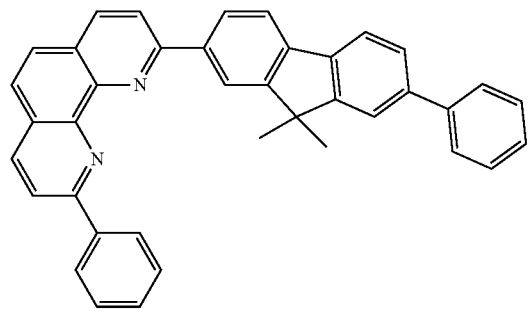
EN-108
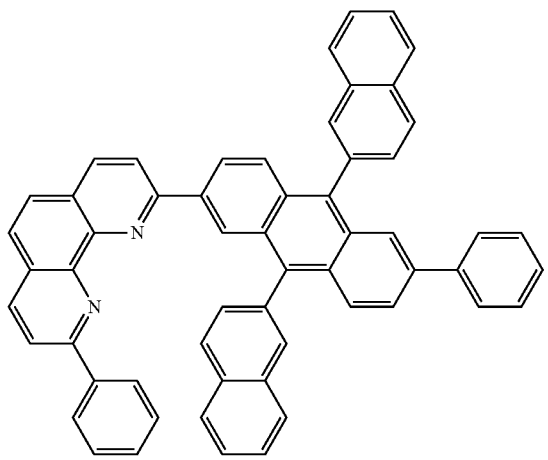
EN-109
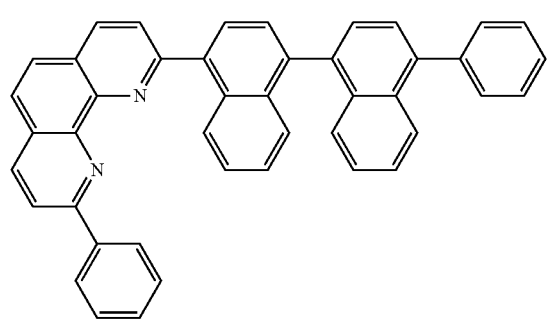
EN-110
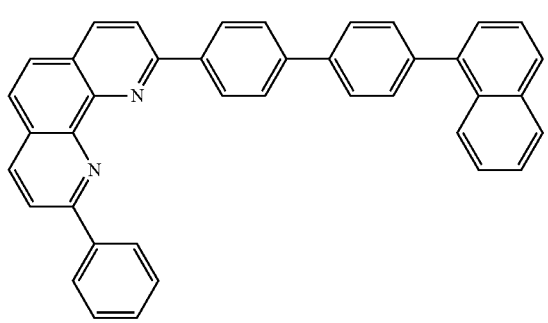
EN-111
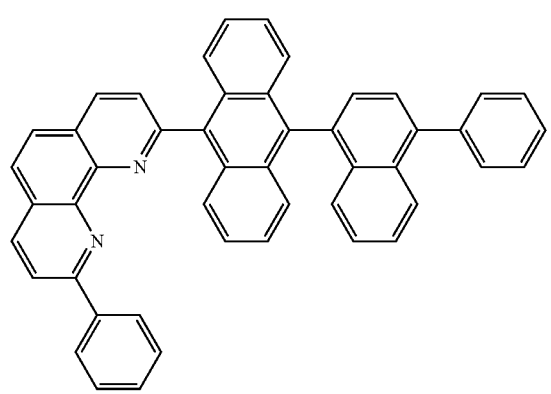
EN-112
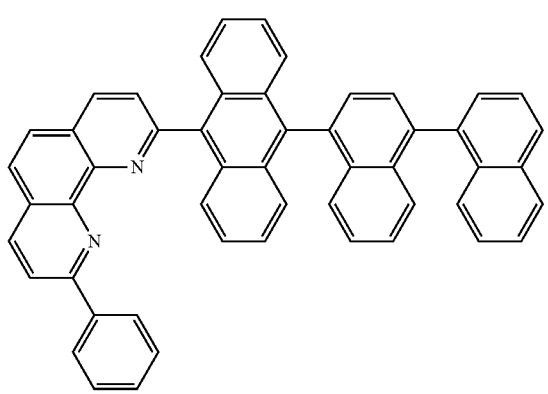
EN-113
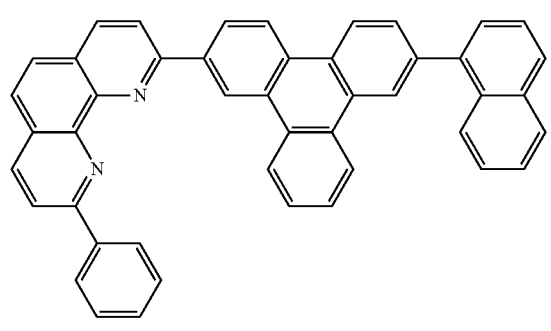
EN-114
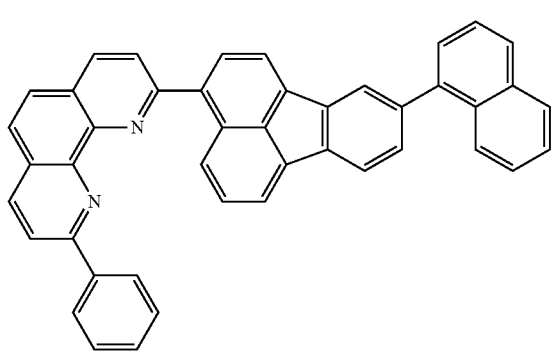

-continued
EN-115
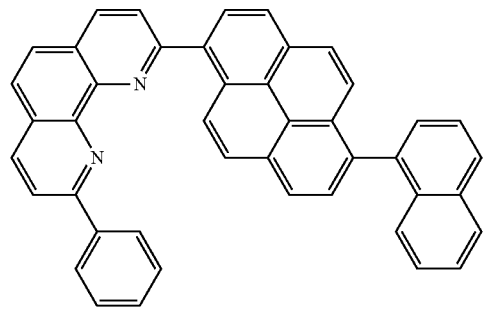
EN-116
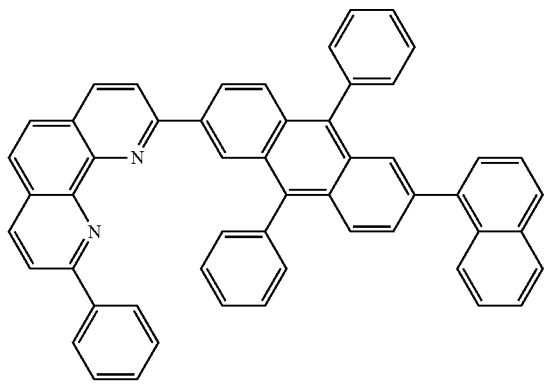
EN-117
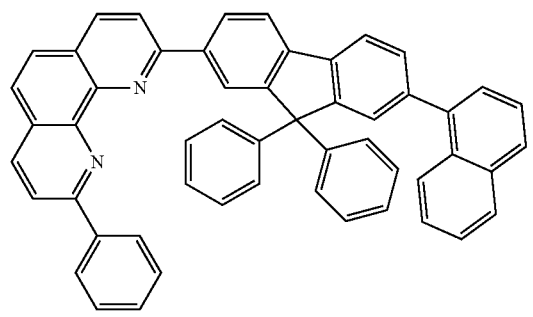
EN-118
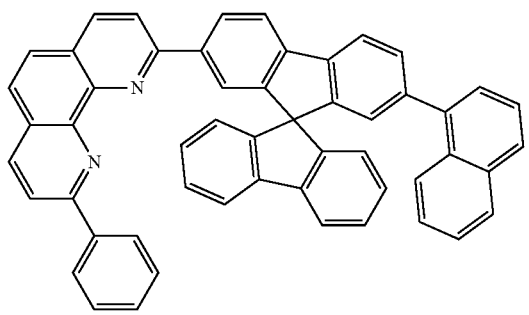
EN-119
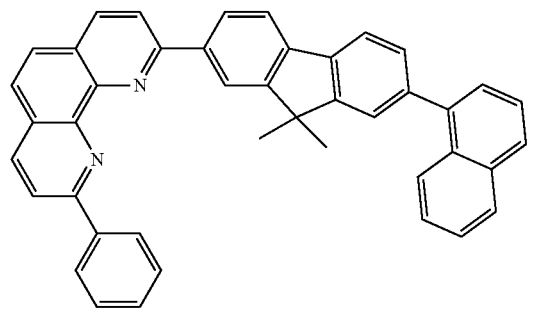
EN-120
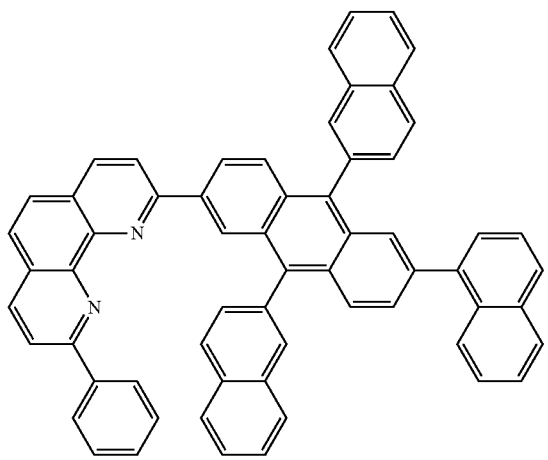
EN-121
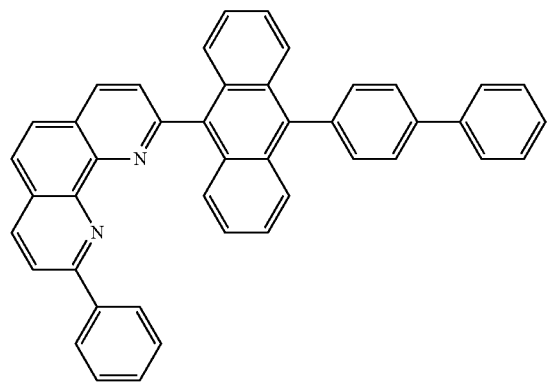
EN-122
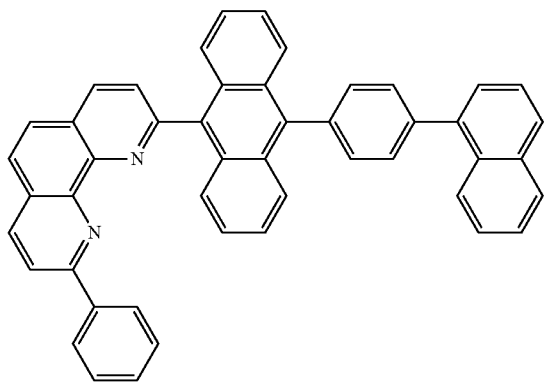

-continued
EN-123
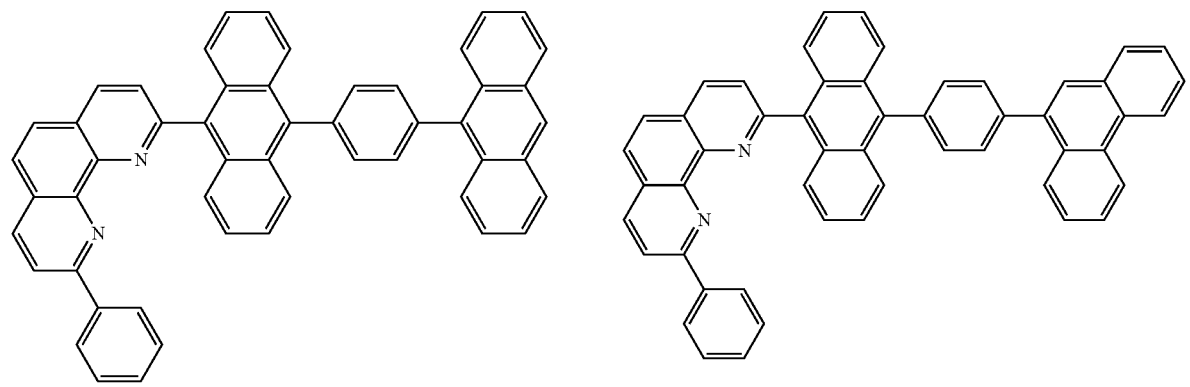
EN-124
EN-125
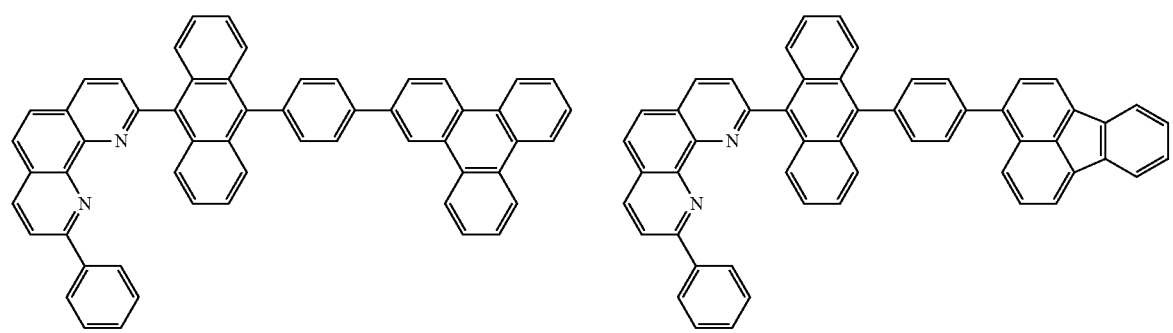
EN-126
EN-127
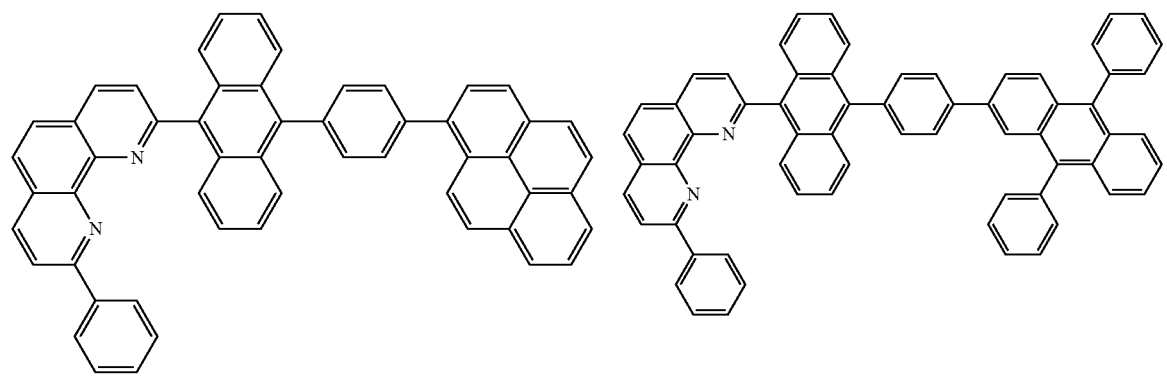
EN-128
EN-129
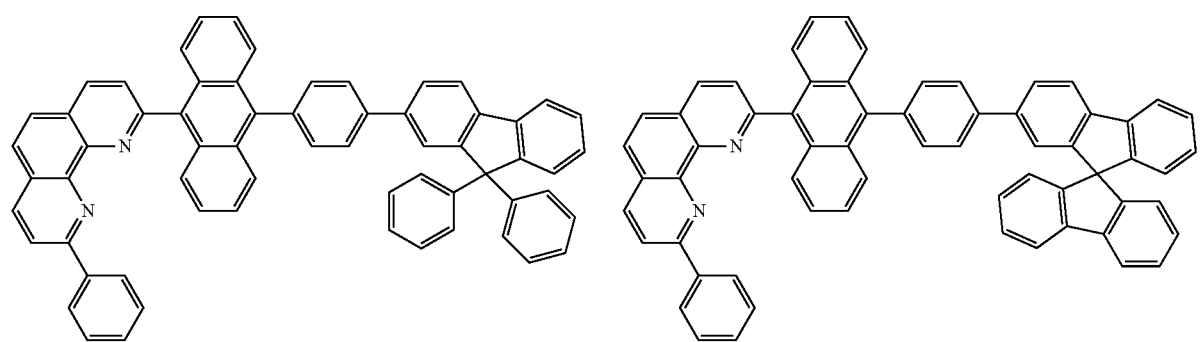
EN-130

-continued
EN-131
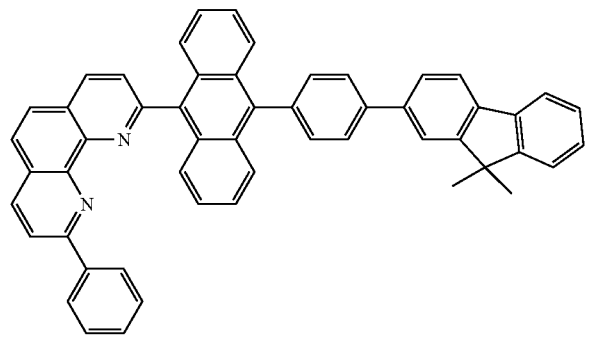
EN-132
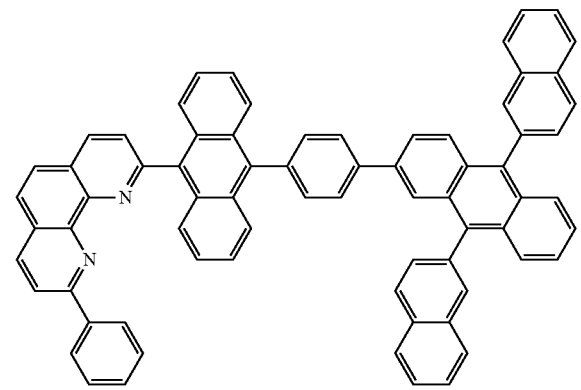
EN-133
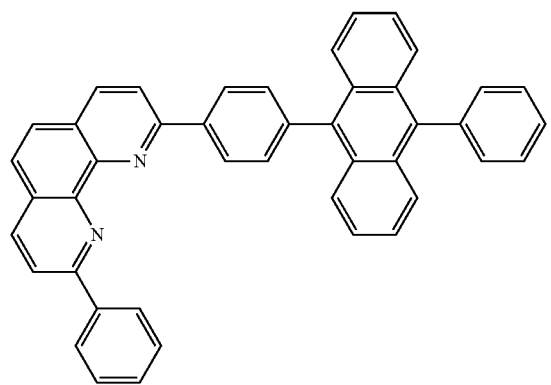
EN-134
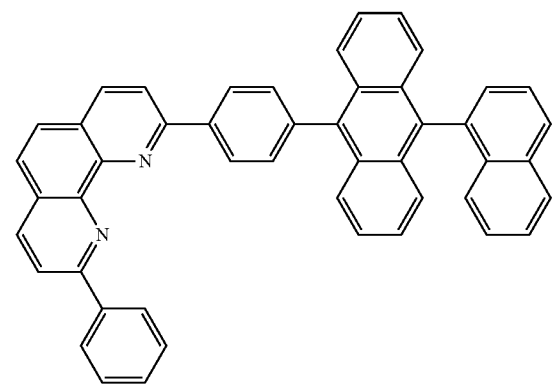
EN-135
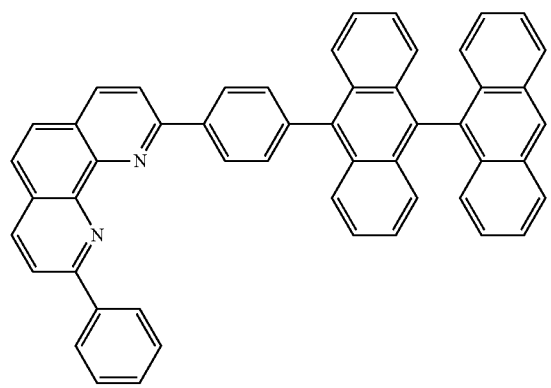
EN-136
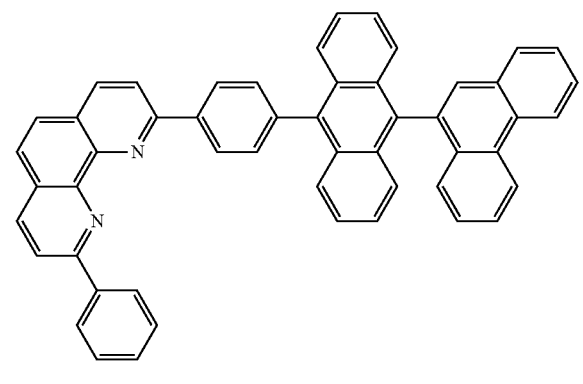
EN-137
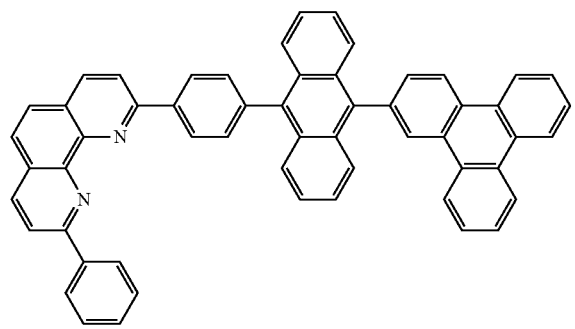
EN-138
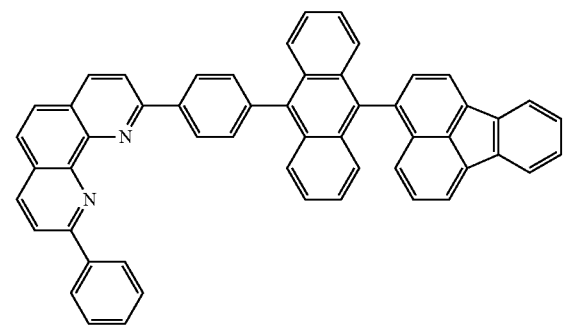

-continued
EN-139
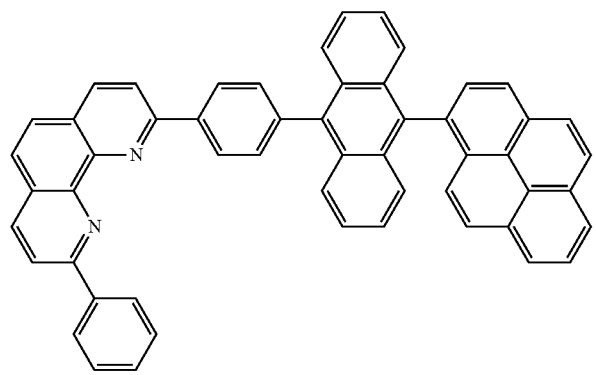
EN-140
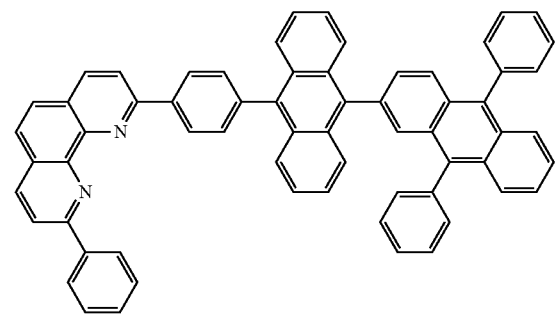
EN-141
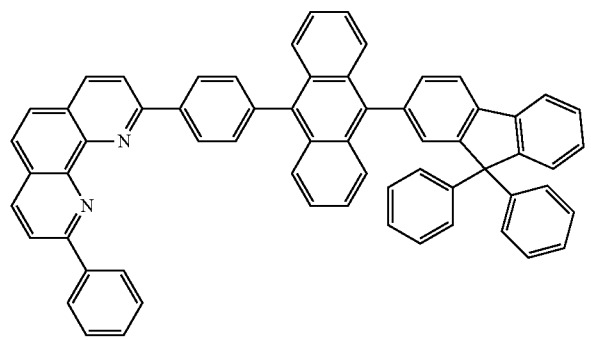
EN-142
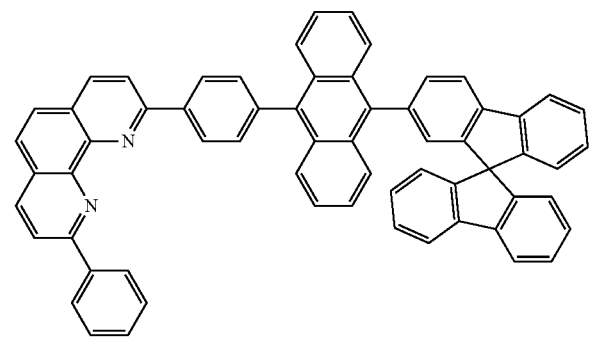
EN-143
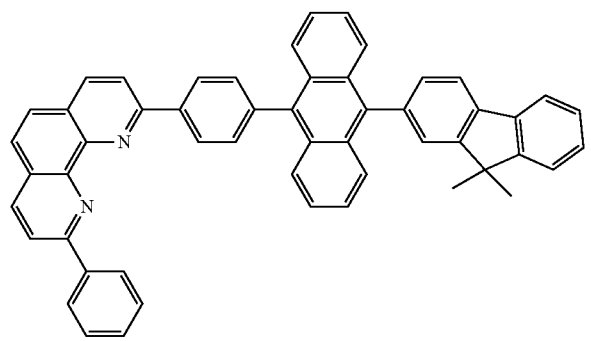
EN-144
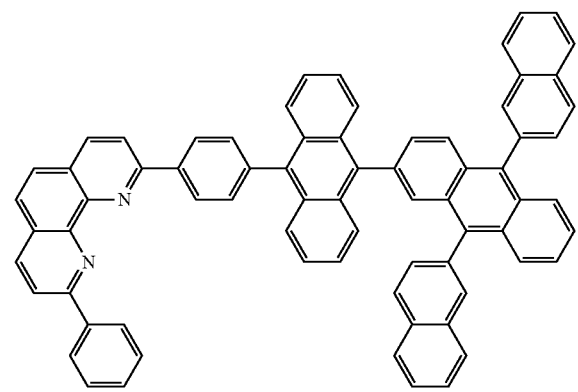
EN-145
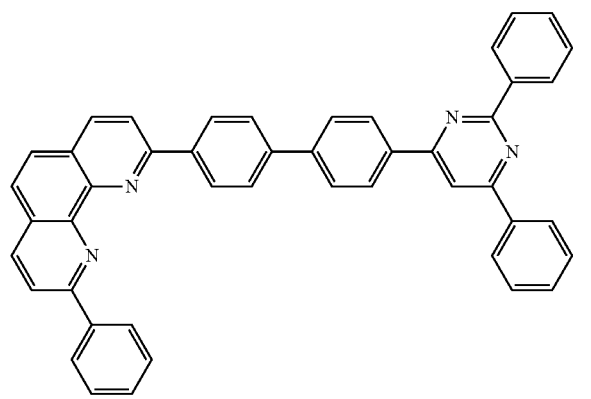
EN-146
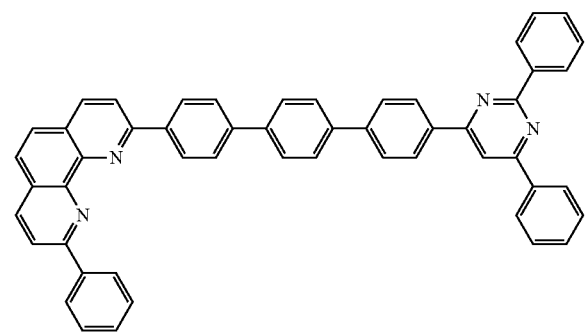

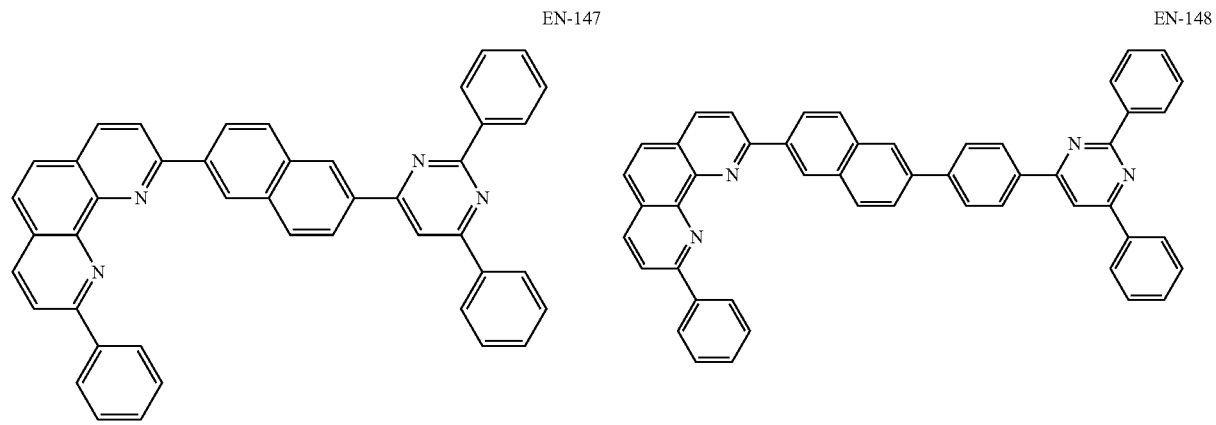
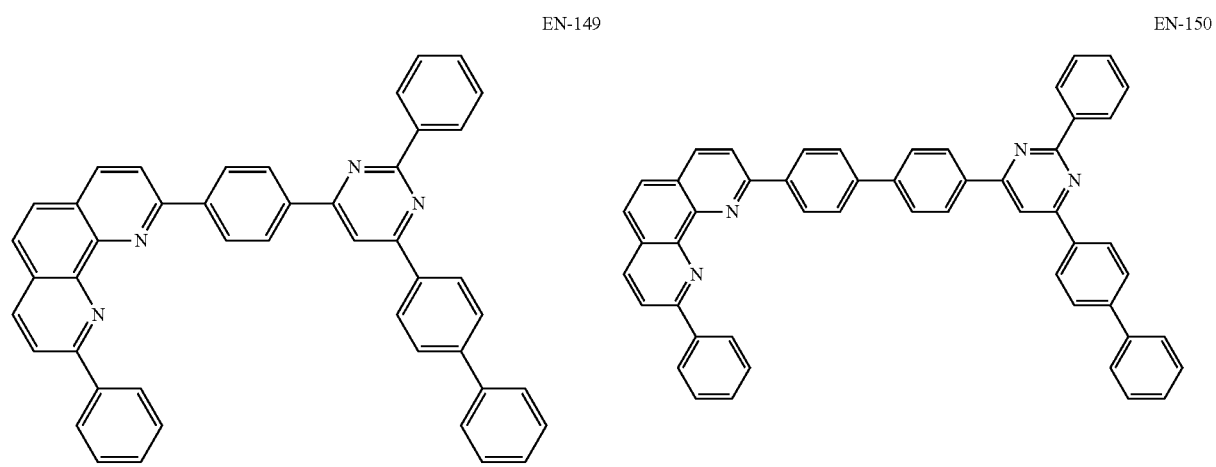
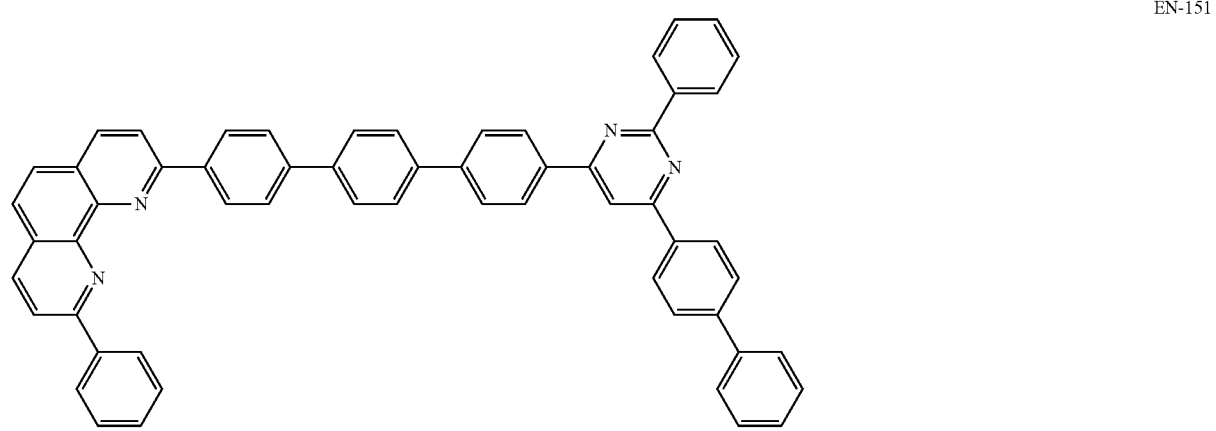

-continued
EN-152
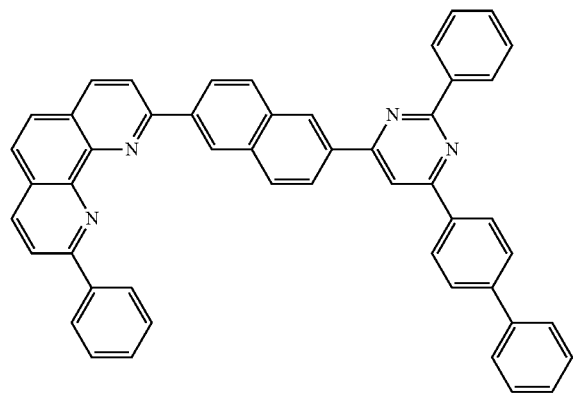
1N-153
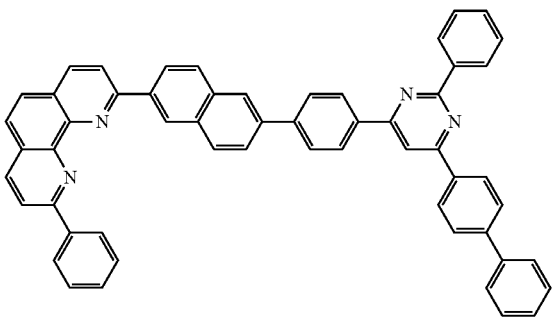
EN-154
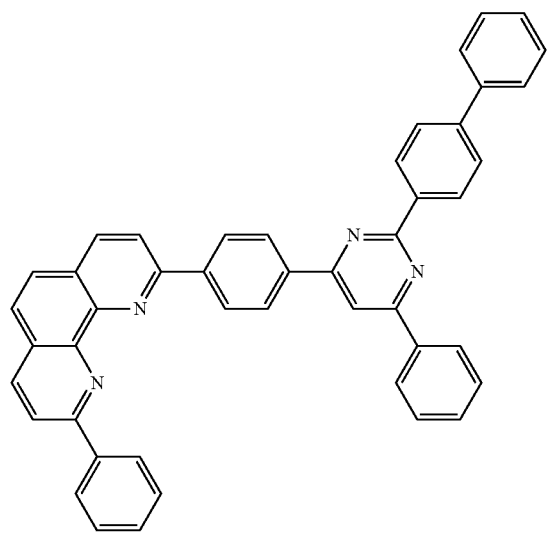
EN-155
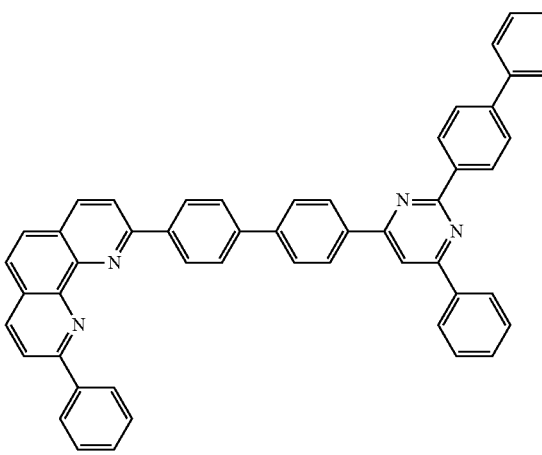
EN-156
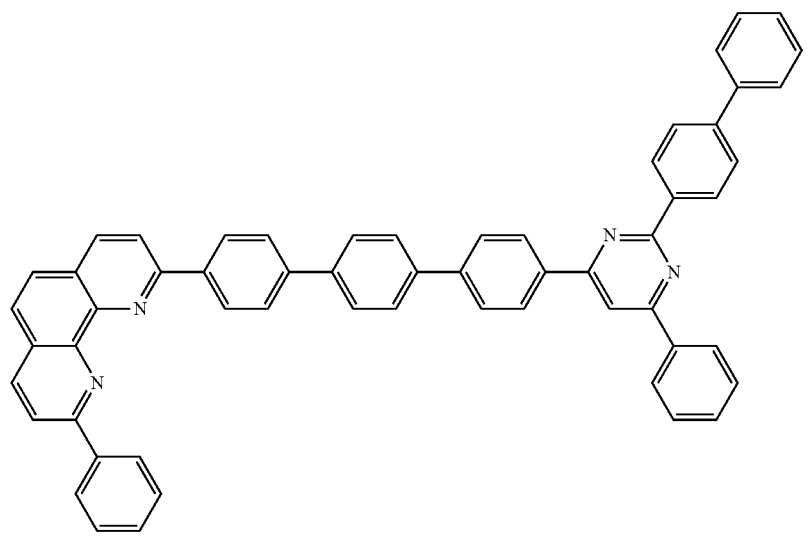

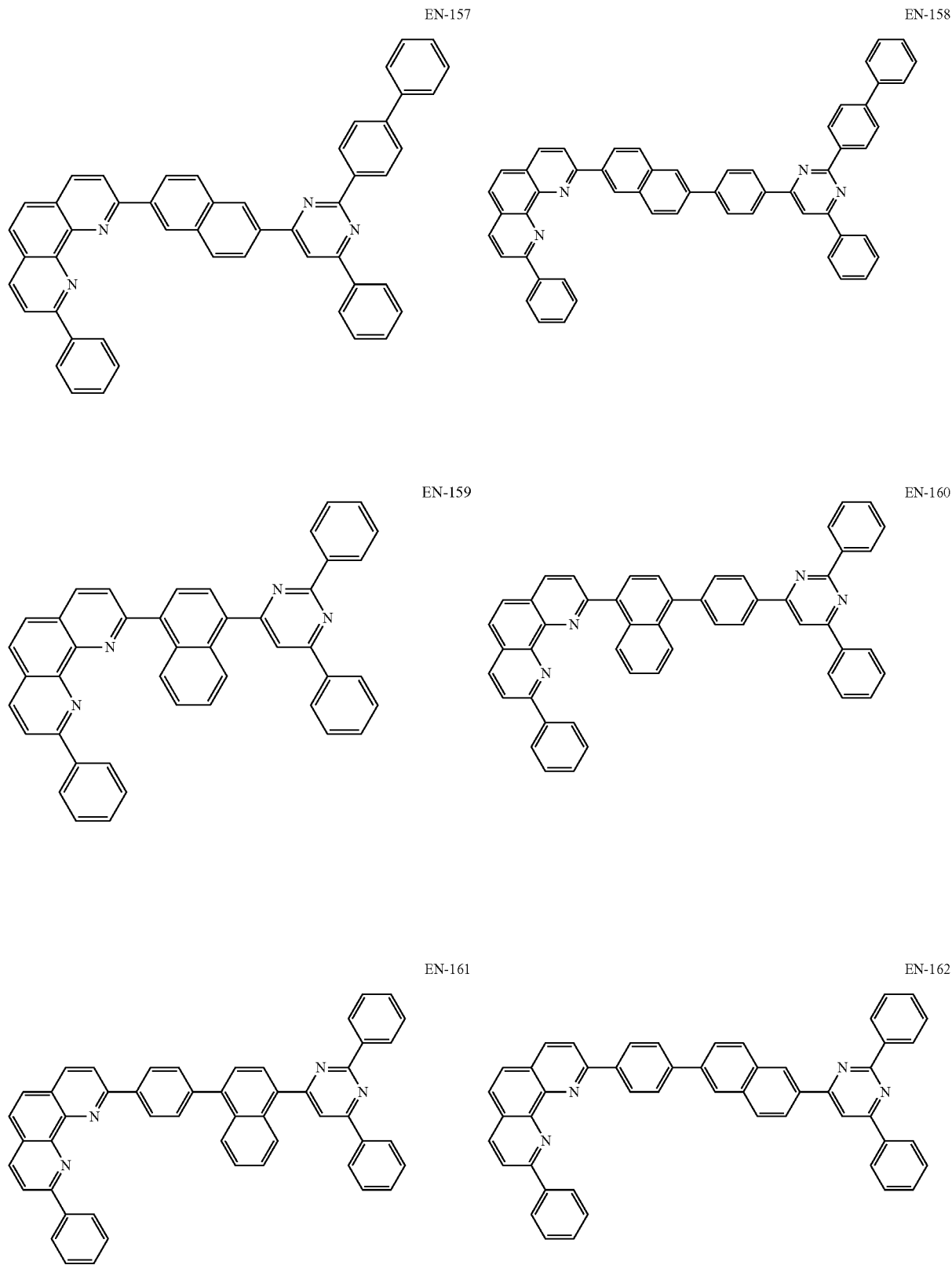

-continued
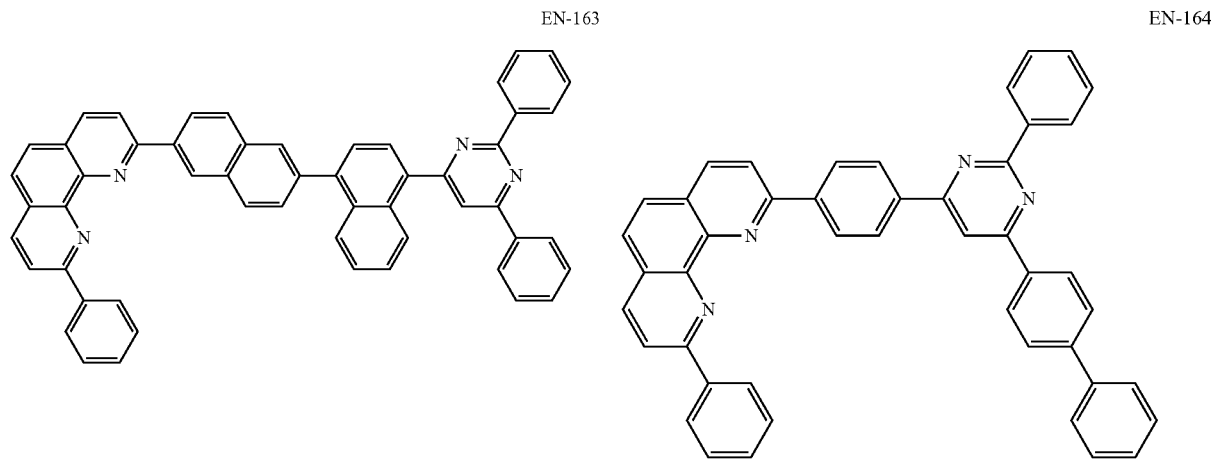
EN-163
EN-164
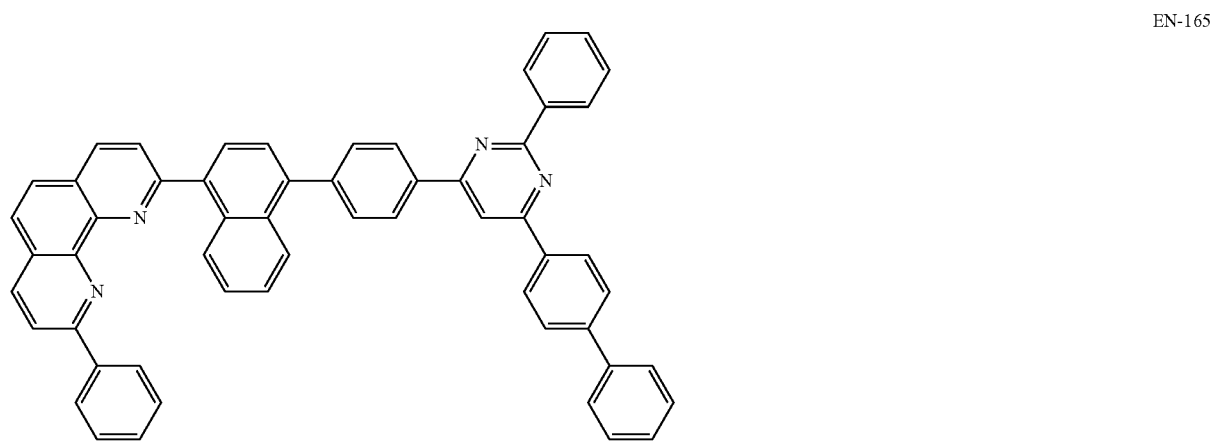
EN-165
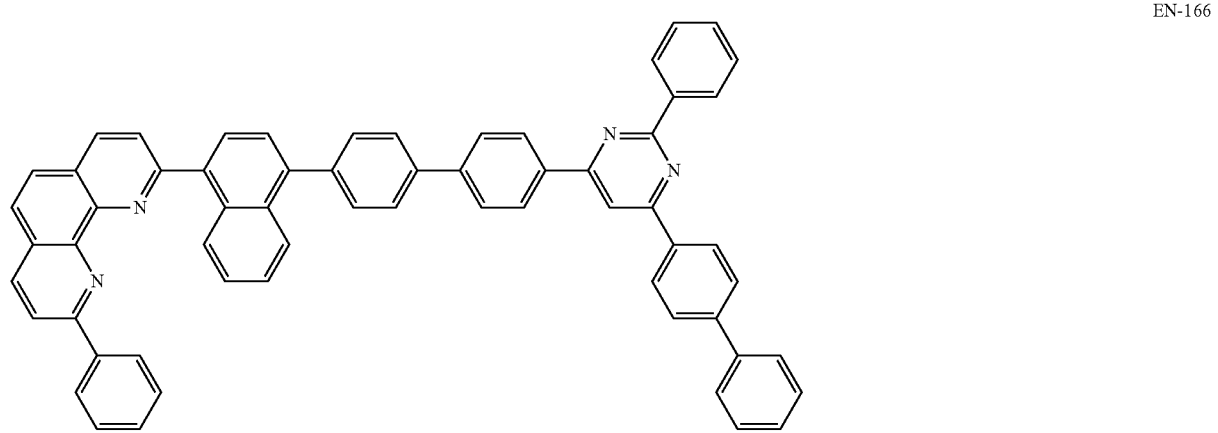
EN-166

-continued
EN-167
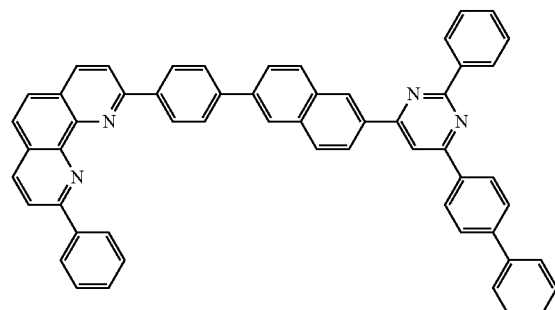
EN-168
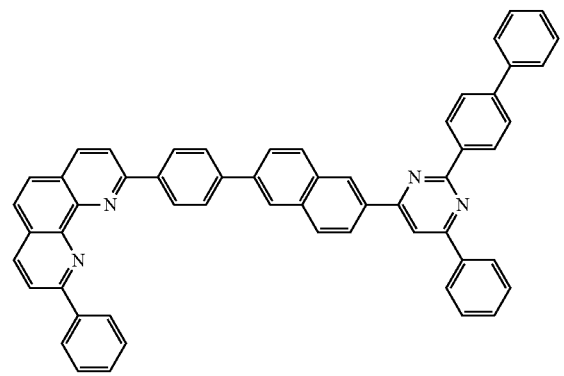
EN-169
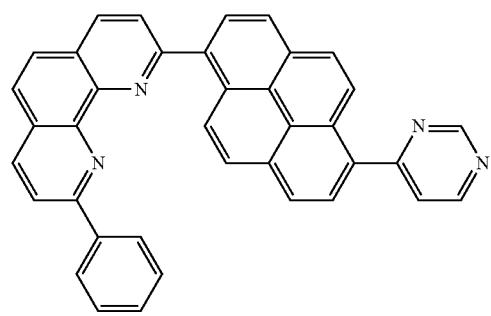
EN-170
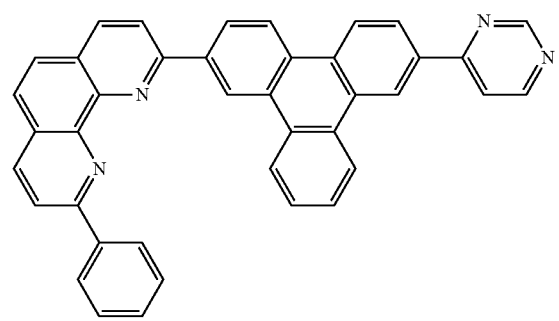
EN-171
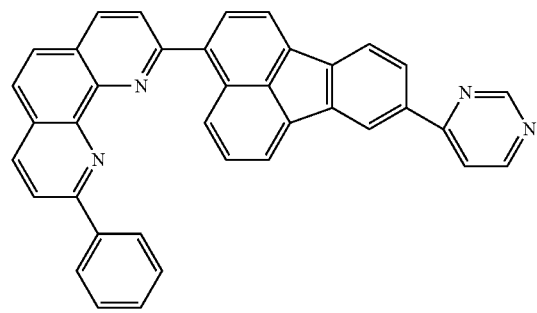
EN-172
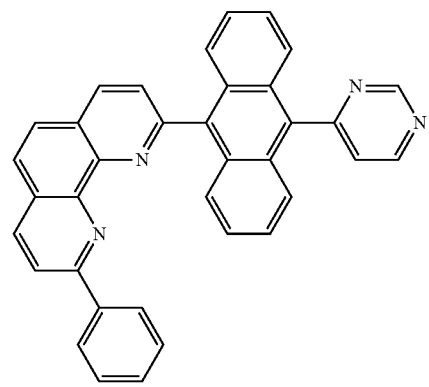
EN-173
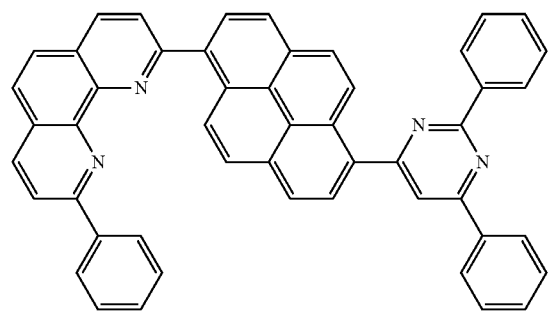
EN-174
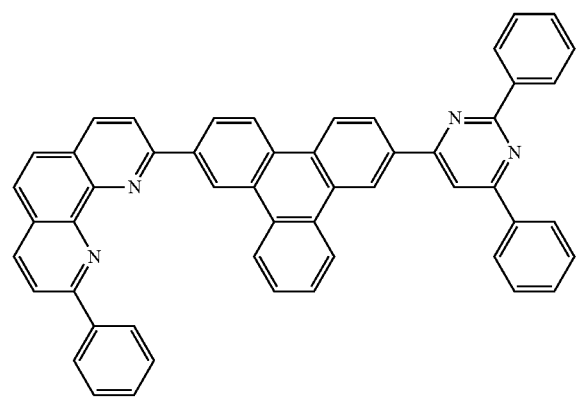

-continued
EN-175
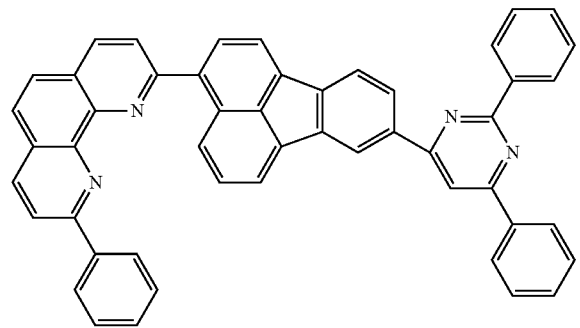
EN-176
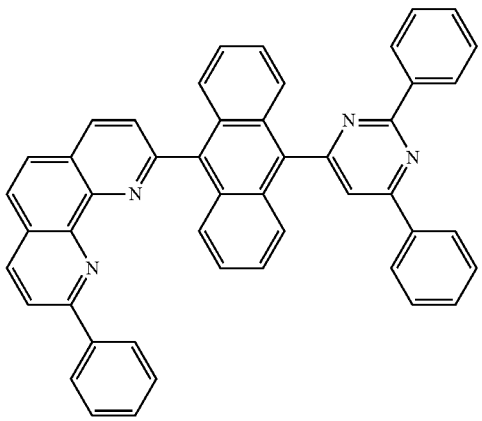
EN-177
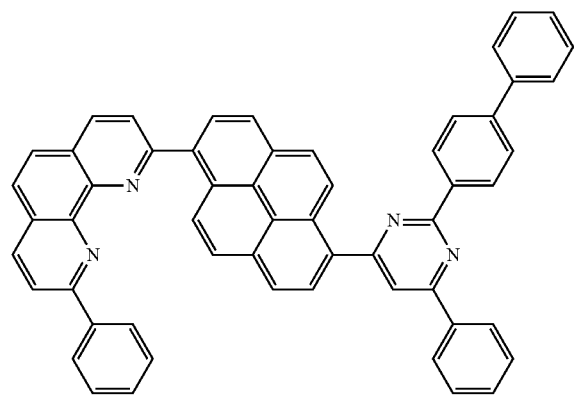
EN-178
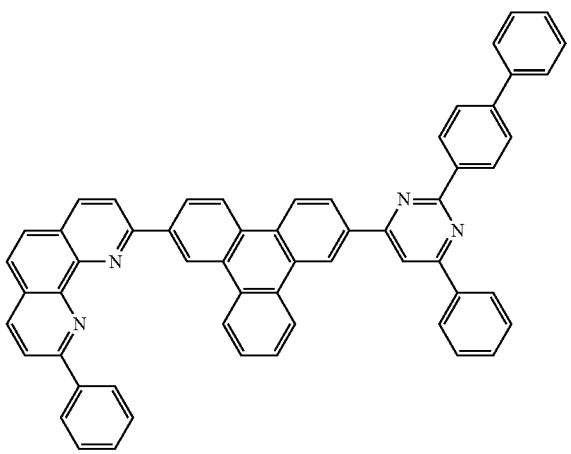
EN-179
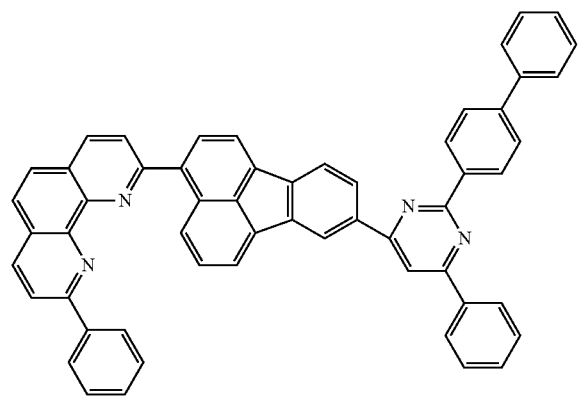
EN-180
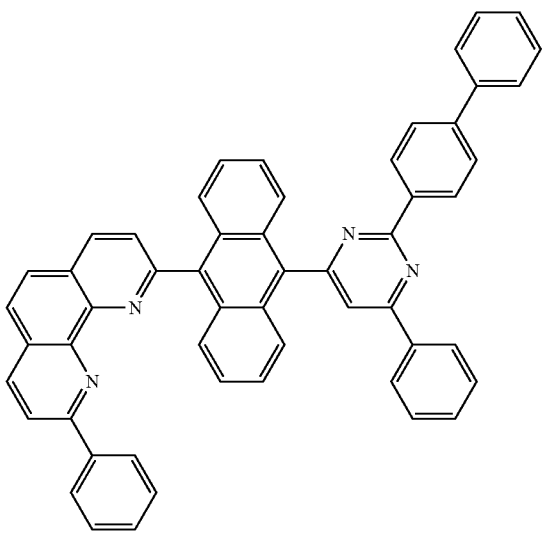

EN-181
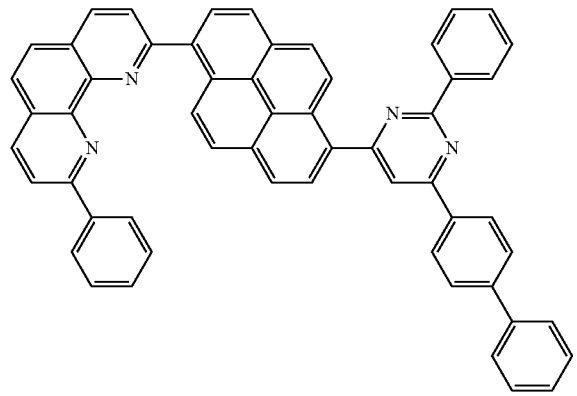
EN-182
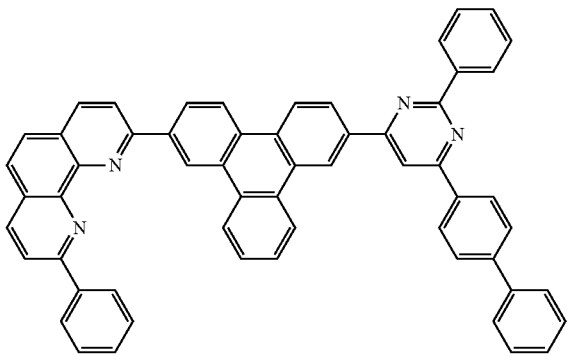
EN-183
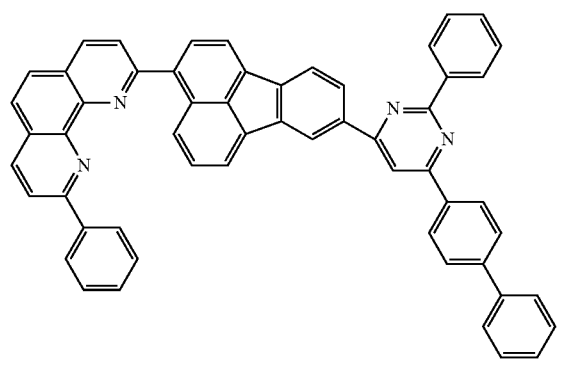
EN-184
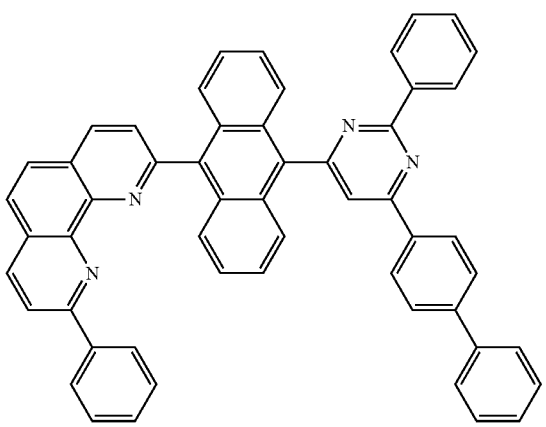
EN-185
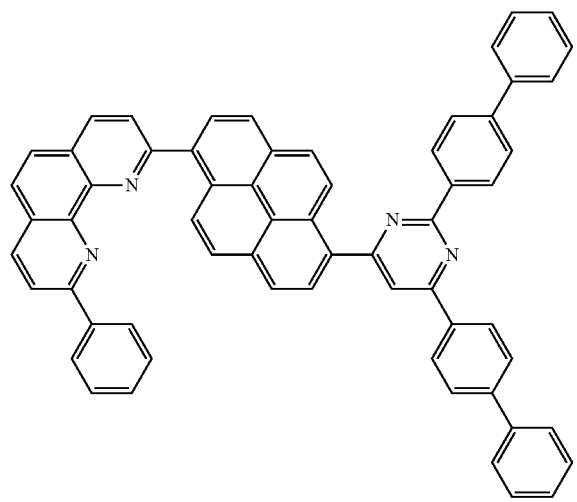
EN-186
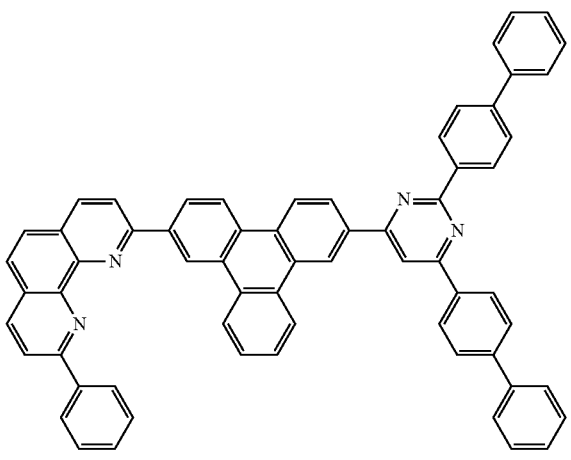

-continued
EN-187
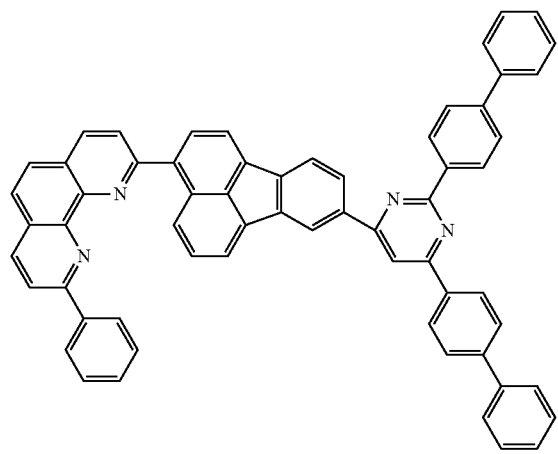
EN-188
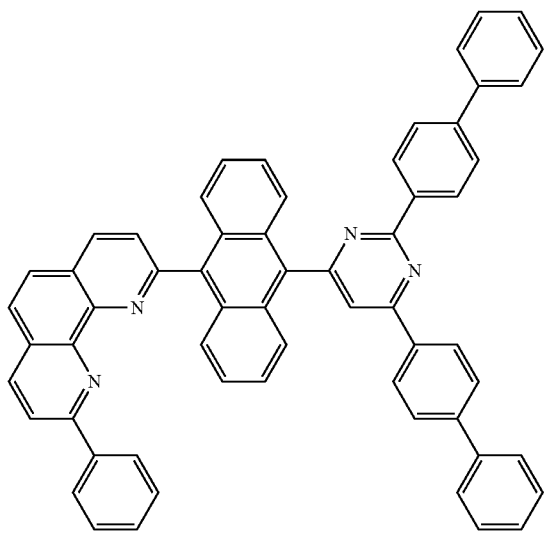
EN-189
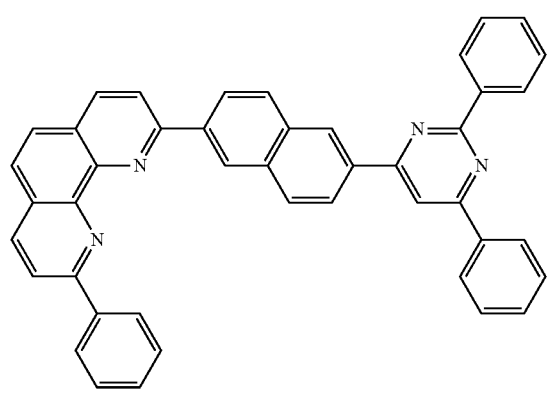
EN-190
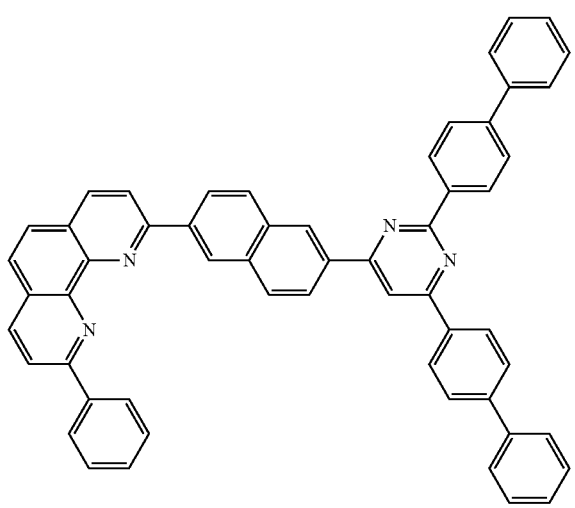
EN-191
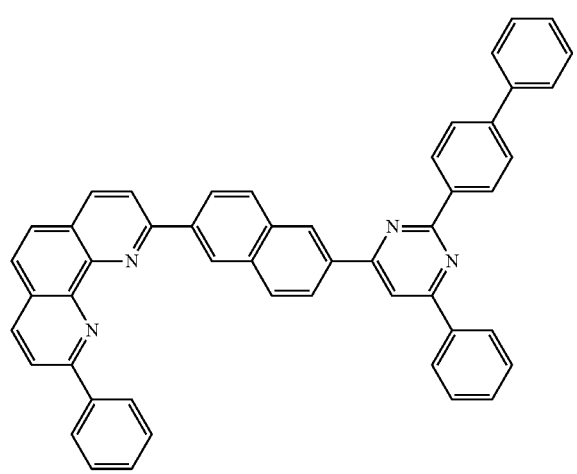
EN-192
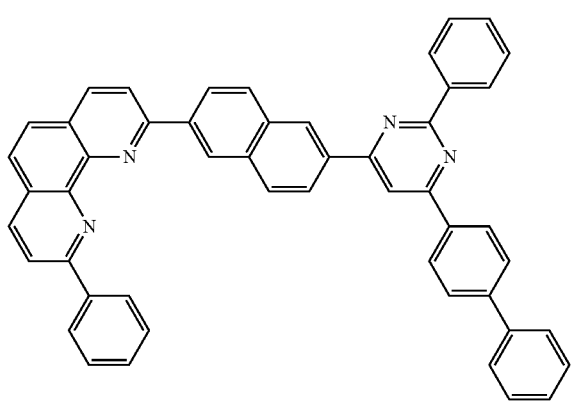

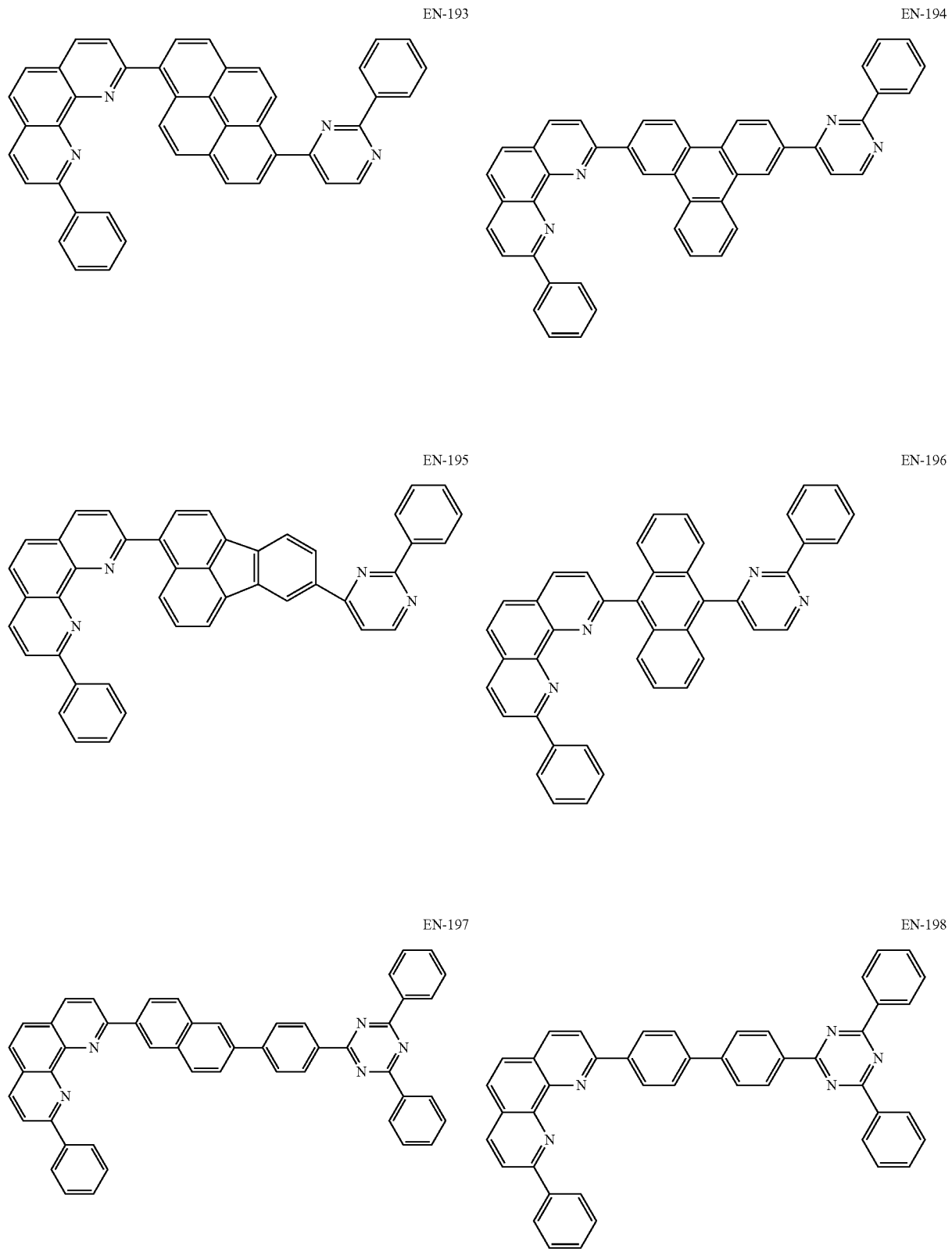

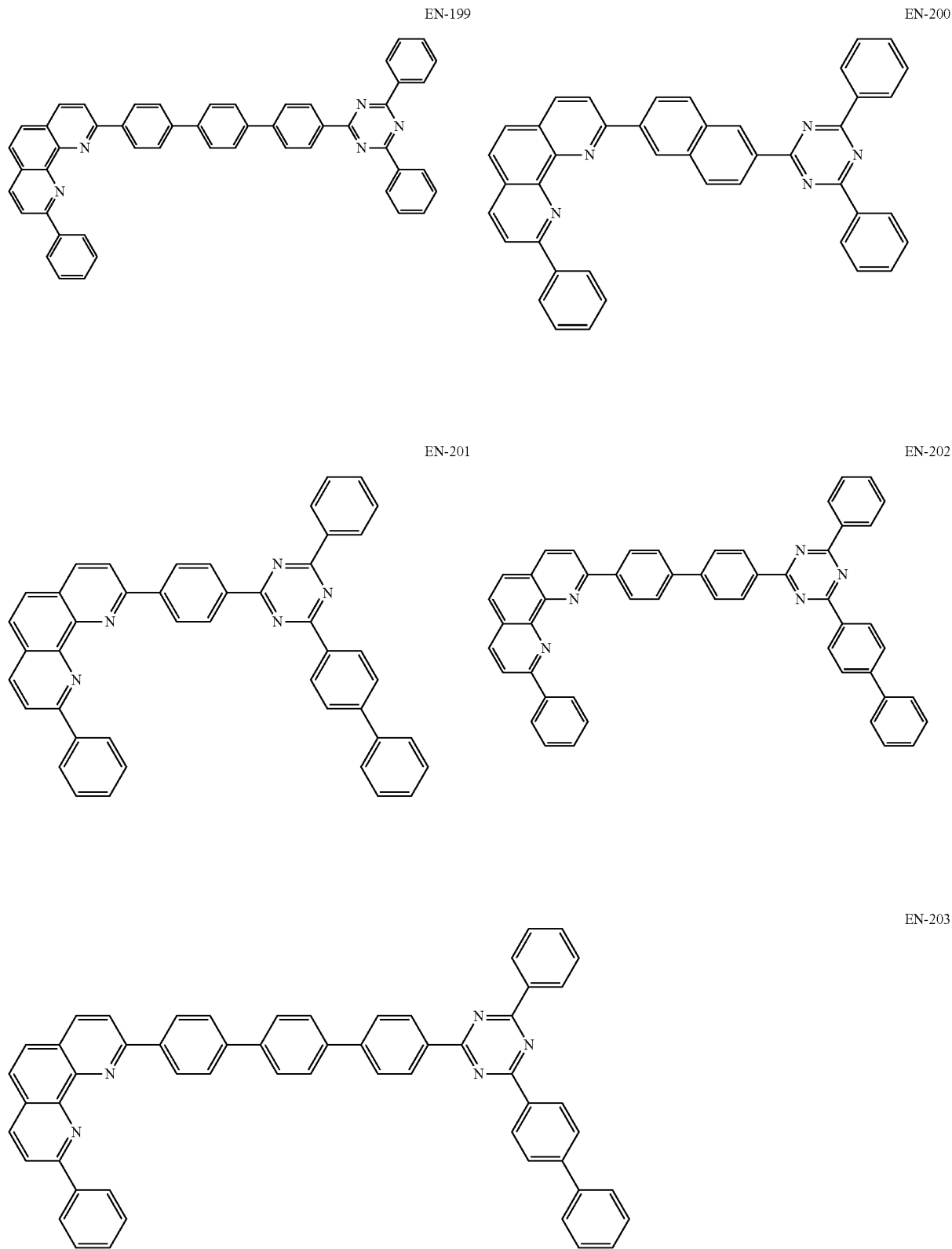

-continued
EN-204
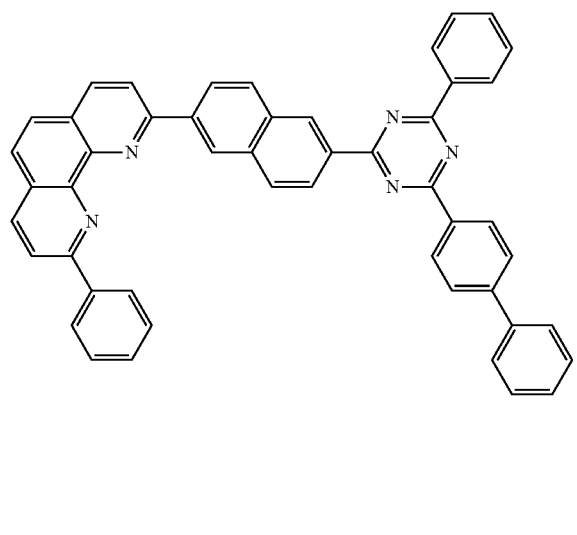
EN-205
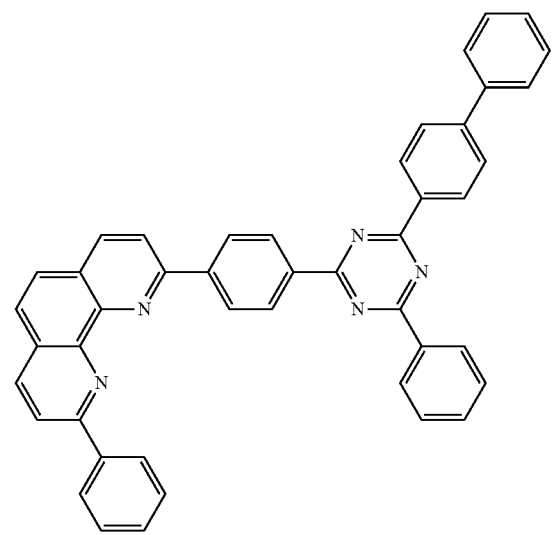
EN-206
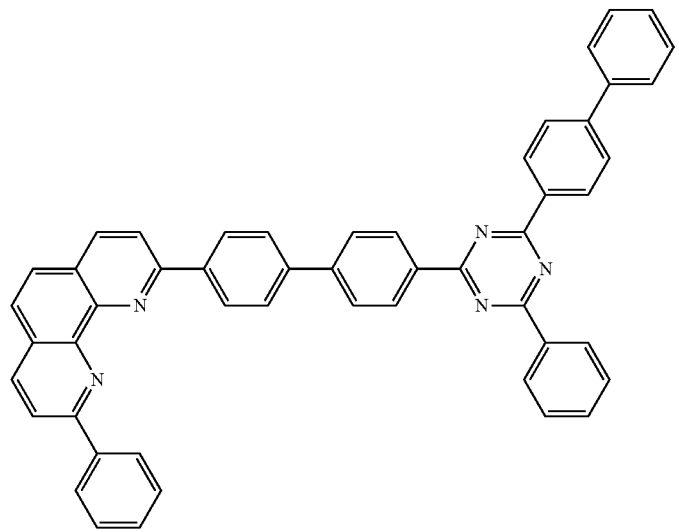
EN-207
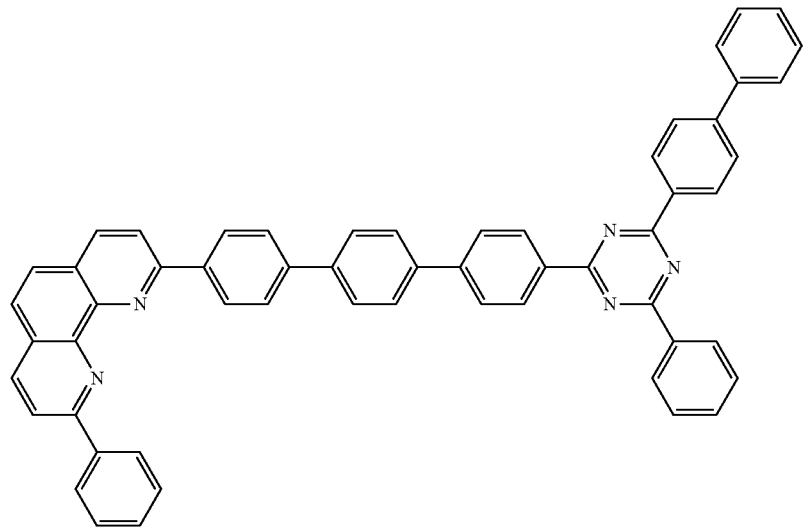

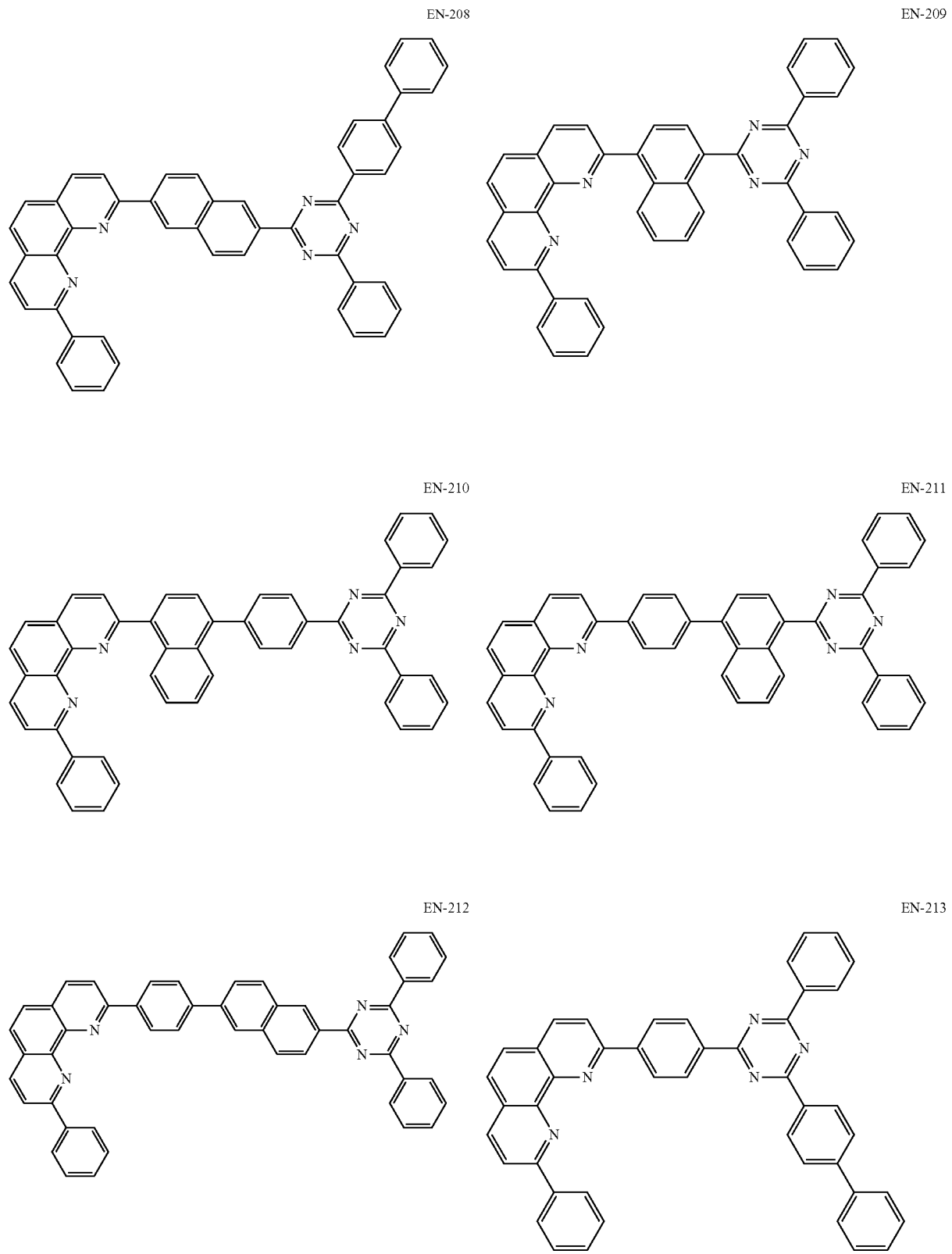

-continued
EN-214
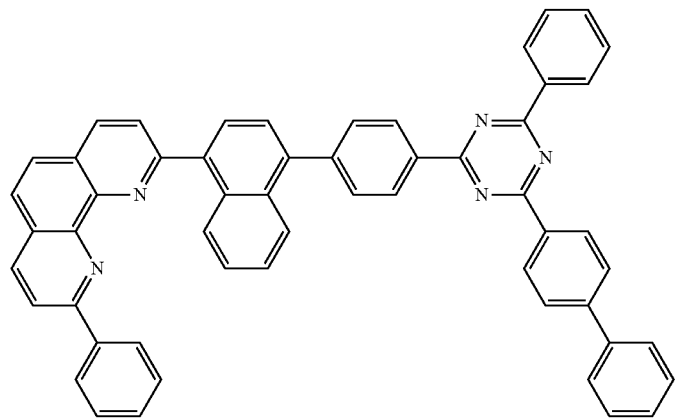
EN-215
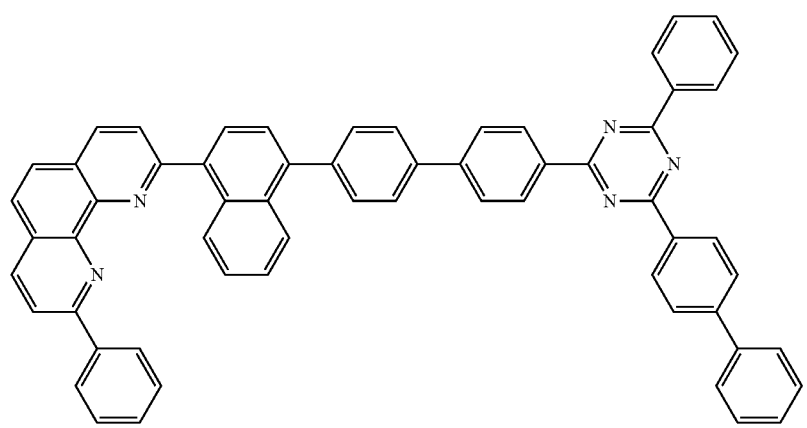
EN-216
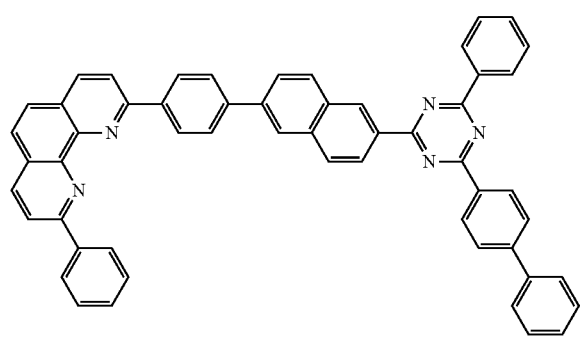
EN-217
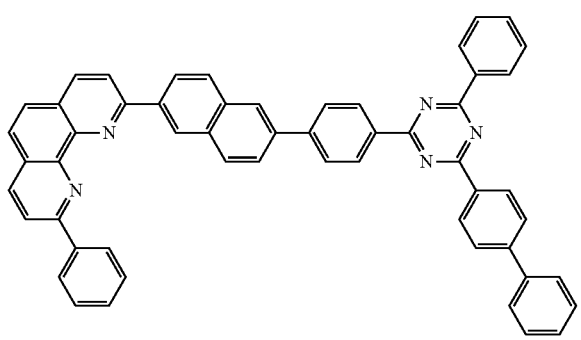
EN-218
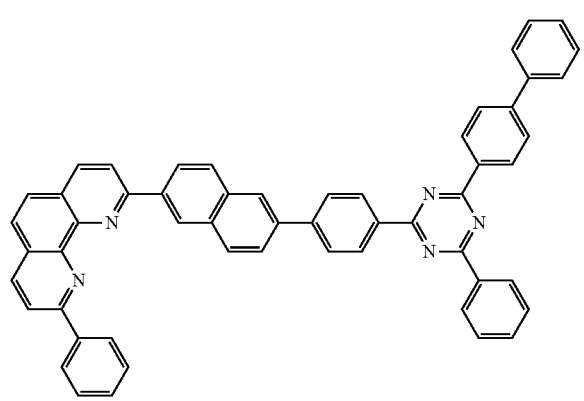
EN-219
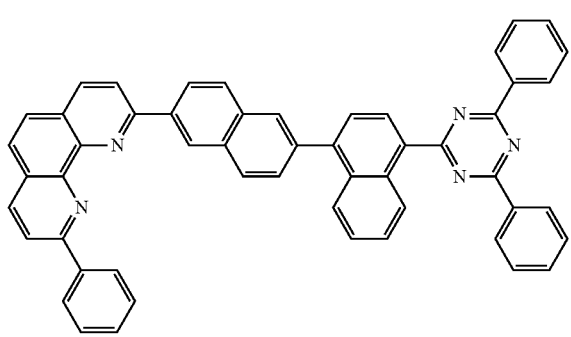

EN-220 EN-221
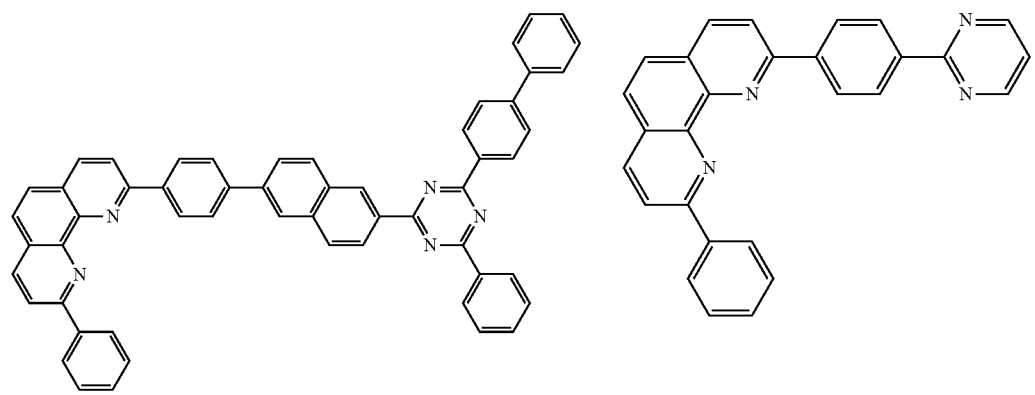
EN-222 EN-223
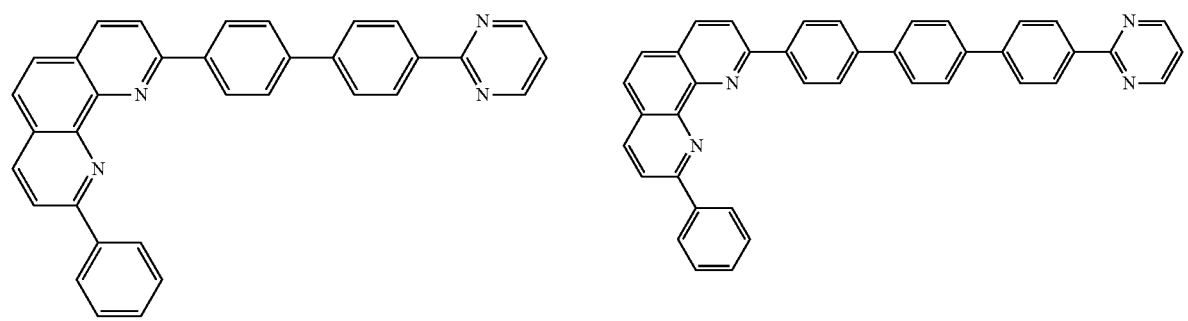
EN-224 EN-225
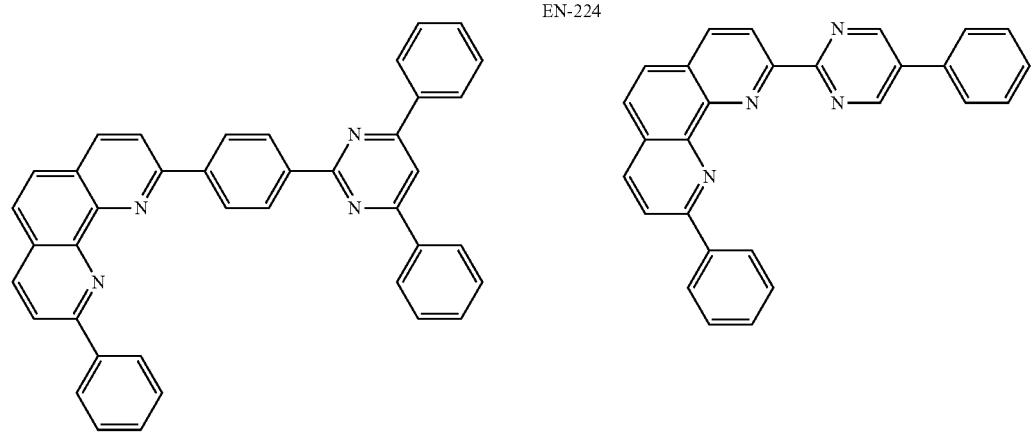
EN-226 EN-227
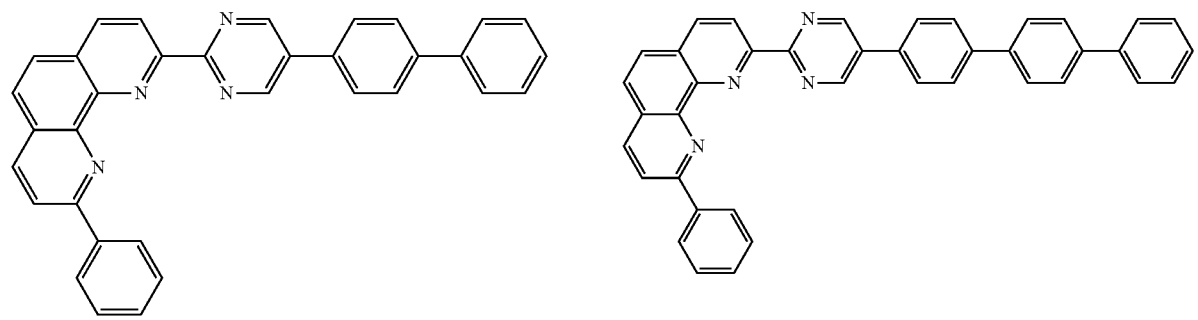

-continued
EN-228
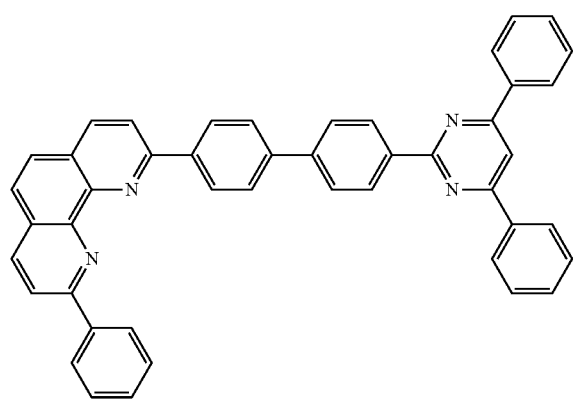
EN-229
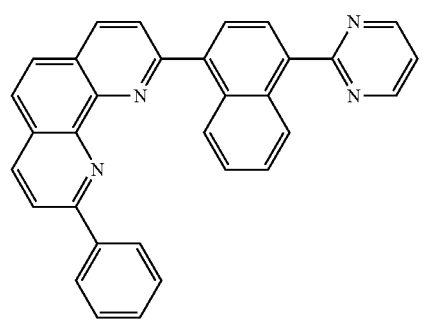
EN-230
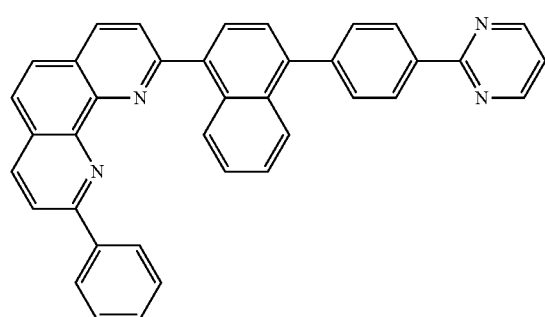
EN-231
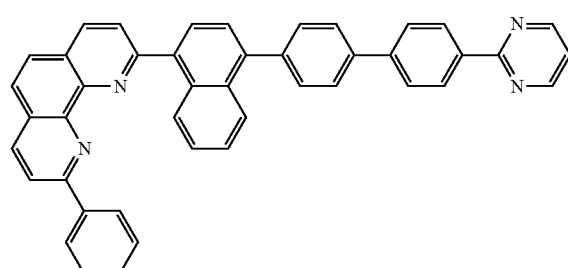
EN-232
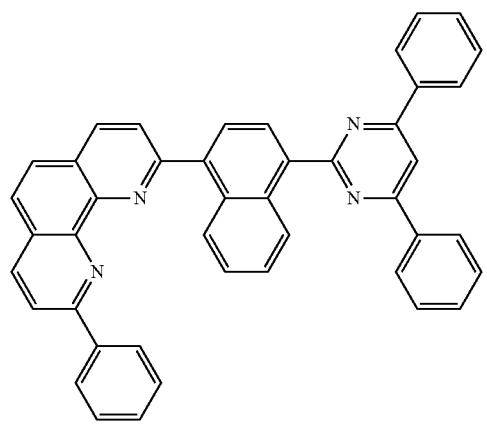
EN-233
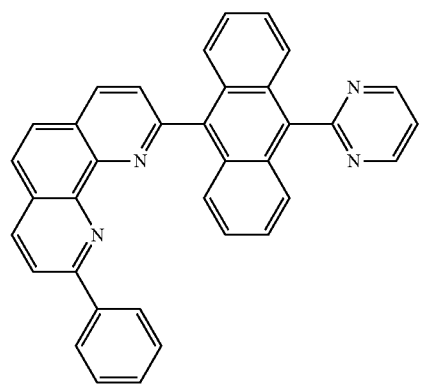
EN-234
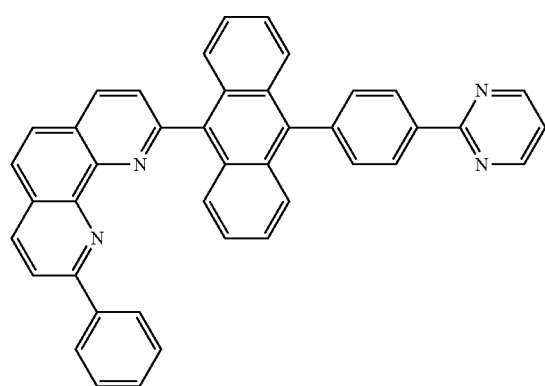
EN-235
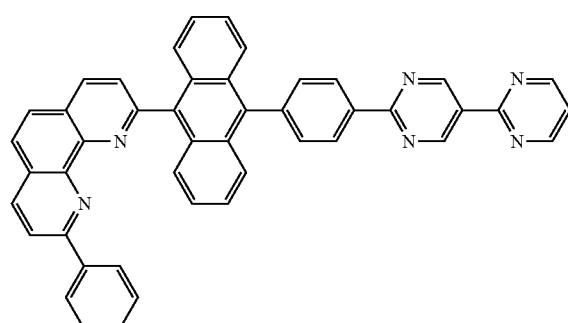

-continued
EN-236
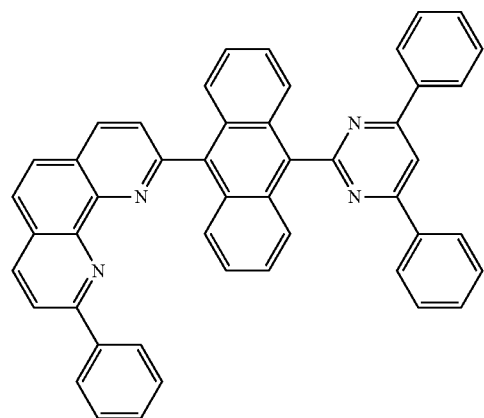
EN-237
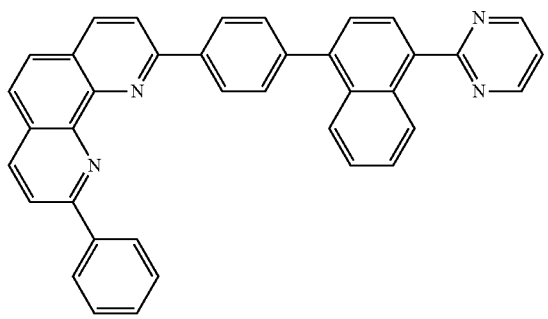
EN-238
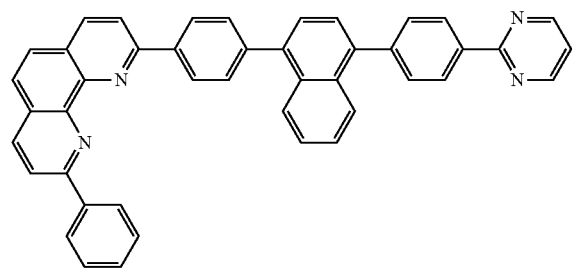
EN-239
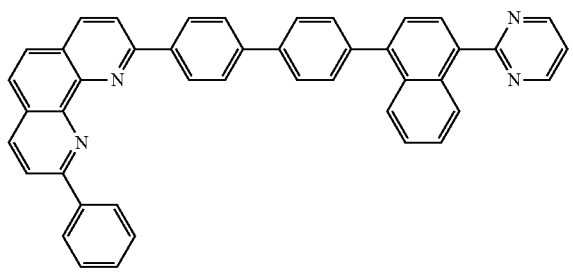
EN-240
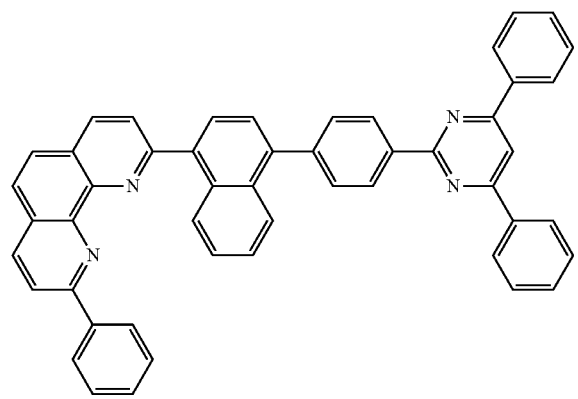
EN-241
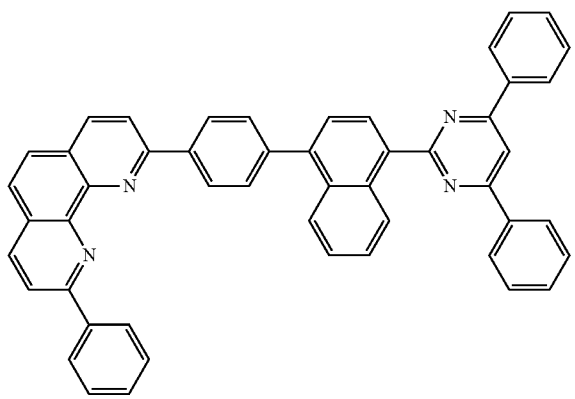
EN-242
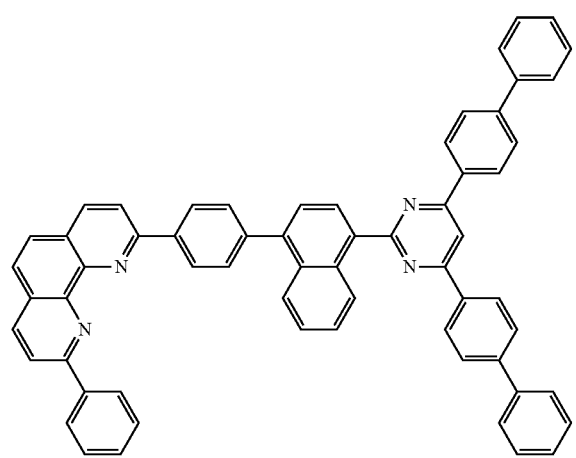
EN-243
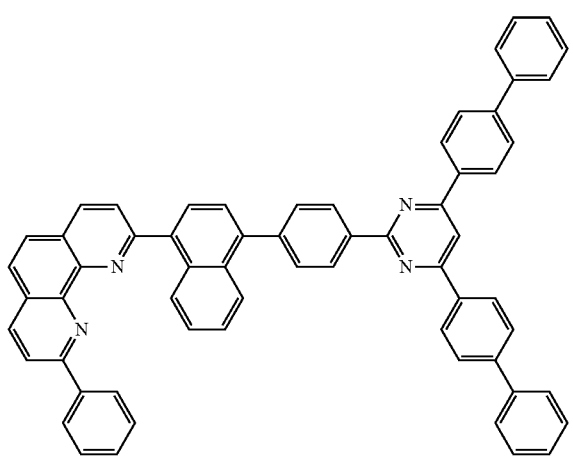

-continued
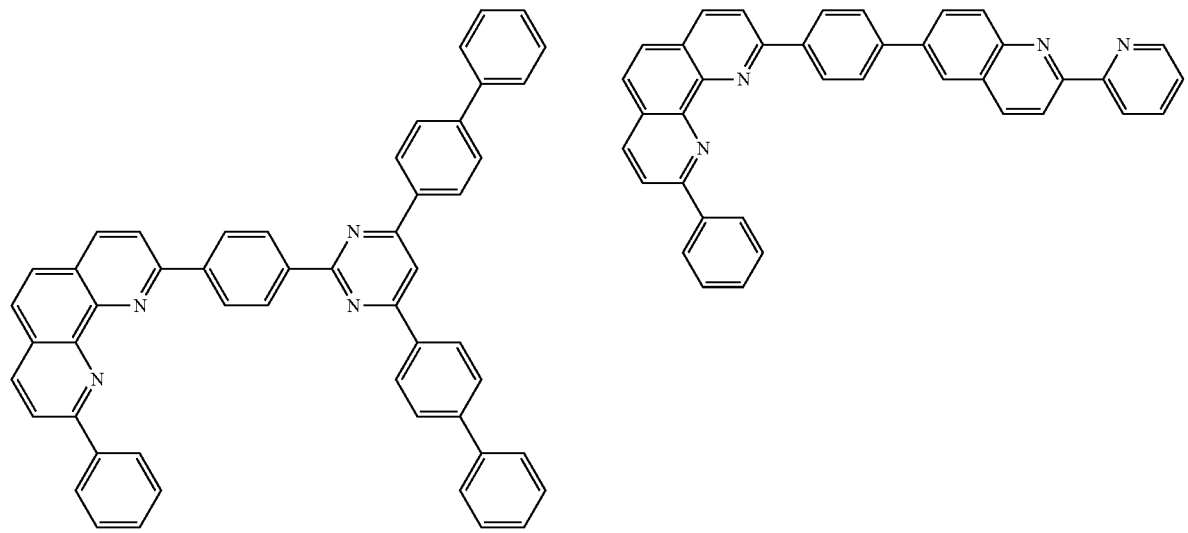
EN-244
EN-245
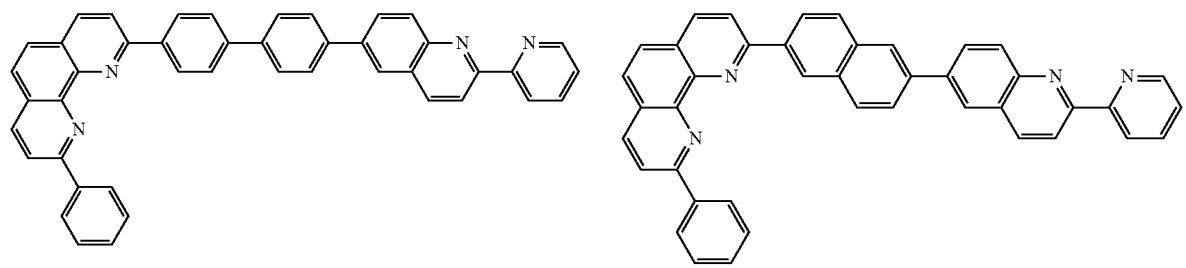
EN-246
EN-247
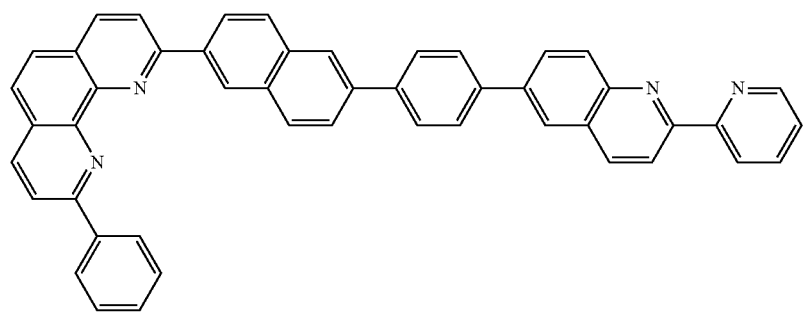
EN-248
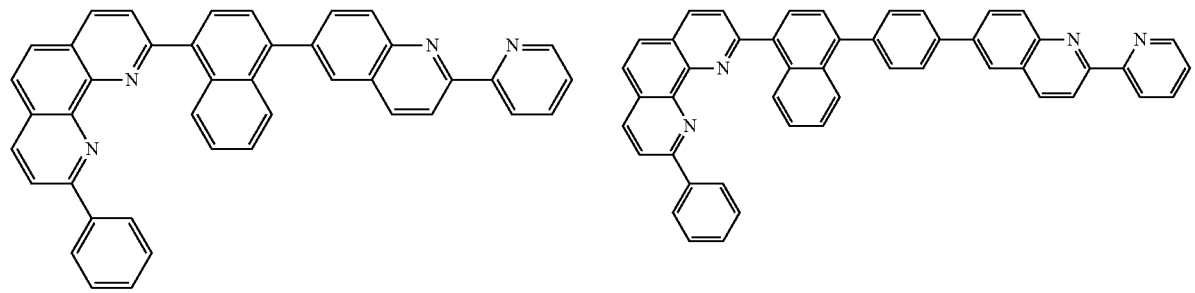
EN-249
EN-250

-continued
EN-251
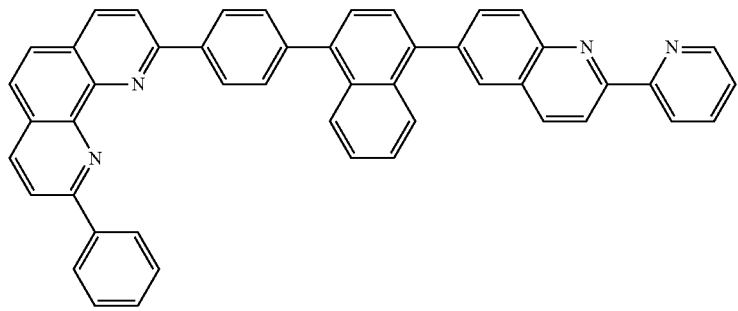
EN-252
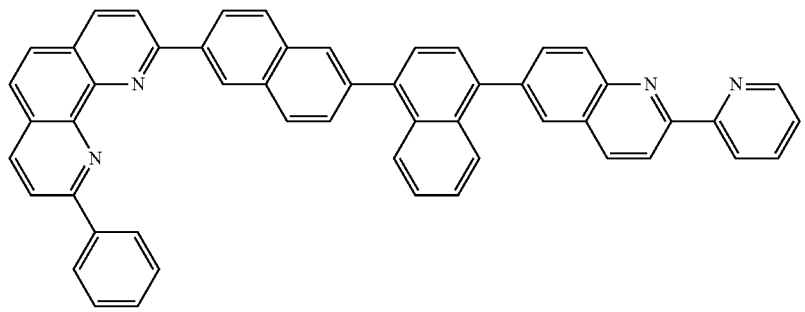
EN-253
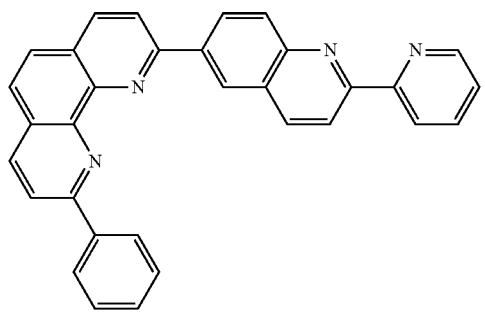
EN-254
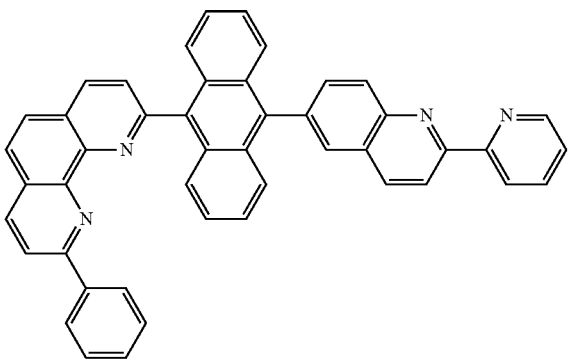
EN-255
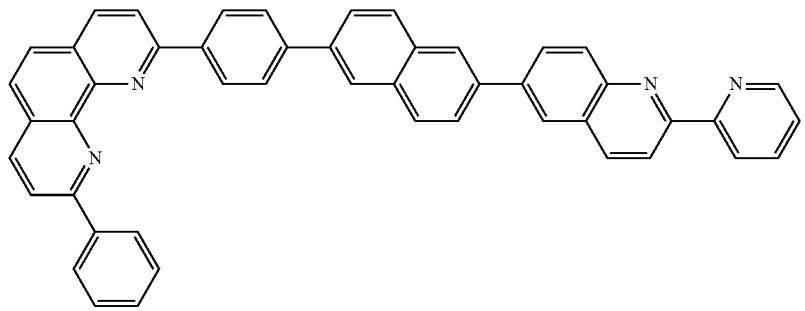
EN-256
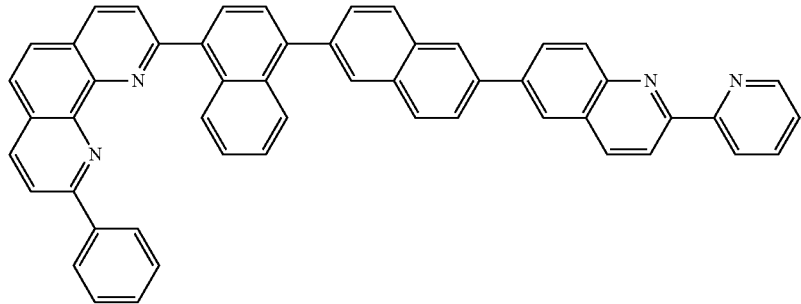

-continued
EN-257
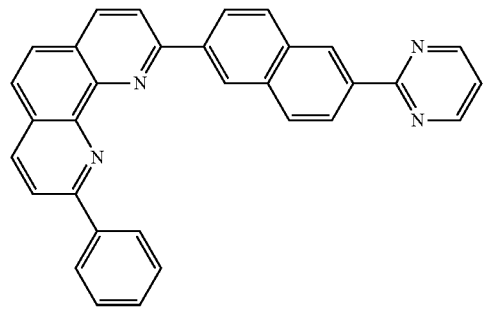
EN-258
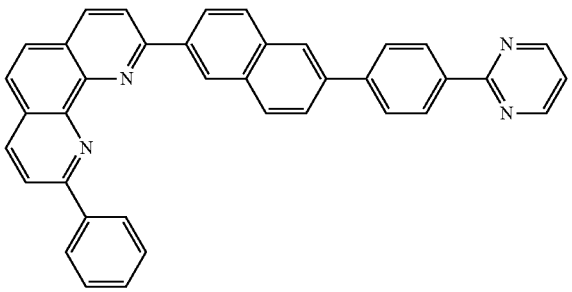
EN-259
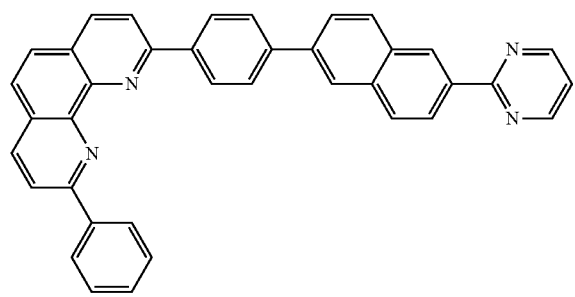
EN-260
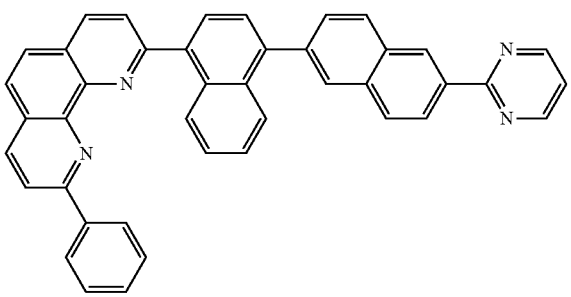
EN-261
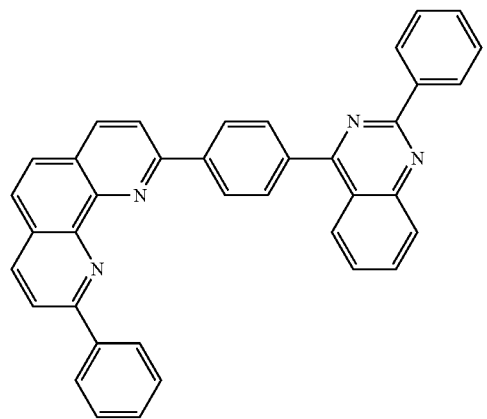
EN-262
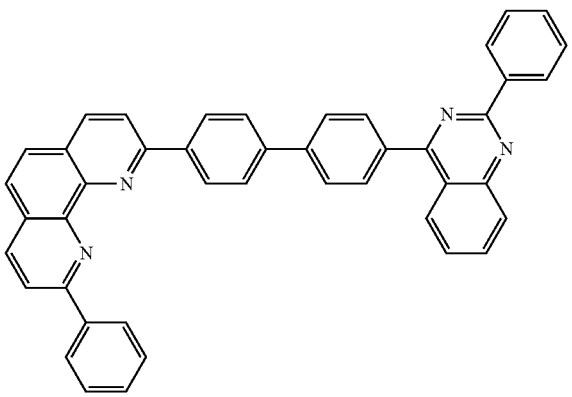
EN-263
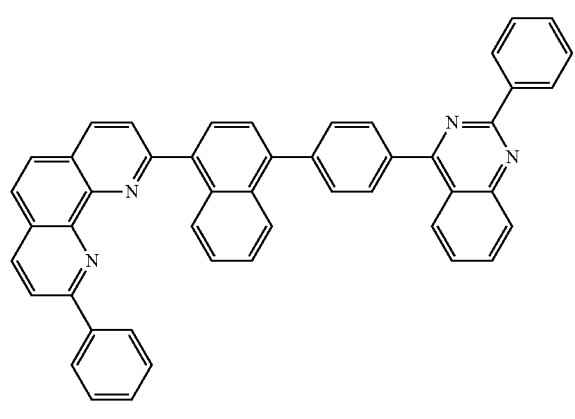
EN-264
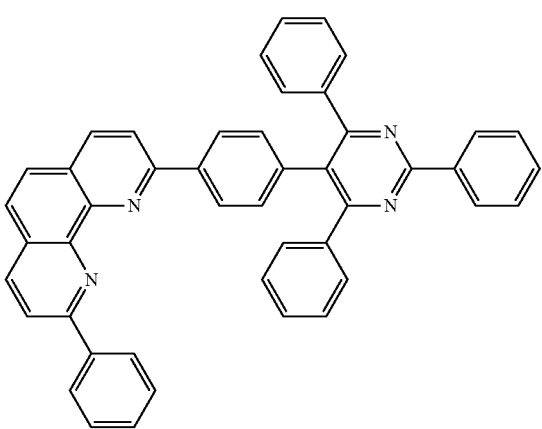

-continued

EN-265
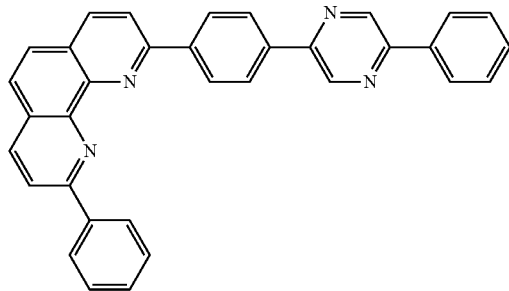

EN-266
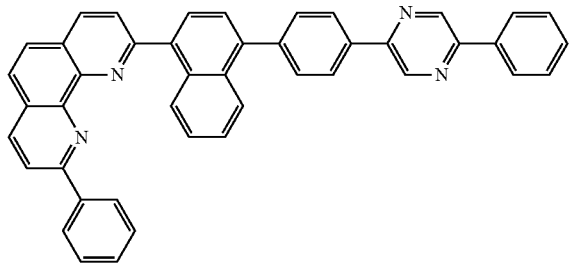

EN-267
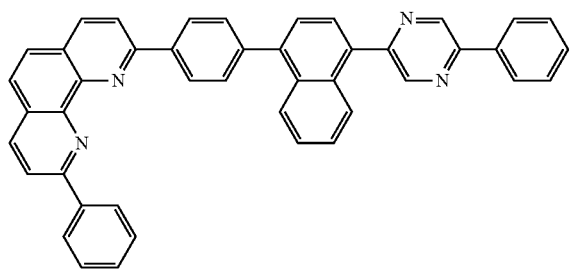

EN-268
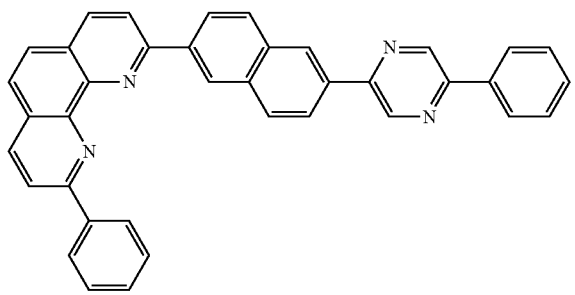

Since the organic compounds above include a phenanthroline substituted with an aromatic ring, a thermal stability, an electron transporting property and an electron moving property are improved as compared with a compound which is not substituted with an aromatic ring. Since one of the organic compounds above is applied to an N type charge generation layer of an LED having a tandem structure, the LED has an extended lifetime, a reduced driving voltage and an improved emission efficiency.

[Light Emitting Diode and Display Device]

Since the organic compound represented by the chemical formula 1includes a phenanthroline moiety substituted with an aromatic ring, the organic compound has an excellent electron transporting property and an excellent thermal stability. As a result, an LED may have a reduced driving voltage, an improved emission efficiency and an extended lifetime by applying the organic compound represented by the chemical formula 1 to an electron transporting layer and/or a charge generation layer of the LED having a tandem structure.

FIG. 1 is a cross-sectional view showing a light emitting diode of a tandem structure having two emitting parts according to a first embodiment of the present disclosure.

In FIG. 1, a light emitting diode (LED) 100 according to a first embodiment of the present disclosure includes first and second electrodes 110 and 120 spaced apart from each other and an organic emitting layer 130 between the first and second electrodes 110 and 120. The organic emitting layer 130 includes a first emitting part (ST1) 140 between the first and second electrodes 110 and 120, a second emitting part (ST2) 150 between the first emitting part 140 and the second electrode 120 and a charge generation layer (CGL) 160 between the first and second emitting parts 140 and 150. The first emitting part 140 includes a first emitting material layer (lower emitting material layer) 144, and the second emitting part 150 includes a second emitting material layer (upper emitting material layer) 154.

The first electrode 110 may be an anode where a hole is injected and may include a material having a relatively high work function. For example, the first electrode 110 may include a transparent conductive material such as indium tin oxide (ITO), indium zinc oxide (IZO) and zinc oxide (ZO). The second electrode 120 may be a cathode where an electron is injected and may include a material having a relatively low work function. For example, the second electrode 120 may include a metallic material such as aluminum (Al), magnesium (Mg) and aluminum magnesium (AlMg) alloy.

The first emitting part 140 may include a hole injecting layer 141 between the first electrode 110 and the first emitting material layer 144, a first hole transporting layer 142 between the hole injecting layer 141 and the first emitting material layer 144 and a first electron transporting layer (lower electron transporting layer) 146 between the first emitting material layer 144 and the charge generation layer 160.

The hole injecting layer 141 may improve an interface property between the first electrode 120 of an inorganic material and the first hole transporting layer 142 of an organic material. For example, the hole injecting layer 141 may include one of 4,4',4''-tris(3-methylphenylphenylamino)triphenylamine(MTDATA), copper phthalocyanine(CuPc), tris(4-carbazoyl-9-ylphenyl)amine(TCTA), N,N'-di(naphthalen-1-yl)-N,N'-diphenylbenzidine(NPB), N,N'-diphenyl-N,N'-bis(1-naphthyl)-1,1'-biphenyl-4,4''-diamine(NPD), 1,4,5,8,9,11-hexaazatriphenylenehexacarbonitrile(HATCN), poly(3,4-ethylenedioxythiophene)polystyrene sulfonate(PEDOT/PSS) 2,3,5,6-tetrafluoro-7,7,8,8-tetracyanoquinodimethane (F4-TCNQ) and/or N-(biphenyl-4-yl)-9,9-dimethyl-N-(4-(9-phenyl-9H-carbazol-3-yl)phenyl)-9H-fluoren-2-amine.

For example, the hole injecting layer 141 may have a thickness of about 1 nm to about 150 nm. A hole injecting property is improved when the thickness of the hole injecting layer 141 is equal to or greater than about 1 nm, and an increase of a driving voltage due to an increase of the thickness is prevented when the thickness of the hole injecting layer 141 is equal to or smaller than about 150 nm. The hole injecting layer 141 may be omitted in another embodiment.

The first hole transporting layer 142 is disposed between the hole injecting layer 141 and the first emitting material layer 144. The first emitting material layer 144 is disposed between the first hole transporting layer 142 and the first electron transporting layer 146. The first electron transporting layer 146 is disposed between the first emitting material layer 144 and the charge generation layer 160.

The second emitting part 150 may include a second hole transporting layer (upper hole transporting layer) 152, a second emitting material layer (upper emitting material layer) 154, a second electron transporting layer (upper electron transporting layer) 156 and an electron injecting layer 158. The second hole transporting layer 152 is disposed between the charge generation layer 160 and the second emitting material layer 154. The second emitting material layer 154 is disposed between the second hole transporting layer 152 and the second electrode 120. Further, the second electron transporting layer 156 is disposed between the second emitting material layer 154 and the second electrode 120, and the electron injecting layer 158 is disposed between the second electron transporting layer 156 and the second electrode 120.

Each of the first and second hole transporting layers 142 and 152 may include one of N,N'-diphenyl-N,N'-bis(3-methylphenyl)-1,1'-biphenyl-4,4'-diamine (TPD),NPD, MTDATA, 1,3-bis(N-carbazolyl)benzene (mCP), CuPC, TCTA, tris(trifluorovinyl ether)-tris(4-carbazoyl-9-yl-phenyl)amine (TFV-TCTA), tris[4-(diethylamino)phenyl]amine), N-(biphenyl-4-yl)-9,9-dimethyl-N-(4-(9-phenyl-9H-carbazol-3-yl)phenyl)-9H-fluorene-2-amine, tri-p-tolylamine,N-[1,1'-biphenyl]-4-yl-9,9-dimethyl-N-[4-(9-phenyl-9H-carbazol-3-yl)phenyl]-amine, 4,4'-bis(N-carbazolyl)-1,1'-biphenyl (CBP) and/or 1,1-bis(4-(N,N'di(ptolyl)amino)phenyl)cyclohexane (TAPC).

For example, each of the first and second hole transporting layers 142 and 152 may have a thickness of about 1 nm to about 150 nm. A hole transporting property is improved when the thickness of each of the first and second hole transporting layers 142 and 152 is equal to or greater than about 1 nm, and an increase of a driving voltage due to an increase of the thickness is prevented when the thickness of the first and second hole transporting layers 142 and 152 is equal to or smaller than about 150 nm. The first and second hole transporting layers 142 and 152 may include the same material or may include different materials.

In an exemplary embodiment, the first and second emitting material layers 144 and 154 may include a host doped with a dopant and may emit different colors. The dopant may be added to the host with a ratio of about 1 wt % to about 30 wt %.

For example, the first emitting material layer 144 may emit a blue (B), red (R), green (G) or yellow (Y) light. When the first emitting material layer 144 is a blue emitting layer, the first emitting material layer 144 may include one of a blue emitting material layer, a dark blue emitting material layer and a sky blue emitting material layer. Alternatively, the first emitting material layer 144 may include one of a blue emitting material layer and a red emitting material layer, a blue emitting material layer and a yellow-green emitting material layer, and a red emitting material layer and a green emitting material layer.

The second emitting material layer may include one of a red emitting material layer, a green emitting material layer, a blue emitting material layer and a yellow-green emitting material layer. In an exemplary embodiment, the first emitting material layer 144 may emit a blue light, and the second emitting material layer 154 may emit a green light, a yellow-green light or an orange light having a wavelength longer than a blue light.

For example, when the first emitting material layer 144 emits a blue light, the first emitting material layer 144 may include at least one fluorescent host material selected from a group including anthracene and derivatives thereof, pyrene and derivatives thereof, and perylene and derivatives thereof doped with a fluorescent dopant.

A blue fluorescent host material for the first emitting material layer 144 may include one of 4,4'-bis(2,2'-diphenylyinyl)-1,1'-biphenyl (DPVBi), 9,10-di-(2-naphtyl)anthracene (ADN), 2,5,8,11-tetra-t-butylperylene (TBADN), 2-tert-butyl-9,10-di(2-naphthyl)anthracene, 2-methyl-9,10-di(2-naphtyl)anthracene (MADN) and/or 2,2',2"-(1,3,5-benzinetriyl)-tris(1-phenyl-1-H-benzimidazole (TBPi).

A blue fluorescent dopant material for the first emitting material layer 144 may include one of 4,4'-bis(9-ethyl-3-carbazovinylene)-1,1'-biphenyl (BCzVBi) and/or diphenyl-[4-(2-[1,1,4,1]terphenyl-4-yl-vinyl)-phenyl]-amine (BD-1) and may include one selected from a group including spiro-DPVBi, spiro-CBP, distyrylbenzene (DSB) and derivatives thereof, distyryl arylene (DSA) and derivatives thereof, polyfluoorene (PF) polymer and polyphenylene vinylene (PPV) polymer. Alternatively, a blue dopant may include an iridium dopant as a phosphorescent dopant. Here, the first emitting material layer 144 may include a sky blue emitting material layer or a deep blue emitting material layer as well as a blue emitting material layer. The light emitted from the first emitting material layer 144 may have a wavelength of about 440 nm to about 480 nm.

When the first emitting material layer 144 emits a green light, the first emitting material layer 144 may be a phosphorescent emitting material layer including a host such as CBP and a dopant of an iridium group (e.g., $dp_2Ir(acac)$, $op_2Ir(acac)$). However, the first emitting material layer 144 is not limited to that set forth herein. Alternatively, the first emitting material layer 144 may be a fluorescent emitting material layer including tris(8-hydroxyquinolinato)aluminum (Alq). Here, the light emitted from the first emitting material layer 144 may have a wavelength of about 510 nm to about 570 nm.

When the first emitting material layer 144 emits a red light, the first emitting material layer 144 may be a phosphorescent emitting material layer including a host such as CBP and a dopant of one selected from a group including bis(1-phenylisoquinoline)acetylacetonate iridium (PIQIr(acac)), bis(1-phenylquinoline)acetylacetonate iridium (PQIr(acac)) and octaethylporphyrin platinum (PtOEP). However, the first emitting material layer 144 is not limited to that set forth herein.

Alternatively, the first emitting material layer 144 may be a fluorescent emitting material layer including 1,3,4-oxadiazole:tris(dibenzoylmethane)mono(1,10-phentathroline)europium(III) (PBD:Eu(DBM)3(Phen)), perylene and derivatives thereof. The light emitted from the first emitting material layer 144 may have a wavelength of about 600 nm to about 650 nm.

When the first emitting material layer 144 emits a yellow light, the first emitting material layer 144 may have a single layered structure of a yellow-green emitting material layer or a double layered structure of a yellow-green emitting material layer and a green emitting material layer. For example, a yellow emitting material layer for the first emitting material layer 144 may have at least one host selected from CBP and bis(2-methyl-8-quinolinolate)-4-(phenylphenolato)aluminium (BAlq) and a yellow-green phosphorescent dopant. Here, the light emitted from the first emitting material layer 144 may have a wavelength of about 510 nm to about 590 nm.

In an exemplary embodiment, to increase a red efficiency of the LED 100 having a tandem structure, the first emitting material layer 144 may include two emitting material layers, for example, a pair of a yellow-green emitting material layer and a red emitting material layer or a pair of a blue emitting material layer and a red emitting material layer.

When the second emitting material layer 154 is a yellow-green emitting material layer, the second emitting material layer 154 may have a single layered structure of a yellow-green emitting material layer or a double layered structure of a yellow-green emitting material layer and a green emitting material layer. When the second emitting material layer 154 has a single layered structure of a yellow-green emitting material layer, the second emitting material layer 154 may include at least one host selected from CBP and BAlq and a yellow-green phosphorescent dopant. However, the second emitting material layer 154 is not limited to that set forth herein.

When the second emitting material layer 154 is a yellow emitting material layer, the second emitting material layer 154 may include at least one host selected from CBP and BAlq and a yellow phosphorescent dopant.

Each of the first and second electron transporting layers 146 and 156 may improve an electron transporting in the first and second emitting parts 140 and 150. Each of the first and second electron transporting layers 146 and 156 may include oxadiazole, triazole, phenanthroline, benzoxazole, benzothiazole, benzoimidazole, triazine and derivatives thereof.

For example, each of the first and second electron transporting layers 146 and 156 may include an electron transporting material such as Alq3,2-biphenyl-4-yl-5-(4-t-butylphenyl)-1,3,4-oxadiazole (PBD), spiro-PBD, lithium quinolate (LiQ), 2-[4-(9,10-Di-2-naphthalenyl-2-anthracenyl)phenyl]-1-phenyl-1H-benzimidazol, 3-(biphenyl-4-yl)-5-(4-tertbutylphenyl)-4-phenyl-4H-1,2,4-triazole (TAZ), 4,7-diphenyl-1,10-phenanthroline (Bphen), tris(phenylquinoxaline (TPQ), 1,3,5-Tri[(3-pyridyl)-phen-3-yl]benzene (TmPyPB) and/or1,3,5-tris(N-phenylbenzimiazole-2-yl)benzene (TPBI). In addition, each of the first and second electron transporting layers 146 and 156 may include an organic compound represented by the chemical formula 1.

Alternatively, each of the first and second electron transporting layers 146 and 156 may be doped with an alkali metal or an alkali earth metal. The dopant for each of each of the first and second electron transporting layers 146 and 156 may include an alkali metal such as lithium (Li), sodium (Na), potassium (K) and cesium (Cs) and/or an alkali earth metal such as magnesium (Mg), strontium (Sr), barium (Ba) and radium (Ra). However, the dopant for each of the first and second electron transporting layers 146 and 156 is not limited to that set forth herein. The alkali metal or the alkali earth metal may be added with a ratio of about 1 wt % to about 20 wt %. However, the ratio is not limited to that set forth herein.

Each of the first and second electron transporting layers 146 and 156 may have a thickness of about 1 nm to about 150 nm. Decrease of an electron transporting property is prevented when the thickness of each of the first and second electron transporting layers 146 and 156 is equal to or greater than about 1 nm, and an increase of a driving voltage due to an increase of the thickness is prevented when the thickness of the first and second electron transporting layers 146 and 156 is equal to or smaller than about 150 nm.

The electron injecting layer 158 may improve an electron injecting property. The electron injecting layer 158 may include an alkali halide material such as lithium fluoride (LiF), sodium fluoride (NaF), potassium fluoride (KF), rubidium fluoride (RbF), cesium fluoride (CsF), francium fluoride (FrF), beryllium fluoride ($BeF_2$), magnesium fluoride ($MgF_2$), calcium ($CaF_2$), barium fluoride ($BaF_2$) and radium fluoride ($RaF_2$) and/or an organic material such as lithium quinolate (LiQ), lithium benzoate, sodium stearate, $Alq_3$, BAlq, PBD, spiro-PBD and TAZ.

The electron injecting layer 158 may have a thickness of about 0.5 nm to about 50 nm. A decrease of an electron injecting property is prevented when the thickness of the electron injecting layer 158 is equal to or greater than about 0.5 nm, and an increase of a driving voltage due to an increase of the thickness is prevented when the thickness of the electron injecting layer 158 is equal to or smaller than about 50 nm.

In an exemplary embodiment of the present disclosure, to improve a current efficiency in each of the first and second emitting parts 140 and 150 and to improve distribution of charges, the charge generation layer (CGL) 160 is disposed between the first and second emitting parts 140 and 150, and the first and second emitting parts 140 and 150 are connected to each other through the charge generation layer 160. The charge generation layer 160 may include a PN junction charge generation layer where an N type charge generation layer 162 and a P type charge generation layer 164 are adjacently disposed and combined to each other.

The N type charge generation layer 162 is disposed between the first electron transporting layer 146 and the second hole transporting layer 152, and the P type charge generation layer 164 is disposed between the N type charge generation layer 162 and the second hole transporting layer 152. The charge generation layer 160 may supply an electron and a hole to the first and second emitting parts 140 and 150 by generating a charge such as an electron and a hole.

The N type charge generation layer 162 supplies an electron to the first electron transporting layer 146 of the first emitting part 140, and the first electron transporting layer 146 supplies an electron to the first emitting material layer 144 adjacent to the first electrode 110. The P type charge generation layer 164 supplies a hole to the second hole transporting layer 152 of the second emitting part 150, and the second hole transporting layer 152 supplies a hole to the second emitting material layer 154 adjacent to the second electrode 120.

The P type charge generation layer 164 may include an organic material doped with a metal or a P type dopant. For example, the metal may include an alloy of one or two selected from a group including aluminum (Al), copper (Cu), iron (Fe), lead (Pb), zinc (Zn), gold (Au), platinum (Pt), tungsten (W), indium (In), molybdenum (Mo), nickel (Ni) an titanium (Ti). The P type dopant may include F4-TCNQ, iodine (I), iron chloride ($FeCl_3$),iron fluoride ($FeF_3$) and antimony chloride ($SbCl_5$), and the host may include at least one selected from a group including NPB, TPD, N,N,N',N'-tetranaphthalenyl-benzidine (TNB) and HAT-CN.

When an electron moves from the N type charge generation layer 162 to the first electron transporting layer 146, a driving voltage of the LED 100 may increase due to difference in a lowest unoccupied molecular orbital (LUMO) energy level between the first electron transporting layer 146 and the N type charge generation layer 162. To solve the above problem, the organic compound represented by the chemical formula 1 may be used for the N type charge generation layer 162 and/or the first electron transporting layer 146. Alternatively, the N type charge generation layer 162 may include a metallic compound such as an alkali metal compound or an alkali earth metal compound as a dopant. The alkali metal or the alkali earth metal may be added with a ratio of about 1 wt % to about 30 wt %. However, the ratio is not limited to that set forth herein.

An electron injecting property to the N type charge generation layer 162 may be improved by doping the N type charge generation layer 162 with the alkali metal or the alkali earth metal. For example, when the alkali metal or the alkali earth metal is used as a dopant of the N type charge generation layer 162, the alkali metal or the alkali earth metal may combine with the organic compound of the present disclosure to form a gap state. Accordingly, the energy level difference between the N type charge generation layer 162 and the P type charge generation layer 164 is alleviated, and the electron injecting property from the N type charge generation layer 162 to the first electron transporting layer 146 may be improved.

The organic compound of the present disclosure includes a phenanthroline moiety substituted with at least one aromatic ring. Since the organic compound has a relatively high decomposition temperature or a relatively high glass transition temperature due to the phenanthroline moiety, the organic compound has an excellent thermal stability. As a result, the organic compound may not be deteriorated or spoiled even by a Joule's heat generated from driving of an element. Accordingly, the lifetime of the LED 100 including the organic compound is extended and the driving voltage of the LED 100 including the organic compound is reduced.

Further, since the organic compound of the present disclosure includes a phenanthroline moiety having a nitrogen atom of a hybrid orbital of $sp^2$ of sufficient electrons, the organic compound has an excellent electron transporting property. As a result, the organic compound may be used for the electron transporting layers 146 and 156 and/or the charge generation layer 160.

Specifically, a nitrogen atom of a phenanthroline moiety is combined with the alkali metal or the alkali earth metal of the dopant of the N type charge generation layer to form a gap state. As a result, the energy level difference between the N type charge generation layer and the P type charge generation layer is alleviated. Since the injection of an electron into the N type charge generation layer is improved, the electron transporting property to the electron transporting layer adjacent to the N type charge generation layer may be maximized.

An electron may be efficiently transmitted from the N type charge generation layer 162 to the first electron transporting layer 146 by applying the organic compound represented by the chemical formula 1 to the N type charge generation layer 162.

Further, since the compound including a nitrogen atom is combined with the alkali metal compound or the alkali earth metal compound of the N type charge generation layer, diffusion of the alkali metal compound or the alkali earth metal compound to the P type charge generation layer is prevented. Accordingly, reduction of the LED lifetime is prevented.

Figure 2:
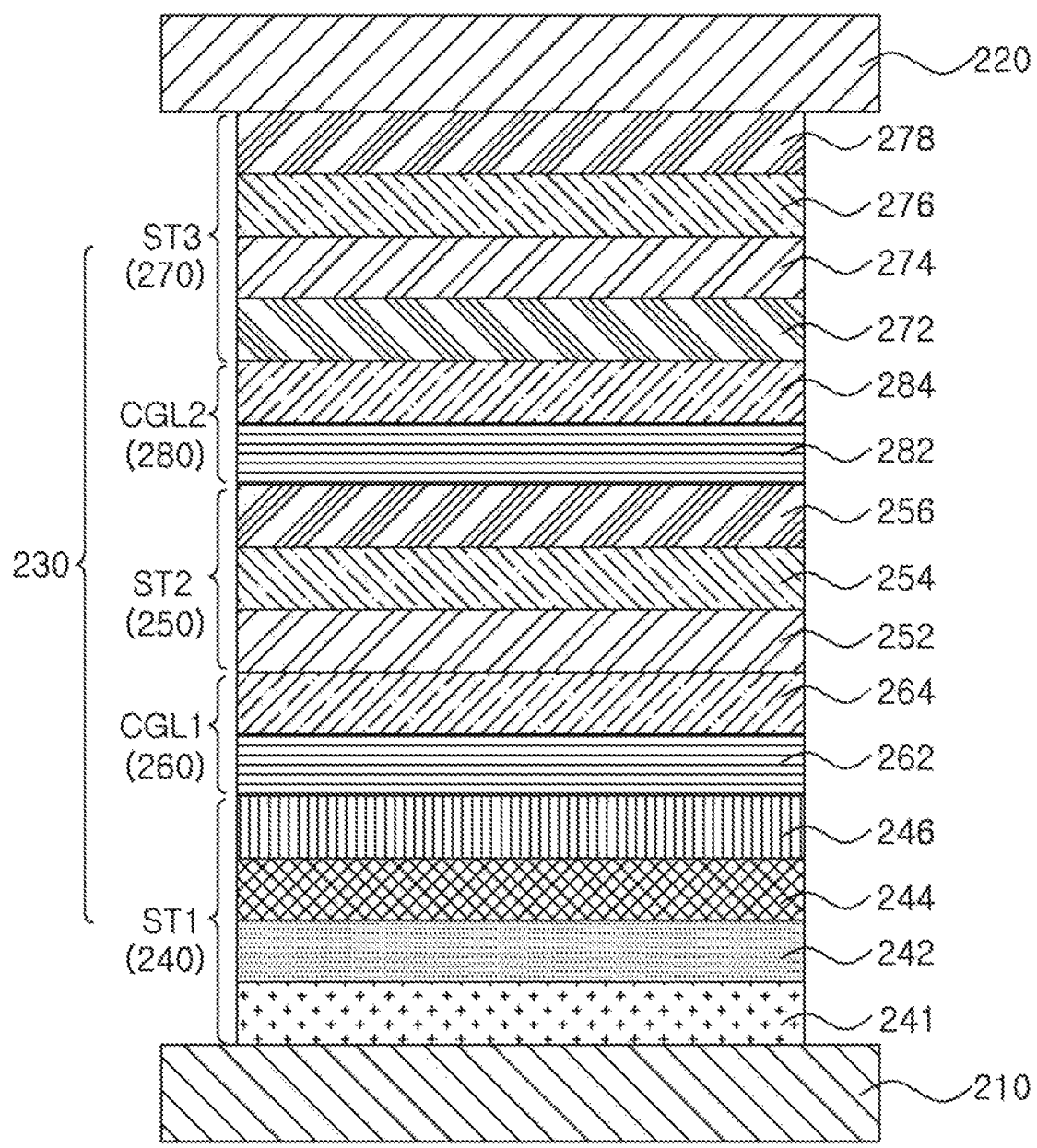
FIG. 2 is a cross-sectional view showing a light emitting diode of a tandem structure having three emitting parts according to a second embodiment of the present disclosure.

FIG. 2 is a cross-sectional view showing a light emitting diode of a tandem structure having three emitting parts according to a second embodiment of the present disclosure.

In FIG. 2, a light emitting diode (LED) 200 according to a second embodiment of the present disclosure includes first and second electrodes 210 and 220 facing and spaced apart from each other and an organic emitting layer 230 between the first and second electrodes 210 and 220. The organic emitting layer 230 includes a first emitting part (ST1) 240, a second emitting part (ST2) 250, a third emitting part (ST3) 270, a first charge generation layer (CGL1) 260 and a second charge generation layer (CGL2) 280. At least four emitting parts and at least three charge generation layers may be disposed between the first and second electrodes 210 and 220 in another embodiment.

The first electrode 210 may be an anode where a hole is injected and may include a material having a relatively high work function. For example, the first electrode 210 may include a transparent conductive material such as indium tin oxide (ITO), indium zinc oxide (IZO) and zinc oxide (ZO). The second electrode 220 may be a cathode where an electron is injected and may include a material having a relatively low work function. For example, the second electrode 220 may include a metallic material such as aluminum (Al), magnesium (Mg) and aluminum magnesium (AlMg) alloy.

The first charge generation layer 260 is disposed between the first and second emitting parts 240 and 250, and the second charge generation layer 280 is disposed between the second and third emitting parts 250 and 270. The first emitting part 240, the first charge generation layer 260, the second emitting part 250, the second charge generation layer 280 and the third emitting part 270 are sequentially formed on the first electrode 210. The first emitting part 240 is disposed between the first electrode 210 and the first charge generation layer 260, the second emitting part 250 is disposed between the first charge generation layer 260 and the second charge generation layer 280, and the third emitting part 270 is disposed between the second electrode 220 and the second charge generation layer 280.

The first emitting part 240 may include a hole injecting layer 241, a first hole transporting layer 242, a first emitting material layer 244 and a first electron transporting layer 246 on the first electrode 210. The hole injecting layer 241 and the first hole transporting layer 242 are disposed between the first electrode 210 and the first emitting material layer 244. The hole injecting layer 241 is disposed between the first electrode 210 and the first hole transporting layer 242. The first electron transporting layer 246 is disposed between the first emitting material layer 244 and the first charge generation layer 260.

The hole injecting layer 241, the first hole transporting layer 242, the first emitting material layer 244 and the first electron transporting layer 246 may have the same property as the hole transporting layer 141, the first hole transporting layer 142, the first emitting material layer 144 and the first electron transporting layer 146, respectively, of FIG. 1 and the illustrations thereof is omitted. For example, the first emitting material layer 244 may be a blue (B) emitting material layer, and the light emitted from the first emitting material layer 244 may have a wavelength of about 440 nm to about 480 nm.

The second emitting part 250 may include a second hole transporting layer 252, a second emitting material layer 254 and a second electron transporting layer 256. The second hole transporting layer 252 is disposed between the first charge generation layer 260 and the second emitting material layer 254, and the second electron transporting layer 256 is disposed between the second emitting material layer 254 and the second charge generation layer 280.

The second hole transporting layer 252, the second emitting material layer 254 and the second electron transporting layer 256 may have the same property as the second hole transporting layer 152, the second emitting material layer 154 and the second electron transporting layer 156, respectively, of FIG. 1 and illustrations thereof is omitted. For example, the second emitting material layer 254 may be a yellow-green (YG) emitting material layer or a yellow emitting material layer, and the light emitted from the second emitting material layer 254 may have a wavelength of about 510 nm to about 590 nm or of about 460 nm to about 510 nm.

The third emitting part 270 may include a third hole transporting layer 272, a third emitting material layer 274, a third electron transporting layer 276 and an electron injecting layer 278. The third hole transporting layer 272 is disposed between the second charge generation layer 280 and the third emitting material layer 274, the third electron transporting layer 276 is disposed between the third emitting material layer 274 and the second electrode 220, and the electron injecting layer 278 is disposed between the third electron transporting layer 276 and the second electrode 220.

The third hole transporting layer 272, the third electron transporting layer 276 and the electron injecting layer 278 may have the same property as the second hole transporting layer 152, the second electron transporting layer 156 and the electron injecting layer 158, respectively, of FIG. 1 and illustrations thereof is omitted. The third emitting material layer 274 may have the same property as the first emitting material layer 144 or the second emitting material layer 154. For example, the third emitting material layer 274 may be a blue (B) emitting material layer, and the light emitted from the third emitting part 270 may have a wavelength of about 440 nm to about 480 nm. In another embodiment, the third emitting material layer 274 may be a yellow-green (YG) emitting material layer or a yellow emitting material layer, and the light emitted from the third emitting part 270 may have a wavelength of about 460 nm to about 590 nm.

For example, at least one of the first electron transporting layer 246, the second electron transporting layer 256 and the third electron transporting layer 276 may include an organic compound represented by the chemical formula 1.

The first charge generation layer 260 is disposed between the first emitting part 240 and the second emitting part 250, and the second charge generation layer 280 is disposed between the second emitting part 250 and the third emitting part 270. Each of the first and second charge generation layers 260 and 280 may include a PN junction charge generation layer where an N type charge generation layer 262 and 282 and a P type charge generation layer 264 and 284 are combined to each other.

In the first charge generation layer 260, the N type charge generation layer 262 is disposed between the first electron transporting layer 246 and the second hole transporting layer 252, and the P type charge generation layer 264 is disposed between the N type charge generation layer 262 and the second hole transporting layer 252.

In the second charge generation layer 280, the N type charge generation layer 282 is disposed between the second electron transporting layer 256 and the third hole transporting layer 272, and the P type charge generation layer 284 is disposed between the N type charge generation layer 282 and the third hole transporting layer 272.

The first and second charge generation layers 260 and 280 may supply an electron and a hole to the first, second and third emitting parts 240, 250 and 270 by generating a charge such as an electron and a hole.

In the first charge generation layer 260, the N type charge generation layer 262 may supply an electron to the first electron transporting layer 246 of the first emitting part 240, and the P type charge generation layer 264 may supply a hole to the second hole transporting layer 252 of the second emitting part 250.

In the second charge generation layer 280, the N type charge generation layer 282 may supply an electron to the second electron transporting layer 256 of the second emitting part 250, and the P type charge generation layer 284 may supply a hole to the third hole transporting layer 272 of the third emitting part 270.

The P type charge generation layers 264 and 284 may include an organic material doped with a metal or a P type dopant. For example, the metal may include an alloy of one or two selected from a group including aluminum (Al), copper (Cu), iron (Fe), lead (Pb), zinc (Zn), gold (Au), platinum (Pt), tungsten (W), indium (In), molybdenum (Mo), nickel (Ni) an titanium (Ti). The P type dopant may include F4-TCNQ, iodine (I), iron chloride ($FeCl_3$),iron fluoride ($FeF_3$) and antimony chloride ($SbCl_5$), and the host may include at least one selected from a group including NPB, TPD, TNB and HAT-CN.

When an electron moves from the N type charge generation layers 262 and 282 to the first and second electron transporting layers 246 and 256, a driving voltage of the LED 200 may increase due to difference in a LUMO energy level between the first and second electron transporting layers 246 and 256 and the N type charge generation layers 262 and 282.

To solve the above problem, the organic compound of the present disclosure may be used for at least one of the N type charge generation layers 262 and 282 and/or at least one of the first and second electron transporting layers 246 and 256. Alternatively, the N type charge generation layers 262 and 282 may include a metallic compound such as an alkali metal or an alkali earth metal as a dopant.

For example, the N type charge generation layers 262 and 282 may further include at least one selected from a group including lithium quinolate (LiQ), lithium fluoride (LiF), sodium fluoride (NaF), potassium fluoride (KF), rubidium fluoride (RbF), cesium fluoride (CsF), francium fluoride (FrF), beryllium fluoride ($BeF_2$), magnesium fluoride ($MgF_2$), calcium fluoride ($CaF_2$), strontium fluoride ($SrF_2$), barium fluoride ($BaF_2$) and radium fluoride ($RaF_2$). However, the material for the N type charge generation layers 262 and 282 is not limited to that set forth herein.

An electron injecting property to the N type charge generation layers 262 and 282 may be improved by doping the N type charge generation layers 262 and 282 with the alkali metal or the alkali earth metal.

The organic compound of the present disclosure includes a phenanthroline moiety substituted with at least one aromatic ring. Since the organic compound has a relatively high decomposition temperature or a relatively high glass transition temperature due to the phenanthroline moiety, the organic compound has an excellent thermal stability. As a result, the organic compound may not be deteriorated or spoiled even by a Joule's heat generated from driving of an element. Accordingly, a lifetime of the LED 200 including the organic compound is extended and a driving voltage of the LED 200 including the organic compound is reduced.

Further, since the organic compound of the present disclosure includes a phenanthroline moiety having a nitrogen atom of a hybrid orbital of sp$^2$ of sufficient electrons, the organic compound has an excellent electron transporting property. As a result, the organic compound may be used for the electron transporting layers 246, 256 and 276 and/or the charge generation layers 260 and 280.

Specifically, a nitrogen atom of a phenanthroline moiety is combined with the alkali metal or the alkali earth metal of the dopant of the N type charge generation layer to form a gap state. As a result, the energy level difference between the N type charge generation layer and the P type charge generation layer is alleviated. Since the injection of an electron into the N type charge generation layer is improved, the electron transporting property to the electron transporting layer adjacent to the N type charge generation layer may be maximized.

Further, since the compound including a nitrogen atom is combined with the alkali metal compound or the alkali earth metal compound of the N type charge generation layer, diffusion of the alkali metal compound or the alkali earth metal compound to the P type charge generation layer is prevented. Accordingly, reduction of the LED lifetime is prevented.

Figure 3:
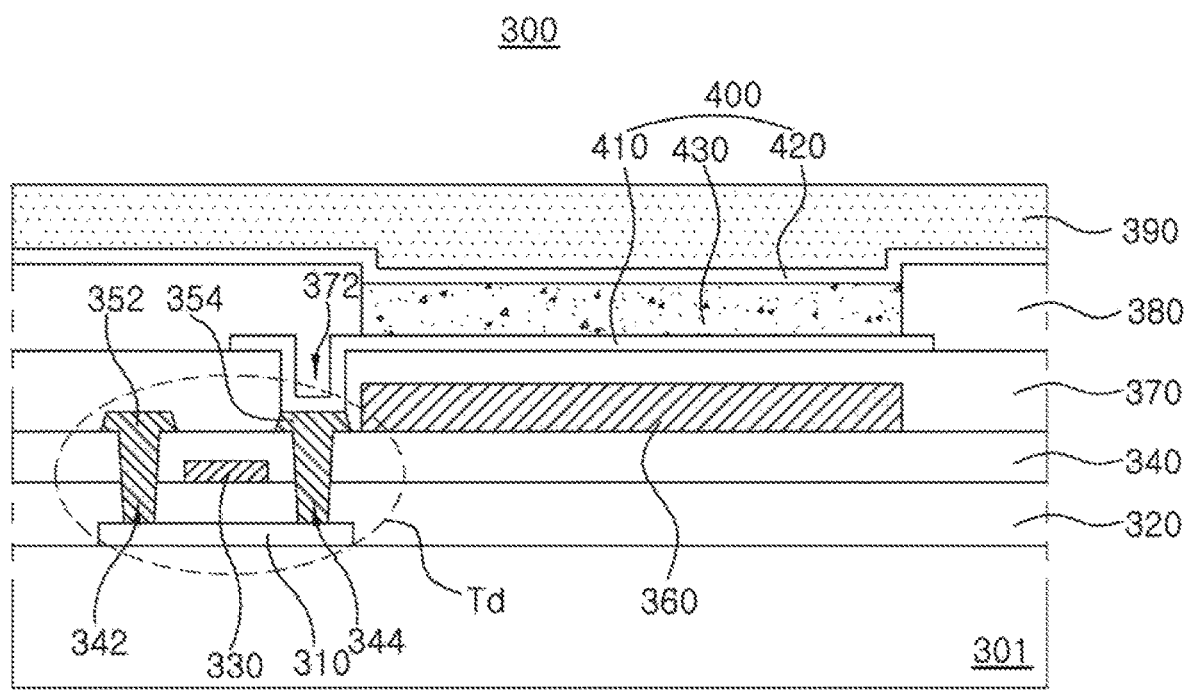
FIG. 3 is a cross-sectional view showing an organic light emitting diode display device according to a third embodiment of the present disclosure.
Figure 4A:
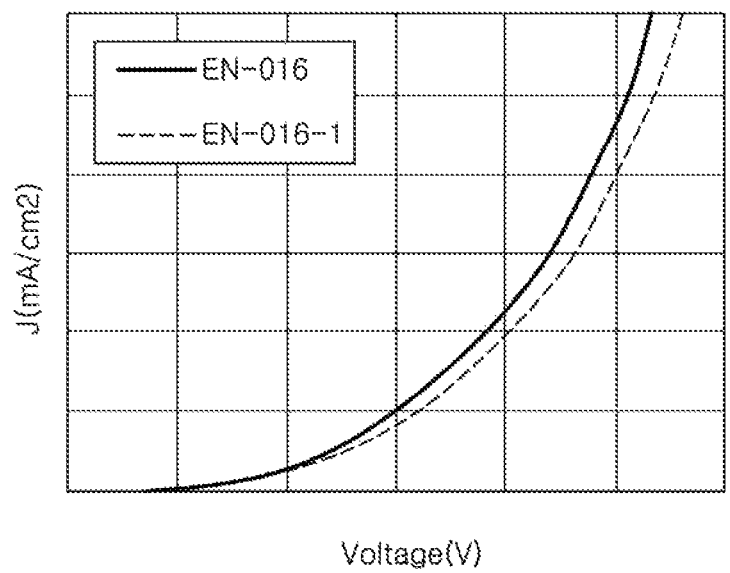
FIG. 4A is a graph showing a voltage-current density property of light emitting diodes of the embodiment 1 and the comparative example 1.
Figure 4B:
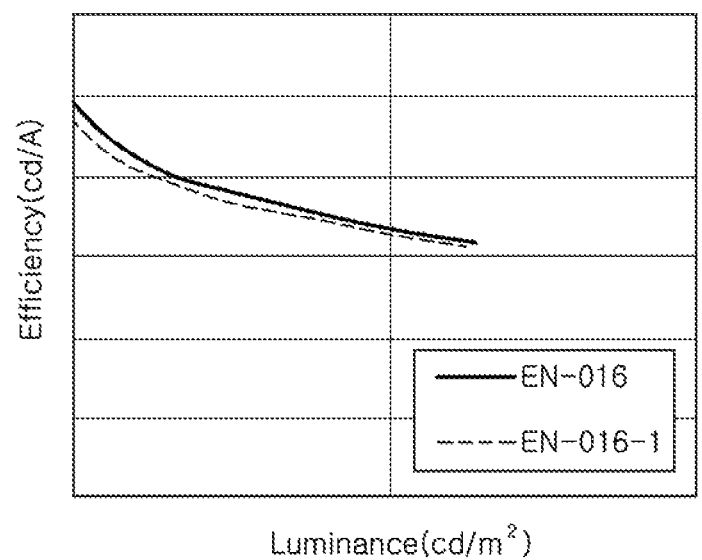
FIG. 4B is a graph showing a brightness-current efficiency property of light emitting diodes of the embodiment 1 and the comparative example 1.
Figure 4C:
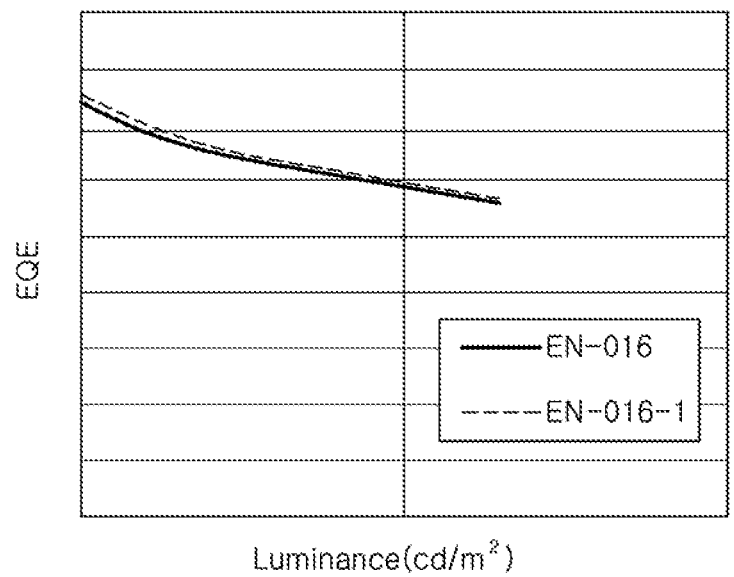
FIG. 4C. is a graph showing a brightness-external quantum efficiency (EQE) property of light emitting diodes of the embodiment 1 and the comparative example 1.
Figure 4D:
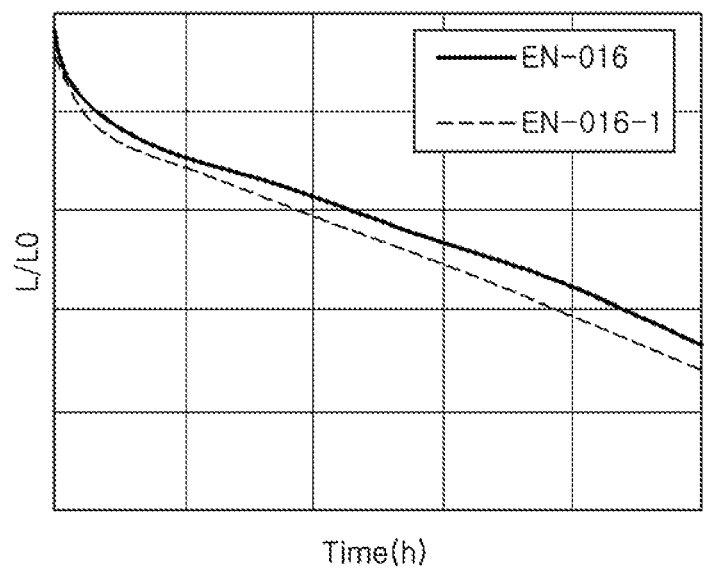
FIG. 4D is a graph showing a lifetime property of light emitting diodes of the embodiment 1 and the comparative example 1.
Figure 5A:
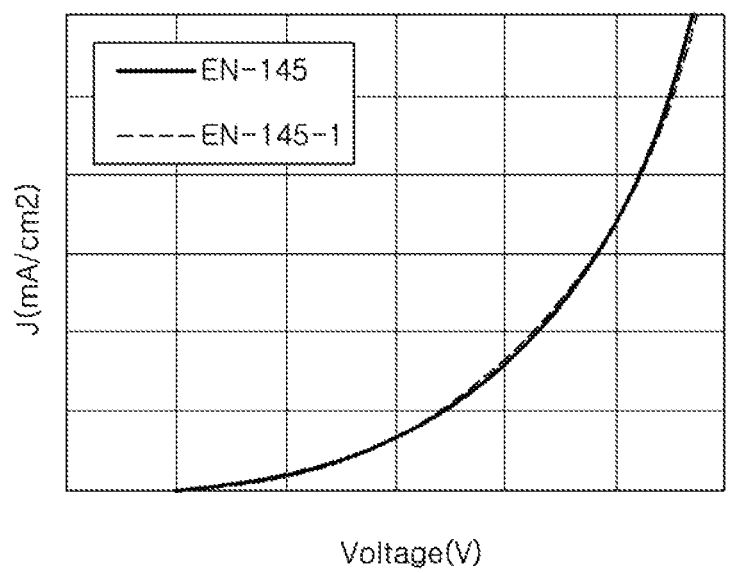
FIG. 5A is a graph showing a voltage-current density property of light emitting diodes of the embodiment 2 and the comparative example 2.
Figure 5B:
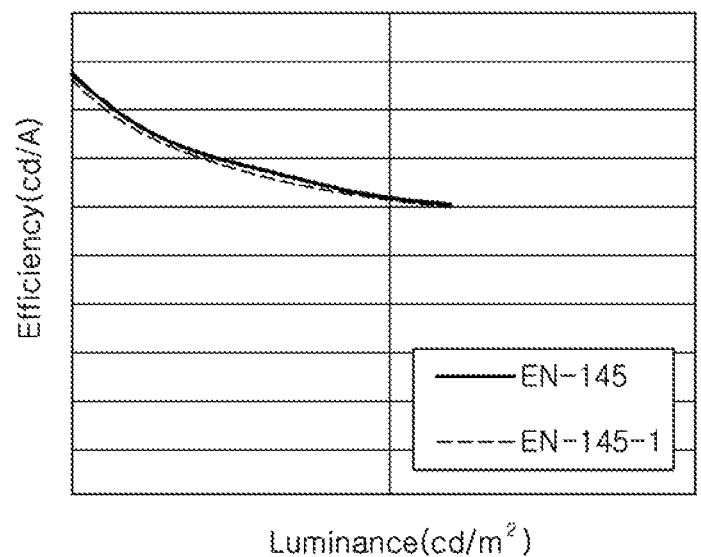
FIG. 5B is a graph showing a brightness-current efficiency property of light emitting diodes of the embodiment 2 and the comparative example 2.
Figure 5C:
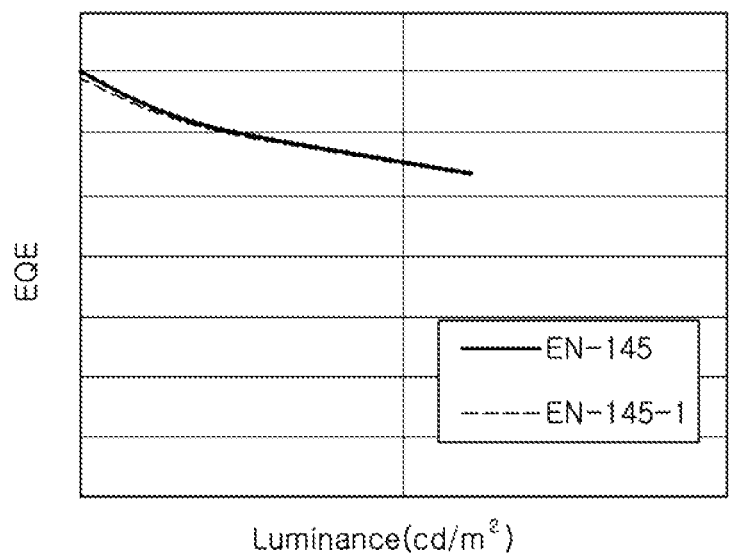
FIG. 5C is a graph showing a brightness-external quantum efficiency (EQE) property of light emitting diodes of the embodiment 2 and the comparative example 2.
Figure 5D:
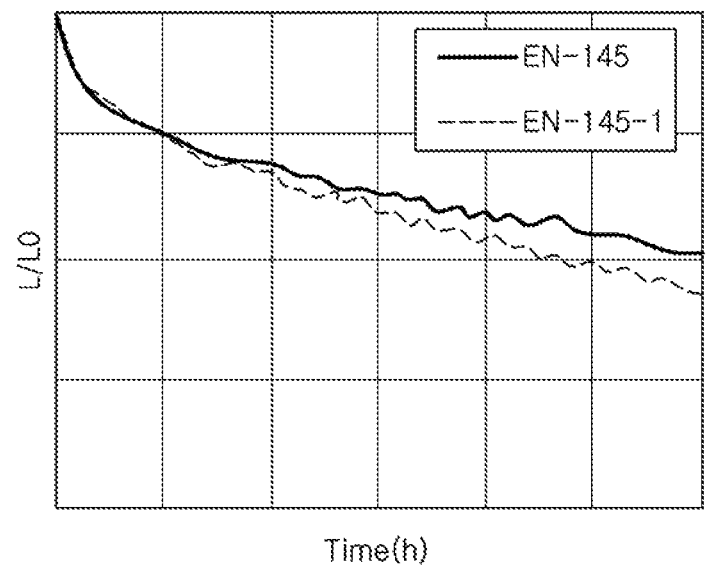
FIG. 5D is a graph showing a lifetime property of light emitting diodes of the embodiment 2 and the comparative example 2.
Figure 6A:
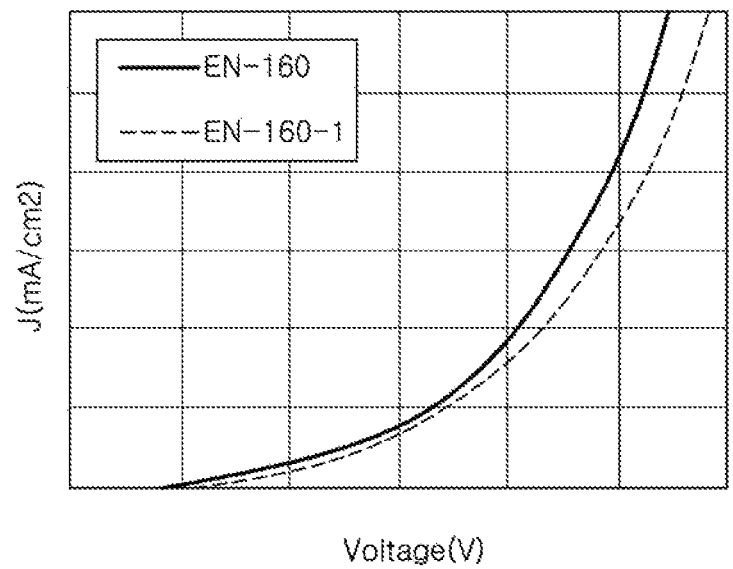
FIG. 6A is a graph showing a voltage-current density property of light emitting diodes of the embodiment 3 and the comparative example 3.
Figure 6B:
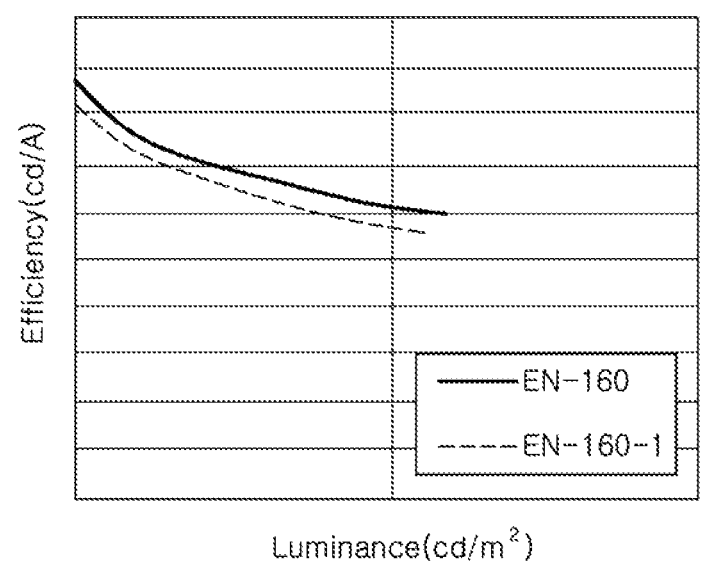
FIG. 6B is a graph showing a brightness-current efficiency property of light emitting diodes of the embodiment 3 and the comparative example 3.
Figure 6C:
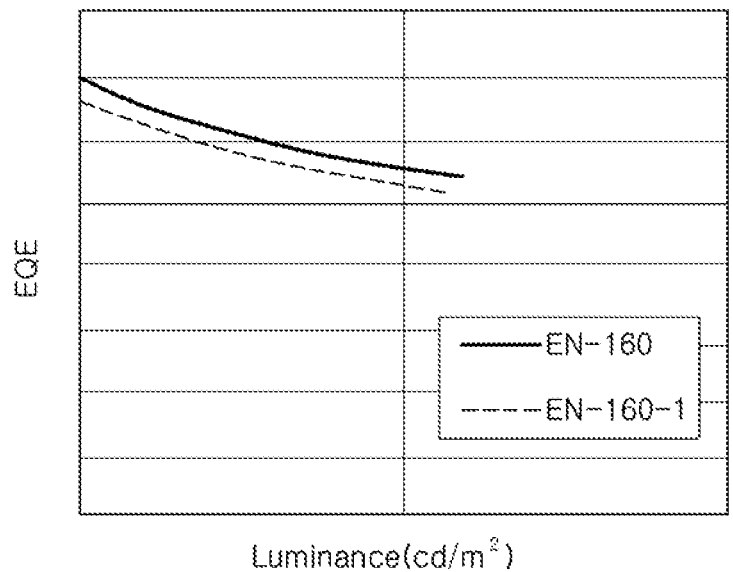
FIG. 6C is a graph showing a brightness-external quantum efficiency (EQE) property of light emitting diodes of the embodiment 3 and the comparative example 3.
Figure 6D:
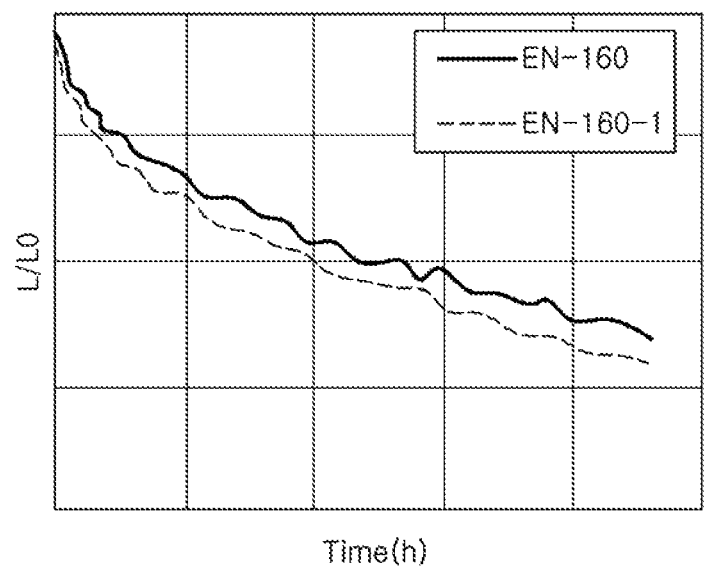
FIG. 6D is a graph showing a lifetime property of light emitting diodes of the embodiment 3 and the comparative example 3.

The LED of the present disclosure may be applied to an OLED display device and a lighting apparatus. FIG. 3 is a cross-sectional view showing an organic light emitting diode display device according to a third embodiment of the present disclosure.

In FIG. 3, an organic light emitting diode (OLED) display device 300 includes a substrate 301, a light emitting diode (LED) 400 and an encapsulation film 390 covering the LED 400. A driving thin film transistor (TFT) Td and the LED 400 connected to the driving TFT Td are formed on the substrate 301.

Although not shown, a gate line, a data line, a power line, a switching TFT and a storage capacitor are formed on the substrate 301. The gate line and the data line cross each other to define a pixel region, and the power line is disposed to be parallel to one of the gate line and the data line. The switching TFT is connected to the gate line and the data line, and the storage capacitor is connected to the power line and the switching TFT.

The driving TFT Td is connected to the switching TFT and includes a semiconductor layer 310, a gate electrode 330, a source electrode 352 and a drain electrode 354.

The semiconductor layer 310 is formed on the substrate 301 and may include an oxide semiconductor material or polycrystalline silicon. When the semiconductor layer 310 includes an oxide semiconductor material, a light shielding pattern (not shown) may be formed under the semiconductor layer 310. Since a light incident to the semiconductor layer 310 is blocked by the light shielding pattern, deterioration of the semiconductor layer 310 due to a light may be prevented. When the semiconductor layer 310 includes polycrystalline silicon, both side portions of the semiconductor layer 310 may be doped with impurities.

A gate insulating layer 320 of an insulating material is formed on an entire surface of the substrate 301 having the semiconductor layer 310. The gate insulating layer 320 may include an inorganic insulating material such as silicon oxide and silicon nitride.

A gate electrode 330 of a conductive material such as a metal is formed on the gate insulating layer 320 corresponding to a central portion of the semiconductor layer 310. The gate electrode 330 is connected to the switching TFT.

An interlayer insulating layer 340 of an insulating material is formed on an entire surface of the substrate 301 having the gate electrode 330. The interlayer insulating layer 340 may include an inorganic insulating material such as silicon oxide and silicon nitride or an organic insulating material such as benzocyclobutene and photoacryl.

The interlayer insulating layer 340 has first and second semiconductor contact holes 342 and 344 exposing both side portions of the semiconductor layer 310. The first and second semiconductor contact holes 342 and 344 are disposed at sides of the gate electrode 330 and spaced apart from the gate electrode 330.

A source electrode 352 and a drain electrode 354 of a conductive material such as a metal are formed on the interlayer insulating layer 340. The source electrode 352 and the drain electrode 354 are spaced apart from each other with respect to the gate electrode 330 as a center and are connected to the both side portions of the semiconductor layer 310 through the first and second semiconductor contact holes 342 and 344, respectively. The source electrode 352 is connected to the power line (not shown).

The semiconductor layer 310, the gate electrode 330, the source electrode 352 and the drain electrode 354 constitute the driving TFT Td having a coplanar structure where the gate electrode 330, the source electrode 352 and the drain electrode 354 are disposed over the semiconductor layer 310.

In another embodiment, the driving TFT Td may have an inverted staggered structure where the gate electrode is formed under the semiconductor layer and the source and drain electrodes are formed over the semiconductor layer. When the driving TFT Td has an inverted staggered structure, the semiconductor layer may include amorphous silicon. The switching TFT may have substantially the same structure as the driving TFT Td.

The OLED display device 300 may include a color filter layer 360 filtering a light emitted from the LED 400. For example, the color filter layer 360 may selectively absorb one of red (R), green (G), blue (B) and white (W) colored lights. Red, green and blue color filters may be formed in pixel regions, respectively, and may be disposed to overlap an organic emitting layer 430 of the LED 400. The OLED display device 300 may display a full color image by using the color filter layer 360.

For example, when the OLED display device 300 has a bottom emission type, the color filter layer 360 may be formed on the interlayer insulating layer 340 corresponding to the LED 400. When the OLED display device 300 has a top emission type, the color filter layer 360 may be formed over a second electrode 420 of the LED 400. The color filter layer 360 may have a thickness of about 2 μm to about 5 μm. The LED 400 may include a white LED having a tandem structure of FIGS. 1 and 2.

A passivation layer 370 is formed on the driving TFT Td and has a drain contact hole exposing the drain electrode 354 of the driving TFT Td.

A first electrode 410 is formed on the passivation layer 370 in each pixel region and is connected to the drain electrode 354 of the driving TFT Td through the drain contact hole 372.

The first electrode 410 may be an anode of a conductive material having a relatively high work function. For example, the first electrode 410 may include a transparent conductive material such as indium tin oxide (ITO), indium zinc oxide (IZO) and zinc oxide (ZO).

When the OLED display device 300 has a top emission type, a reflecting electrode or a reflecting layer may be further formed under the first electrode 410. For example, the reflecting electrode or the reflecting layer may include one of aluminum (Al), silver (Ag), nickel (Ni) and aluminum palladium copper (APC) alloy.

A bank layer 380 is formed on the passivation layer 370 to cover an edge portion of the first electrode 410. The bank layer 380 exposes a central portion of the first electrode 410 corresponding to the pixel region.

An organic emitting layer 430 is formed on the first electrode 410. For example, the organic emitting layer 430 may include at least two emitting parts as shown in FIGS. 1 and 2 such that the LED 400 has a tandem structure.

A second electrode 420 is formed on an entire surface of the substrate 301 having the organic emitting layer 430. The second electrode 420 may be a cathode of a conductive material having a relatively low work function. For example, the second electrode 420 may include a metallic material such as aluminum (Al), magnesium (Mg) and aluminum magnesium (AlMg) alloy.

The first electrode 410, the organic emitting layer 430 and the second electrode 420 constitute the LED 400.

An encapsulation film 390 is formed on the second electrode 420 to prevent penetration of external moisture into the LED 400. Although not shown, the encapsulation film 390 may have a triple layered structure including a first inorganic layer, an organic layer and a second inorganic layer. However, the encapsulation film 390 is not limited to that set forth herein.

The organic compound of the present disclosure includes a phenanthroline moiety substituted with at least one aromatic ring. Since the organic compound has a relatively high decomposition temperature or a relatively high glass transition temperature due to the phenanthroline moiety, the organic compound has an excellent thermal stability. Accordingly, a lifetime of the LED 400 including the organic compound is extended and a driving voltage of the LED 400 including the organic compound is reduced.

Further, since the organic compound of the present disclosure includes a phenanthroline moiety having a nitrogen atom of a hybrid orbital of $sp^2$ of sufficient electrons, the organic compound has an excellent electron transporting property. A nitrogen atom of a phenanthroline moiety is combined with the alkali metal or the alkali earth metal of the dopant of the N type charge generation layer to form a gap state. As a result, the energy level difference between the N type charge generation layer and the P type charge generation layer is alleviated. Since the injection of an electron into the N type charge generation layer is improved, the electron transporting property to the electron transporting layer adjacent to the N type charge generation layer may be maximized.

Further, since the compound including a nitrogen atom is combined with the alkali metal compound or the alkali earth metal compound of the N type charge generation layer, diffusion of the alkali metal compound or the alkali earth metal compound to the P type charge generation layer is prevented. Accordingly, reduction of the LED lifetime is prevented.

SYNTHESIS EXAMPLE 1

Synthesis of Compound EN-016

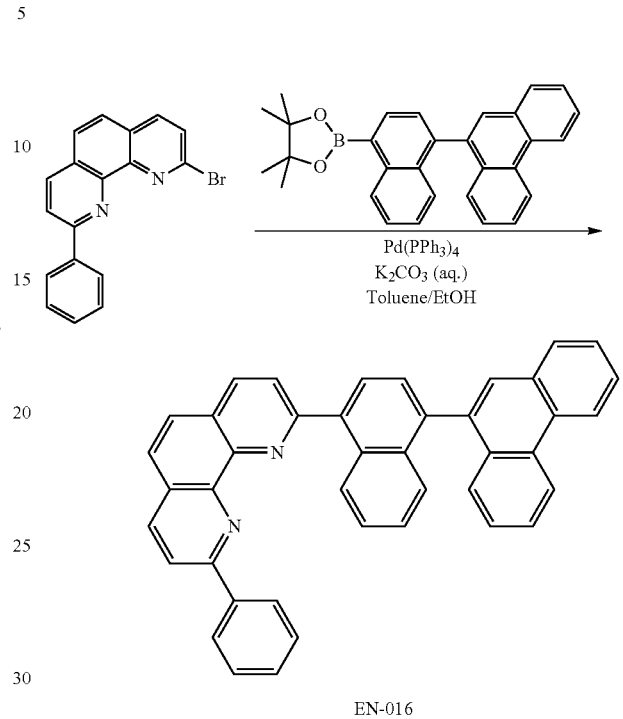

EN-016

After a mixture was formed by dissolving 4,4,5,5-tetramethyl-2-(1-(phenanthren-10-yl)naphthalen-4-yl)-1,3,2-dioxaborolane (6.0 g, 13.94 mmol), 2-bromo-1,10-phenanthroline (4.20 g, 12.57 mmol), tetrakis-triphenylphosphine palladium(0) (Pd(PPh$_3$)$_4$) (0.50 g, 0.70 mmol), 4M potassium carbonate aqueous solution (10 mL), toluene 30 mL, ethanol (EtOH) 10 mL under a nitrogen atmosphere, the mixture was refluxed and stirred for 12 hours. After a reaction was finished, H$_2$O 50 mL was added to the mixture, the mixture was stirred for 3 hours and a vacuum filtration was performed. After the mixture was divided through a column chromatography using methylene chloride (MC) and hexane as an eluent, the mixture was re-crystallized by using MC to obtain a compound EN-016 (6.25 g, transference number of 80.3%).

COMPARATIVE SYNTHESIS EXAMPLE 1

Synthesis of Compound EN-016-1

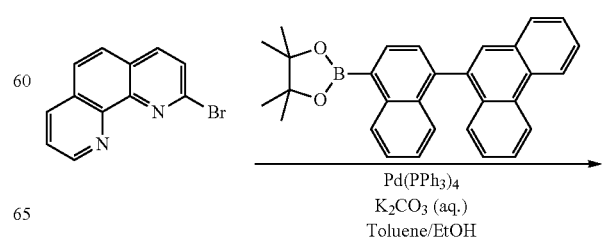

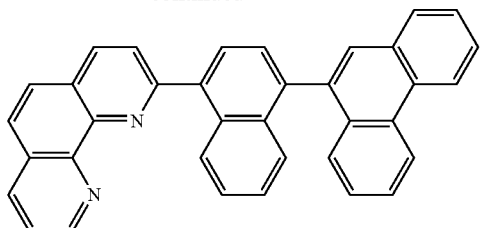

EN-016-1

After a mixture was formed by dissolving 4,4,5,5-tetramethyl-2-(1-(phenanthren-10-yl)naphthalen-4-yl)-1,3,2-dioxaborolane (5.0 g, 19.38 mmol), 2-bromo-9-phenyl-1,10-phenanthroline (8.50 g, 19.76 mmol), tetrakis-triphenylphosphine palladium(0) (Pd(PPh$_3$)$_4$) (1.14 g, 0.99 mmol), 4M potassium carbonate aqueous solution (10 mL), toluene 30 mL, ethanol (EtOH) 10 mL under a nitrogen atmosphere, the mixture was refluxed and stirred for 12 hours. After there action was finished, H$_2$O 50 mL was added to the mixture, the mixture was stirred for 3 hours and vacuum filtration was performed. After the mixture was divided through a column chromatography using methylene chloride (MC) and hexane as an eluent, the mixture was re-crystallized by using MC to obtain a compound EN-016-1 (7.94 g, transference number of 85.1%).

SYNTHESIS EXAMPLE 2

Synthesis of Compound EN-145

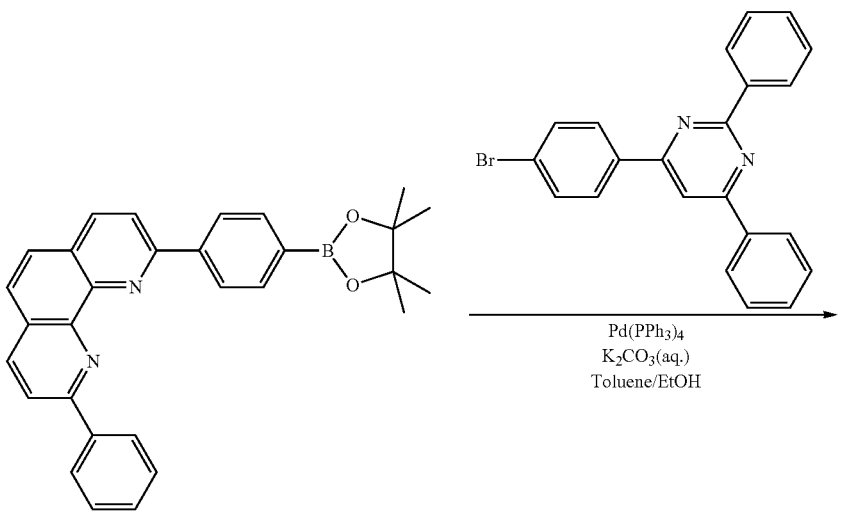

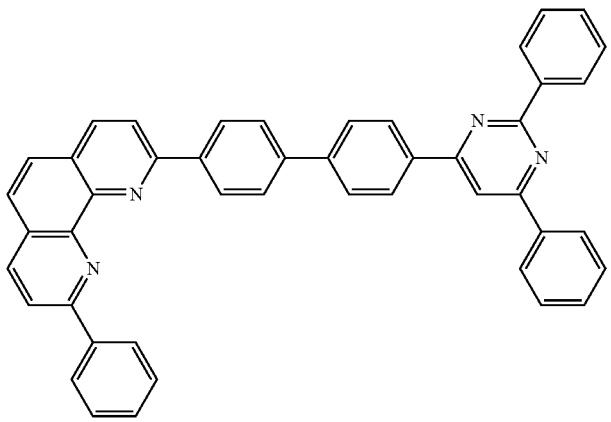

EN-145

After a mixture was formed by dissolving 2-(4-(4,4,5,5-tetramethyl-1,3,2-dioxaborolan-2-yl)phenyl)-9-phenyl-1,10-phenanthroline (5.0 g, 10.91 mmol), 4-(4-bromophenyl)-2,6-diphenylpyrimidine (4.80 g, 12.40 mmol), tetrakis-triphenylphosphine palladium(0) (Pd(PPh$_3$)$_4$) (0.63 g, 0.55 mmol), 4M potassium carbonate aqueous solution (10 mL), toluene 30 mL, ethanol (EtOH) 10 mL under a nitrogen atmosphere, the mixture was refluxed and stirred for 12 hours. After the reaction was finished, H$_2$O 50 mL was added to the mixture, the mixture was stirred for 3 hours and vacuum filtration was performed. After the mixture was divided through a column chromatography using methylene chloride (MC) and hexane as an eluent, the mixture was re-crystallized by using MC to obtain a compound EN-145 (5.01 g, transference number of 72.3%).

COMPARATIVE SYNTHESIS EXAMPLE 2

Synthesis of Compound EN-145-1

After a mixture was formed by dissolving 2-(4-(4,4,5,5-tetramethyl-1,3,2-dioxaborolan-2-yl)phenyl)-1,10-phenanthroline (5.0 g, 13.08 mmol), 4-(4-bromophenyl)-2,6-diphenylpyrimidine (6.10 g, 15.96 mmol), tetrakis-triphenylphosphine palladium(0) (Pd(PPh$_3$)$_4$) (0.75 g, 0.65 mmol), 4M potassium carbonate aqueous solution (10 mL), toluene 30 mL, ethanol (EtOH) 10 mL under a nitrogen atmosphere, the mixture was refluxed and stirred for 12 hours. After there action was finished, H$_2$O 50 mL was added to the mixture, the mixture was stirred for 3 hours and vacuum filtration was performed. After the mixture was divided through a column chromatography using methylene chloride (MC) and hexane as an eluent, the mixture was re-crystallized by using MC to obtain a compound EN-145-1 (5.56 g, transference number of 75.6%).

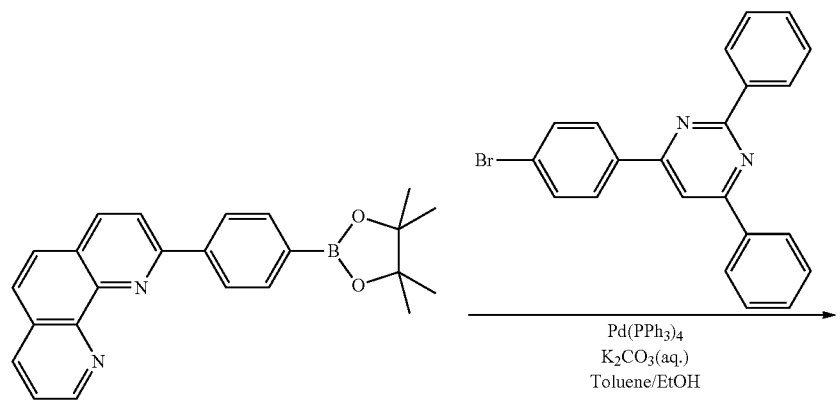

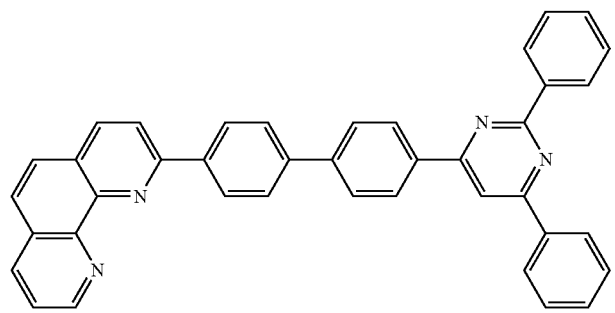

EN-145-1

SYNTHESIS EXAMPLE 3

Synthesis of Compound EN-160

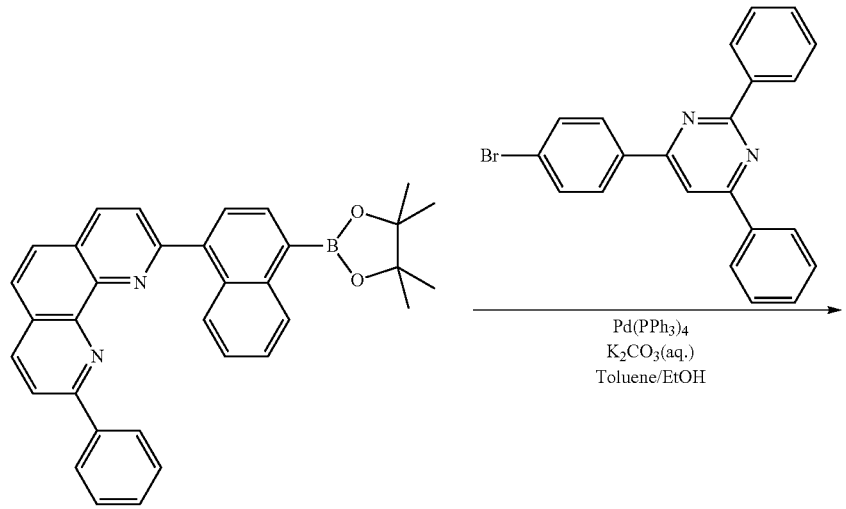

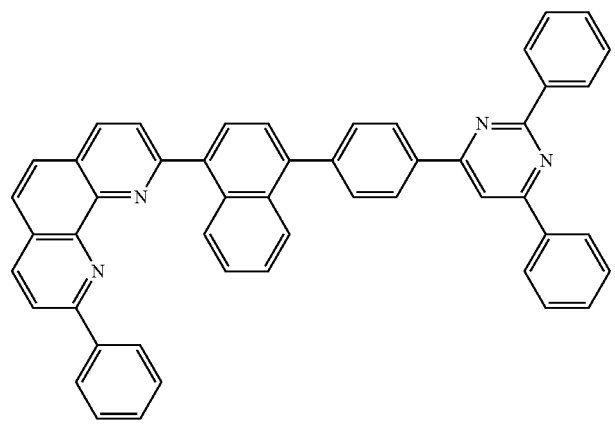

EN-160

After a mixture was formed by dissolving 2-(1-(4,4,5,5-tetramethyl-1,3,2-dioxaborolan-2-yl)naphthalen-4-yl)-1,10-phenanthroline (5.5 g, 10.82 mmol), 4-(4-bromophenyl)-2,6-diphenylpyrimidine (4.50 g, 11.63 mmol), tetrakis-triphenylphosphine palladium(0) (Pd(PPh$_3$)$_4$) (0.63 g, 0.54 mmol), 4M potassium carbonate aqueous solution (10 mL), toluene 30 mL, ethanol (EtOH) 10 mL under a nitrogen atmosphere, the mixture was refluxed and stirred for 12 hours. After there action was finished, H$_2$O 50 mL was added to the mixture, the mixture was stirred for 3 hours and vacuum filtration was performed. After the mixture was divided through a column chromatography using methylene chloride (MC) and hexane as an eluent, the mixture was re-crystallized by using MC to obtain a compound EN-160 (5.03 g, transference number of 72.8%).

COMPARATIVE SYNTHESIS EXAMPLE 3

Synthesis of Compound EN-160-1

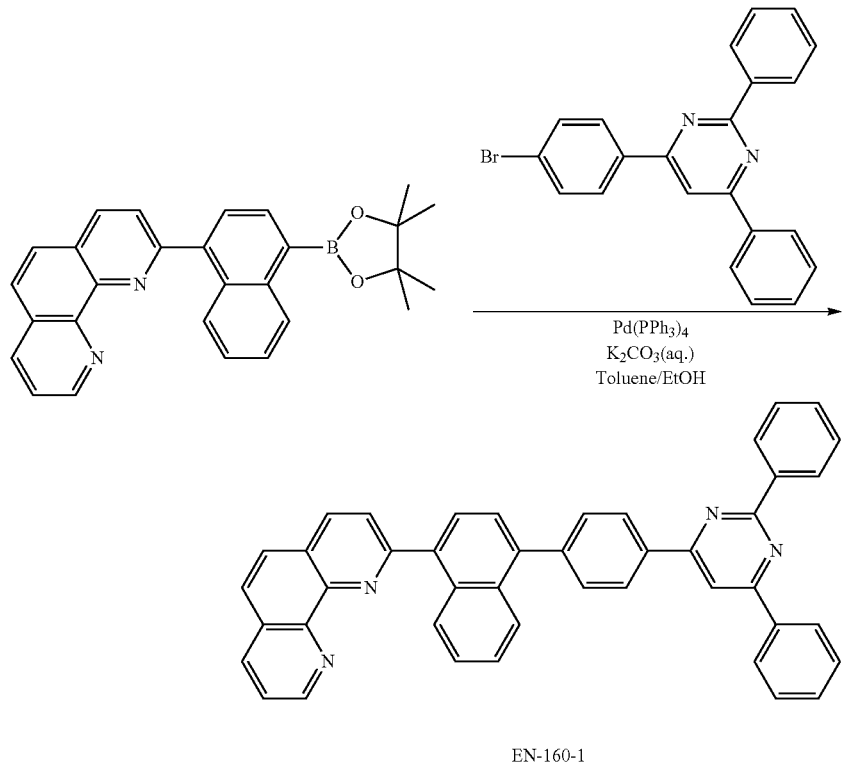

EN-160-1

After a mixture was formed by dissolving 2-(1-(4,4,5,5-tetramethyl-1,3,2-dioxaborolan-2-yl)naphthalen-4-yl)-9-phenyl-1,10-phenanthroline (6.0 g, 13.88 mmol), 4-(4-bromophenyl)-2,6-diphenylpyrimidine (6.0 g, 15.50 mmol), tetrakis-triphenylphosphine palladium(0) (Pd(PPh$_3$)$_4$) (0.80 g, 0.69 mmol), 4M potassium carbonate aqueous solution (10 mL), toluene 30 mL, ethanol (EtOH) 10 mL under a nitrogen atmosphere, the mixture was refluxed and stirred for 12 hours. After there action was finished, H$_2$O 50 mL was added to the mixture, the mixture was stirred for 3 hours and vacuum filtration was performed. After the mixture was divided through a column chromatography using methylene chloride (MC) and hexane as an eluent, the mixture was re-crystallized by using MC to obtain a compound EN-160-1 (6.11 g, transference number of 71.8%).

EXPERIMENTAL EXAMPLE 1

Estimation of Thermal Stability and Electron Moving Property

A thermal stability and an electron moving property of the compounds of the synthesis examples 1 to 3 and the comparative synthesis examples 1 to 3 were estimated. A thermal stability was obtained by measuring a decomposition temperature (1%, 5%) and a glass transition temperature (Tg) through a thermogravimetric analysis (TGA) and a differential scanning calorimeter (DSC). An electron moving property was obtained by calculating an electron affinity (EA), a reorganization energy ($\lambda_{electron}$) and a ratio of rate constants of an electron and a hole ($k_{et}(e)/k_{et}(h)$) using a density functional theory (B3LYP/6-31G*). Results of measurement and estimation are illustrated in a following table.

TABLE 1

| | Thermal Analysis (° C.) | | | Simulation Analysis | | |
|---|---|---|---|---|---|---|
| | Td (1%) | Td (5%) | Tg | Electron Affinity | $\lambda_{electron}$ | $k_{et}(e)/k_{et}(h)$ |
| EN-016 | 415 | 456 | 157 | 0.57 | 0.29 | 1.18 |
| EN-016-1 | 401 | 442 | 151 | 0.44 | 0.38 | 1.11 |
| EN-145 | 465 | 506 | 138 | 0.96 | 0.27 | 0.30 |
| En-145-1 | 436 | 477 | 131 | 0.89 | 0.29 | 0.27 |
| EN-160 | 471 | 510 | 147 | 0.92 | 0.31 | 0.43 |
| EN-160-1 | 445 | 588 | 141 | 0.72 | 0.35 | 0.31 |

In TABLE 1, the compound according to the present disclosure including a phenanthroline moiety where a phenyl group corresponding to an aryl group is substituted has a higher decomposition temperature and a higher glass transition temperature as compared with the compound where a phenyl group is not substituted. As a result, the thermal stability is improved. Further, the compound including a phenanthroline moiety where a phenyl group is substituted has a greater electron affinity (EA) as compared with the compound where a phenyl group is not substituted. As a result, the compound including a phenanthroline moiety where a phenyl group is substituted may receive an electron more easily as compared with the compound where a phenyl group is not substituted. Specifically, a material for the N type charge generation layer (n-CGL) is required to have an excellent property of receiving an electron from the P type charge generation layer (p-CGL) and transmitting an electron to the electron transporting layer (ETL). Since the compound including a phenanthroline moiety where a phenyl group is substituted has a reduced reorganization energy ($\lambda_{electron}$) and a increased ratio of rate constants of an electron and a hole ($k_{et}(e)/k_{et}(h)$), the compound including a phenanthroline moiety where a phenyl group is substituted has a superior negative ion stability and a superior electron moving property as compared with the compound where a phenyl group is not substituted.

Embodiment 1: Fabrication of Light Emitting Diode of Tandem Structure

A light emitting diode (LED) of a tandem structure including three emitting parts by using the compound EN-016 of the synthesis example 1 for the N type charge generation layer was fabricated. After an indium tin oxide (ITO) substrate was patterned to have an emission area of 2 mm*2 mm, the ITO substrate was cleaned using an ultraviolet (UV) and ozone. In a vacuum deposition chamber having a pressure of $5*10^{-8}$ to $7*10^{-8}$ torr, the following layers were sequentially formed on the ITO substrate.

Hole Injecting Layer (NPD doped with 10% of F4-TCNQ) 100 Å, First Hole Transporting Layer (NPD) 1200 Å, First Emitting Material Layer (Blue Emitting Material Layer, anthracene host doped with 4% of pyrene dopant) 200 Å, First Electron Transporting Layer (1,3,5-tri[(3-pyridyl)-phen-3-yl]benzene (TmPyPB) 100 Å, First N Type Charge Generation Layer (EN-016 doped with 2% of Li) 100 Å, First P Type Charge Generation Layer (NPD doped with 10% of F4-TCNQ) 200 Å, Second Hole Transporting Layer (NPD) 200 Å, Second Emitting Material Layer (Yellow Emitting Material Layer, CBP host doped with 10% of Ir complex) 200 Å, Second Electron Transporting Layer (Alq3), Second N Type Charge Generation Layer(EN-016 doped with 2% of Li) 100 Å,Second P Type Charge Generation Layer (NPD doped with 10% of F4-TCNQ)200 Å,Third Hole Transporting Layer (NPD) 200 Å,Third Emitting Material Layer (Yellow Emitting Material Layer, CBP host doped with 10% of Ir complex)200 Å,Third Electron Transporting Layer (TmPyPB) 100 Å, Electron Injecting Layer (LiF) 10 Å, Cathode (aluminum) 200 Å.

COMPARATIVE EXAMPLE 1

Fabrication of Light Emitting Diode of Tandem Structure

Through a process the same as that of the embodiment 1 except that the compound EN-016-1 of the comparative synthesis example 1 was used for the host of the first and second N type charge generation layers instead of the compound EN-016, the LED was fabricated.

EXPERIMENTAL EXAMPLE 2

Estimation of Property of Light Emitting Diode

Driving properties of the LED of a tandem structure of the embodiment 1 and the comparative example 1 were estimated. FIGS. 4A to 4D are graphs showing a voltage-current density property, a brightness-current efficiency property, a brightness-external quantum efficiency (EQE) property and a lifetime property, respectively, of light emitting diodes of the embodiment 1 and the comparative example 1. The driving voltage of the LED of the embodiment 1 is reduced by about 0.2V as compared with the driving voltage of the LED of the comparative example 1. The current efficiency of the LED of the embodiment 1 is increased by about 2% as compared with the current efficiency of the LED of the comparative example 1. The external quantum efficiency of the LED of the embodiment 1 is similar to the external quantum efficiency of the LED of the comparative example 1. The lifetime of the LED of the embodiment 1 is extended by about 10% as compared with the lifetime of the LED of the comparative example 1.

Embodiment 2: Fabrication of Light Emitting Diode of Tandem Structure

Through a process the same as that of the embodiment 1 except that the compound EN-145 of the synthesis example 2 was used for the host of the first and second N type charge generation layers instead of the compound EN-016, the LED was fabricated.

COMPARATIVE EXAMPLE 2

Fabrication of Light Emitting Diode of Tandem Structure

Through a process the same as that of the embodiment 1 except that the compound EN-145-1 of the comparative synthesis example 2 was used for the host of the first and second N type charge generation layers instead of the compound EN-016, the LED was fabricated.

EXPERIMENTAL EXAMPLE 3

Estimation of Property of Light Emitting Diode

Driving properties of the LED of a tandem structure of the embodiment 2 and the comparative example 2 were estimated. FIGS. 5A to 5D are graphs showing a voltage-current density property, a brightness-current efficiency property, a brightness-external quantum efficiency (EQE) property and a lifetime property, respectively, of light emitting diodes of the embodiment 2 and the comparative example 2. The driving voltage of the LED of the embodiment 2 is similar to the driving voltage of the LED of the comparative example 2. The current efficiency of the LED of the embodiment 2 is increased by about 1% as compared with the current efficiency of the LED of the comparative example 2. The external quantum efficiency of the LED of the embodiment 2 is increased by about 1% as compared with the external quantum efficiency of the LED of the comparative example 2. The lifetime of the LED of the embodiment 2 is extended by about 29% as compared with the lifetime of the LED of the comparative example 2.

Embodiment 3: Fabrication of Light Emitting Diode of Tandem Structure

Through a process the same as that of the embodiment 1 except that the compound EN-160 of the synthesis example 3 was used for the host of the first and second N type charge generation layers instead of the compound EN-016, the LED was fabricated.

COMPARATIVE EXAMPLE 3

Fabrication of Light Emitting Diode of Tandem Structure

Through a process the same as that of the embodiment 1 except that the compound EN-160-1 of the comparative synthesis example 3 was used for the host of the first and second N type charge generation layers instead of the compound EN-016, the LED was fabricated.

EXPERIMENTAL EXAMPLE 4

Estimation of Property of Light Emitting Diode

Driving properties of the LED of a tandem structure of the embodiment 3 and the comparative example 3 were estimated. FIGS. 6A to 6D are graphs showing a voltage-current density property, a brightness-current efficiency property, a brightness-external quantum efficiency (EQE) property and a lifetime property, respectively, of light emitting diodes of the embodiment 3 and the comparative example 3. The driving voltage of the LED of the embodiment 3 is reduced by about 0.2V as compared with the driving voltage of the LED of the comparative example 3. The current efficiency of the LED of the embodiment 3 is increased by about 5% as compared with the current efficiency of the LED of the comparative example 3. The external quantum efficiency of the LED of the embodiment 3 is increased by about 1% as compared with the external quantum efficiency of the LED of the comparative example 3. The lifetime of the LED of the embodiment 3 is extended by about 15% as compared with the lifetime of the LED of the comparative example 3.

As shown in the results of the experimental examples 2 to 4, the organic compound including a phenanthroline moiety where a phenyl group is substituted has the similar or reduced driving voltage as compared with the organic compound where a phenyl group is not substituted. The organic compound including a phenanthroline moiety where a phenyl group is substituted has the similar or improved current efficiency and the similar or improved external quantum efficiency as compared with the organic compound where a phenyl group is not substituted. Specifically, since the thermal stability and the electron moving property are improved due to a phenyl group, the lifetime of the LED is greatly extended.

Consequently, the organic compound of the present disclosure includes a phenanthroline moiety substituted with at least one aromatic ring. Since the organic compound has a relatively high decomposition temperature or a relatively high glass transition temperature due to the phenanthroline moiety, the organic compound has an excellent thermal stability. As a result, the organic compound may not be deteriorated or spoiled even by a Joule's heat generated from driving of an element. Accordingly, a lifetime of the LED including the organic compound is extended and a driving voltage of the LED including the organic compound is reduced.

Further, since the organic compound of the present disclosure includes a phenanthroline moiety having a nitrogen atom of a hybrid orbital of $sp^2$ of sufficient electrons, the organic compound has an excellent electron transporting property. Accordingly, the organic compound of the present disclosure may be used for the electron transporting layer. A nitrogen atom of a phenanthroline moiety is combined with the alkali metal or the alkali earth metal of the dopant of the N type charge generation layer to form a gap state. As a result, the energy level difference between the N type charge generation layer and the P type charge generation layer is alleviated. Since the injection of an electron into the N type charge generation layer is improved, the electron transporting property to the electron transporting layer adjacent to the N type charge generation layer may be maximized.

An electron may be efficiently transmitted from the N type charge generation layer to the electron transporting layer by applying the organic compound of the present disclosure to the N type charge generation layer.

Further, since the compound including a nitrogen atom is combined with the alkali metal compound or the alkali earth metal compound of the N type charge generation layer, diffusion of the alkali metal compound or the alkali earth metal compound to the P type charge generation layer is prevented. Accordingly, reduction of the LED lifetime is prevented.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:
1. An organic compound selected from:

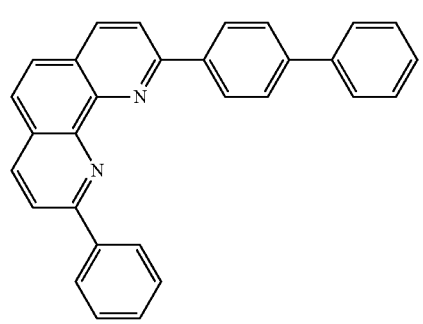

EN-001

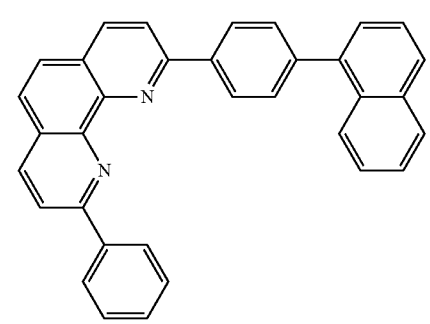

EN-002

-continued
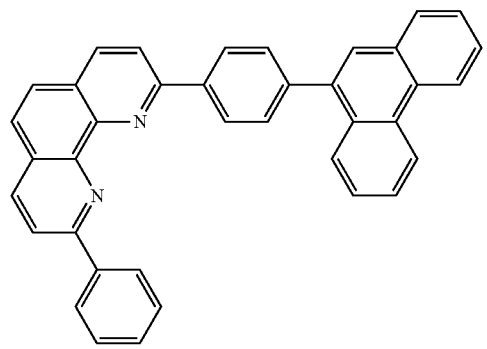
EN-003
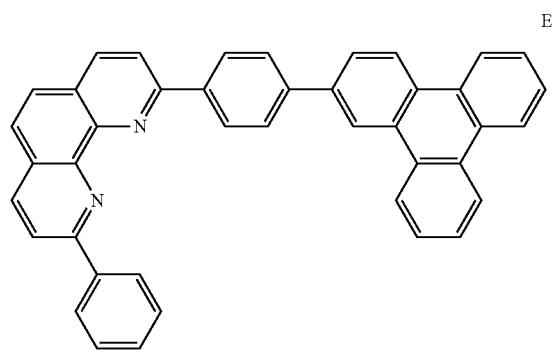
EN-005
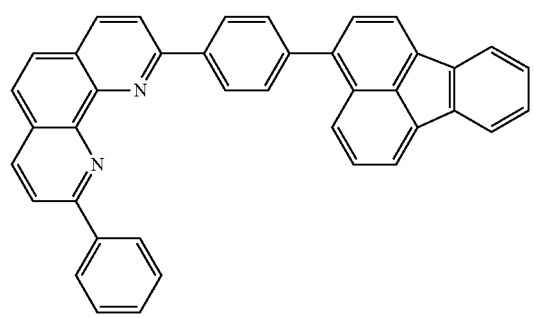
EN-006
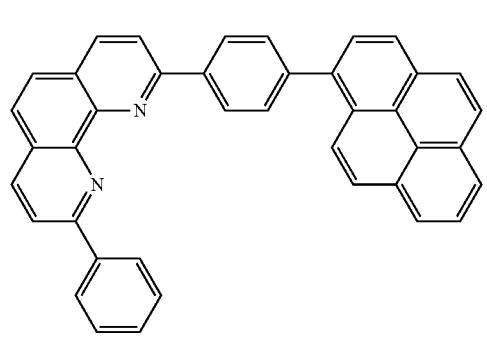
EN-007
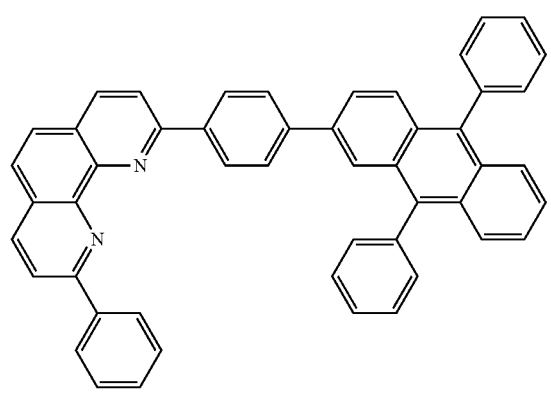
EN-008
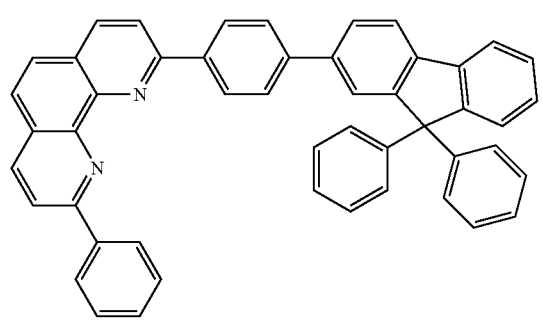
EN-009
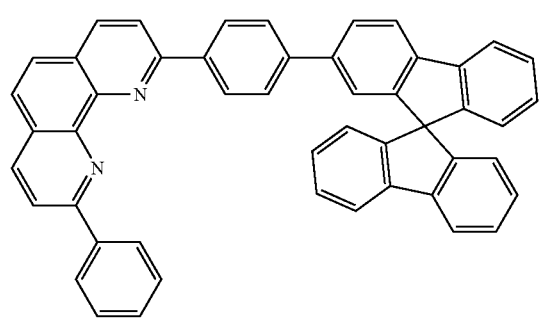
EN-010

-continued
EN-011
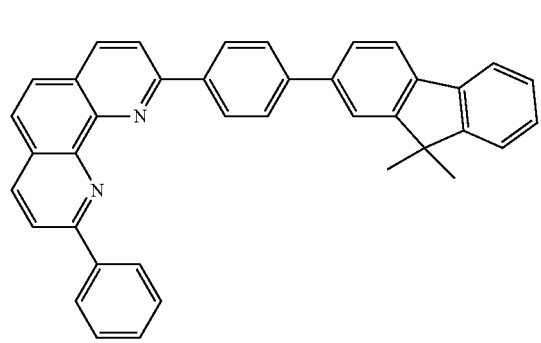
EN-013
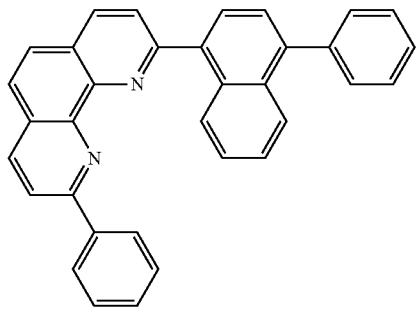
EN-014
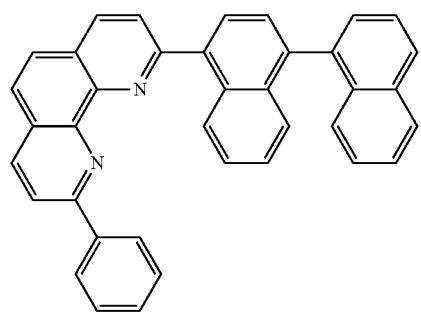
EN-016
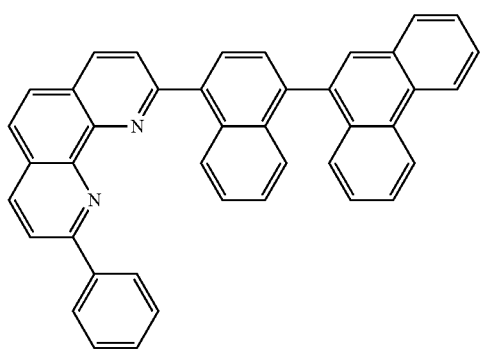
EN-017
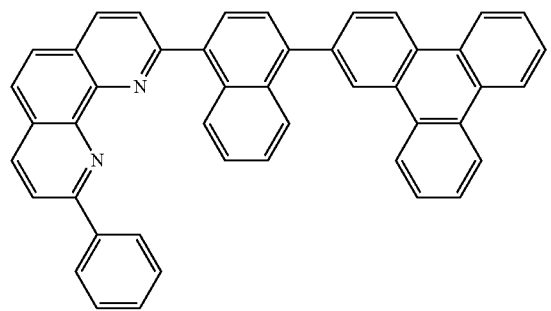
EN-018
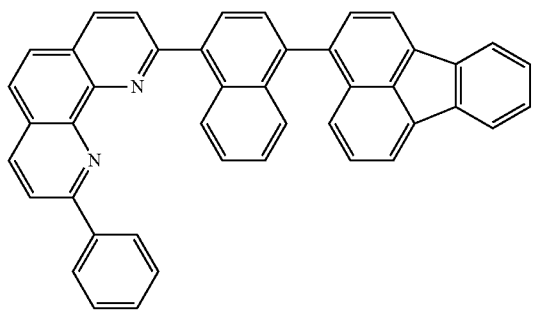
EN-019
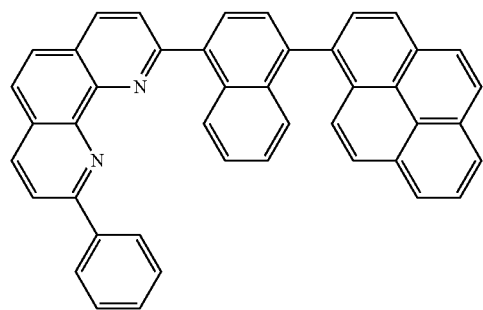
EN-020
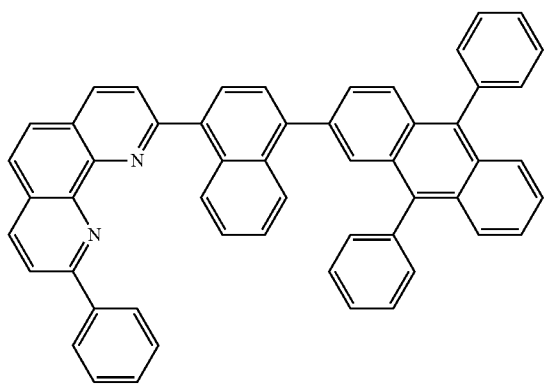

-continued
EN-021
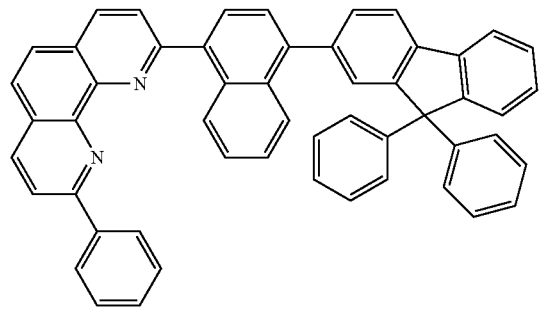
EN-022
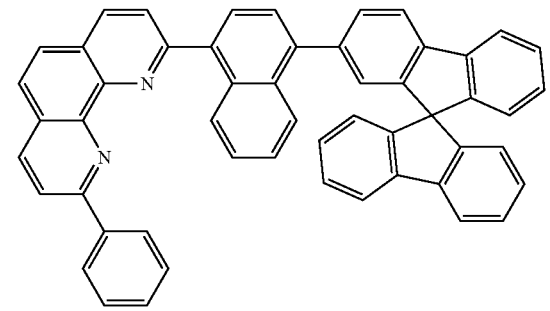
EN-023
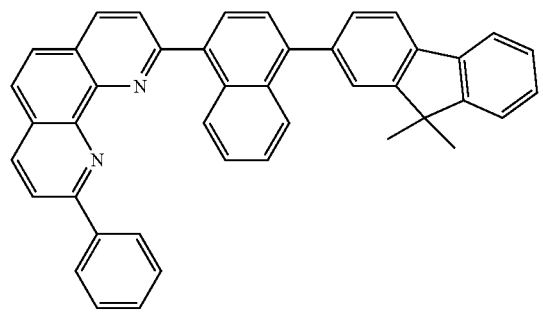
EN-024
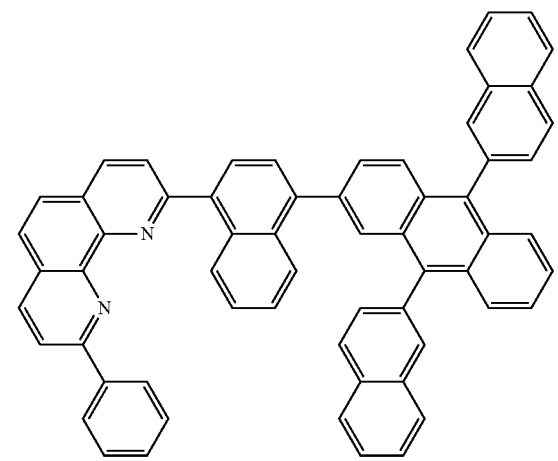
EN-025
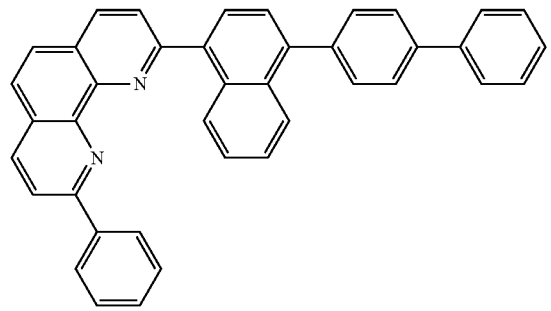
EN-026
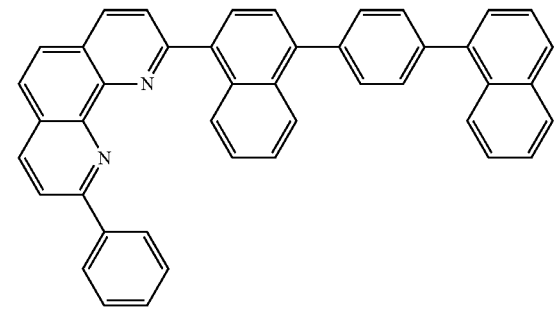
EN-027
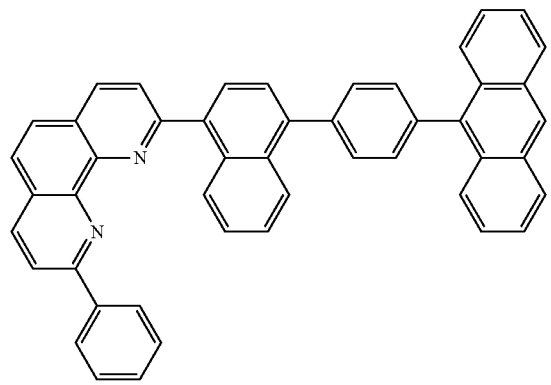
EN-028
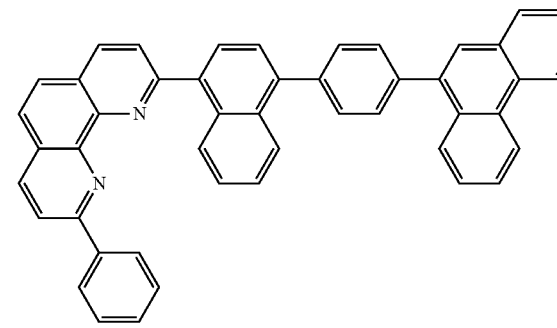

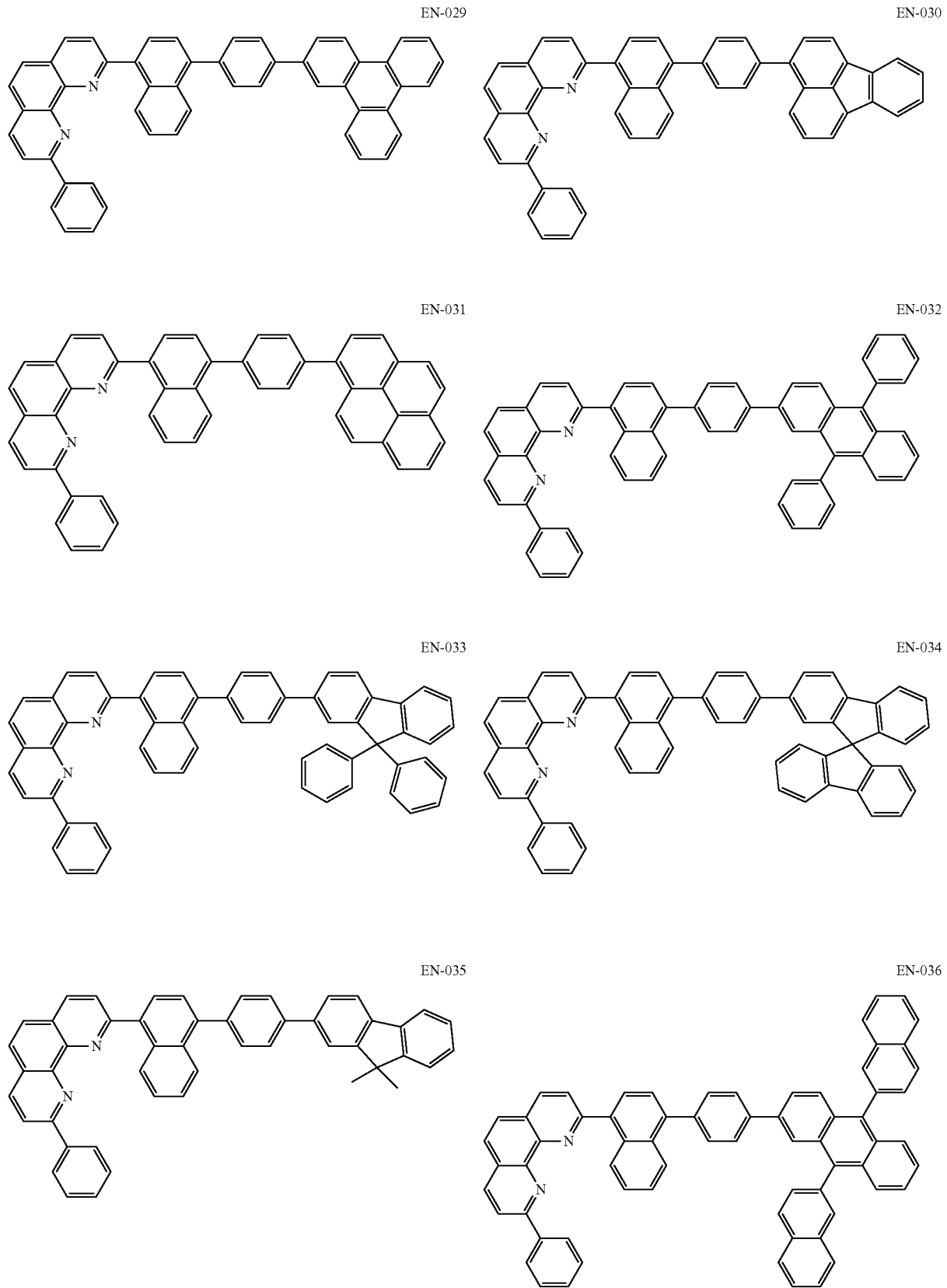

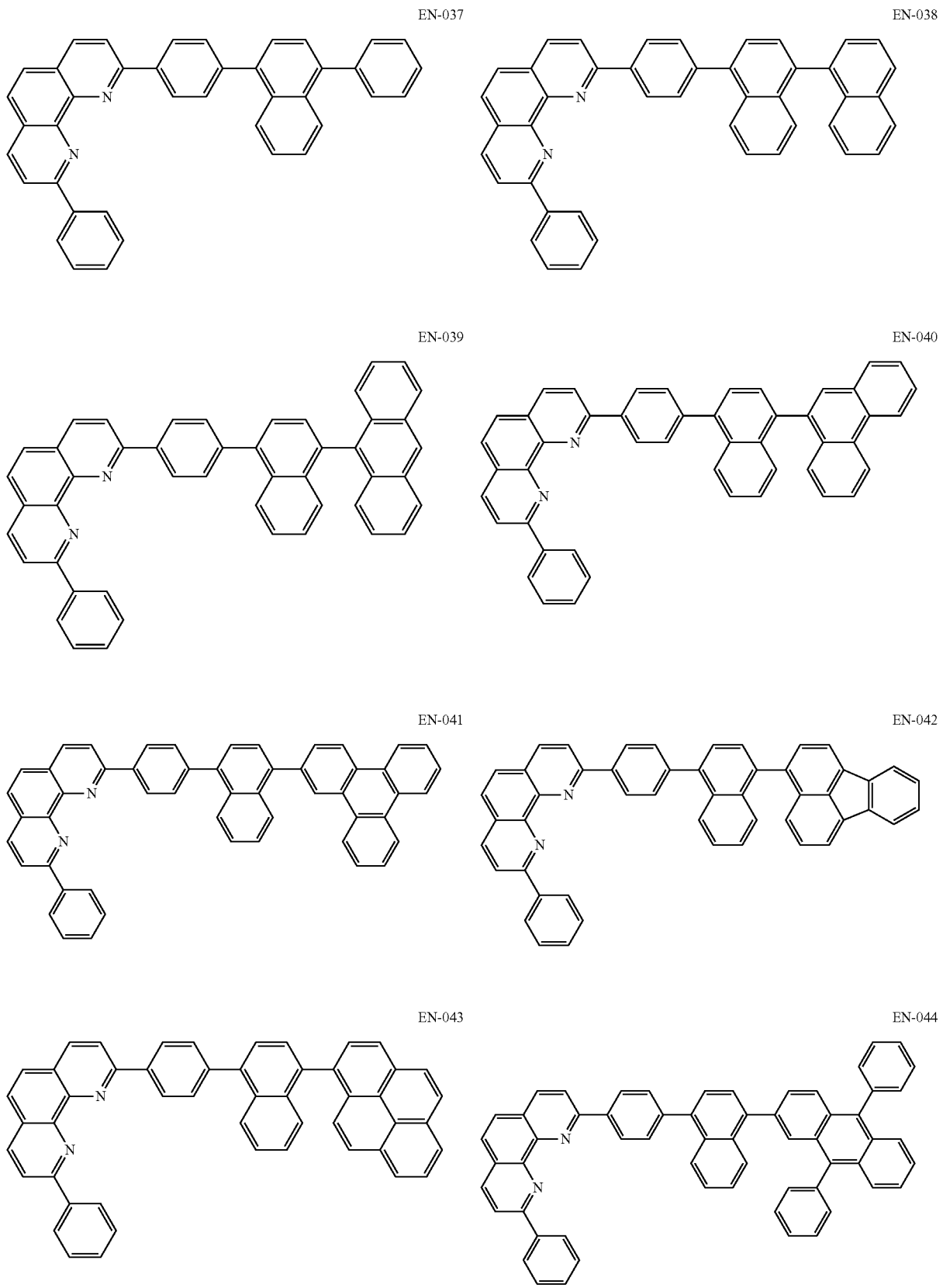

-continued
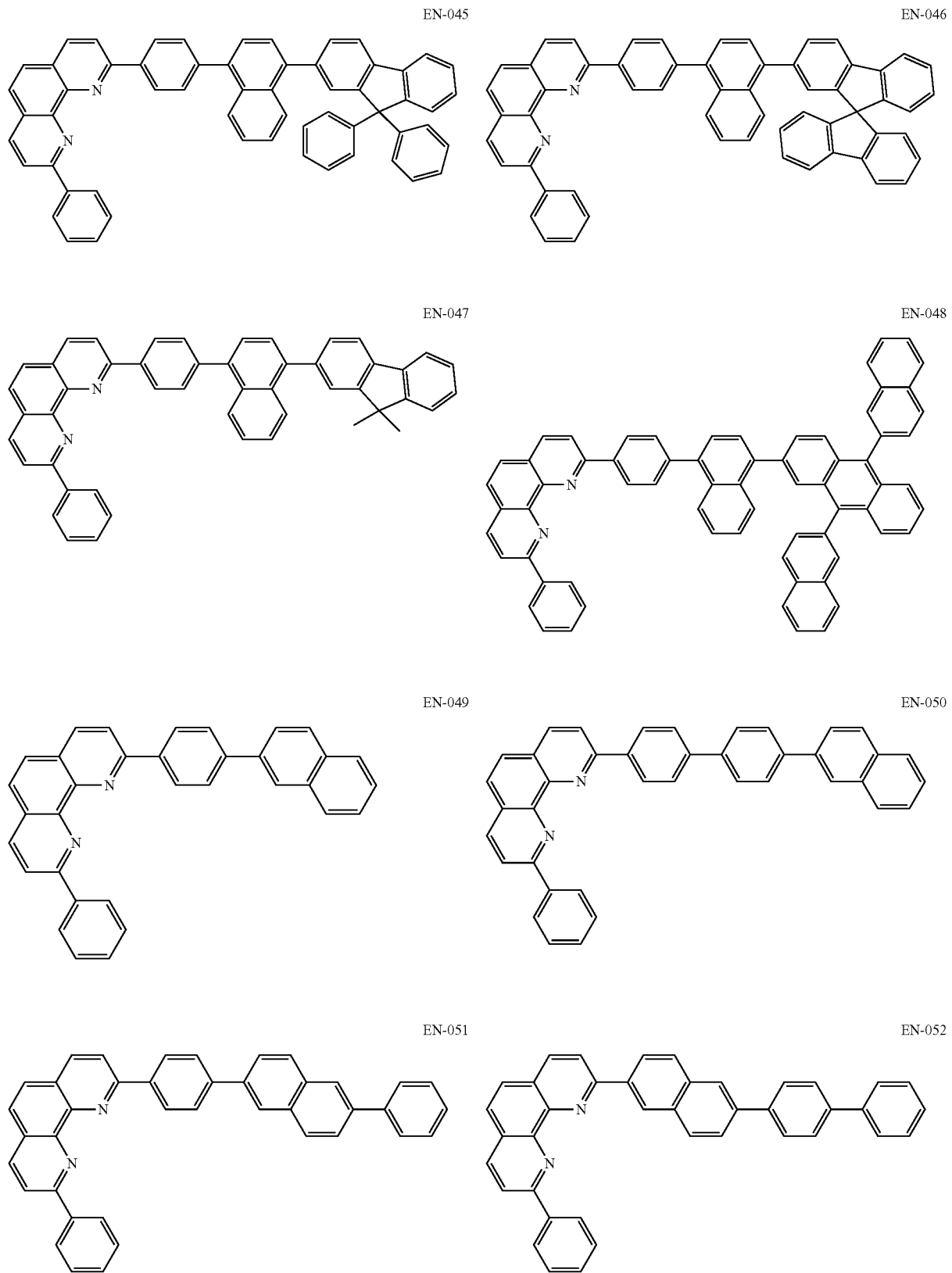

EN-053
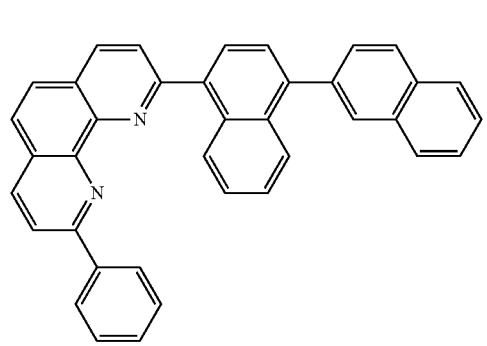
EN-054
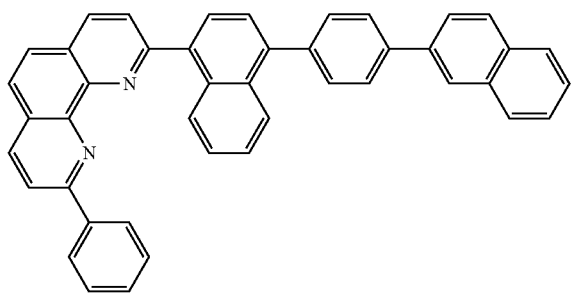
EN-055
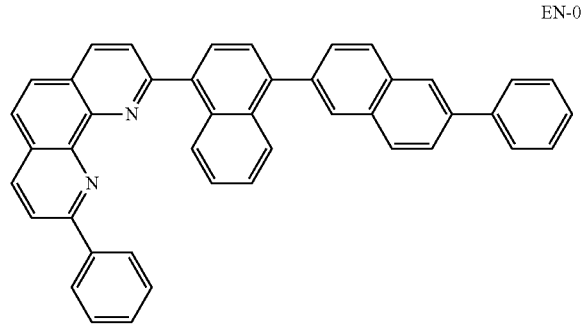
EN-056
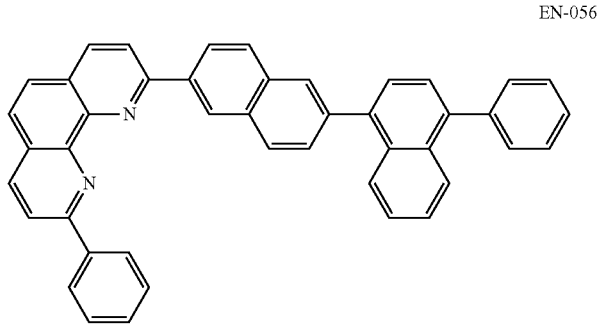
EN-057
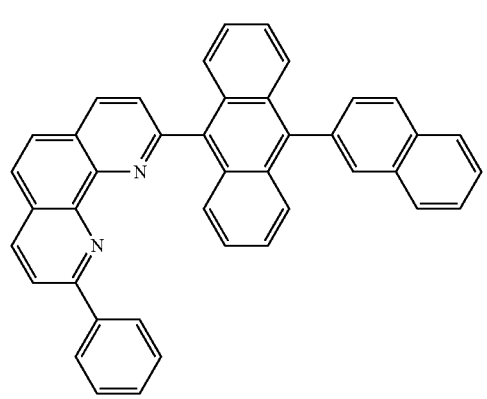
EN-058
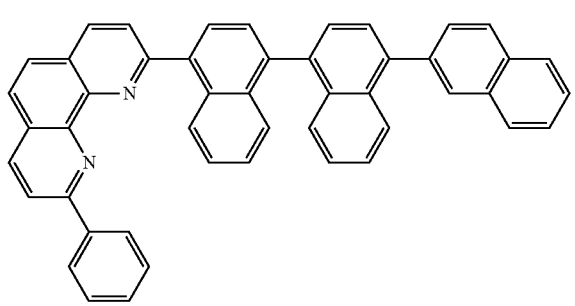
EN-059
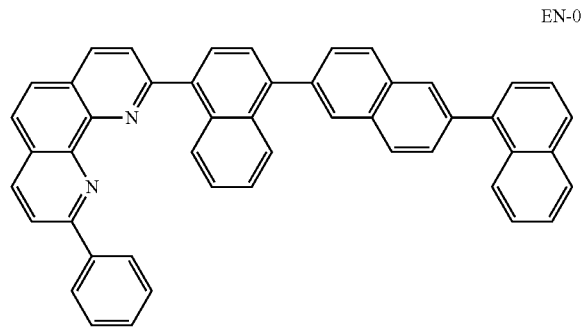
EN-060
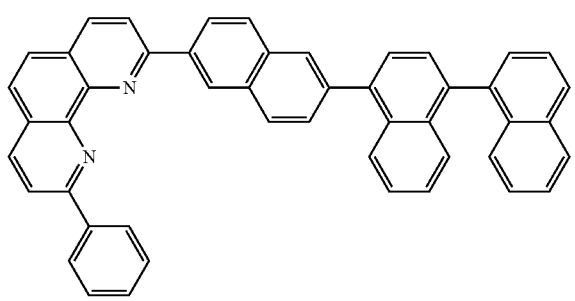

EN-061
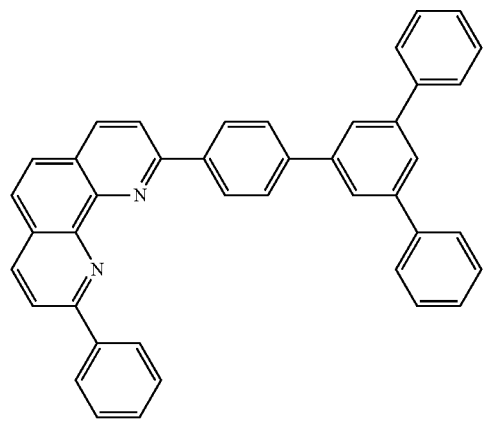
EN-062
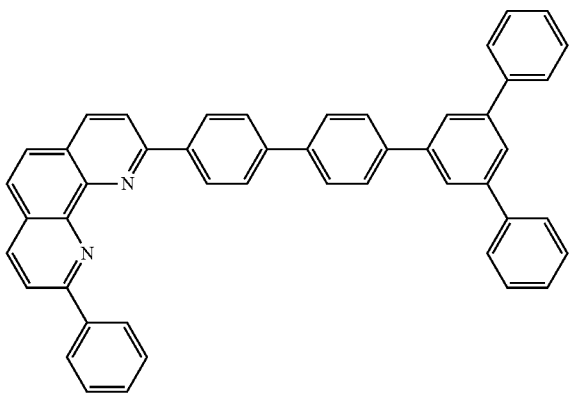
EN-063
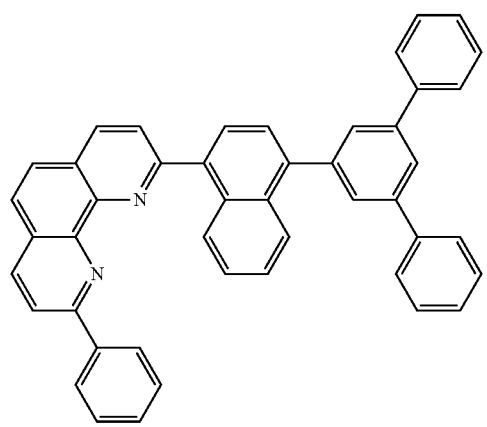
EN-064
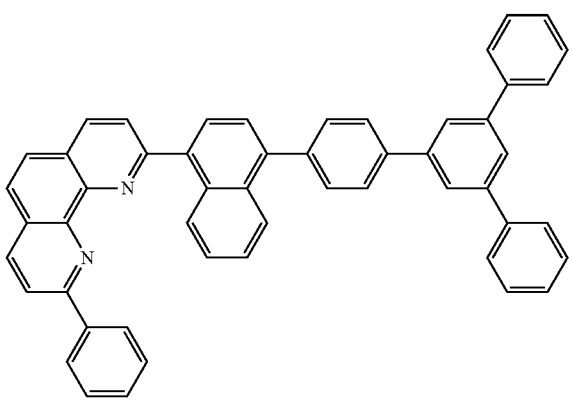
EN-065
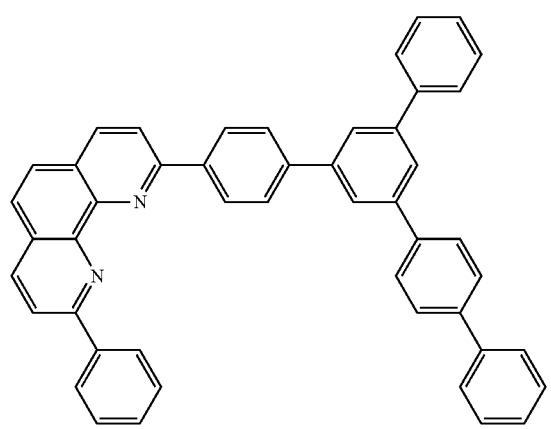
EN-066
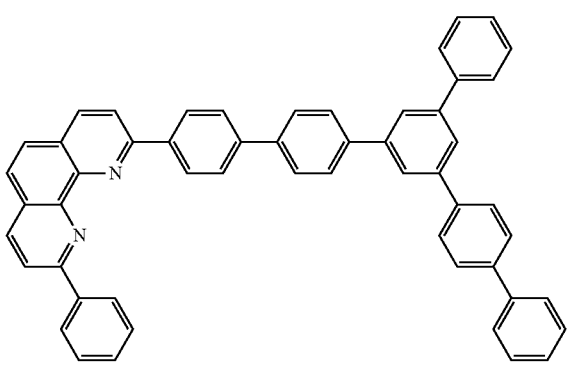

-continued
EN-067
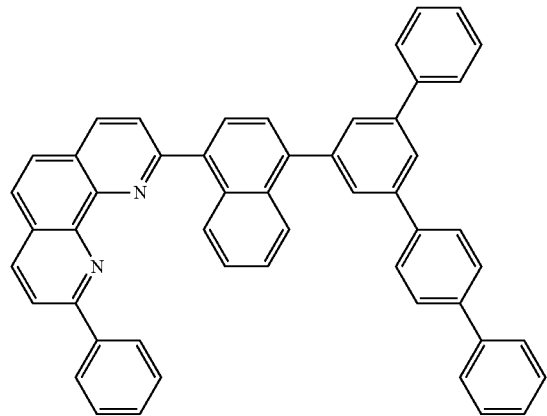
EN-068
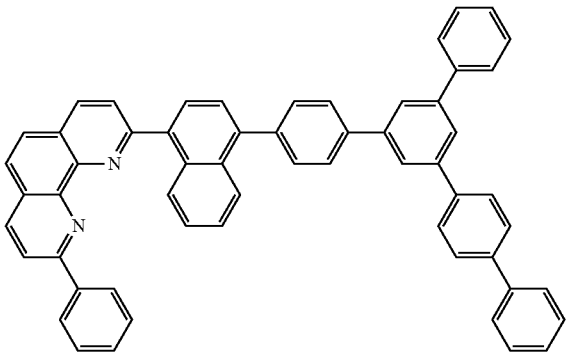
EN-069
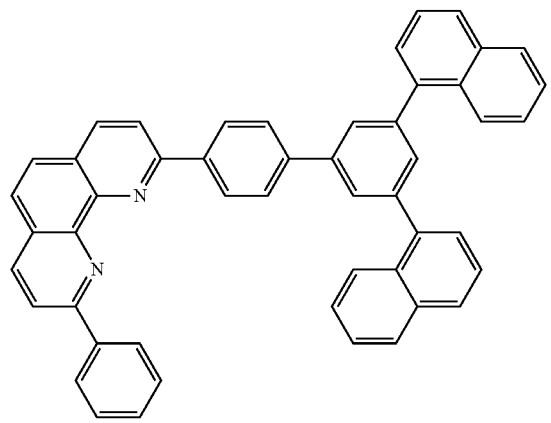
EN-070
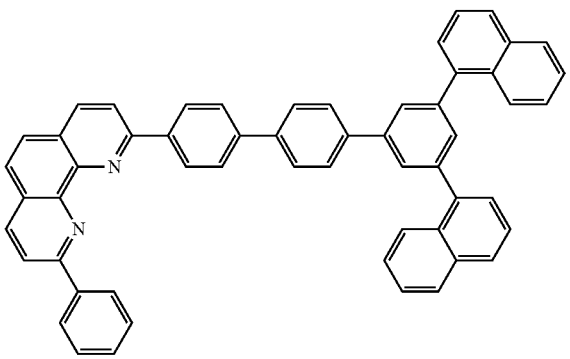
EN-071
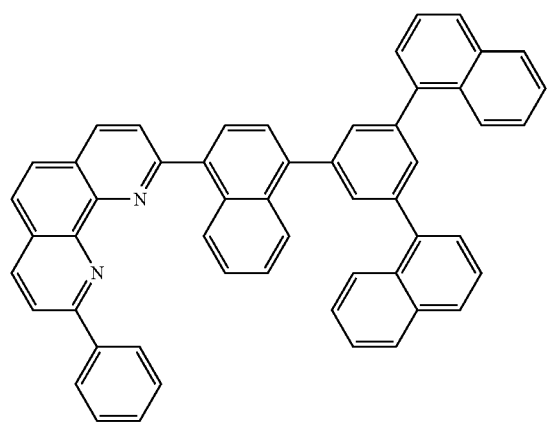
EN-072
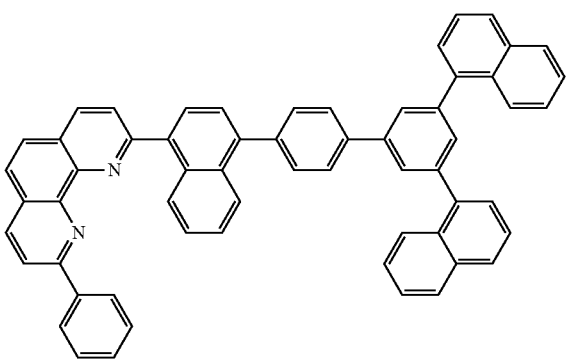

-continued
EN-073
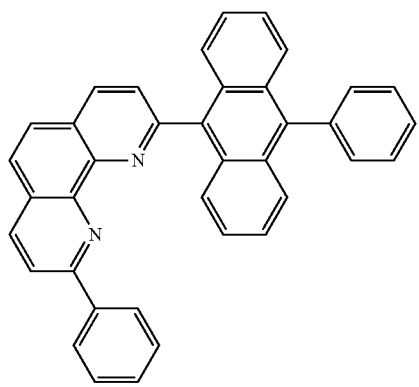
EN-074
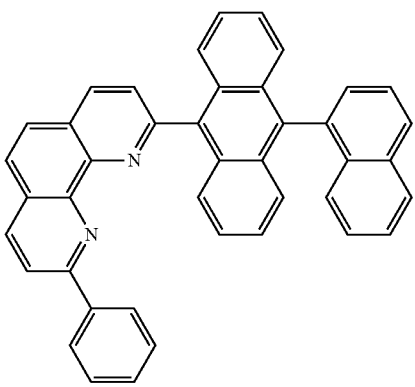
EN-075
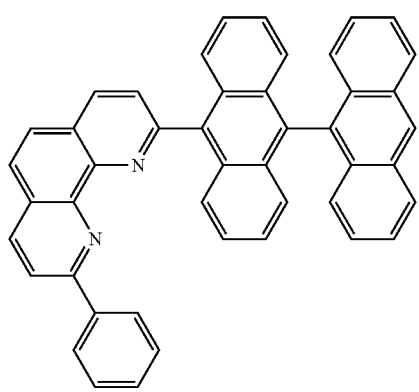
EN-076
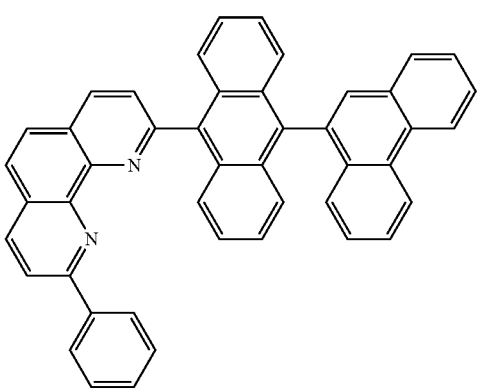
EN-077
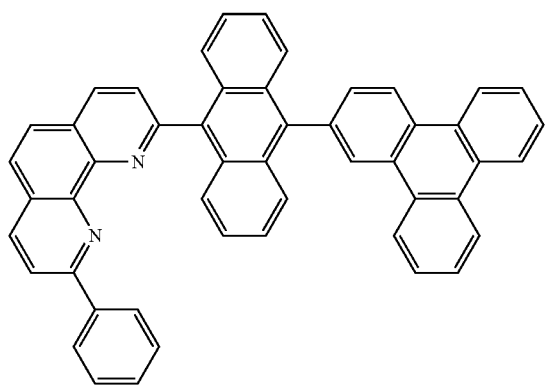
EN-078
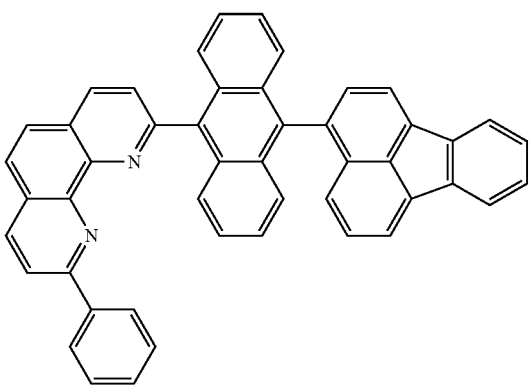
EN-079
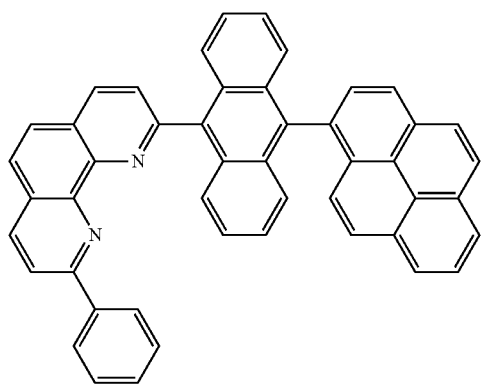
EN-080
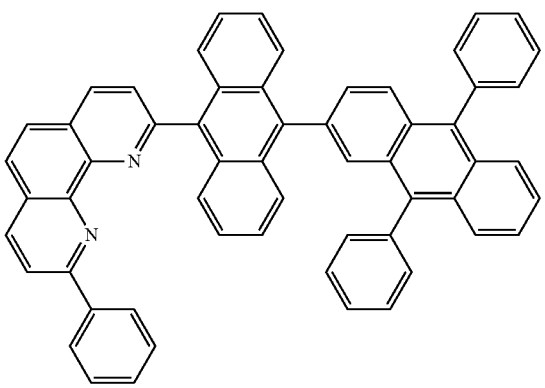

-continued
EN-081
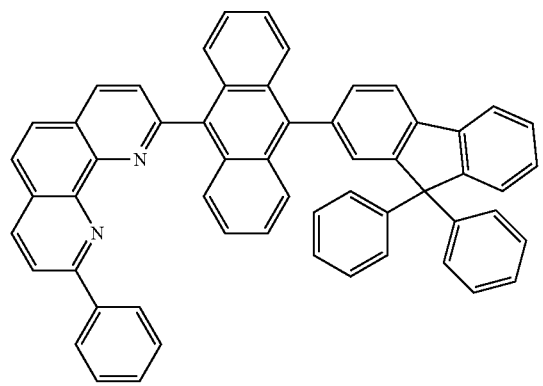
EN-082
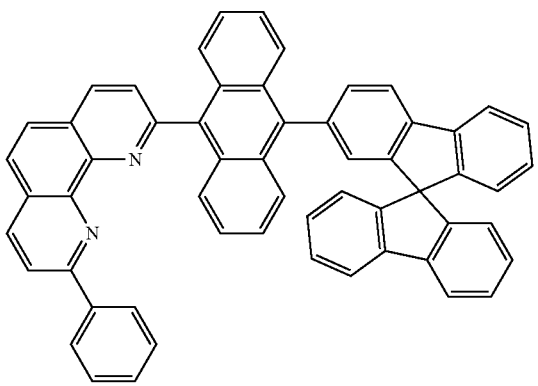
EN-083
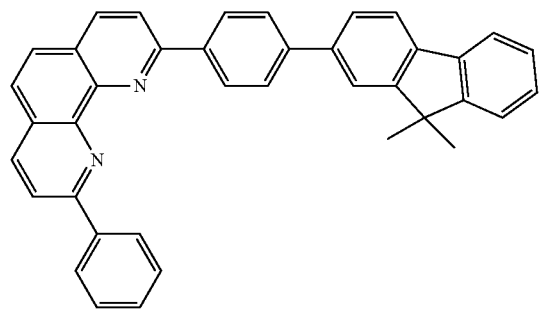
EN-084
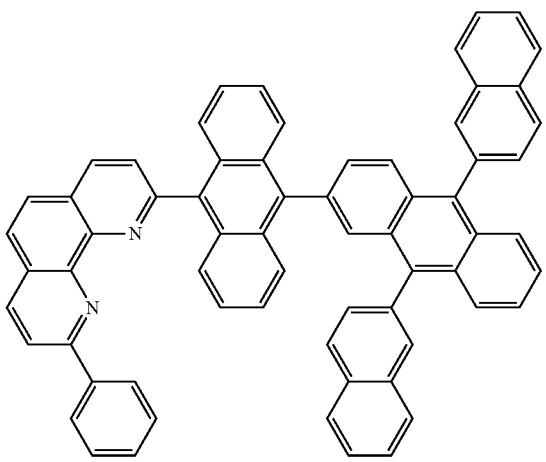
EN-085
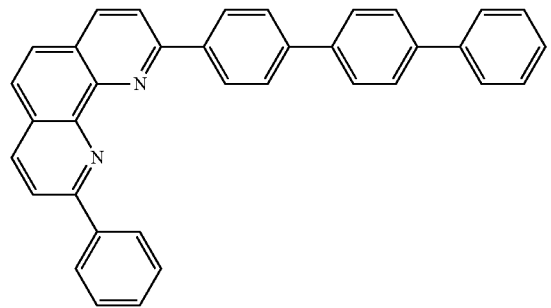
EN-086
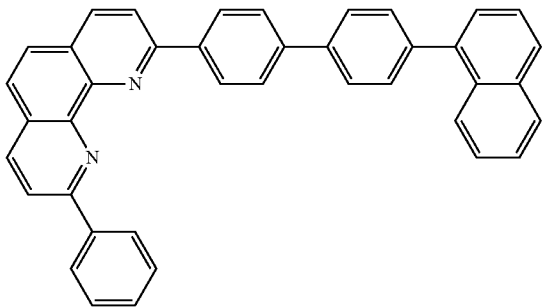
EN-087
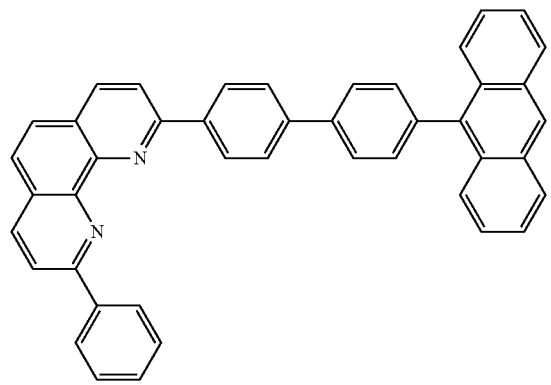
EN-088
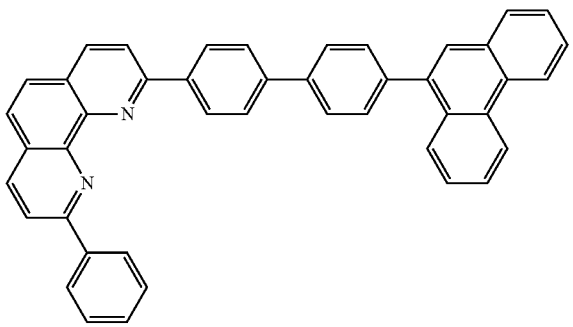

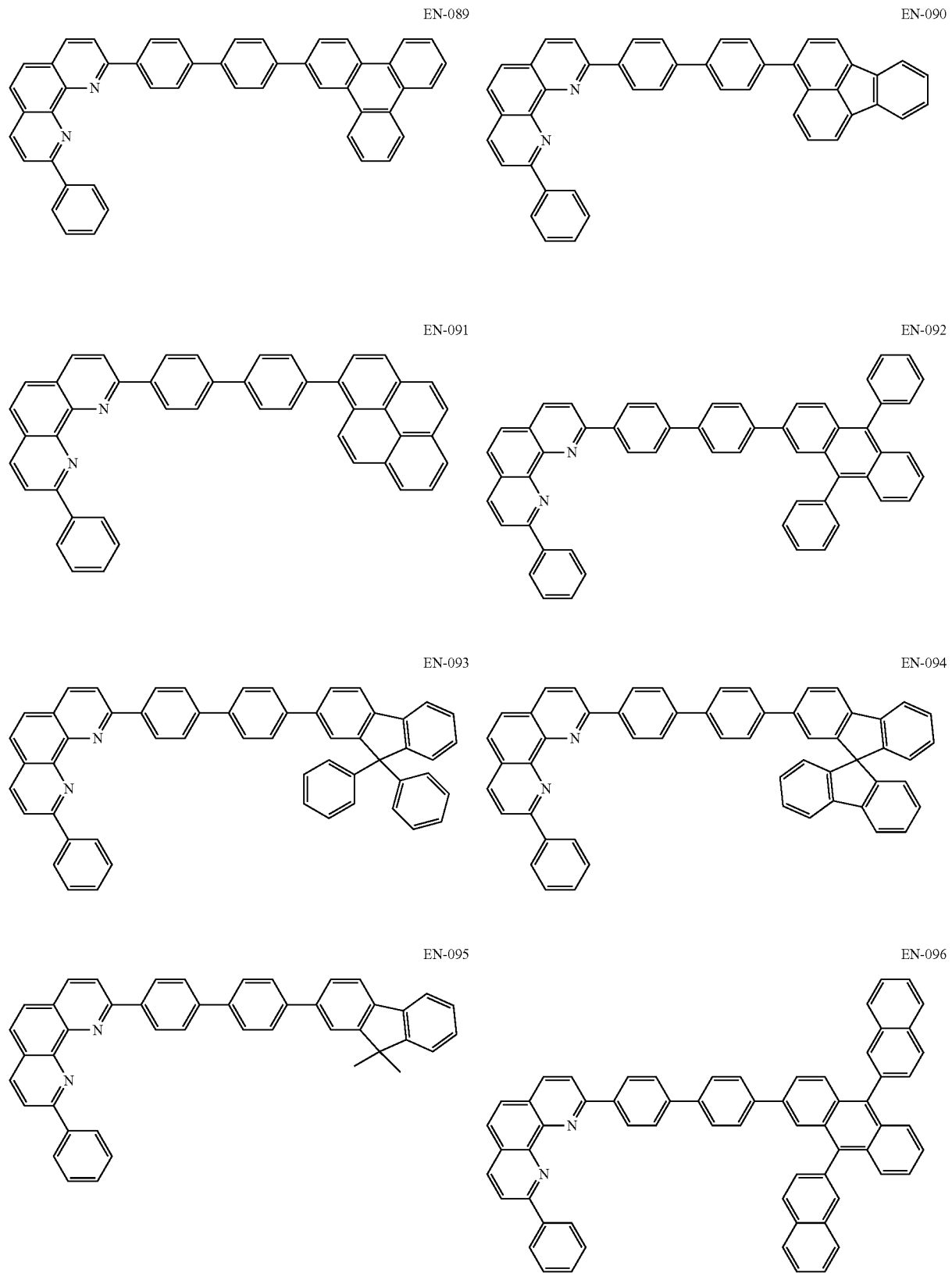

-continued
EN-097
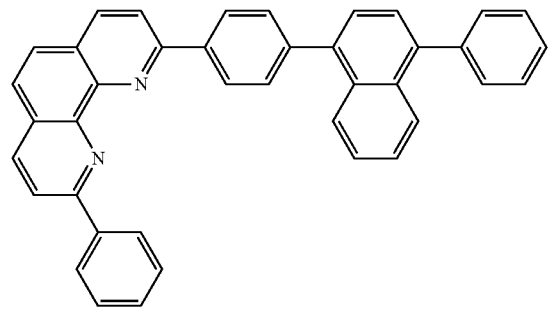
EN-098
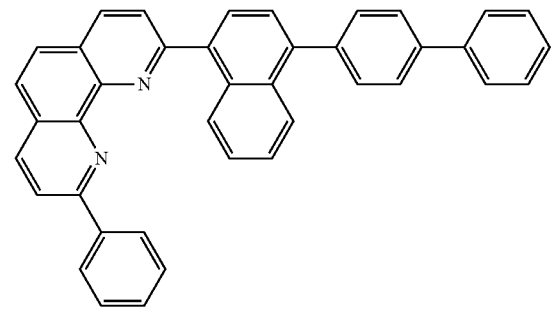
EN-099
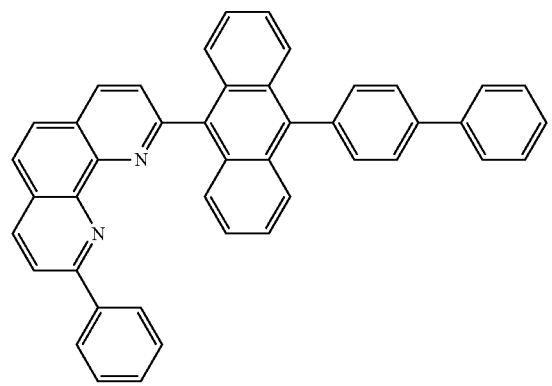
EN-100
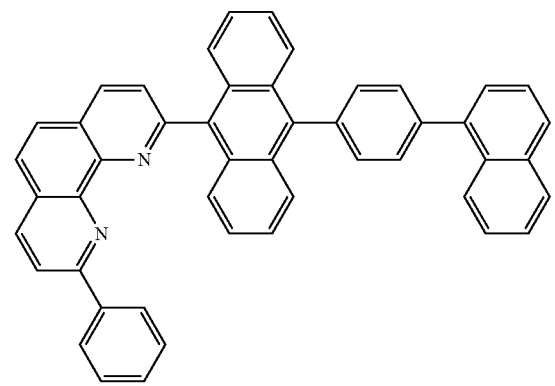
EN-101
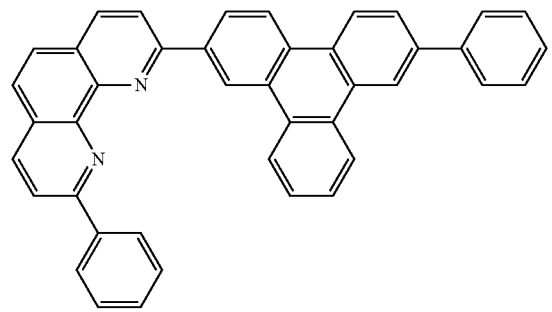
EN-102
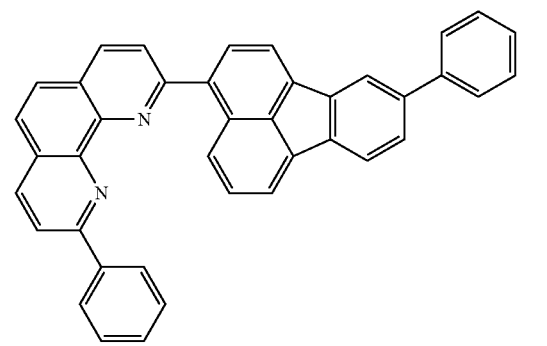
EN-103
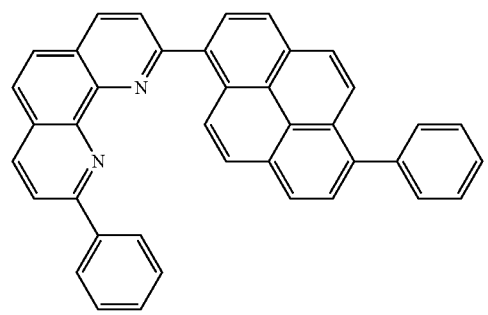
EM-104
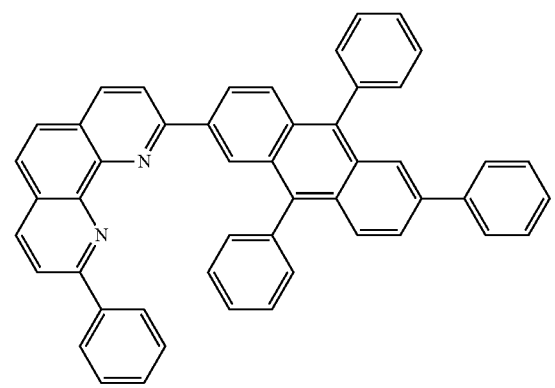

-continued
EN-105
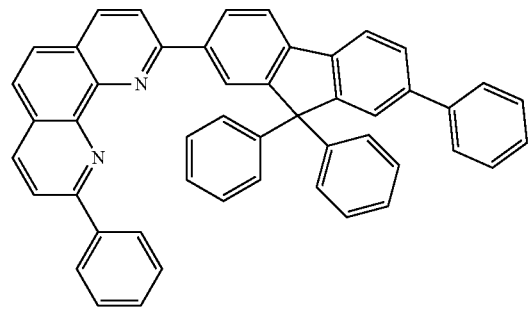
EN-106
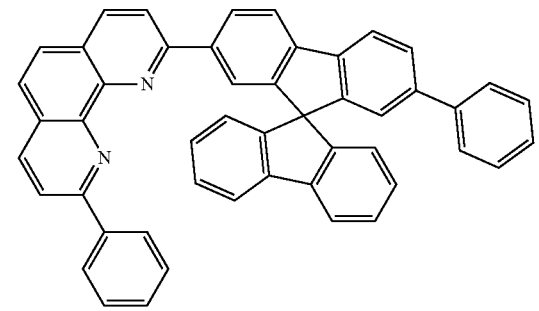
EN-107
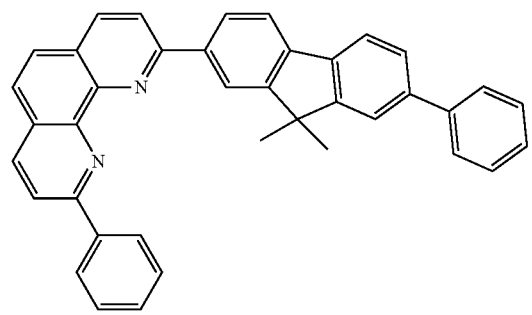
EN-108
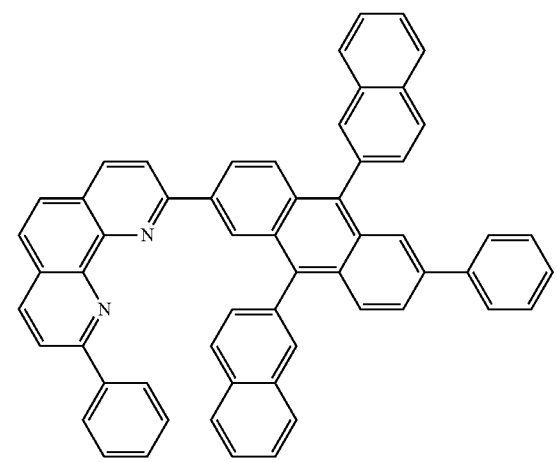
EN-109
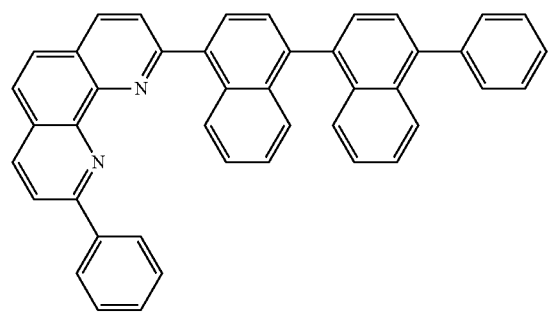
EN-110
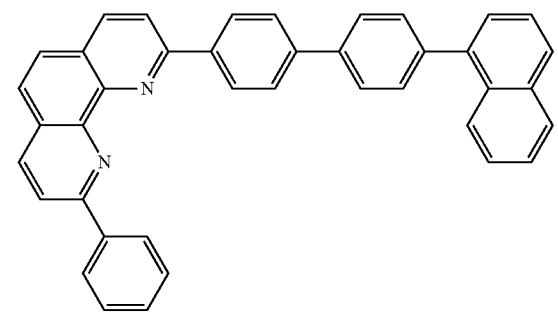
EN-111
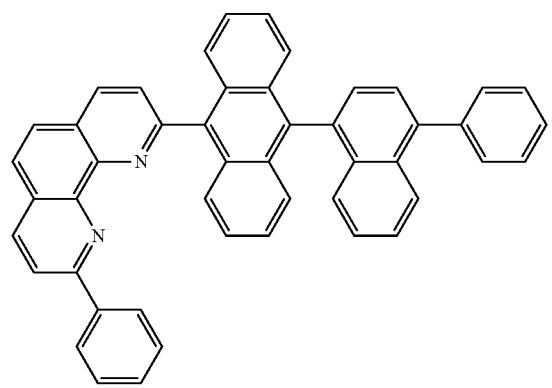
EN-112
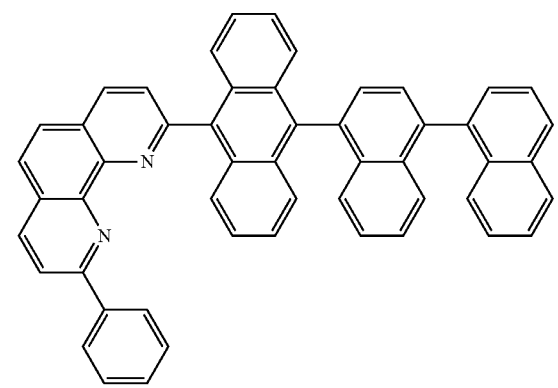

-continued
EN-113
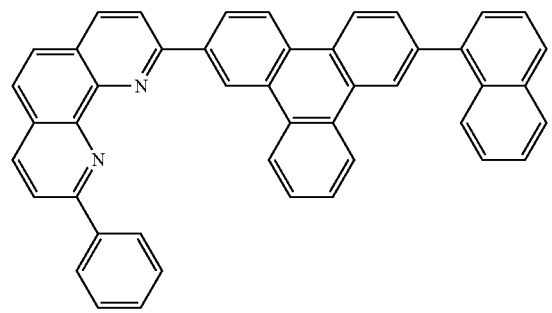
EN-114
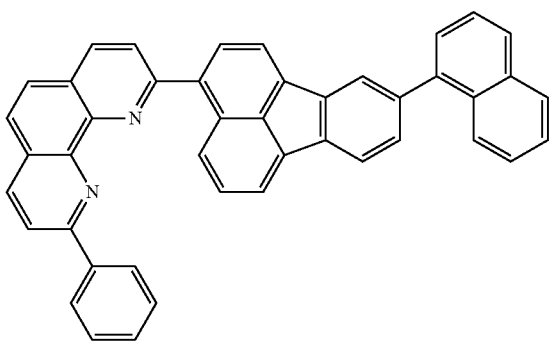
EN-115
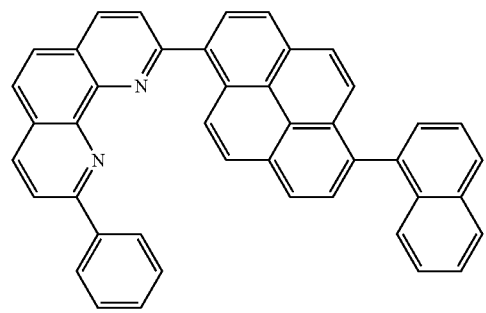
EN-116
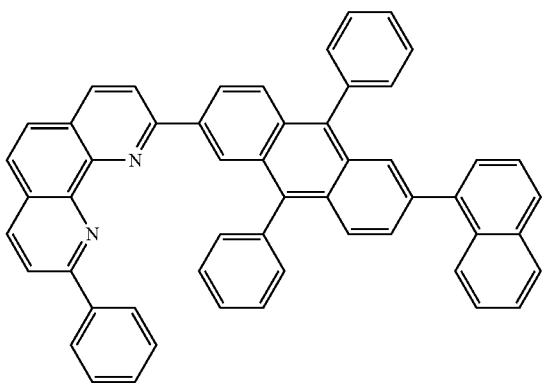
EN-117
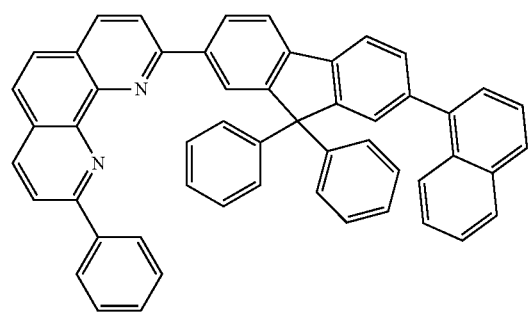
EN-118
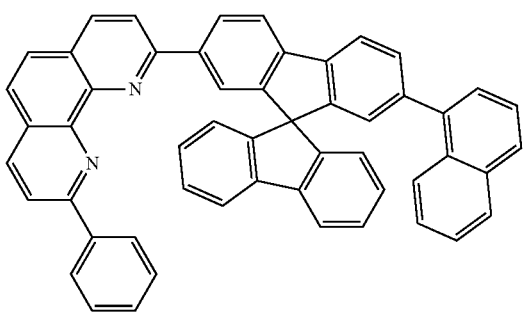
EN-119
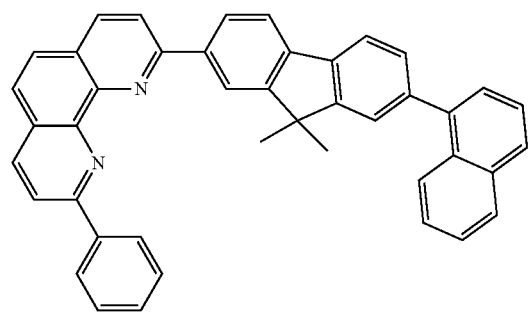
EN-120
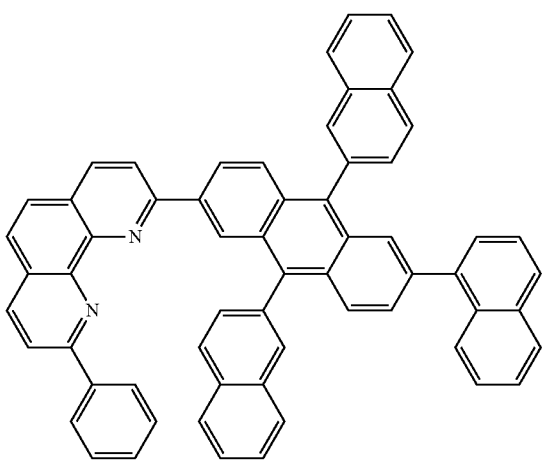

-continued
EN-121
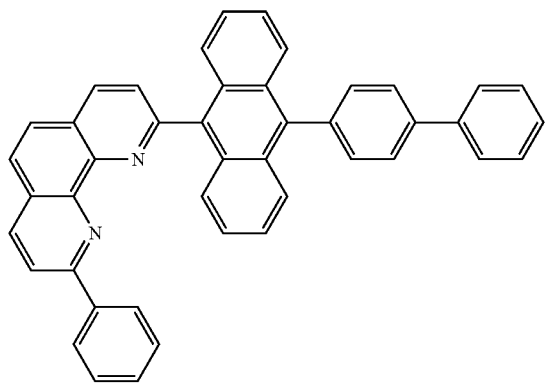
EN-122
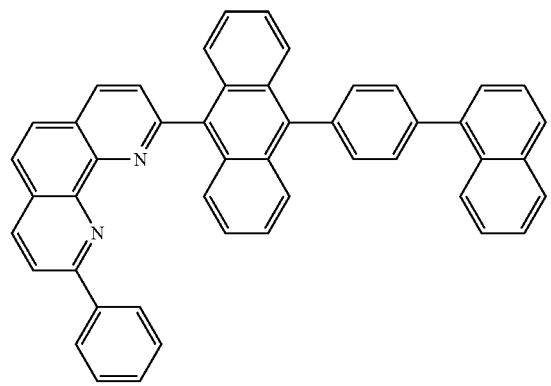
EN-123
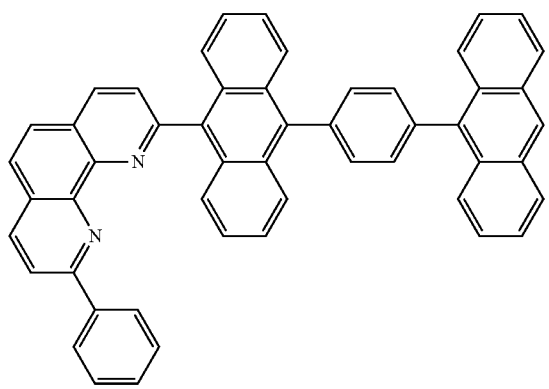
EN-124
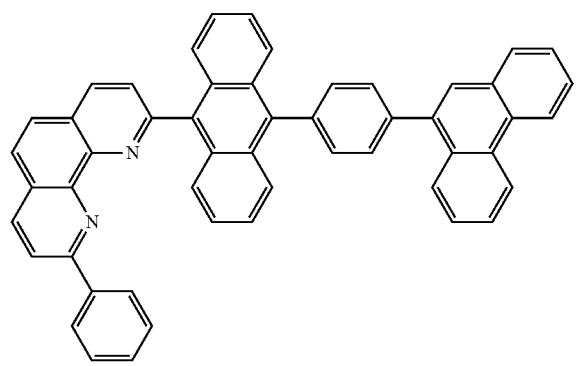
EN-125
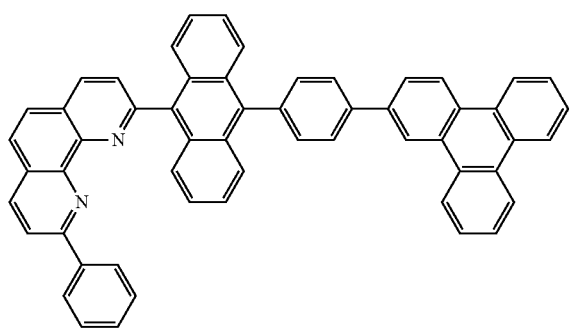
EN-126
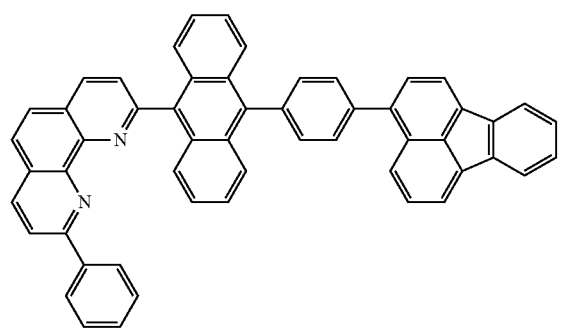
EN-127
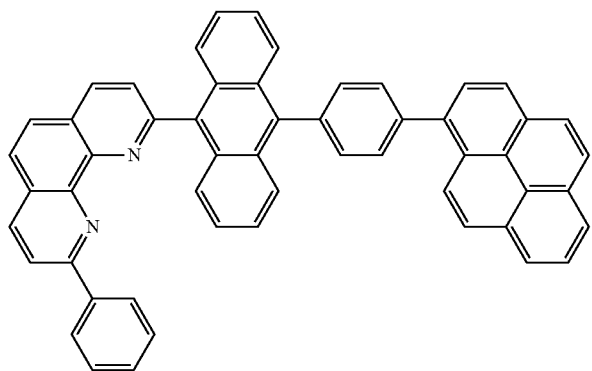
EN-128
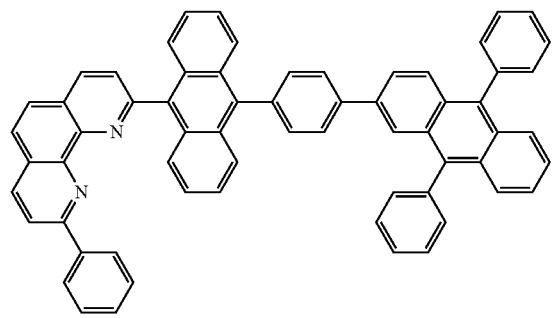

-continued
EN-129
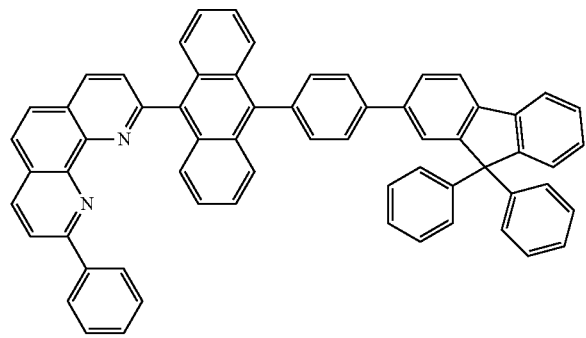
EN-130
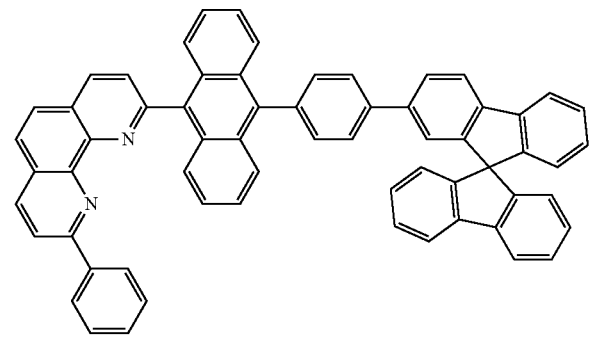
EN-131
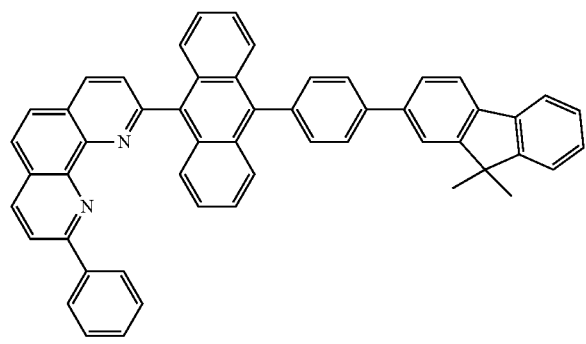
EN-132
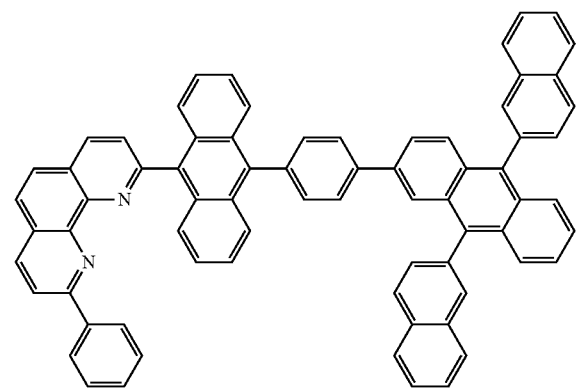
EN-133
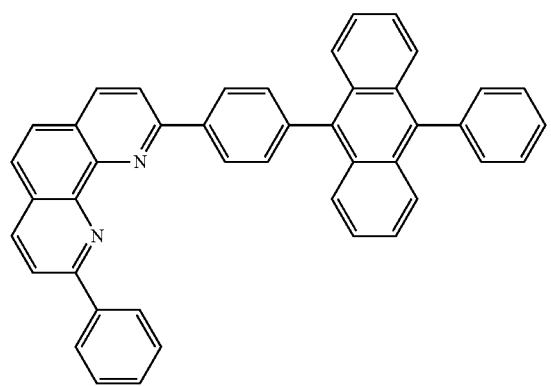
EN-135
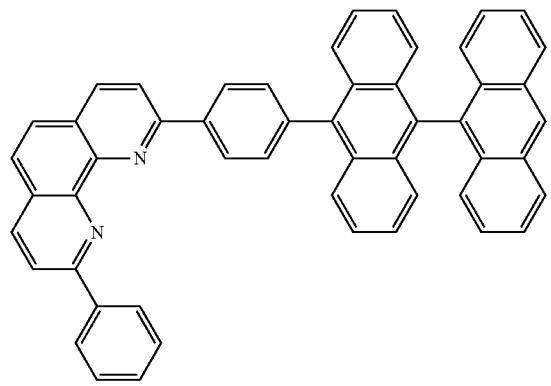
EN-136
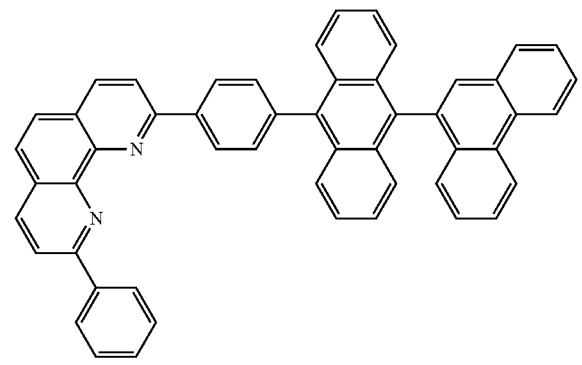

-continued
EN-137
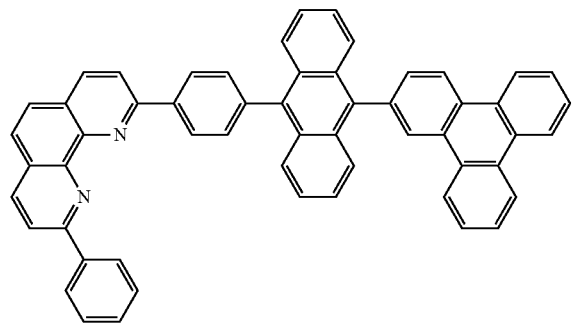
EN-138
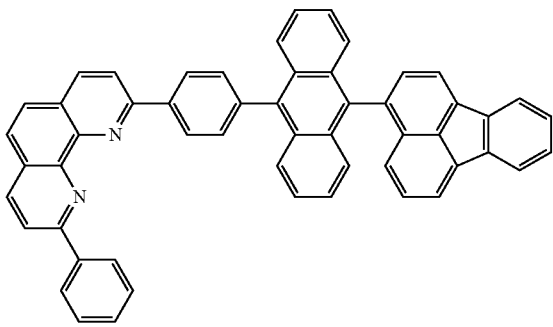
EN-139
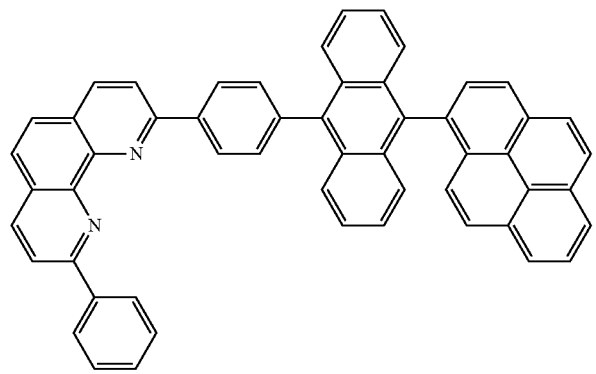
EN-140
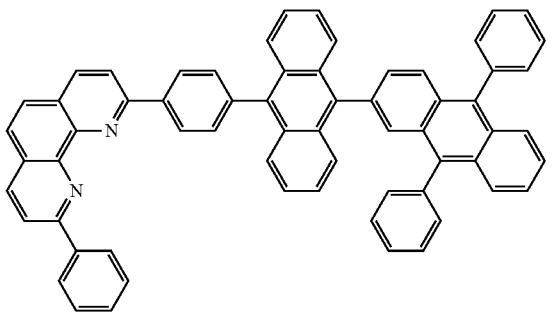
EN-141
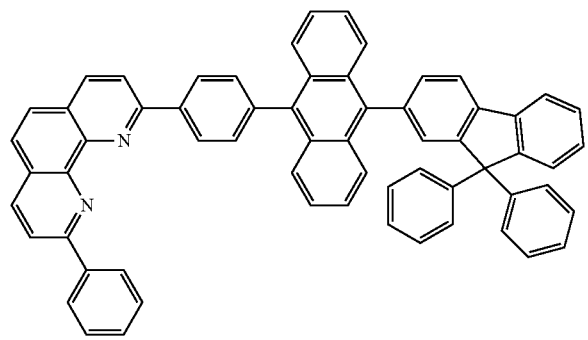
EN-142
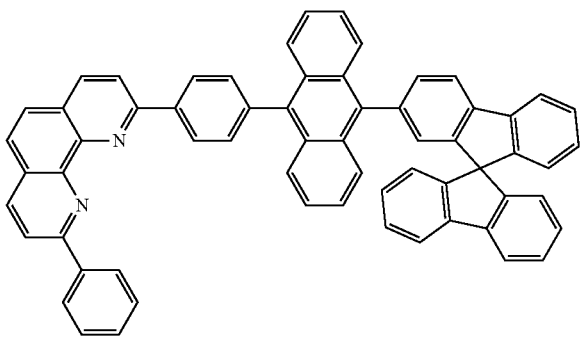
EN-143
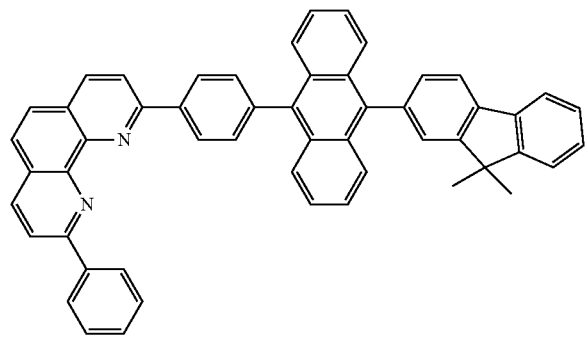
EN-144
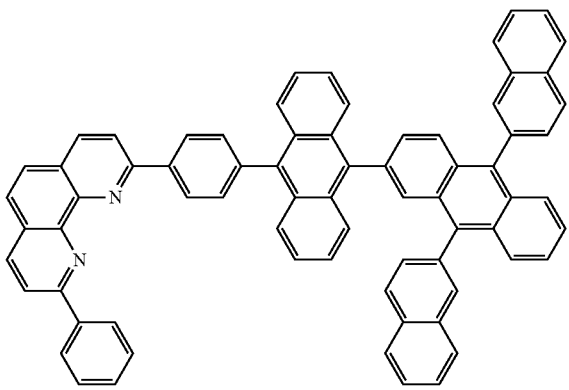

-continued
EN-145
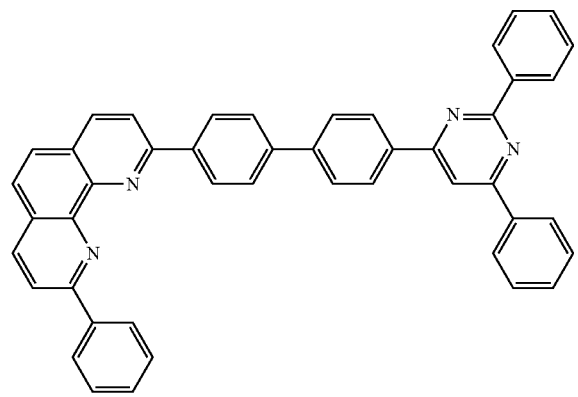
EN-146
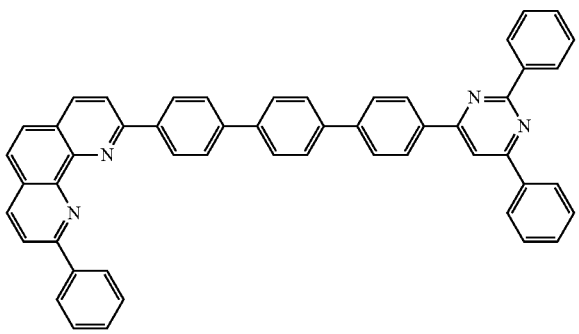
EN-147
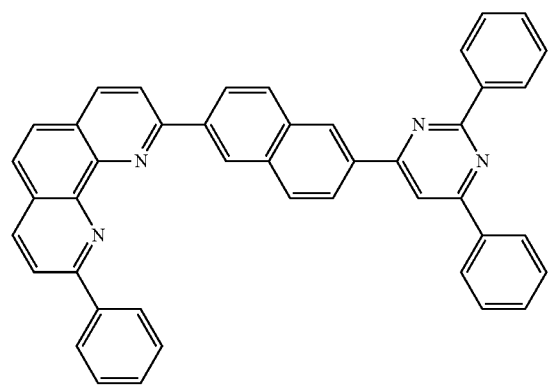
EN-148
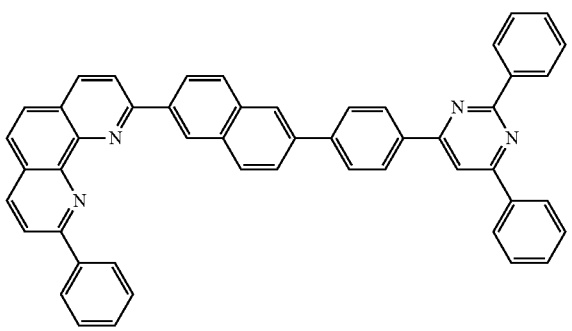
EN-149
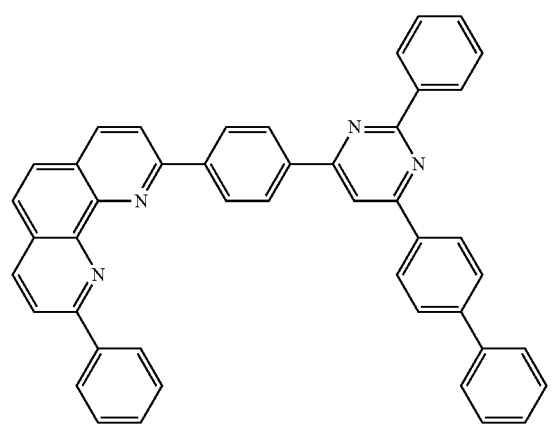
EN-150
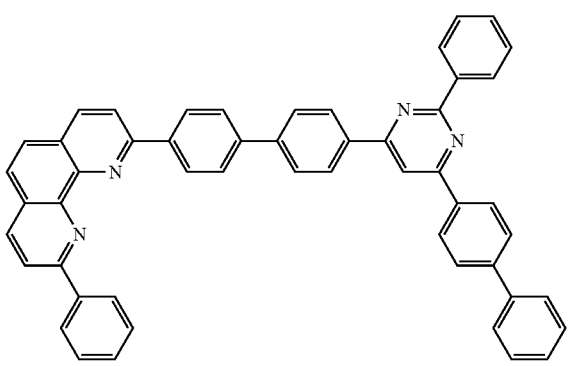

EN-151
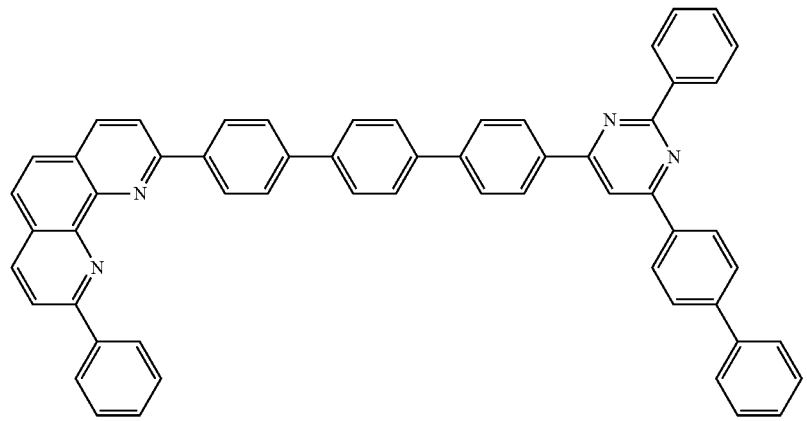
EN-152 1N-153
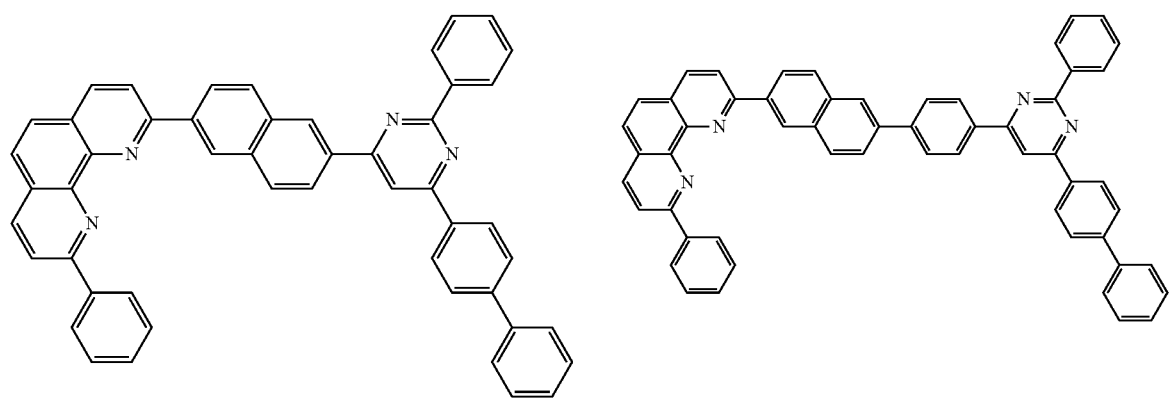
EN-154 EN-155
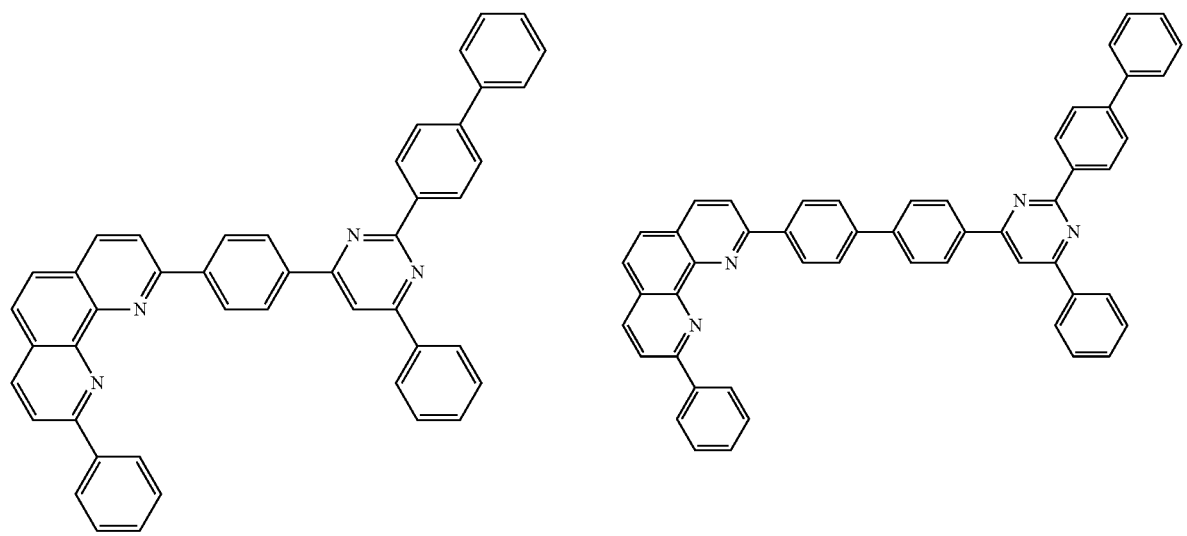

-continued
EN-156
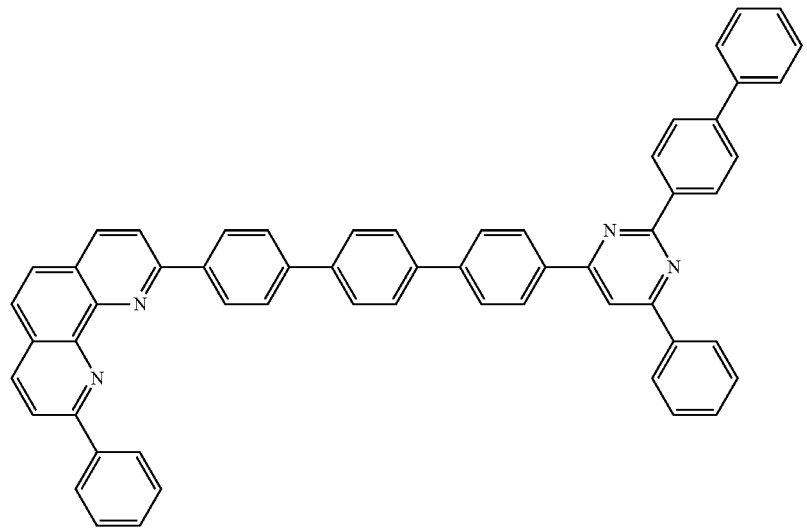
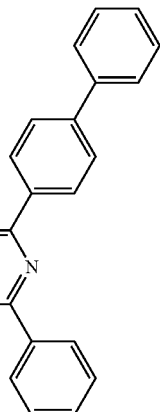
EN-157
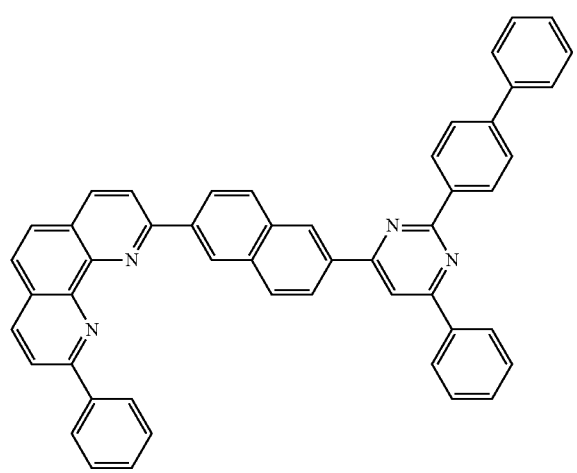
EN-158
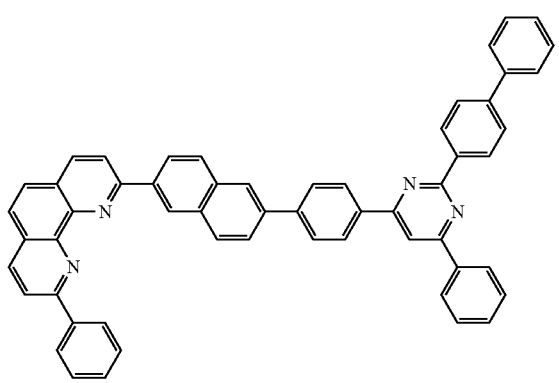
EN-159
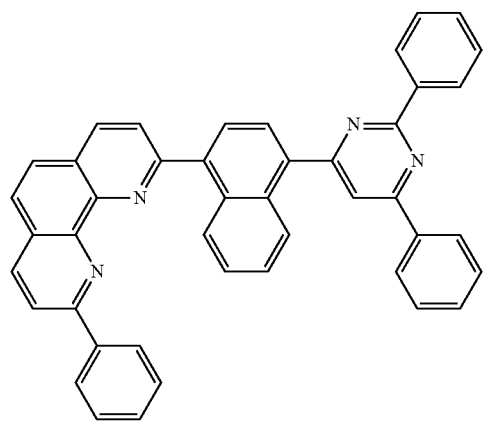
EN-160
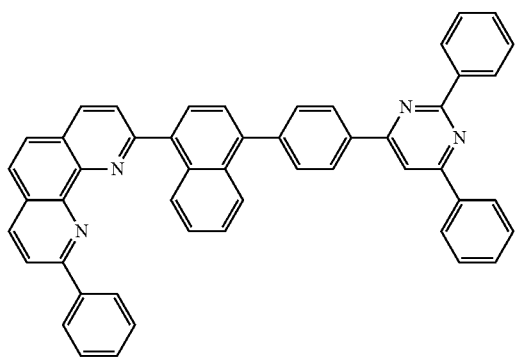

-continued
EN-161
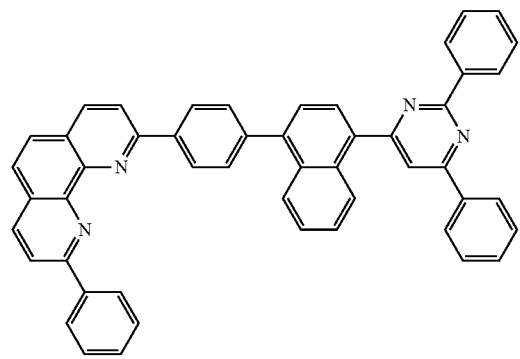
EN-162
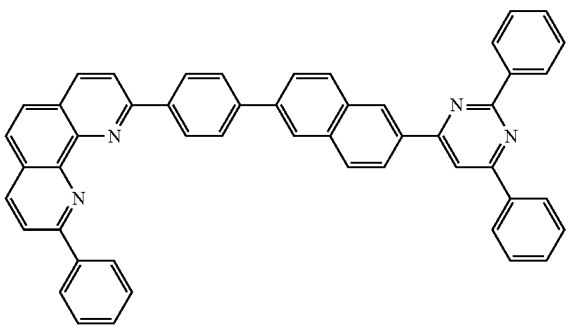
EN-163
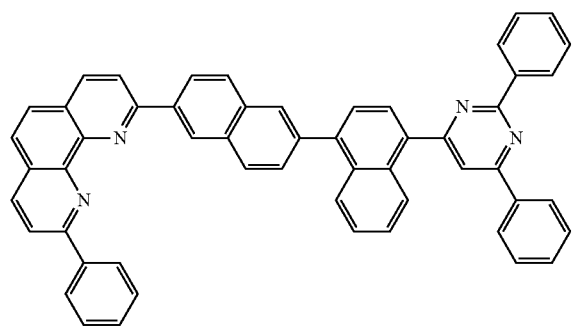
EN-164
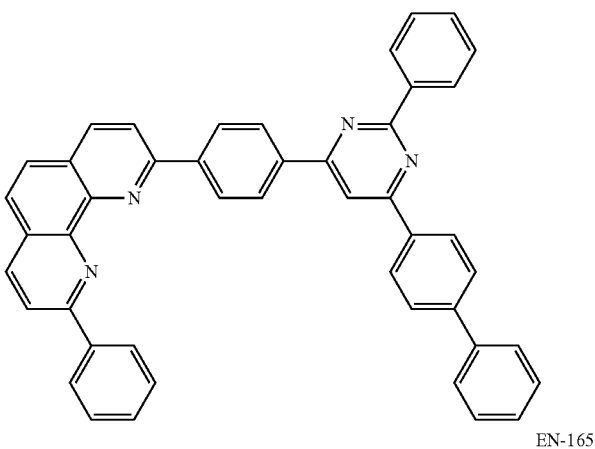
EN-165
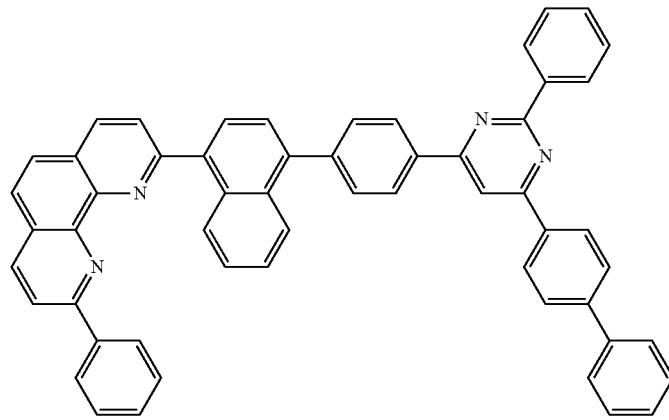
EN-166
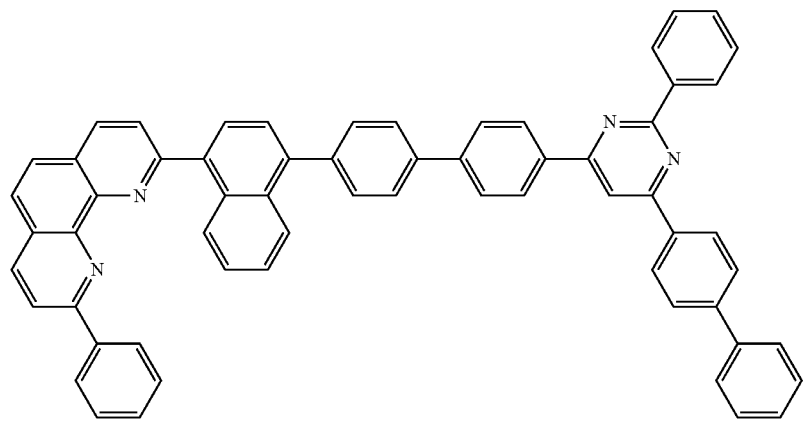

-continued
EN-167
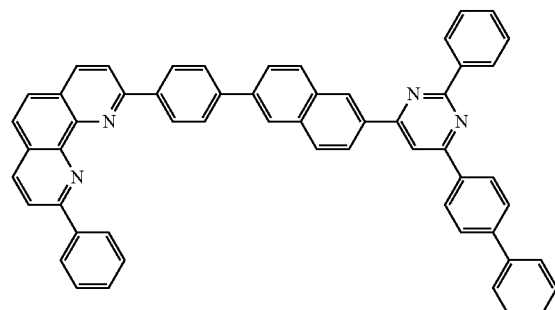
EN-168
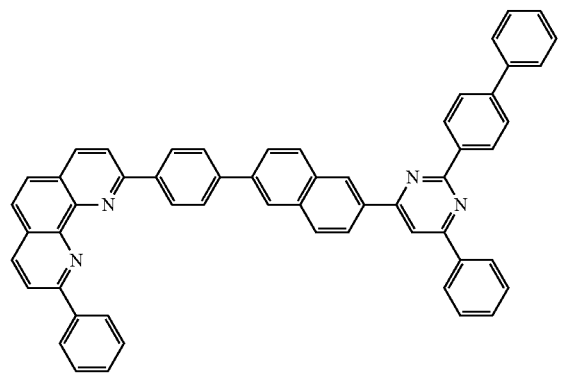
EN-169
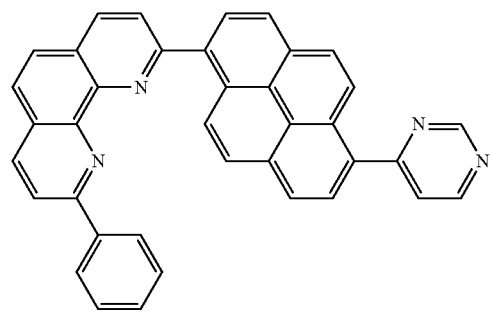
EN-170
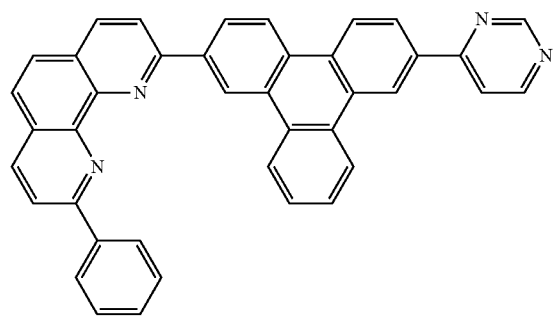
EN-171
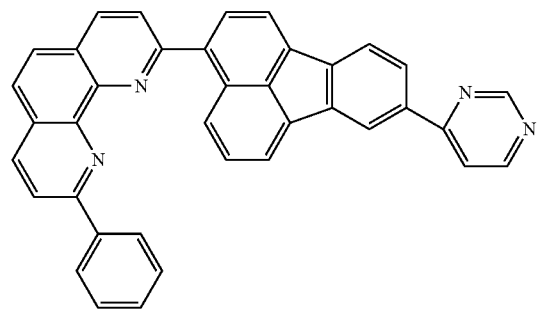
EN-172
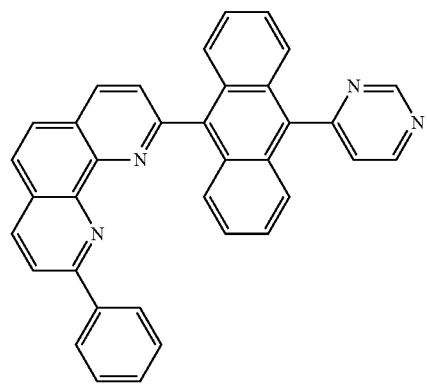
EN-173
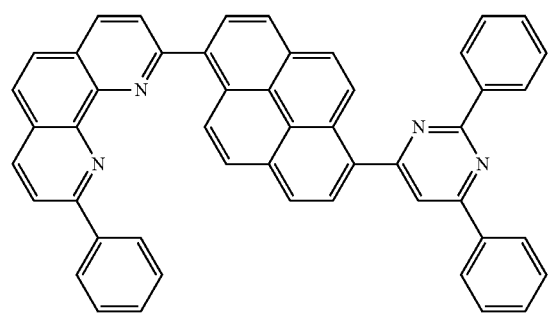
EN-174
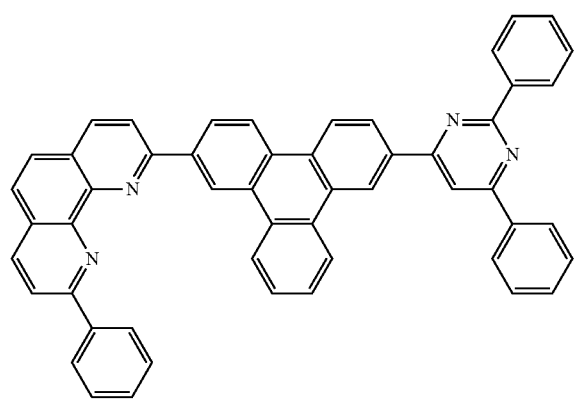

EN-175
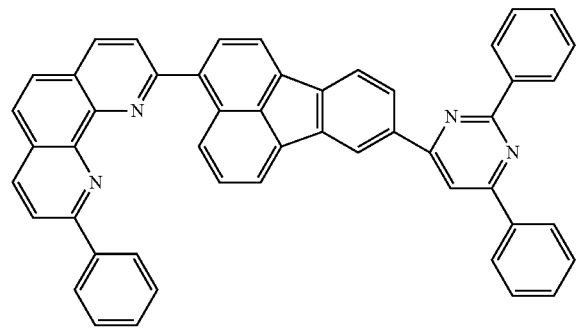
EN-176
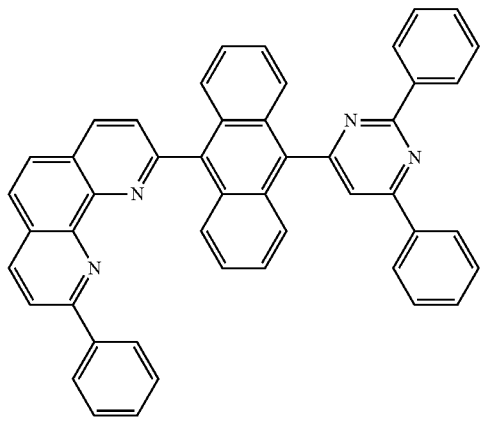
EN-177
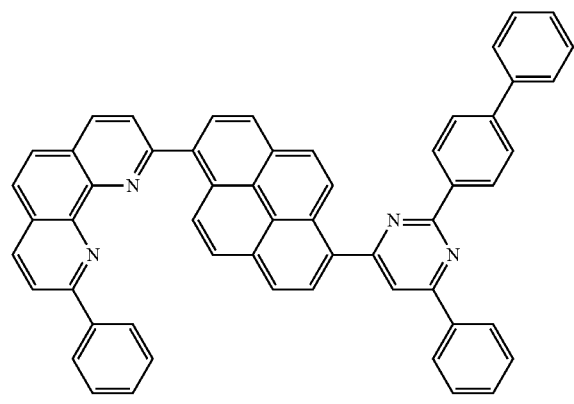
EN-178
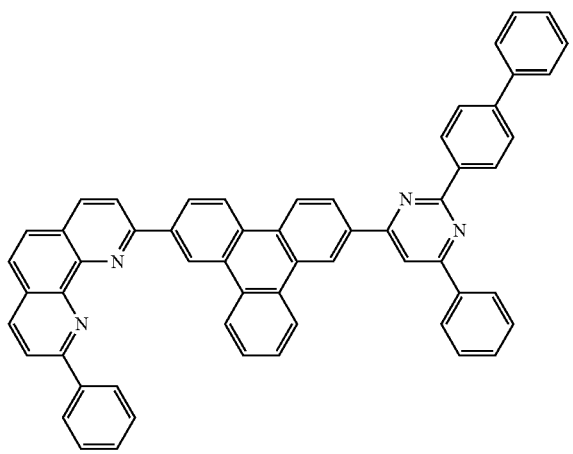
EN-179
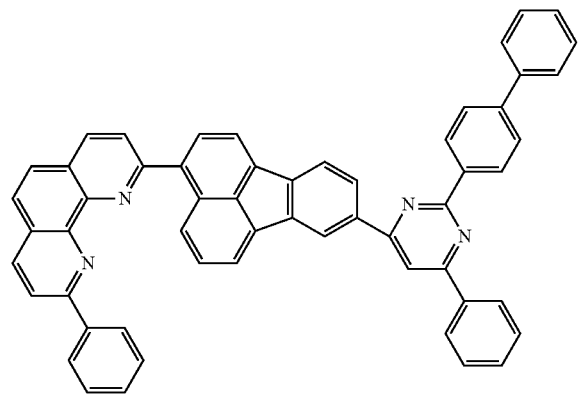
EN-180
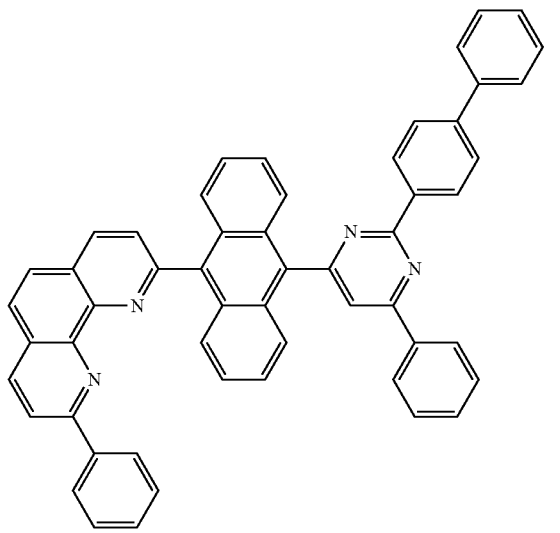

-continued
EN-181
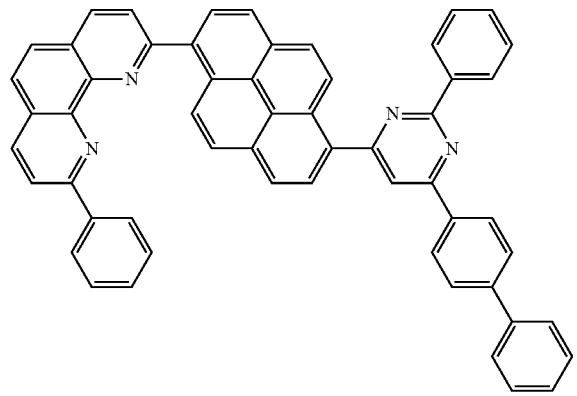
EN-182
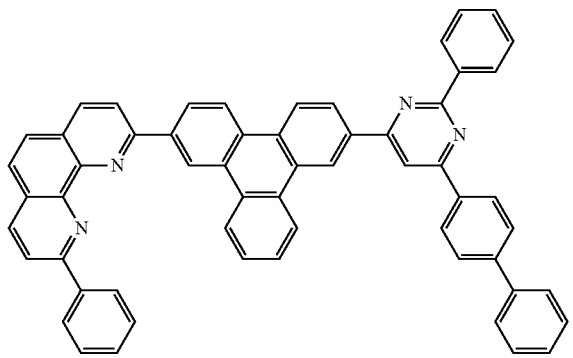
EN-183
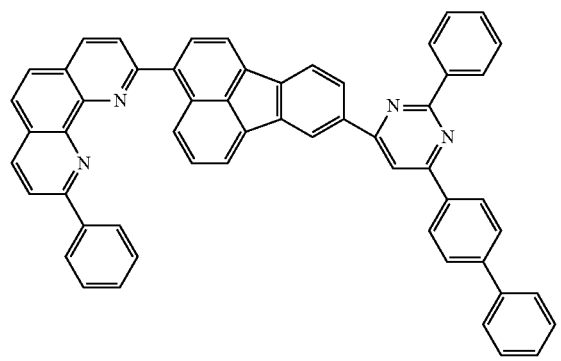
EN-184
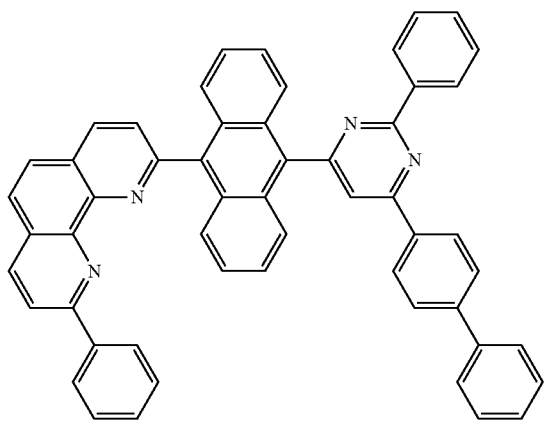
EN-185
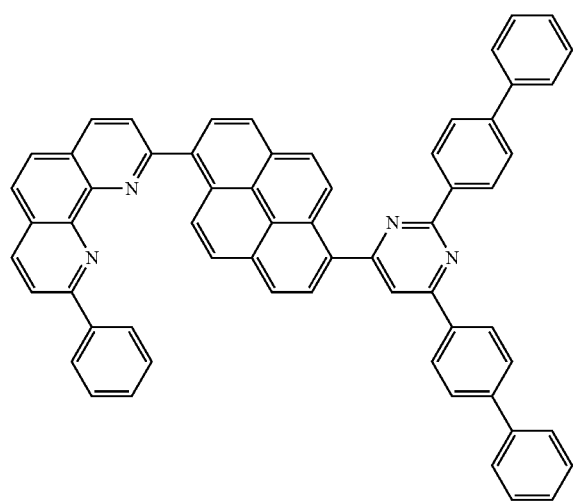
EN-186
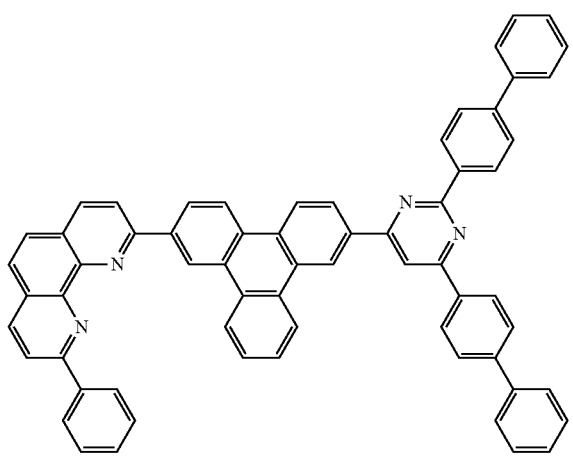

-continued
EN-187
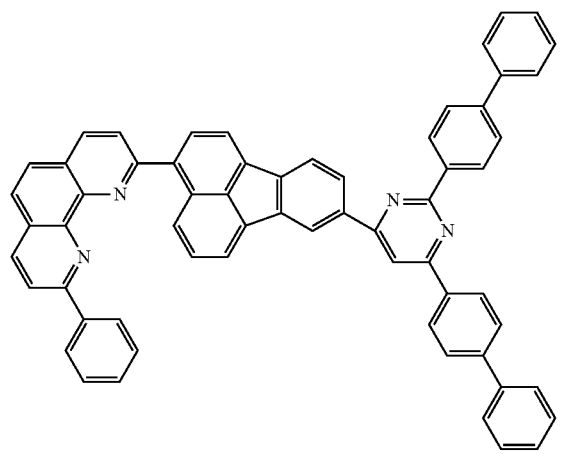
EN-188
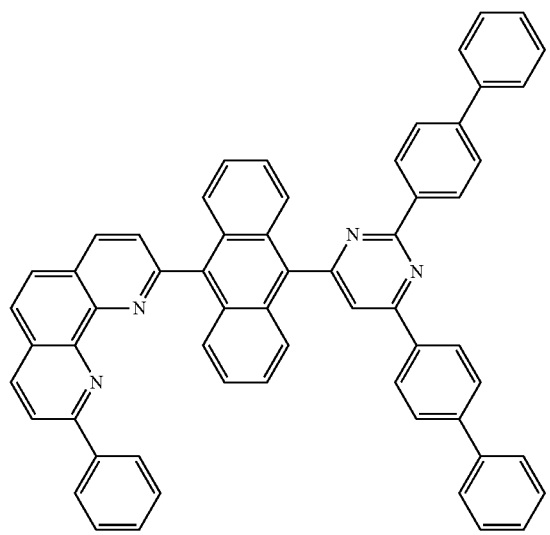
EN-189
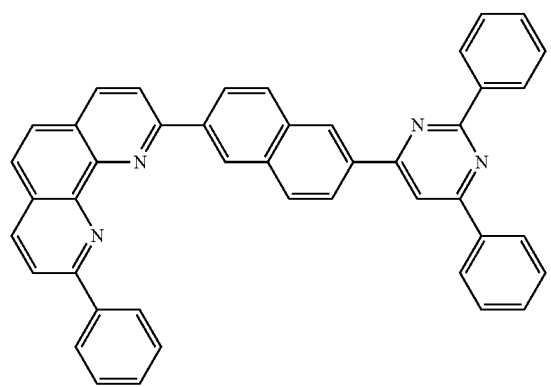
EN-190
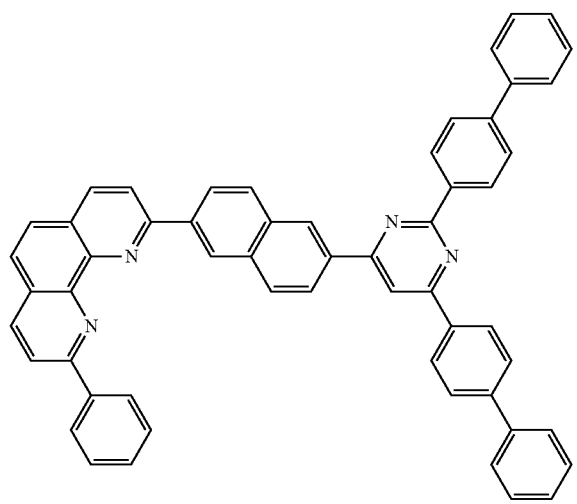
EN-191
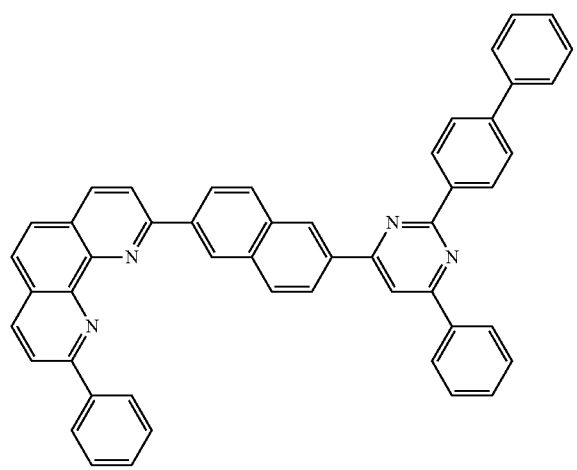
EN-192
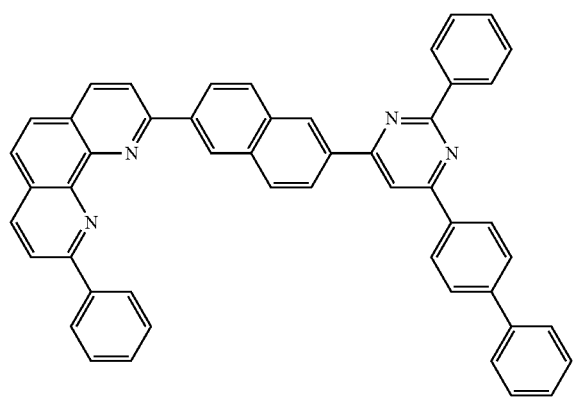

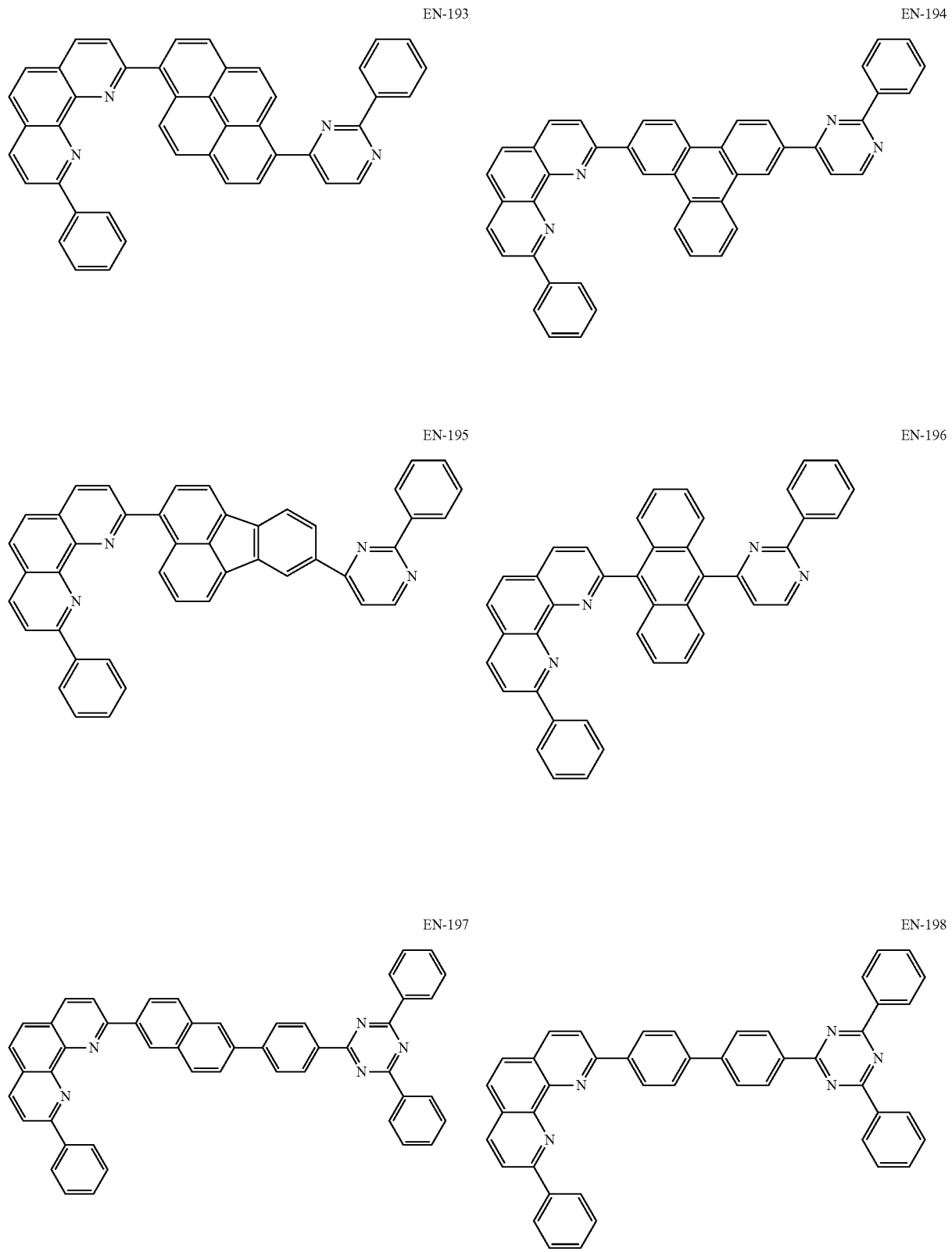

EN-199
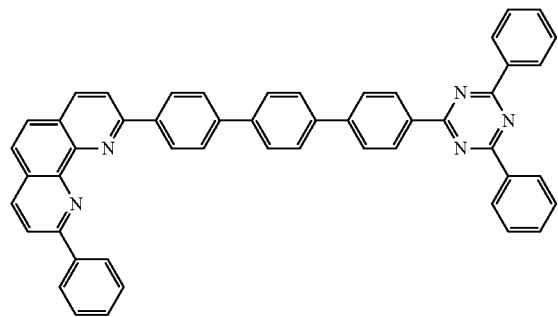
EN-200
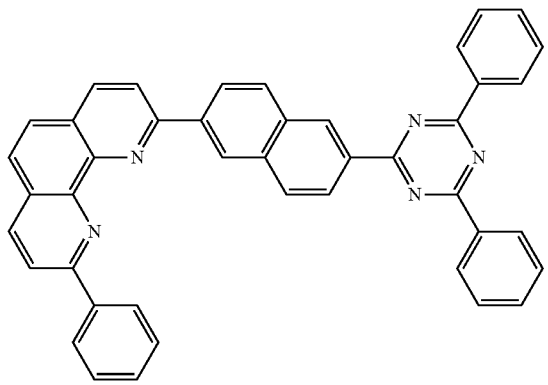
EN-201
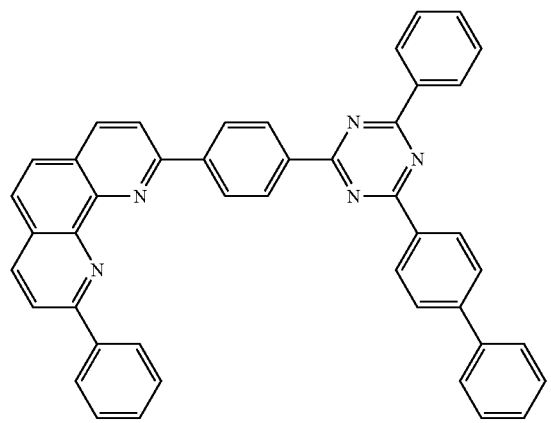
EN-202
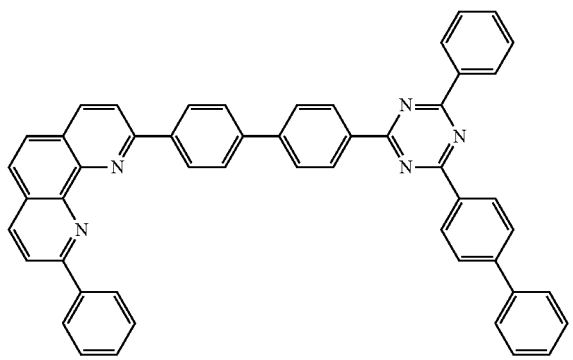
EN-203
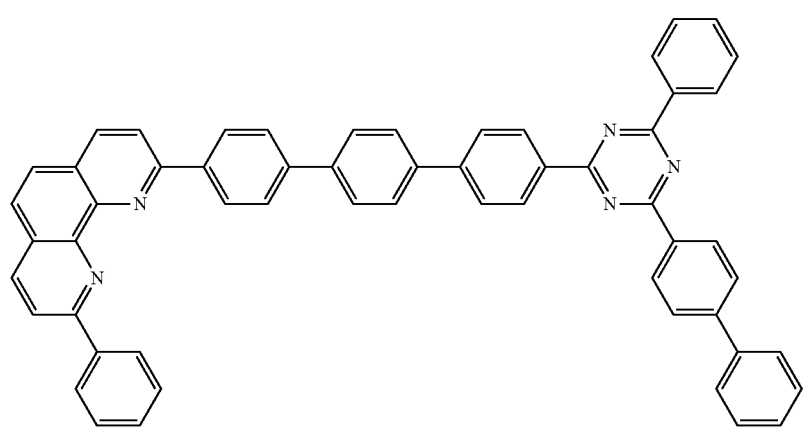

-continued
EN-204
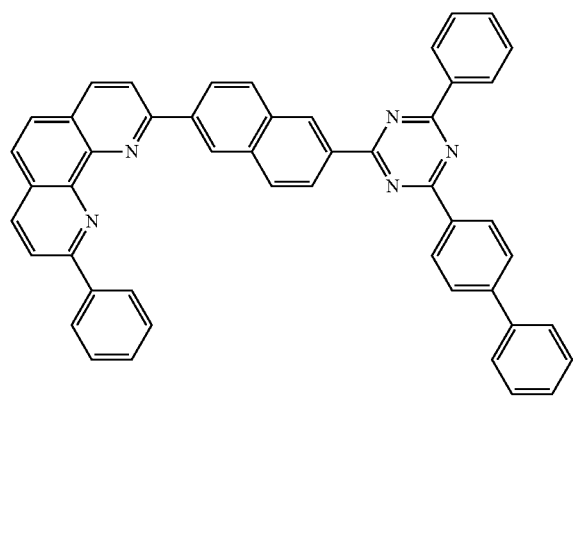
EN-205
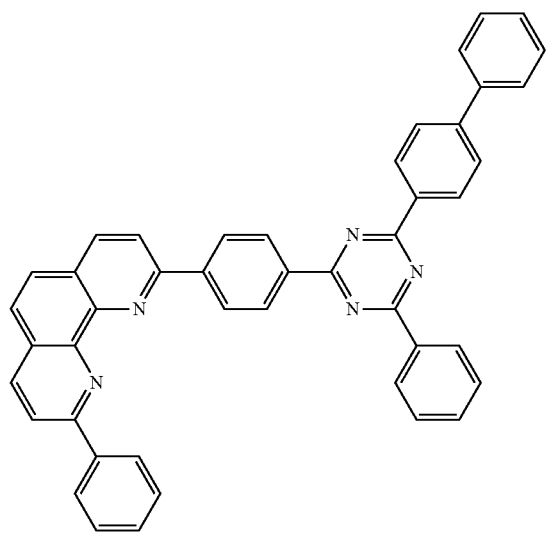
EN-206
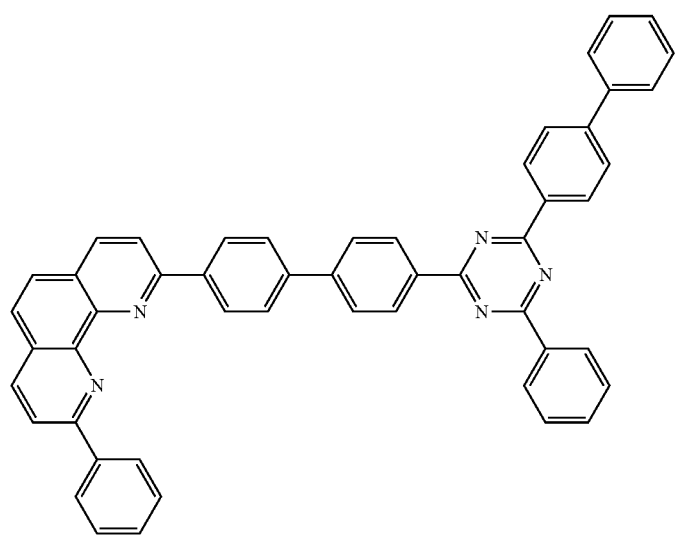
EN-207
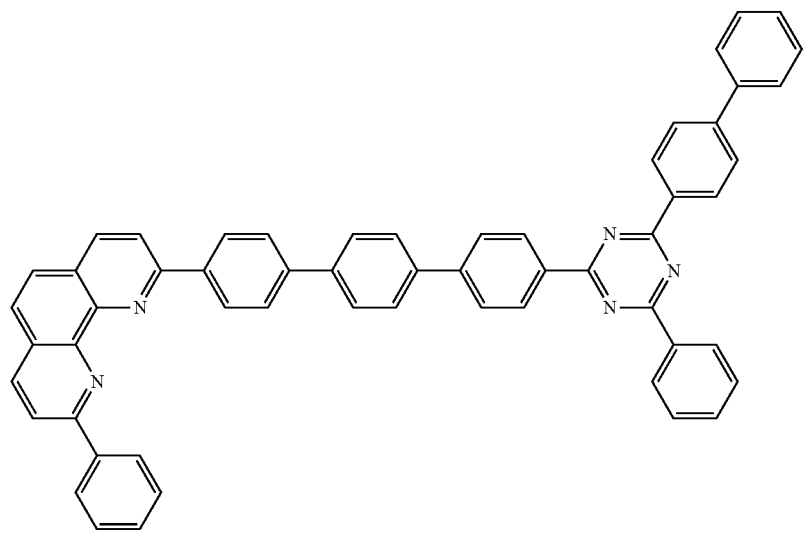

-continued
EN-208
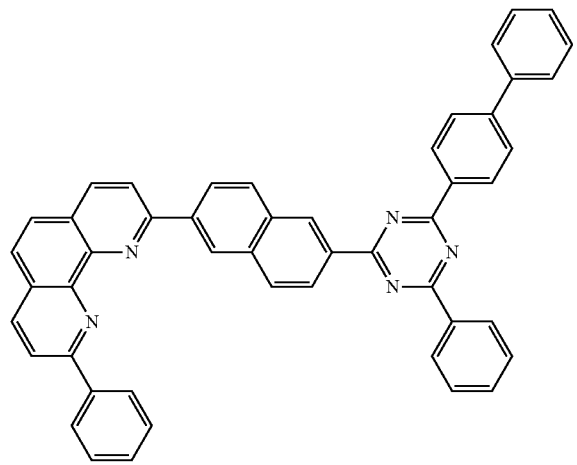
EN-209
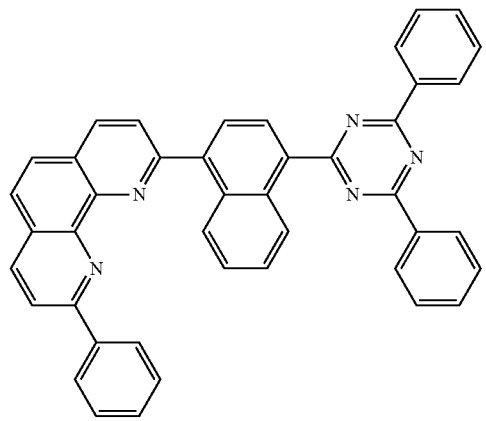
EN-210
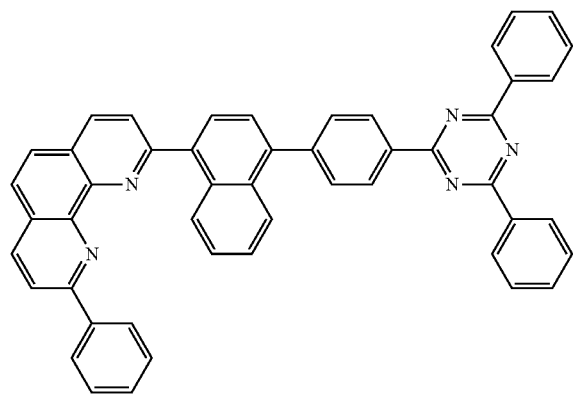
EN-211
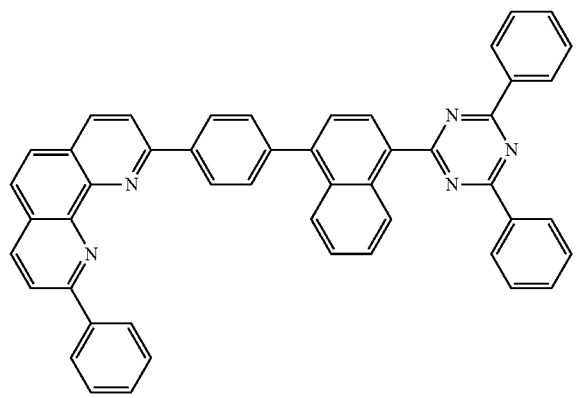
EN-212
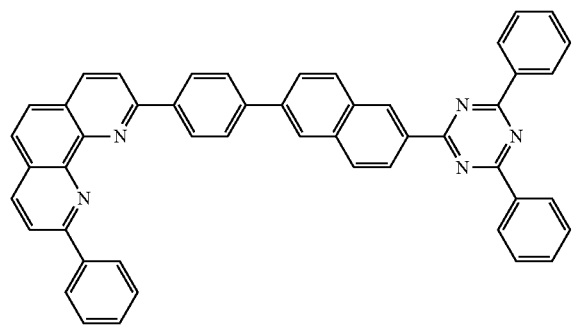
EN-213
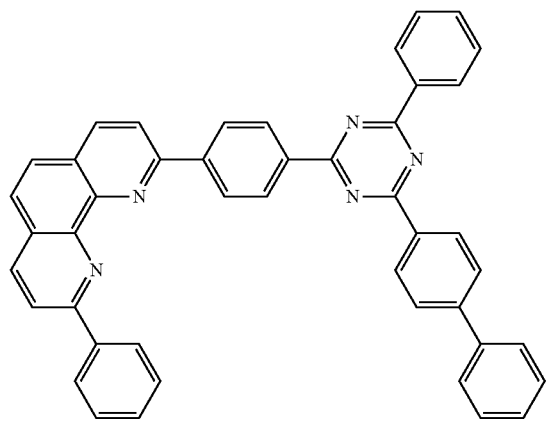

EN-214
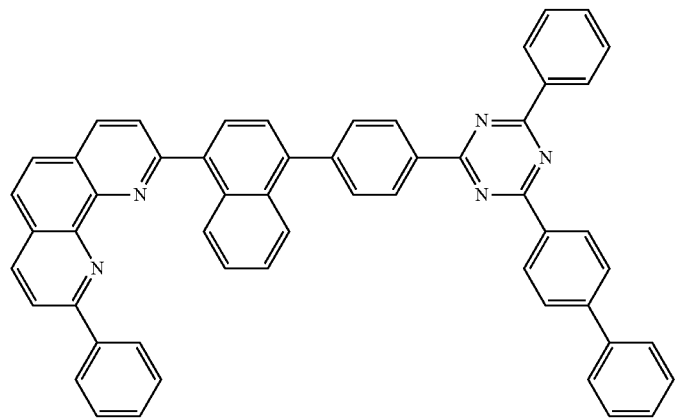
EN-215
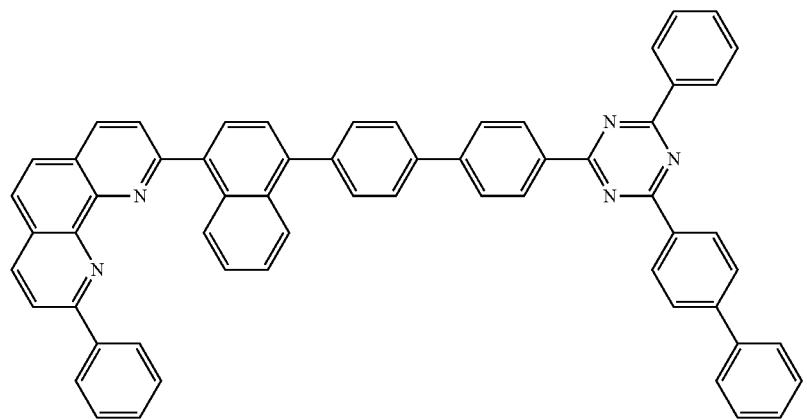
EN-216
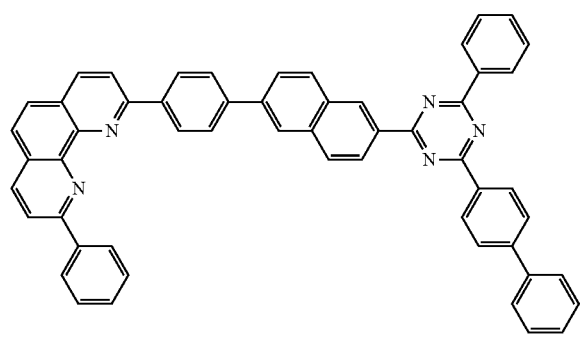
EN-217
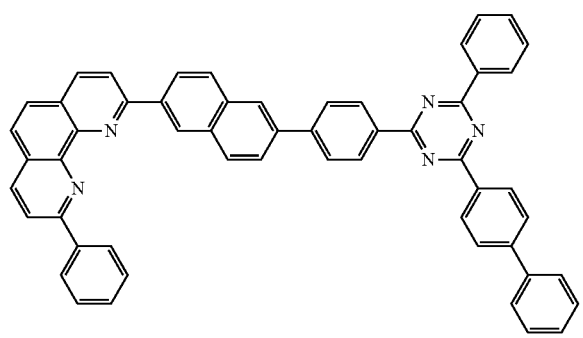
EN-218
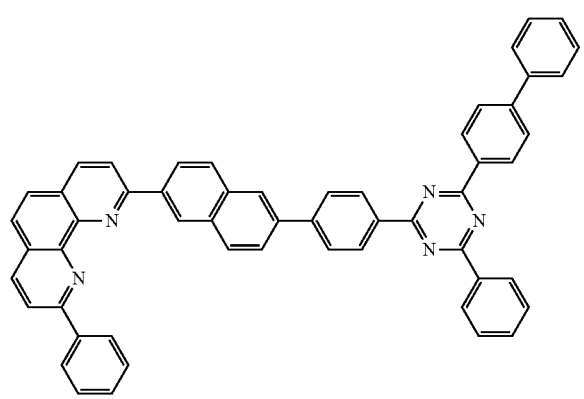
EN-219
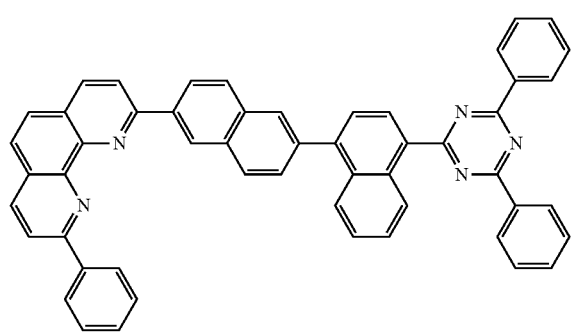

-continued
EN-220
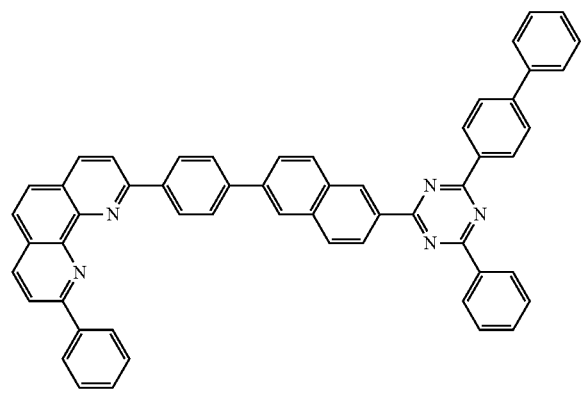
EN-221
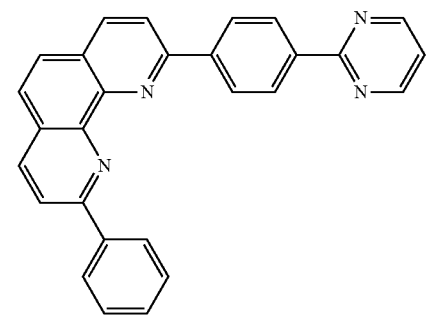
EN-222
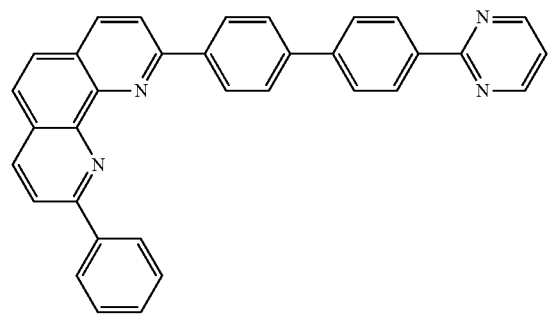
EN-223
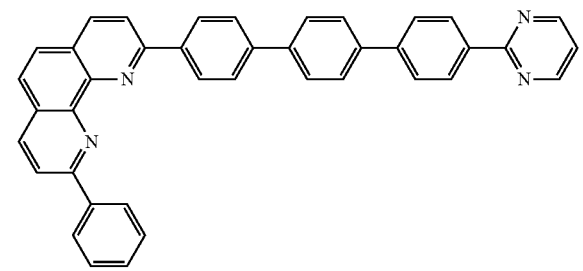
EN-224
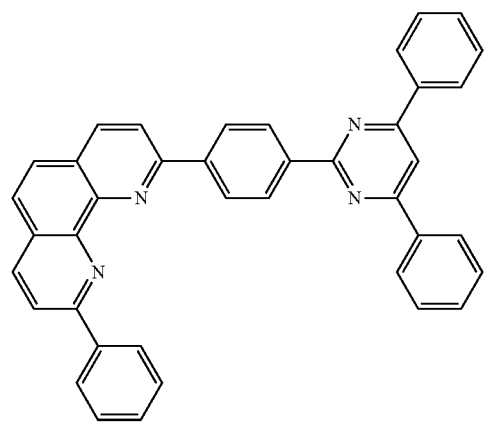
EN-225
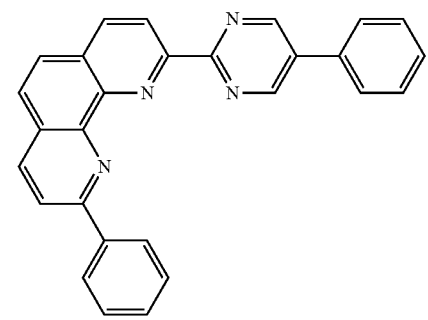
EN-226
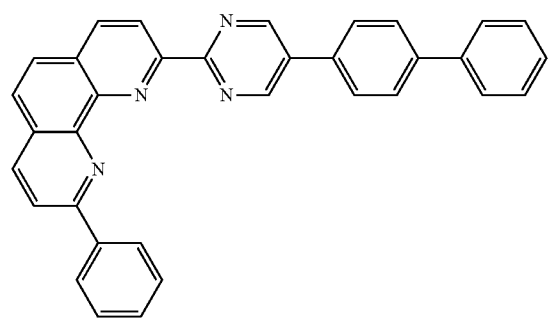
EN-227
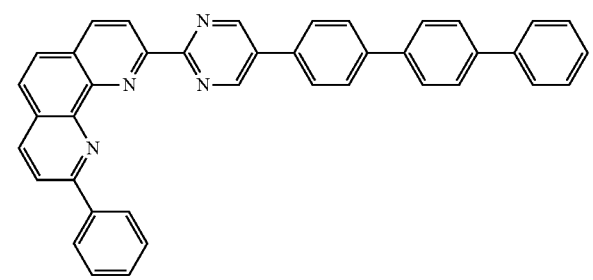

-continued
EN-228
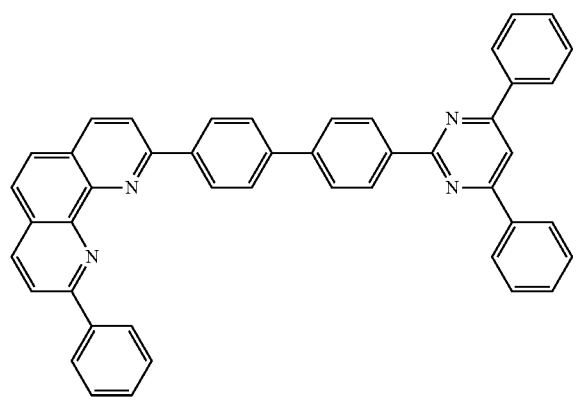
EN-229
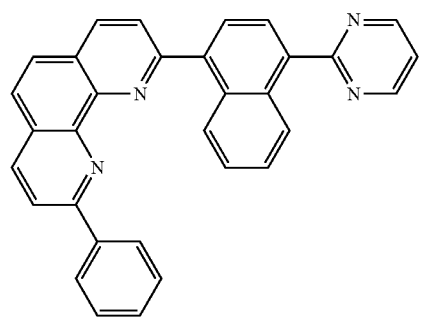
EN-230
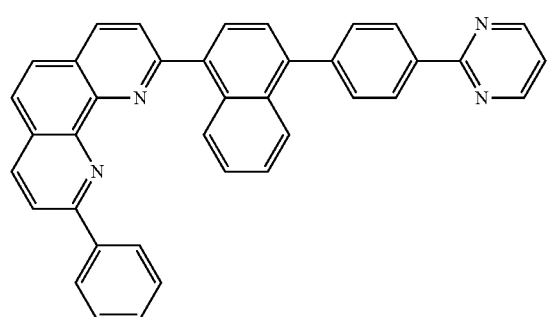
EN-231
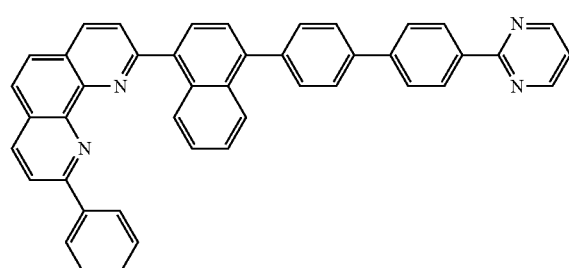
EN-232
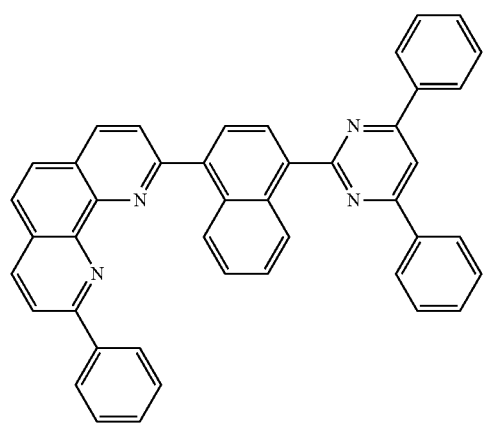
EN-233
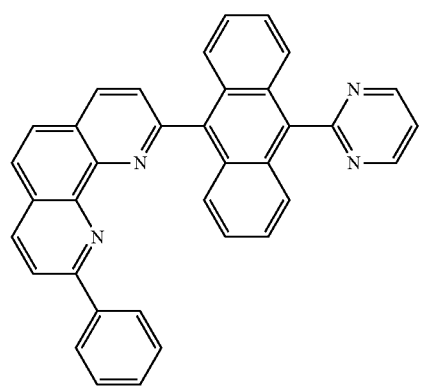
EN-234
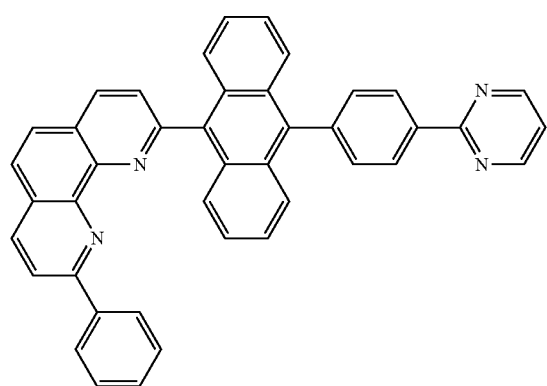
EN-235
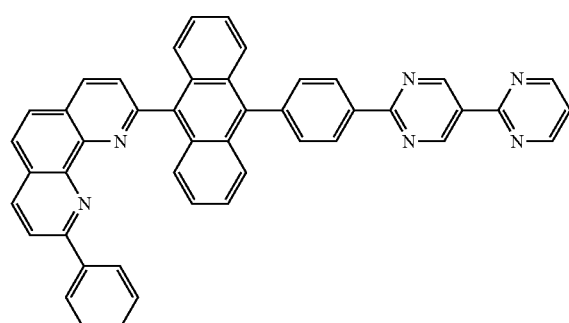

-continued
EN-236
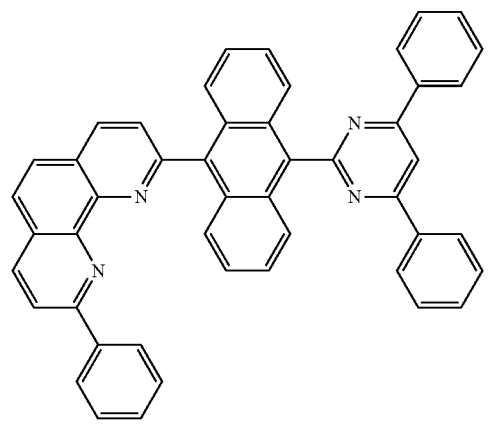
EN-237
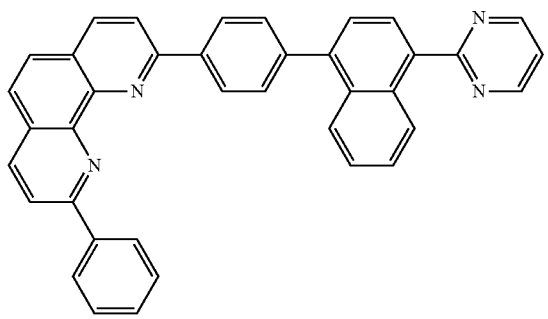
EN-238
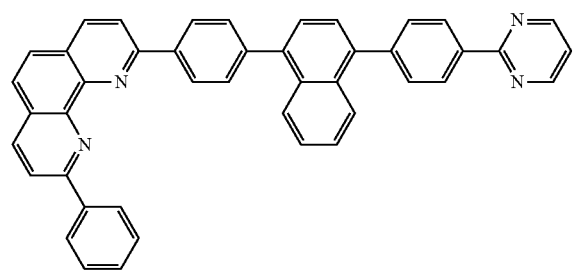
EN-239
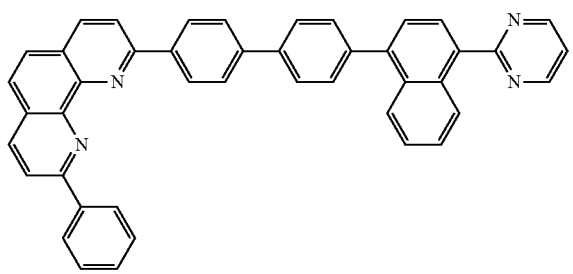
EN-240
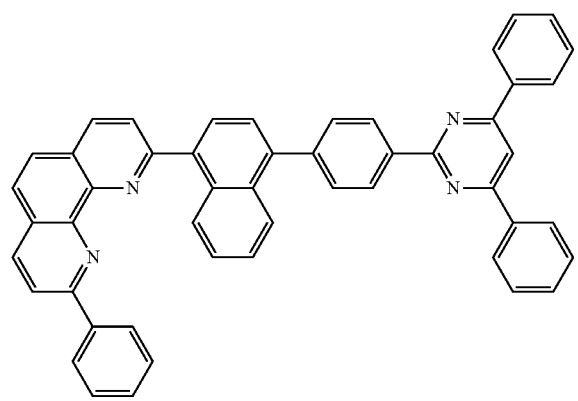
EN-241
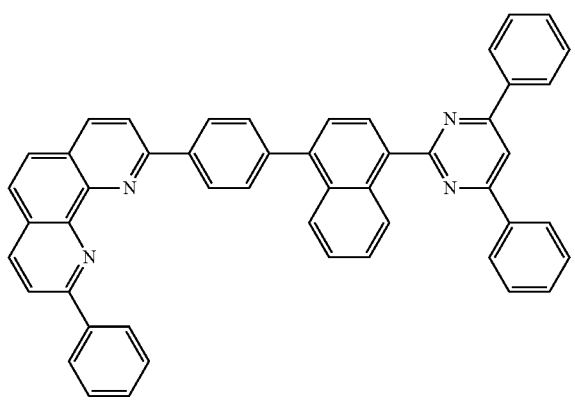
EN-242
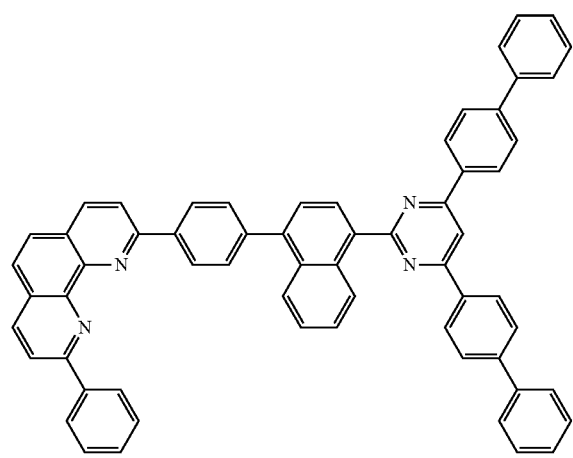
EN-243
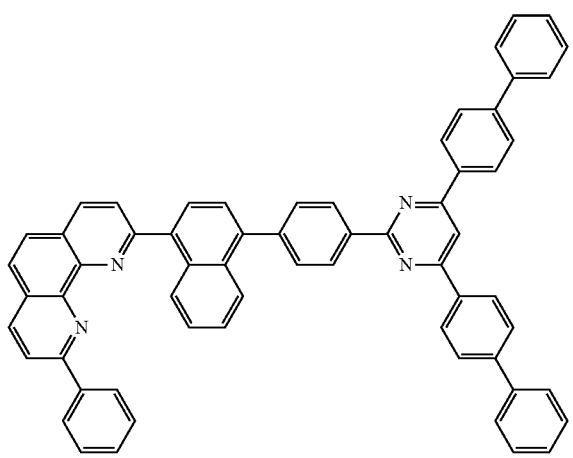

-continued
EN-244
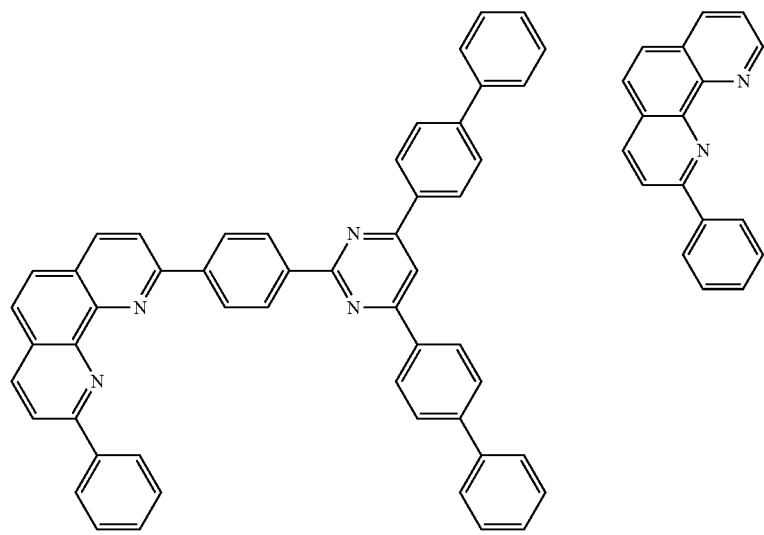
EN-245
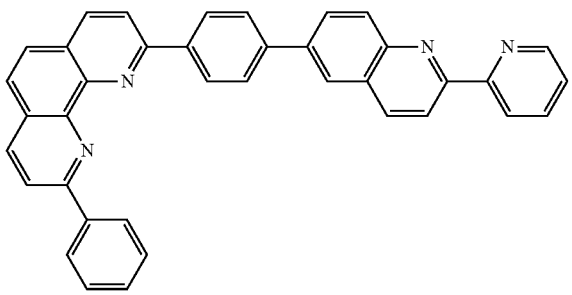
EN-246
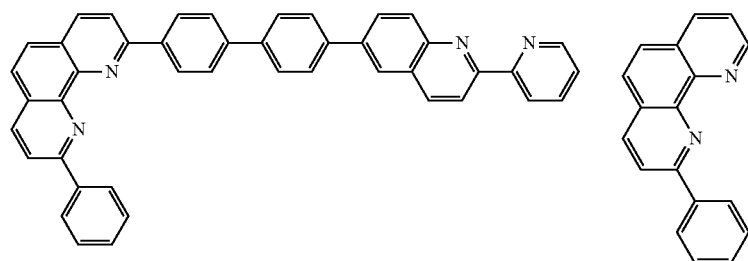
EN-247
EN-248
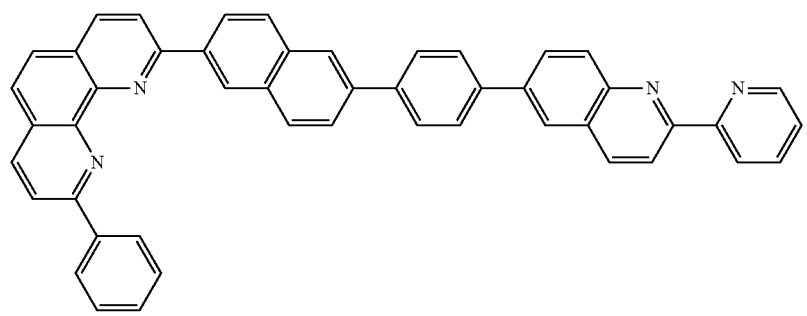
EN-249
EN-250
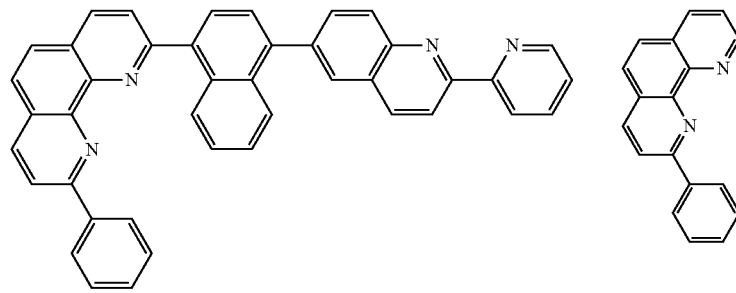

-continued
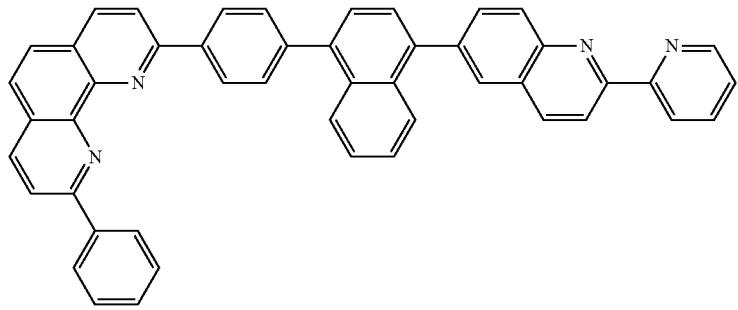
EN-251
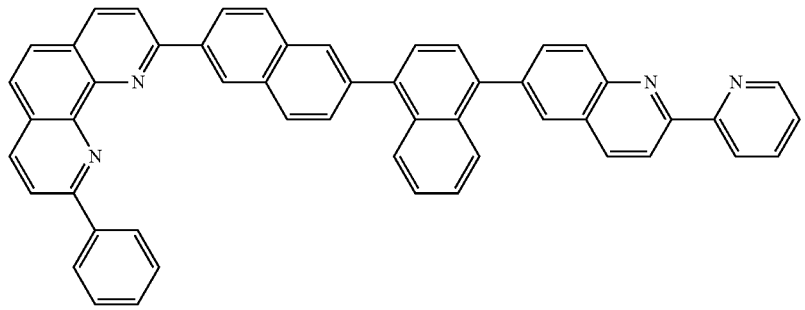
EN-252
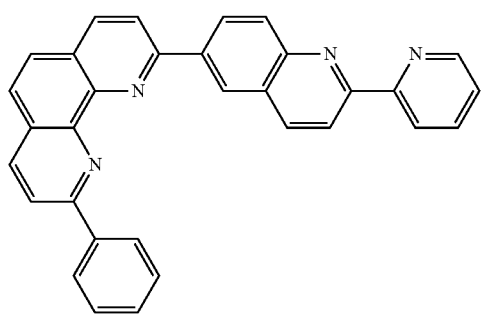
EN-253
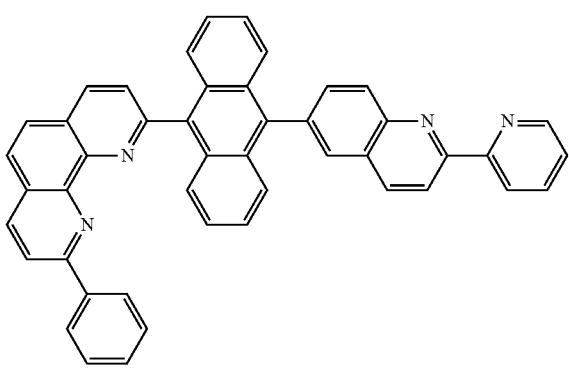
EN-254
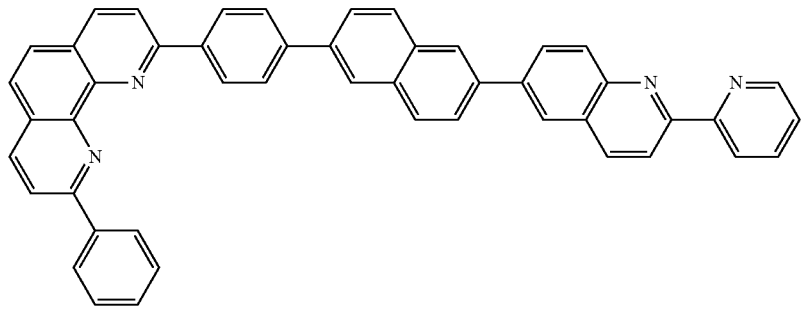
EN-255
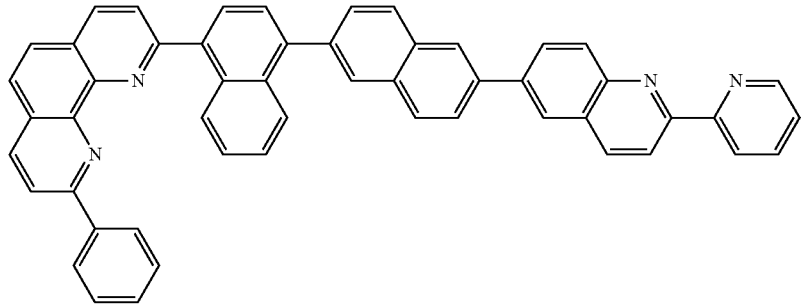
EN-256

-continued
EN-257
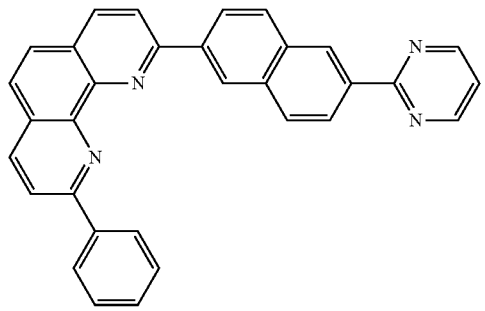
EN-258
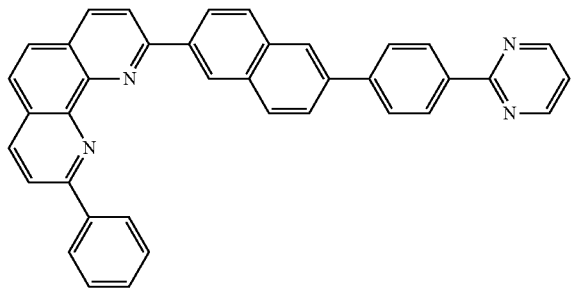
EN-259
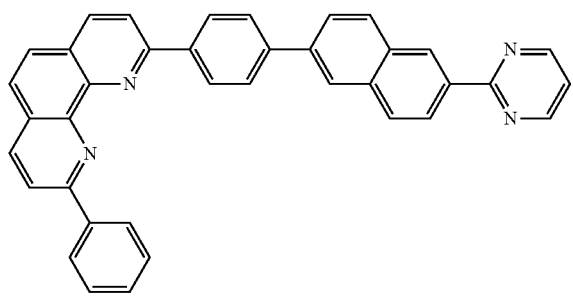
EN-260
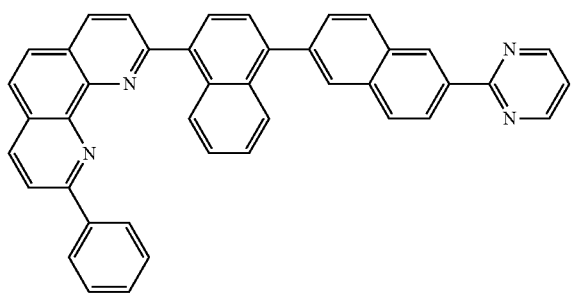
EN-261
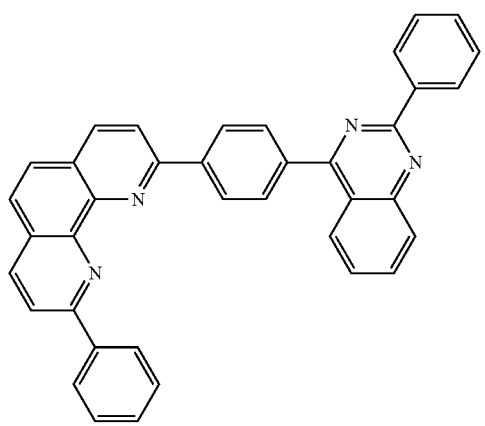
EN-262
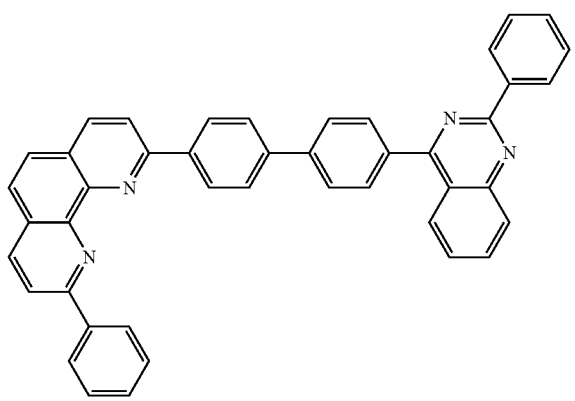
EN-263
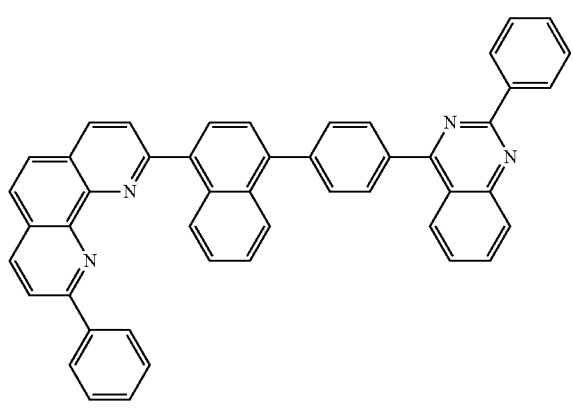
EN-264
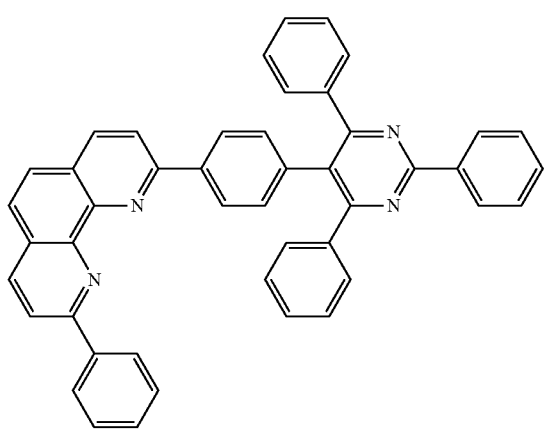

EN-265

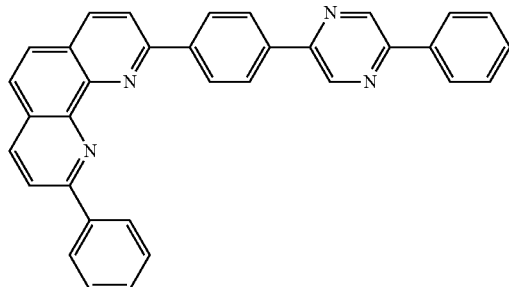

EN-266

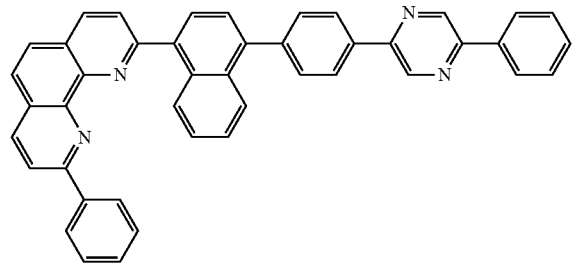

EN-267

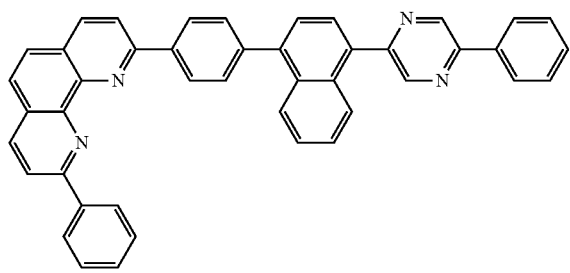

EN-268

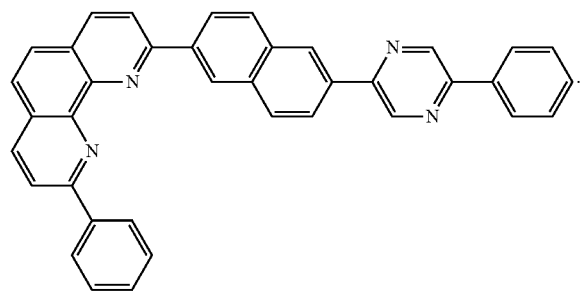

2. A light emitting diode, comprising:

first and second electrodes facing each other;

a first emitting part between the first and second electrodes and including a first emitting material layer and an electron transporting layer;

a second emitting part between the first emitting part and the second electrode and including a second emitting material layer; and a first charge generation layer between the first and second emitting parts, wherein at least one of the electron transporting layer and the first charge generation layer includes an organic compound represented by the following chemical formula 1, wherein the first charge generation layer includes an N type charge generation layer and a P type charge generation layer, and the N type charge generation layer includes the organic compound:

Chemical Formula 1

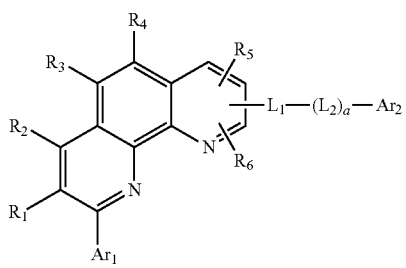

wherein, each of $R_1$ to $R_6$ is independently one of hydrogen, deuterium, tritium, a non-substituted alkyl group of C1 to C20, a substituted alkyl group of C1 to C20, a non-substituted alkoxy group of C1 to C20, a substituted alkoxy group of C1 to C20, a non-substituted aryl group of C5 to C60, a substituted aryl group of C5 to C60 and a non-substituted hetero aryl group of C4 to C60, and a substituted hetero aryl group of C4 to C60;

each of $L_1$ and $L_2$ is independently one of a non-substituted arylene group of C5 to C60, a substituted arylene group of C5 to C60, a non-substituted hetero arylene group of C5 to C60, and a substituted hetero arylene group of C5 to C60;

a is 1; and each of $Ar_1$ and $Ar_2$ is independently one of a non-substituted aryl group of C5 to C60, a substituted aryl group of C5 to C60, a non-substituted hetero aryl group of C4 to C30, and a substituted hetero aryl group of C4 to C30;

with the proviso that when $R_1$ to $R_6$ are each hydrogen, $L_1$ is phenylene, $L_2$ is anthracenylene and $Ar_1$ is phenyl, then $Ar_2$ cannot be a naphthyl group.

3. The light emitting diode of claim 2, wherein the N type charge generation layer includes one of an alkali metal and an alkali earth metal.

4. The light emitting diode of claim 2, further comprising:

a third emitting part between the second emitting part and the second electrode; and a second charge generation layer between the second emitting part and the third emitting part, wherein the second charge generation layer includes the organic compound.

5. An organic light emitting diode display device, comprising:

a substrate;

a light emitting diode on the substrate; and a driving element between the substrate and the light emitting diode, wherein the light emitting diode comprises:

first and second electrodes facing each other;

a first emitting part between the first and second electrodes and including a first emitting material layer and an electron transporting layer;

a second emitting part between the first emitting part and the second electrode and including a second emitting material layer; and a first charge generation layer between the first and second emitting parts, wherein at least one of the electron transporting layer and the first charge generation layer includes an organic compound selected from:

EN-008

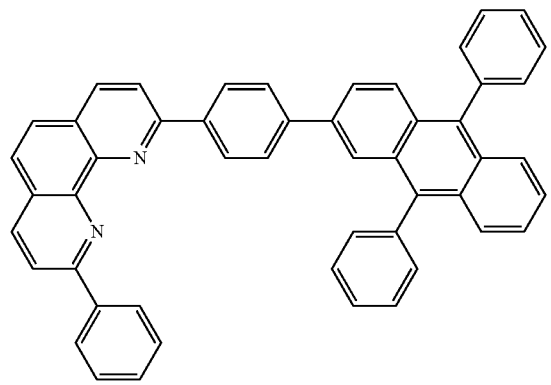

EN-020

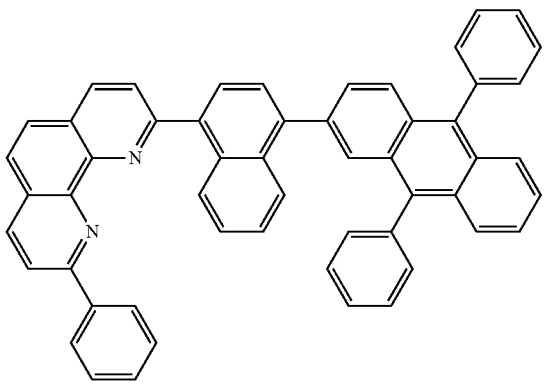

EN-024

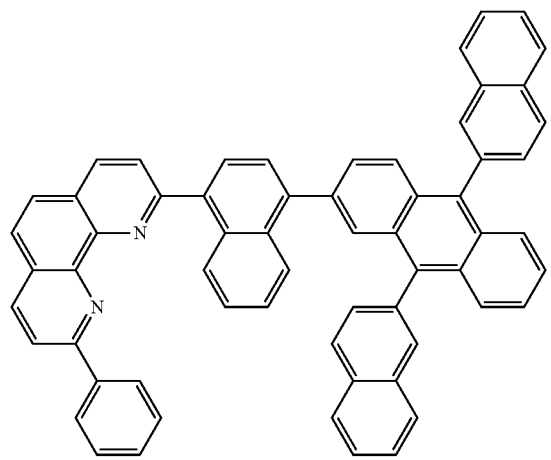

EN-025

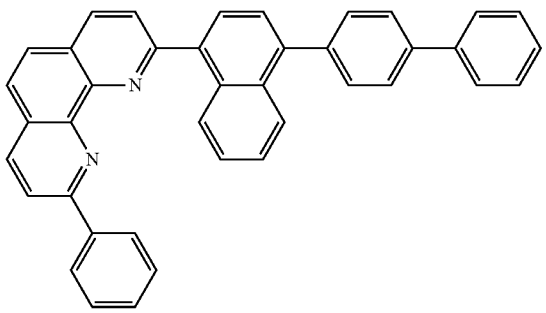

EN-026

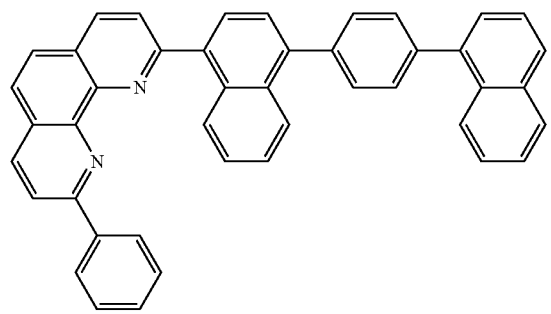

EN-027

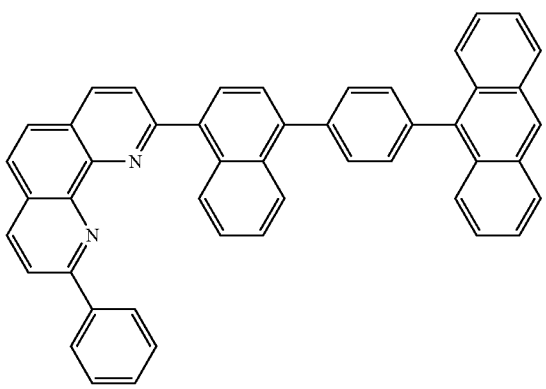

-continued
EN-028
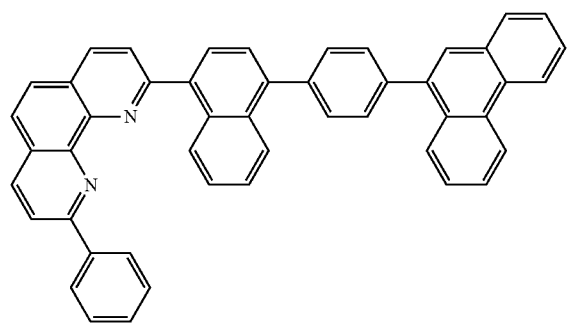
EN-029
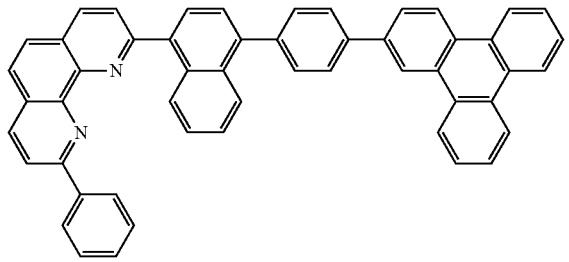
EN-030
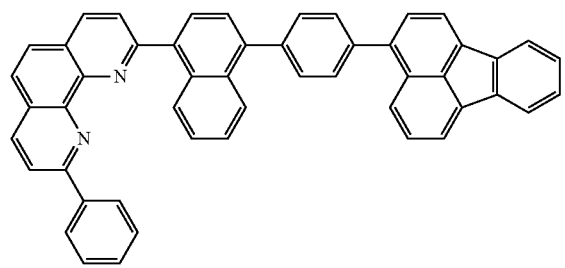
EN-031
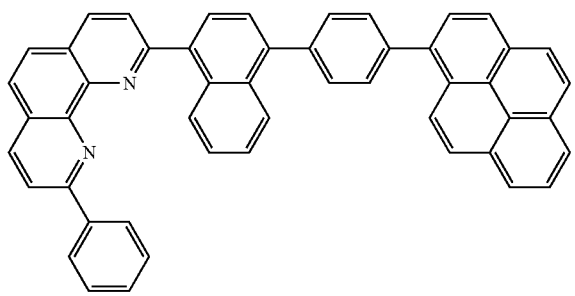
EN-032
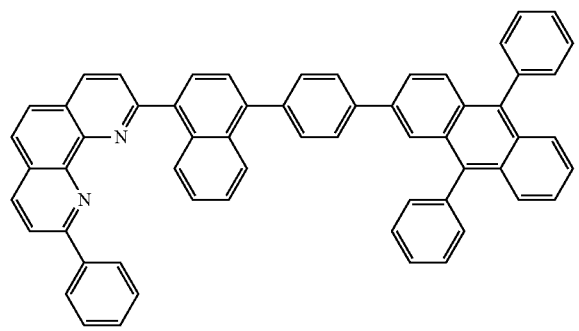
EN-033
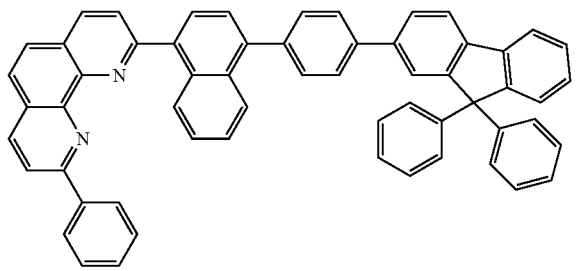
EN-034
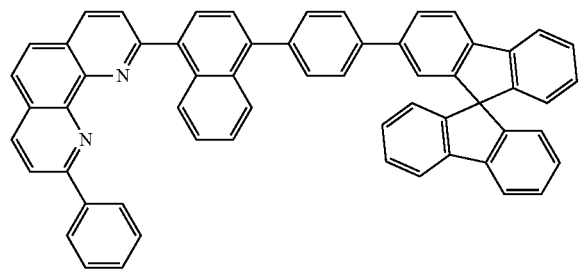
EN-035
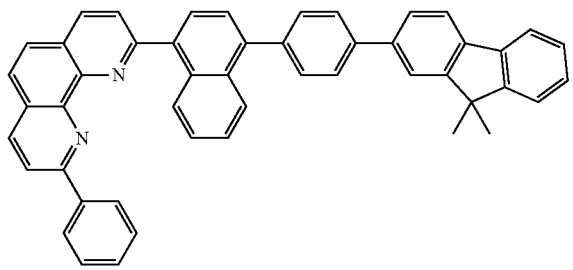

-continued
EN-036
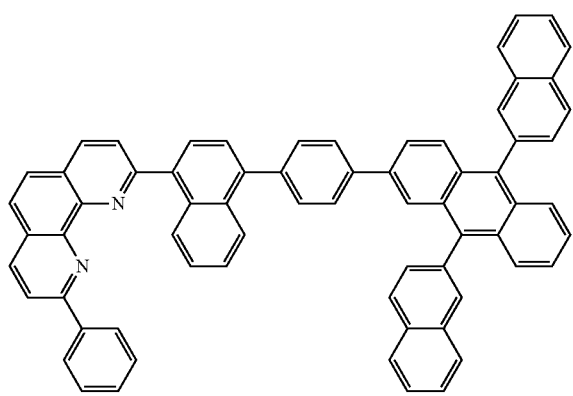
EN-037
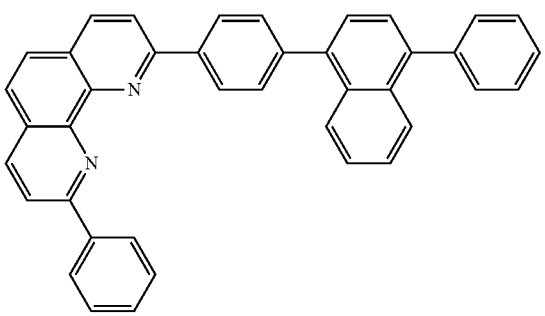
EN-038
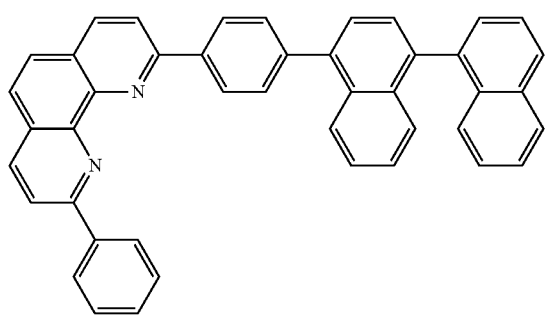
EN-039
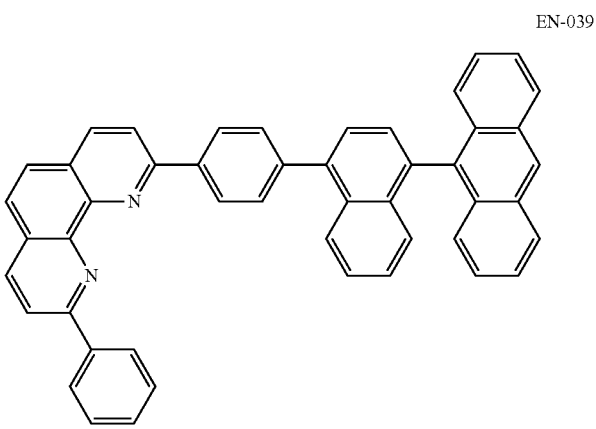
EN-040
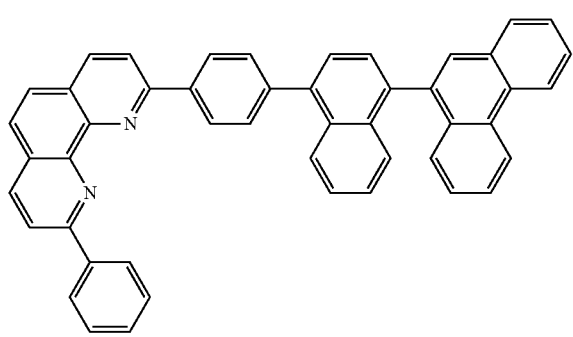
EN-041
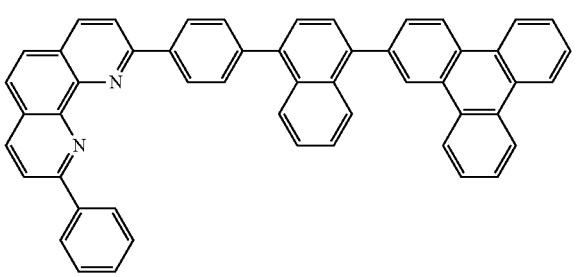
EN-042
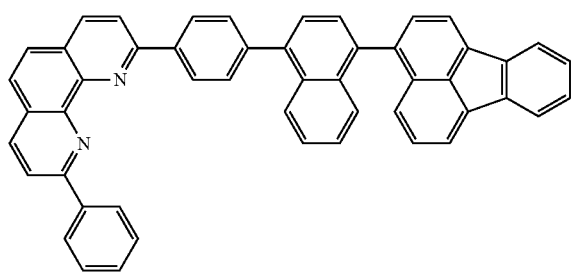
EN-043
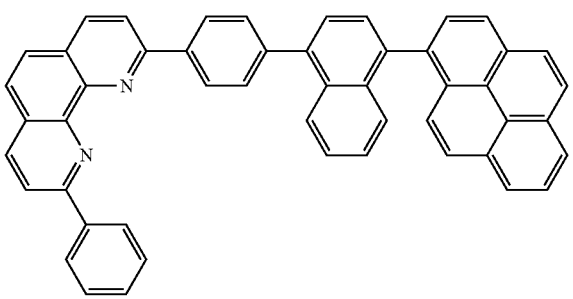

-continued
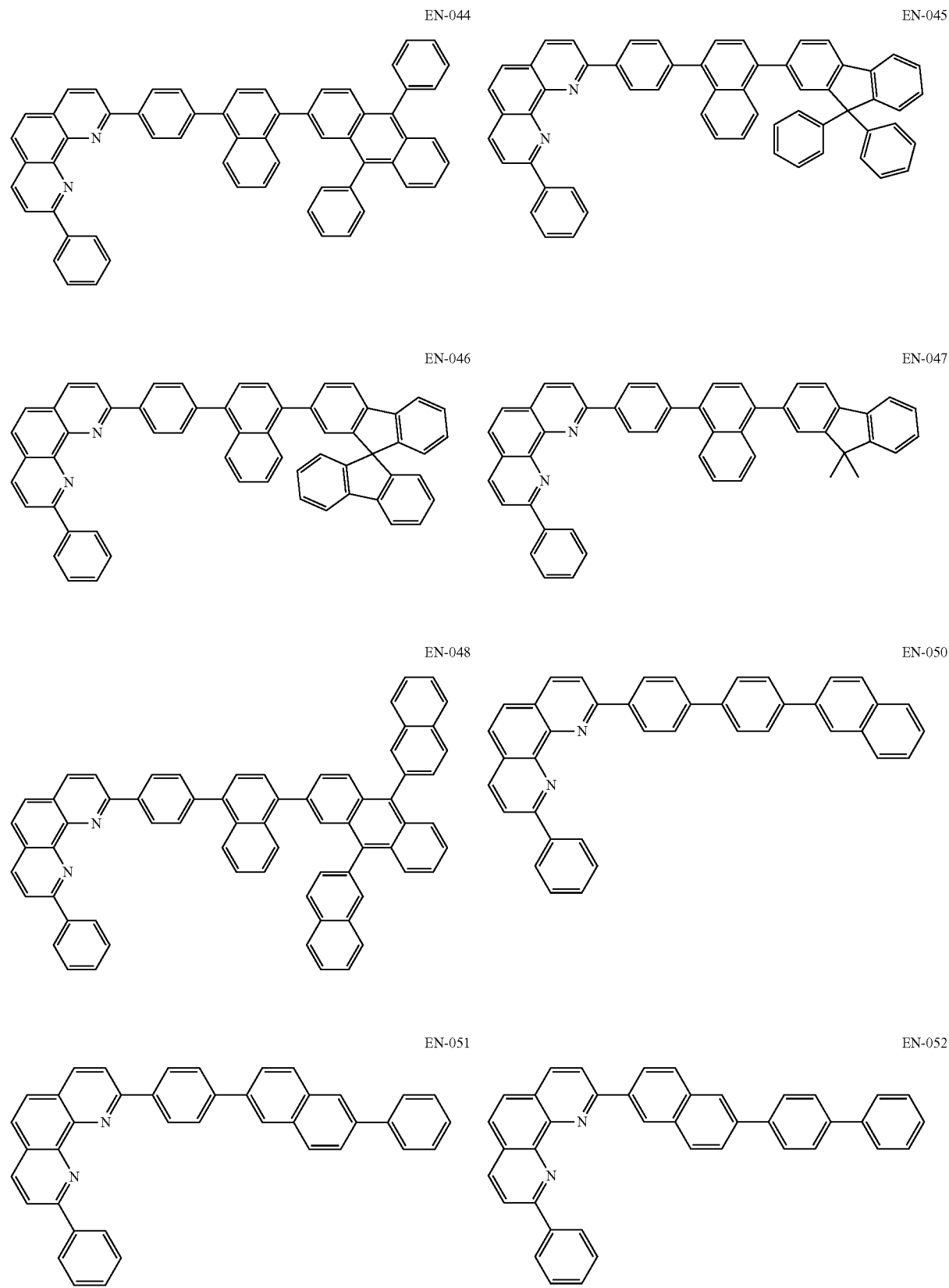

EN-054
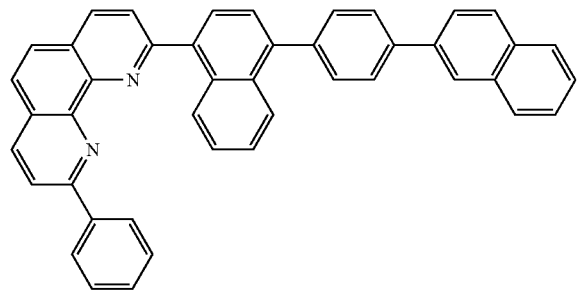
EN-055
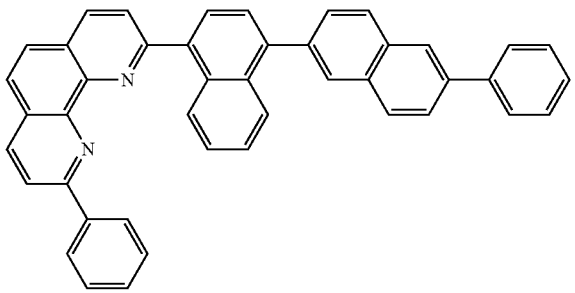
EN-056
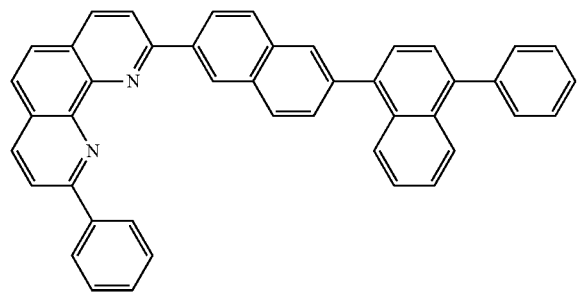
EN-058
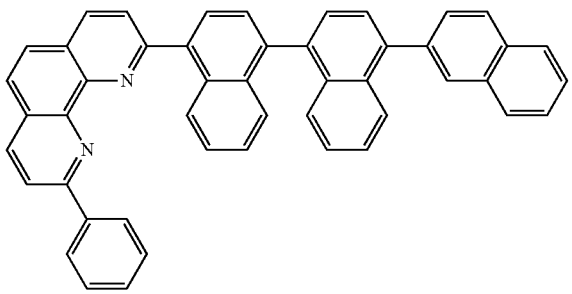
EN-059
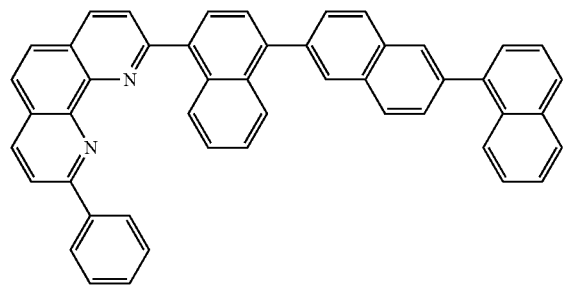
EN-060
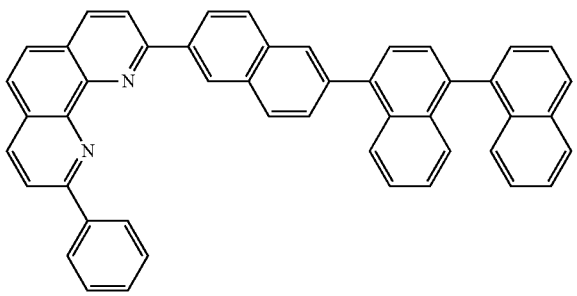
EN-061
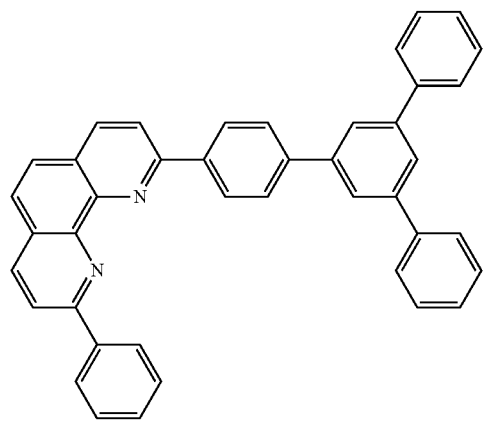
EN-062
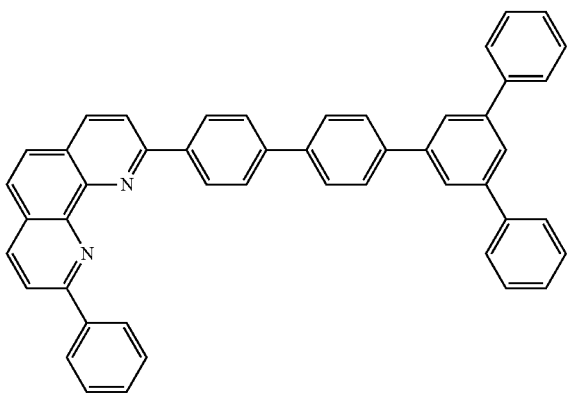

-continued
EN-063
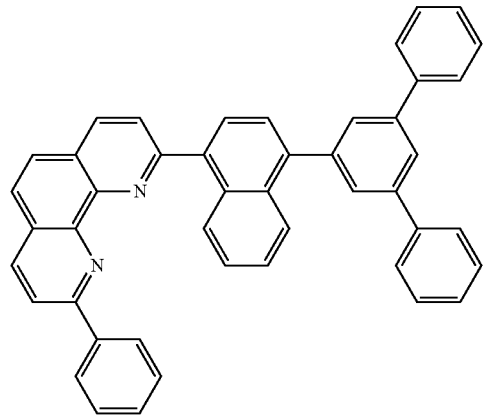
EN-064
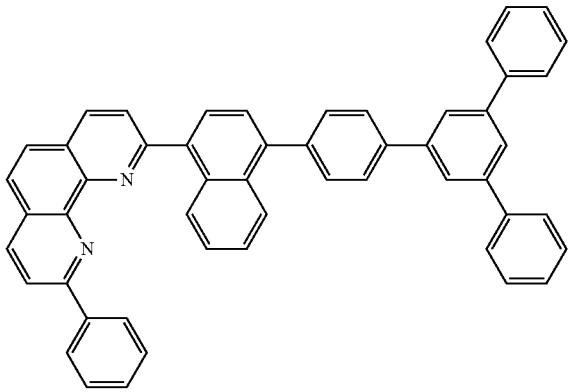
EN-065
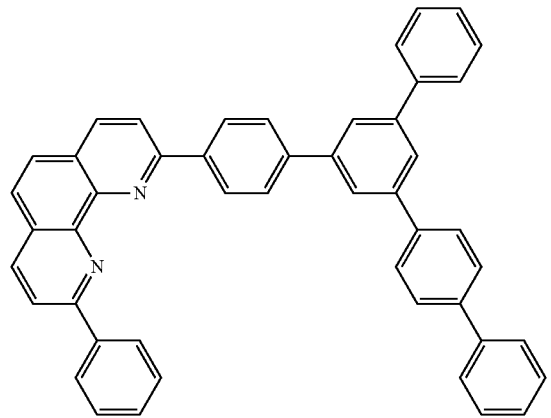
EN-066
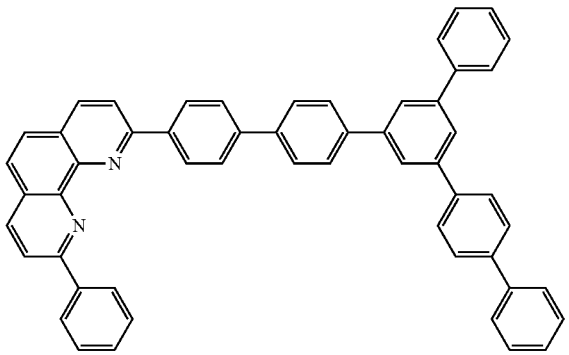
EN-067
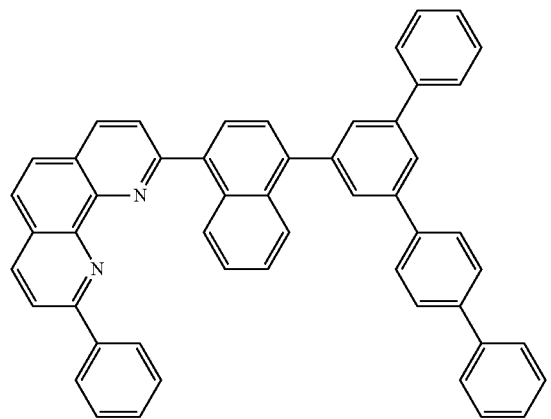
EN-068
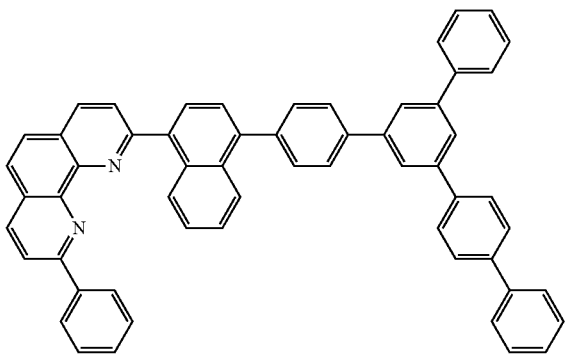

-continued
EN-069
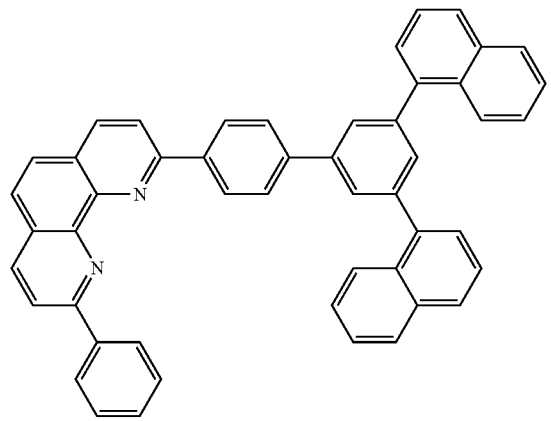
EN-070
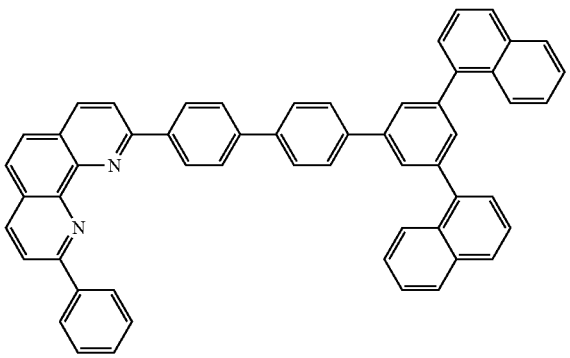
EN-071
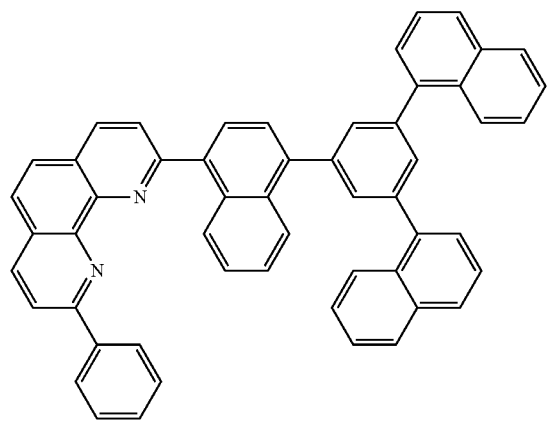
EN-072
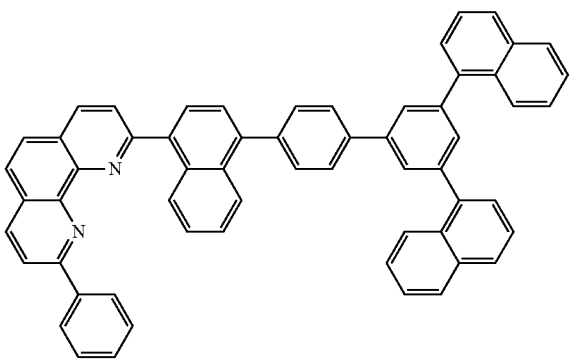
EN-080
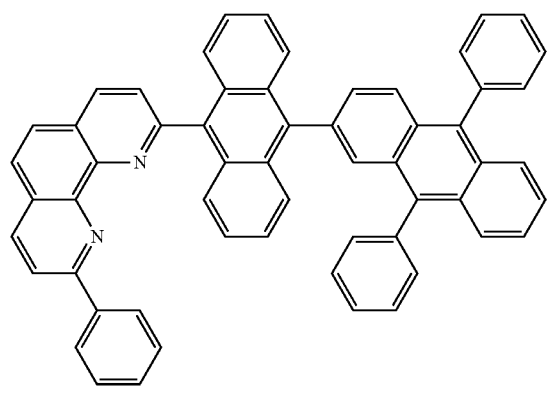
EN-084
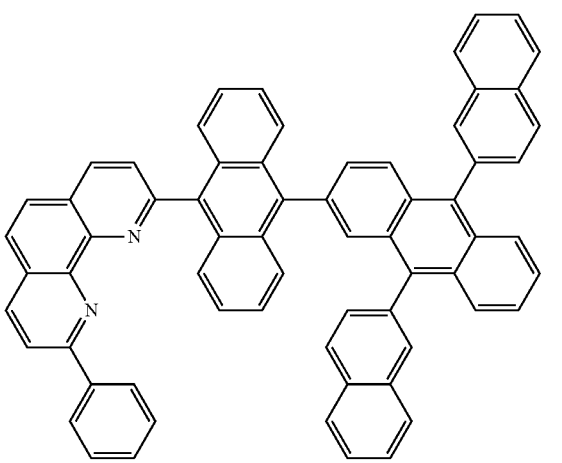

EN-085
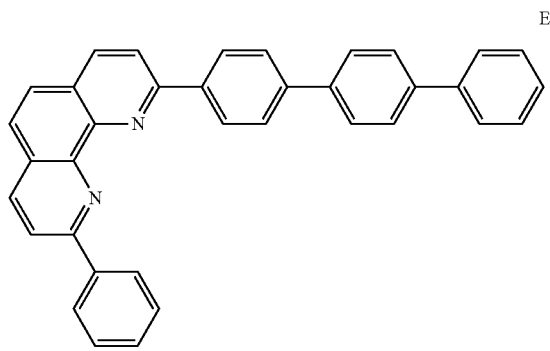
EN-086
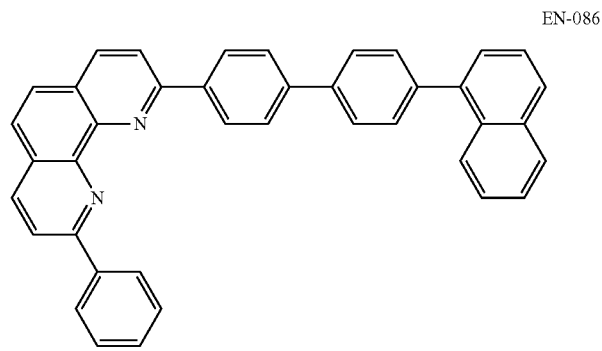
EN-087
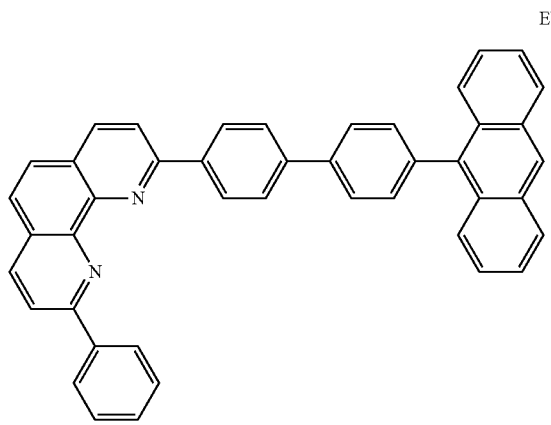
EN-088
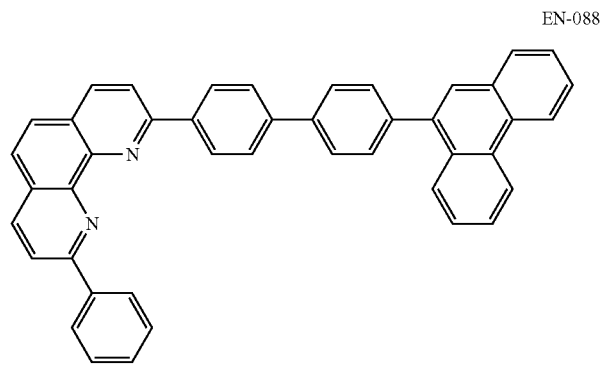
EN-089
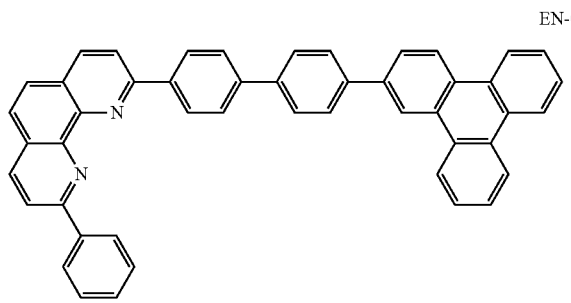
EN-090
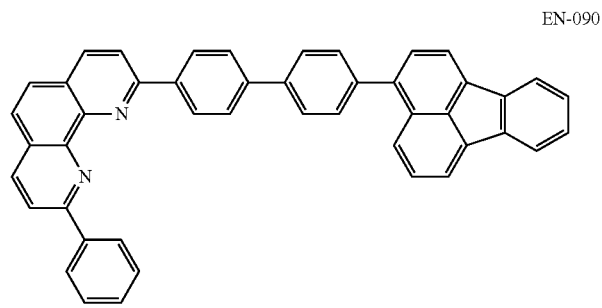
EN-091
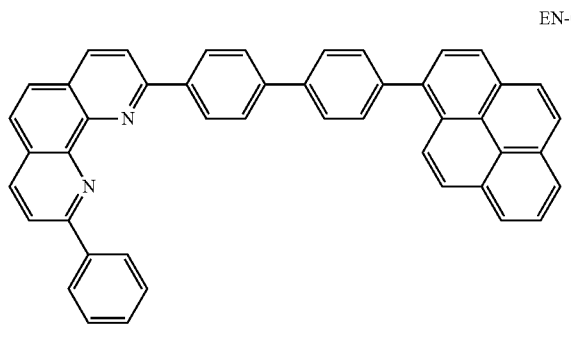
EN-092
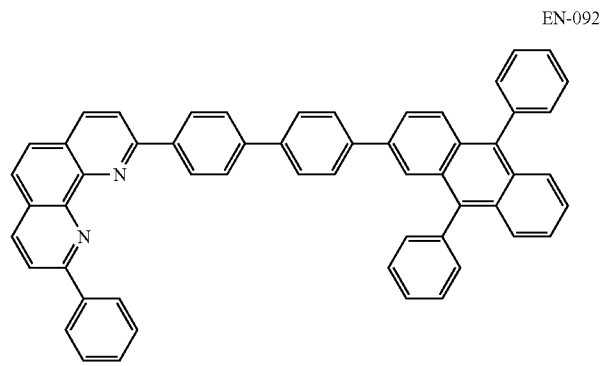

-continued
EN-093
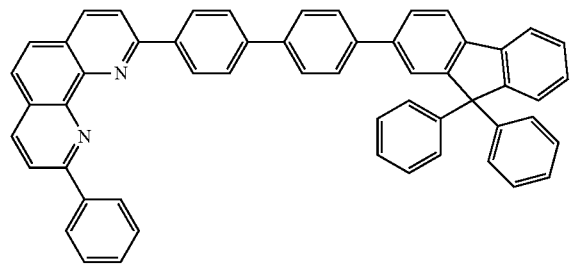
EN-094
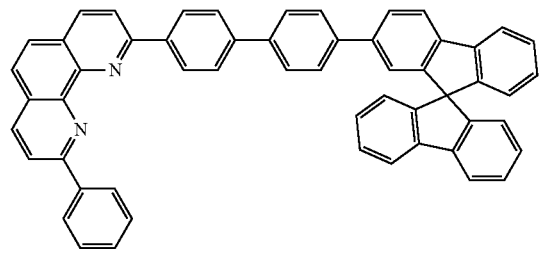
EN-095
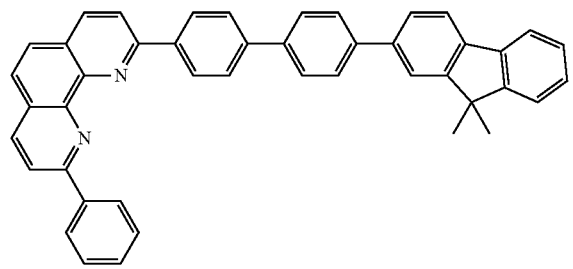
EN-096
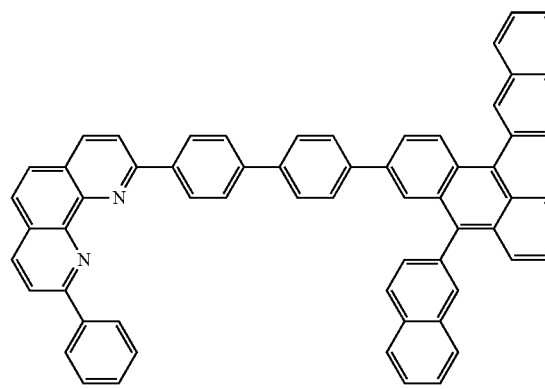
EN-097
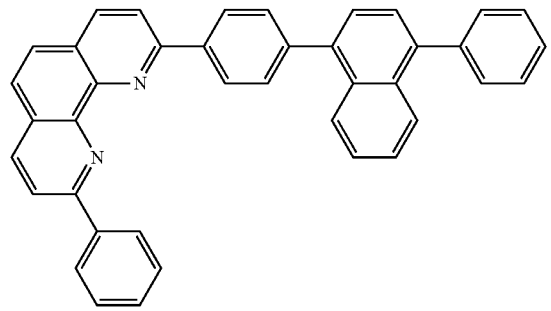
EN-098
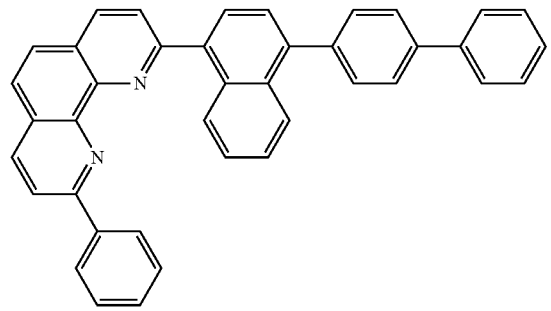
EN-099
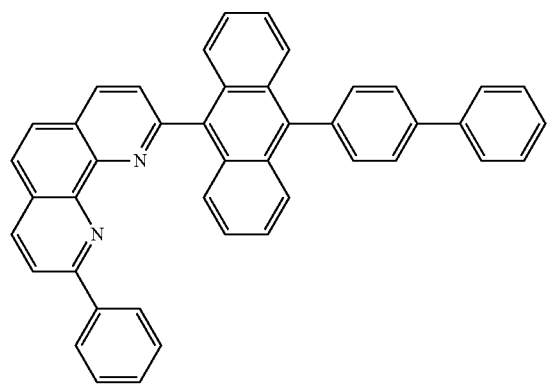
EN-100
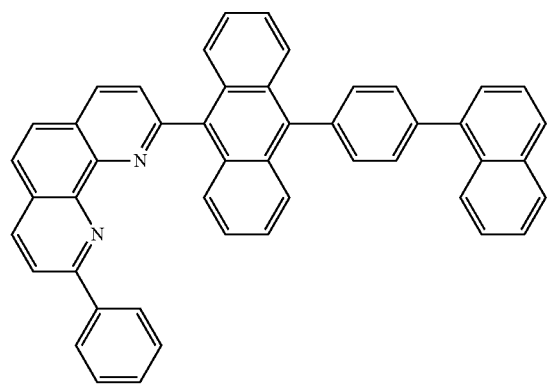

-continued
EN-109
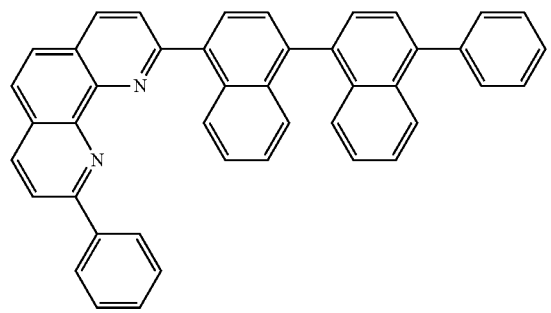
EN-110
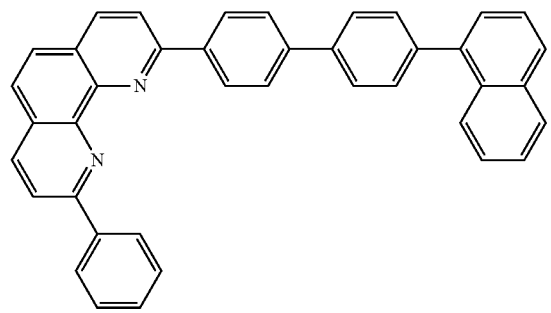
EN-111
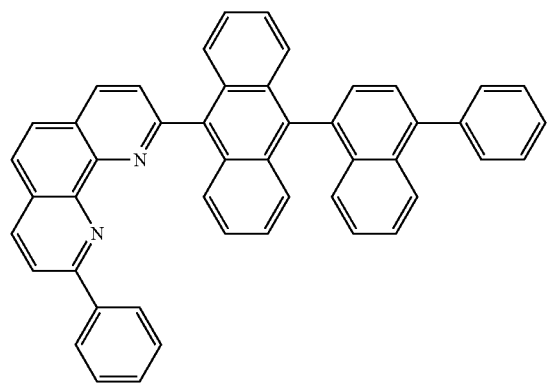
EN-112
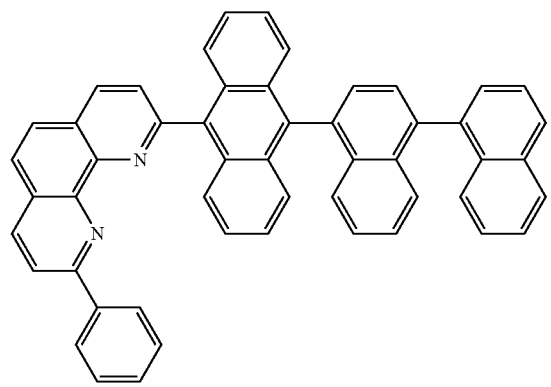
EN-121
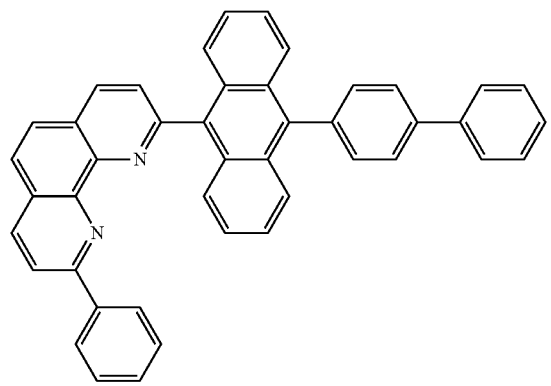
EN-122
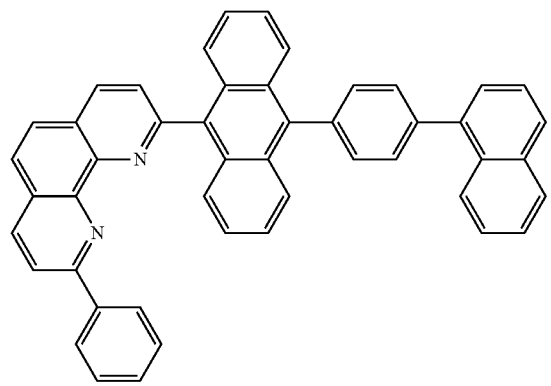
EN-123
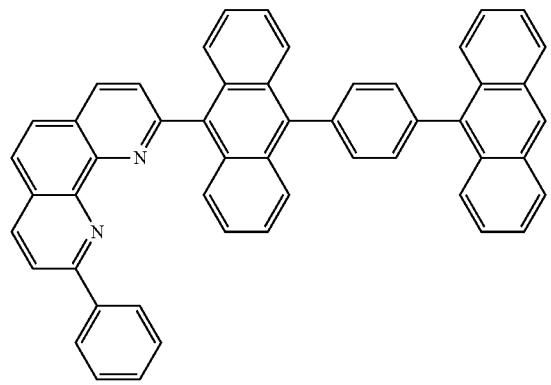
EN-124
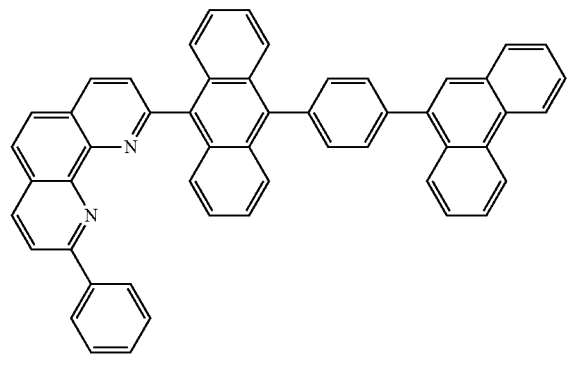

-continued
EN-125
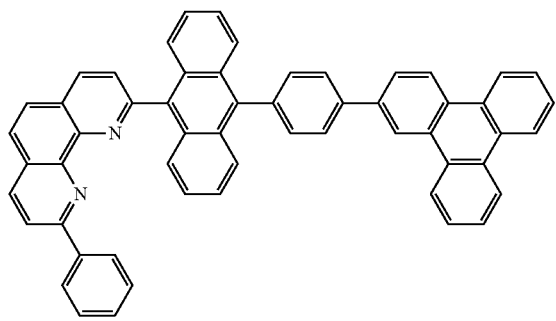
EN-126
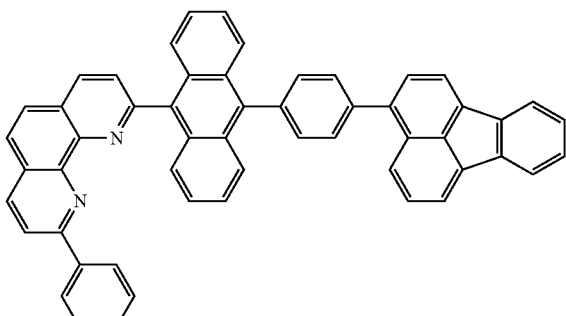
EN-127
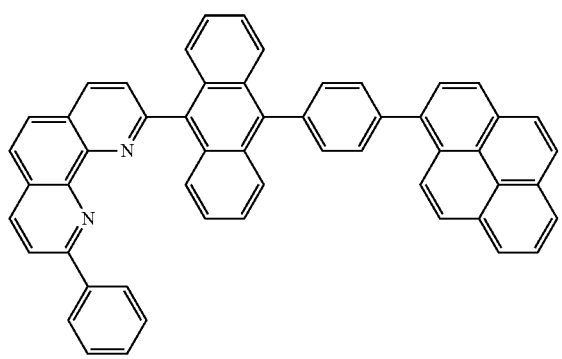
EN-128
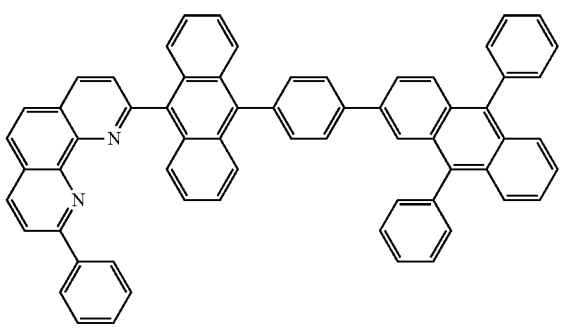
EN-129
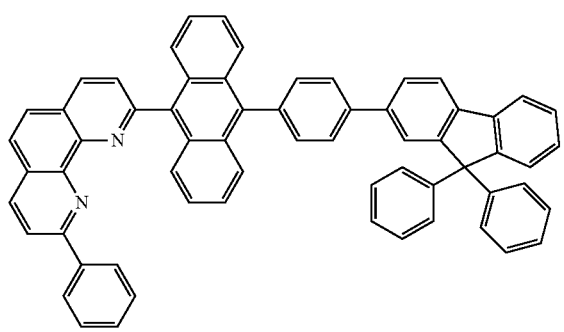
EN-130
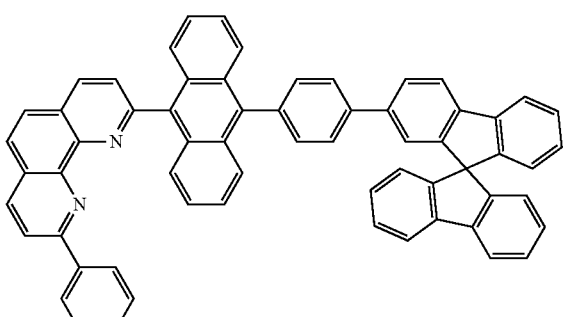
EN-131
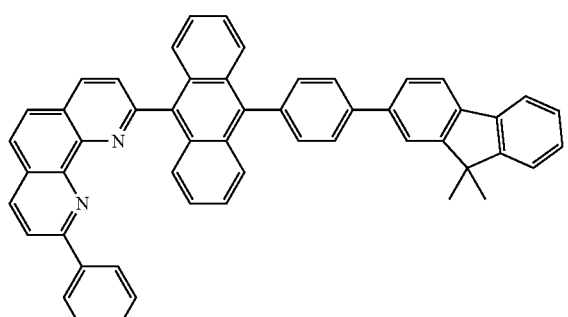
EN-132
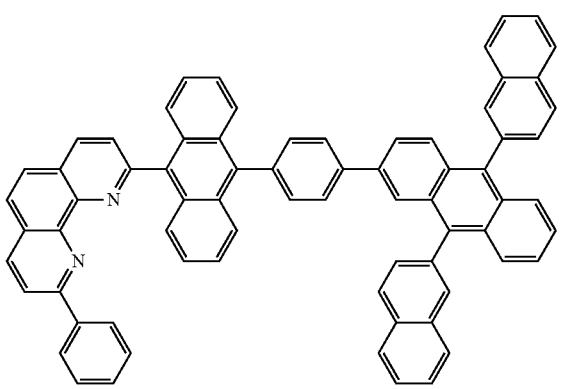

-continued
EN-133
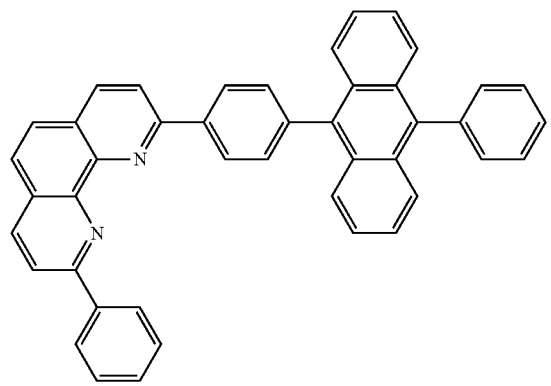
EN-135
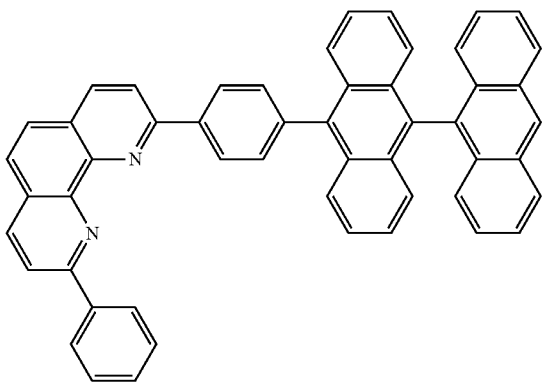
EN-136
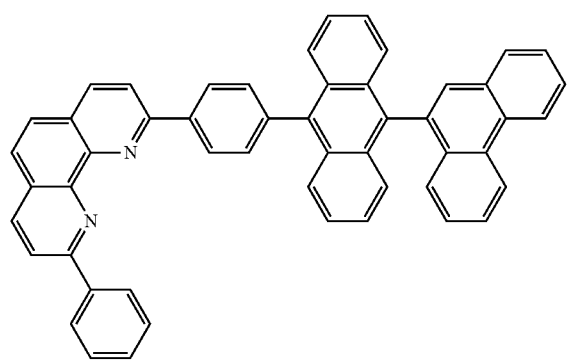
EN-137
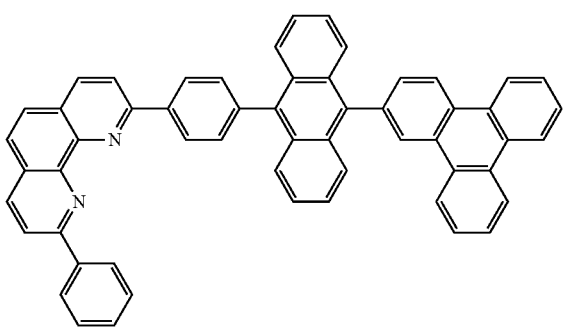
EN-138
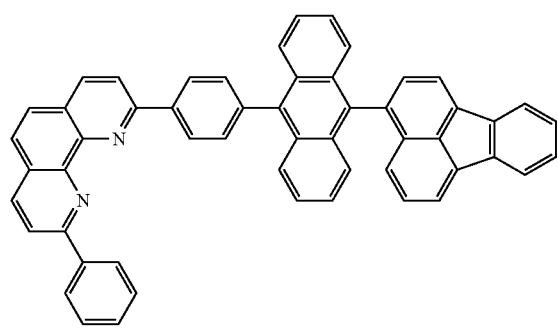
EN-139
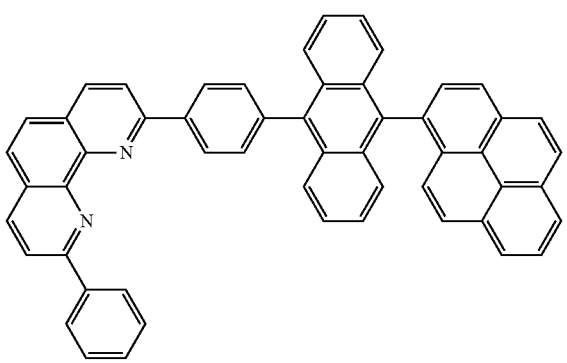
EN-140
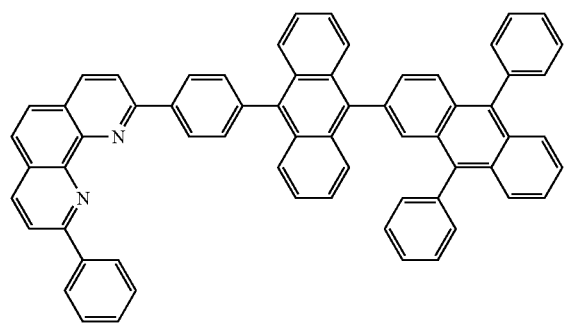
EN-141
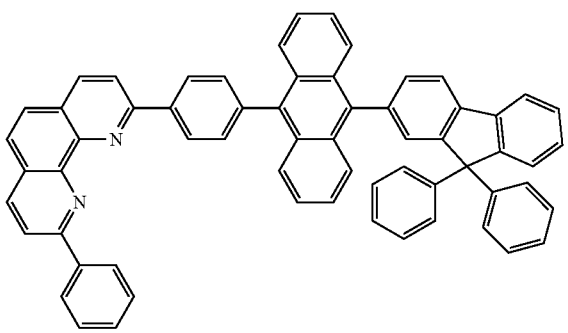

-continued
EN-142
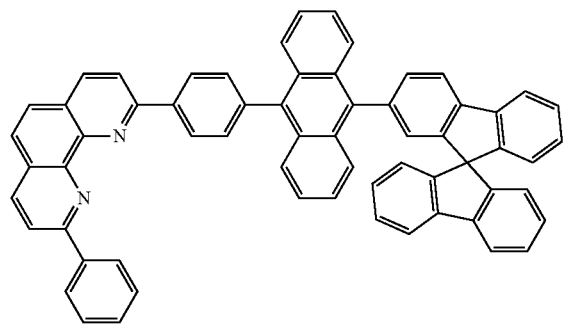
EN-143
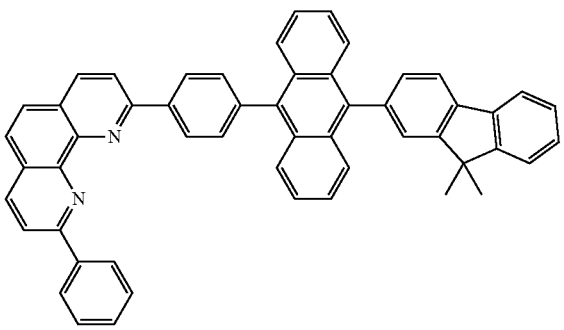
EN-144
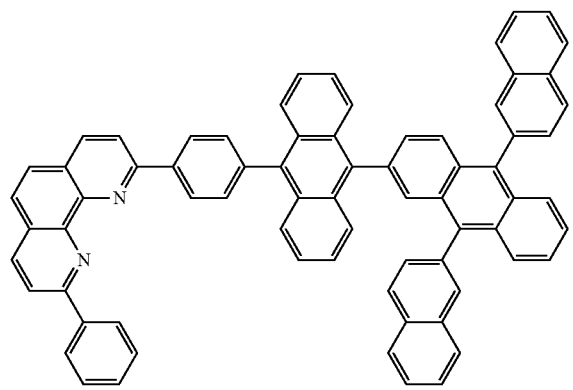
EN-145
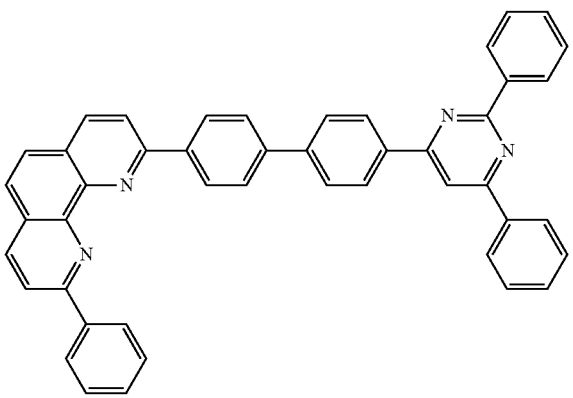
EN-146
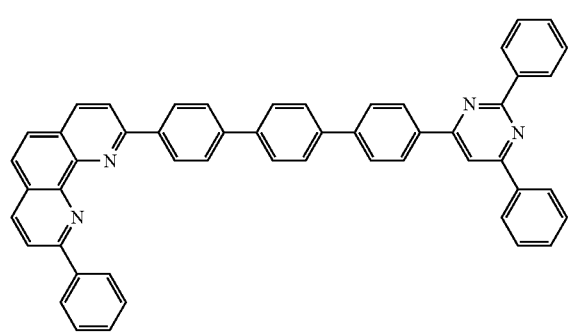
EN-147
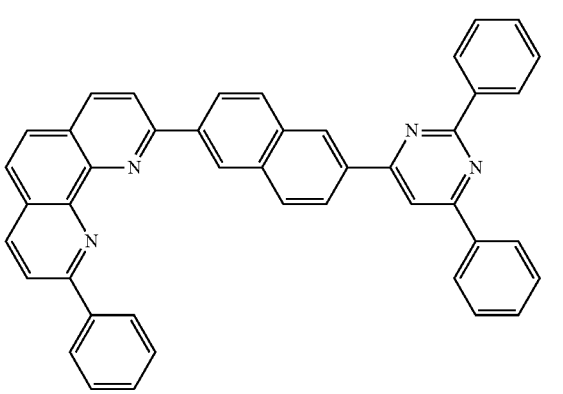
EN-148
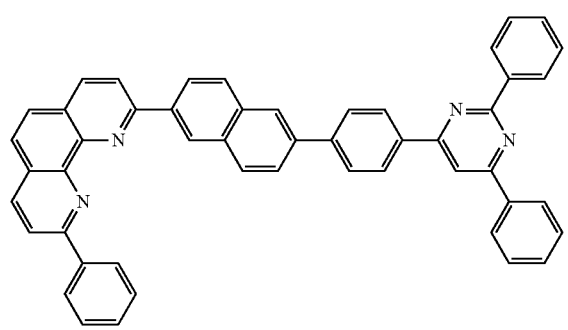
EN-149
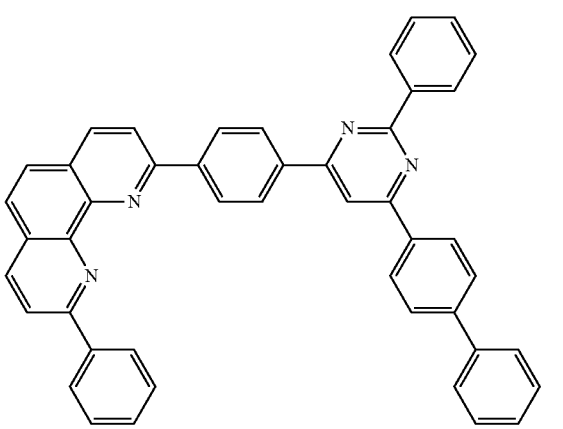

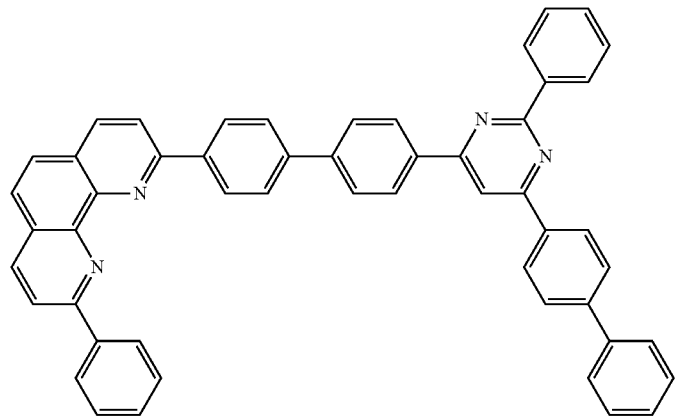
EN-150
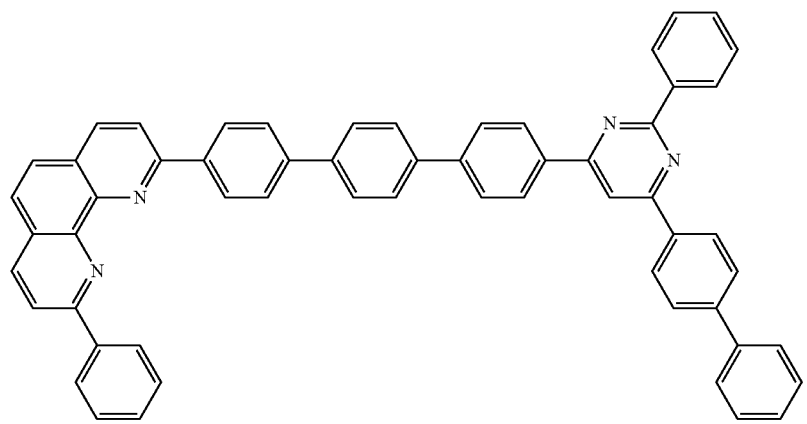
EN-151
EN-152
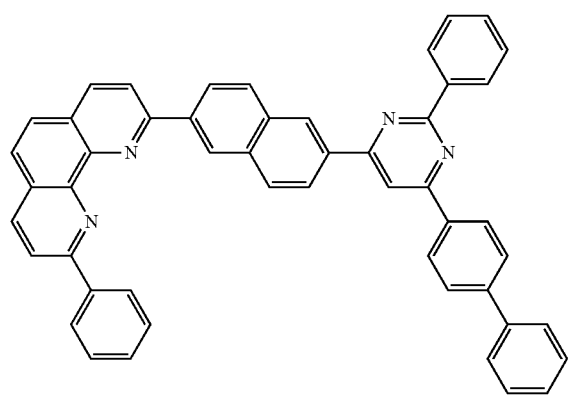
EN-153
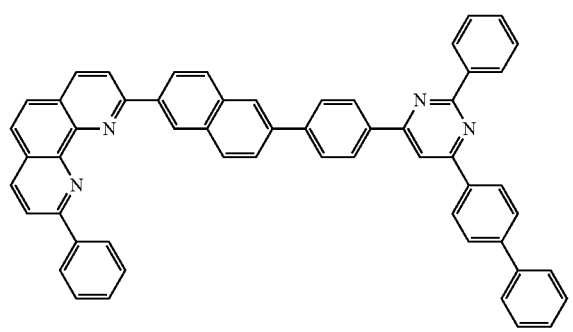

-continued
EN-154
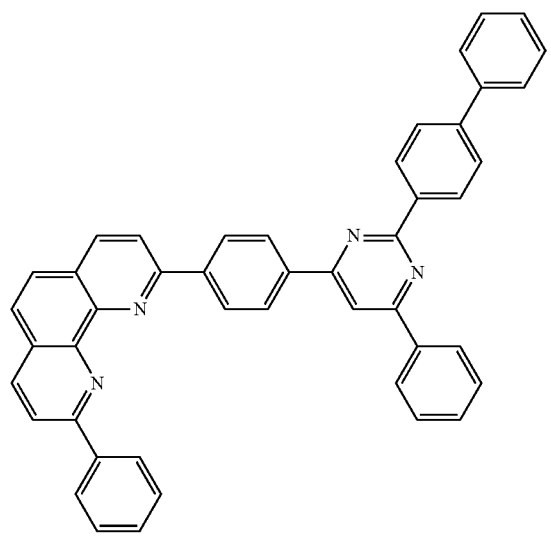
EN-155
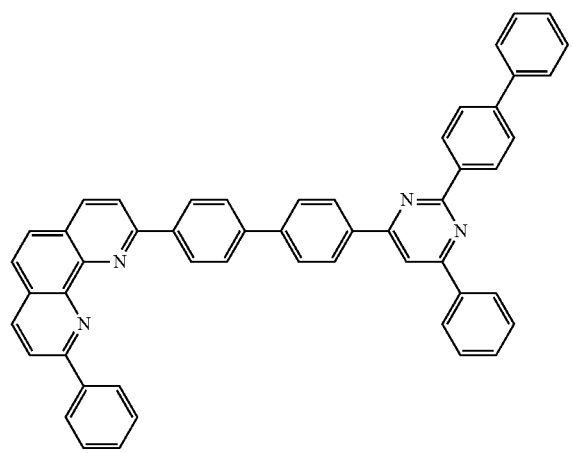
EN-156
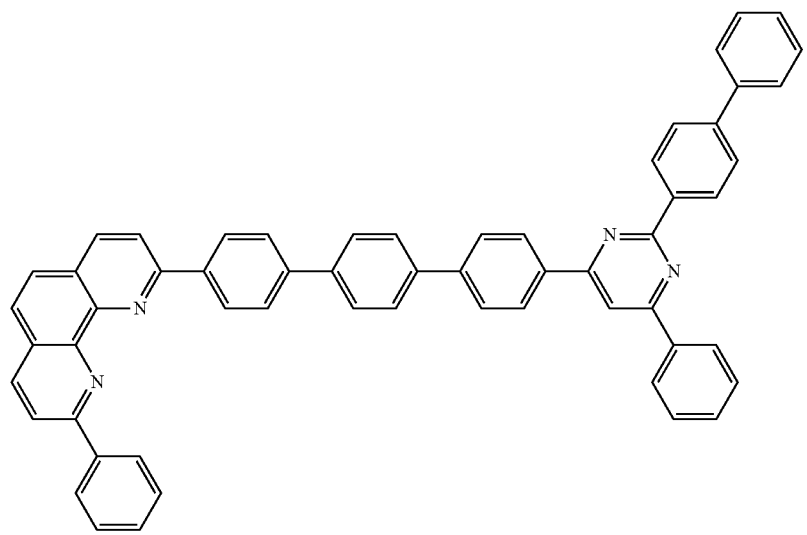
EN-157
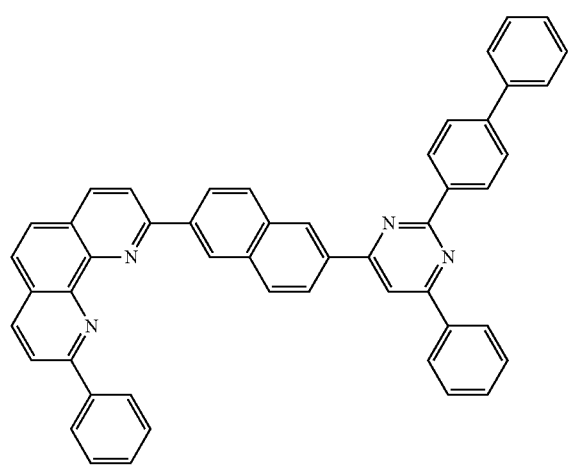
EN-158
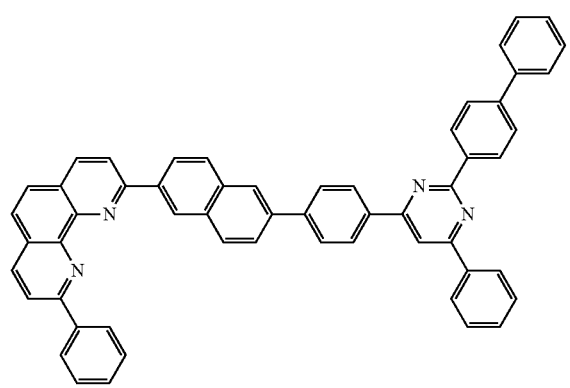

EN-159
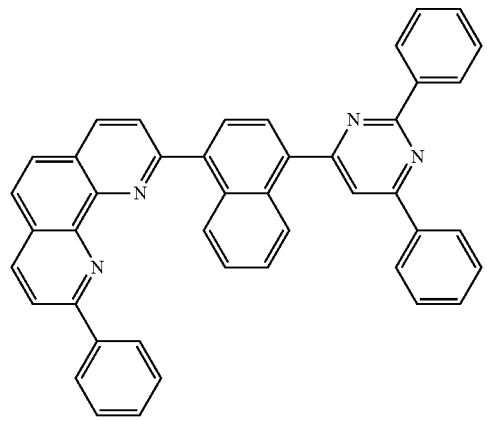
EN-160
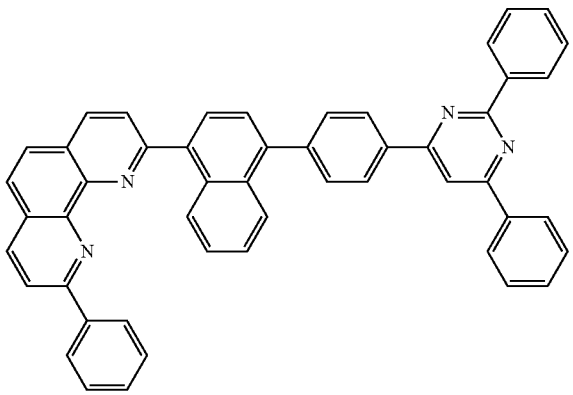
EN-161
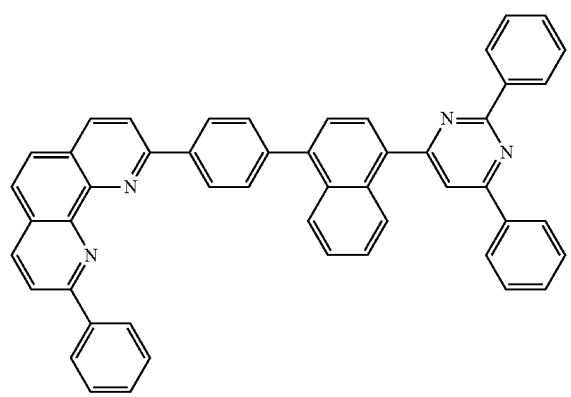
EN-162
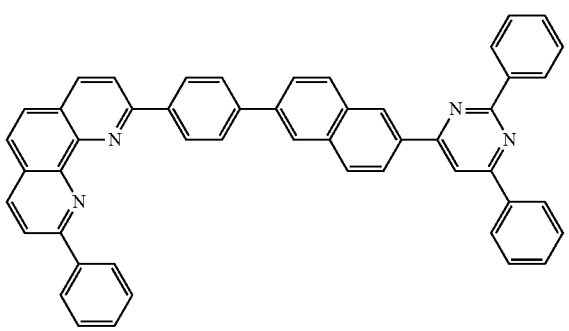
EN-163
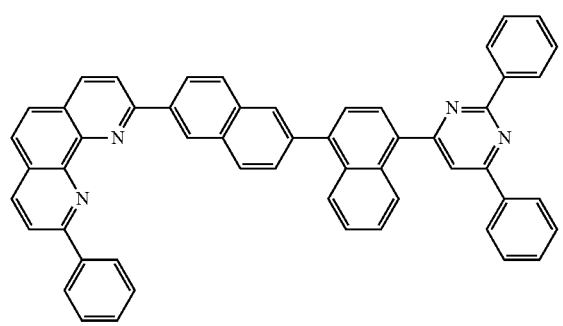
EN-164
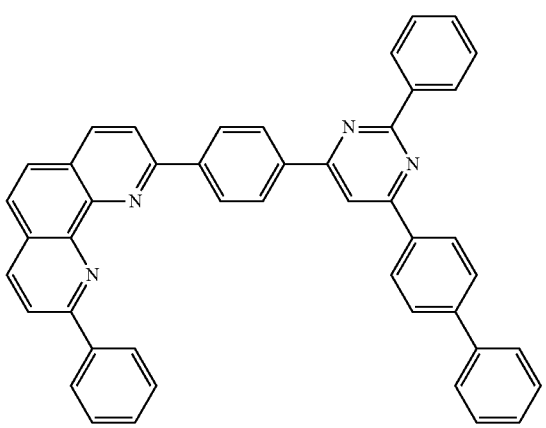

-continued
EN-165
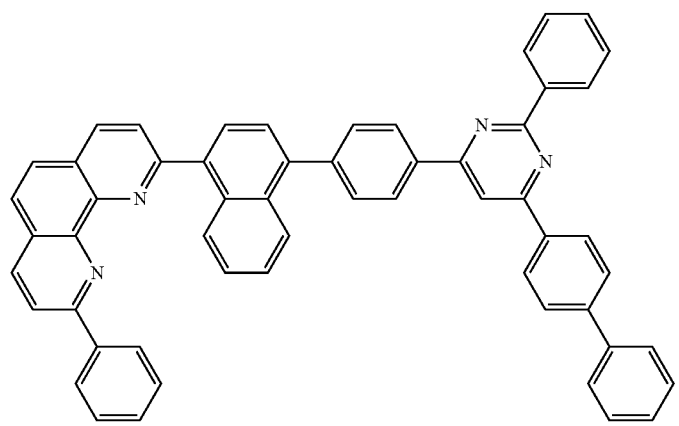
EN-166
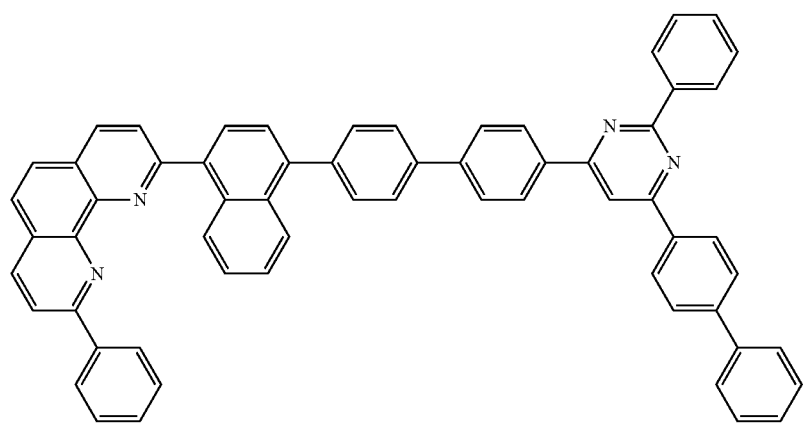
EN-167
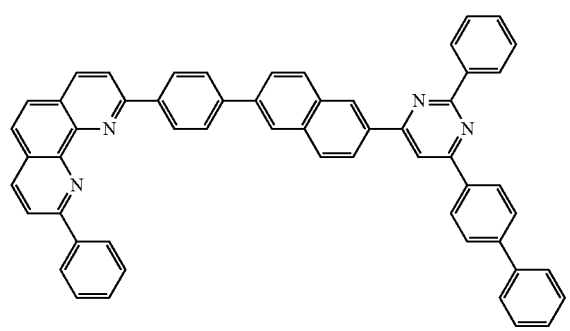
EN-168
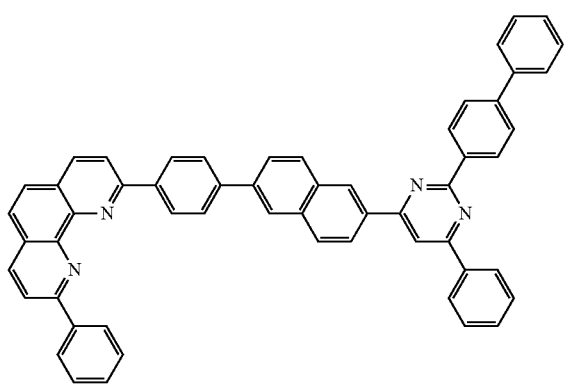
EN-173
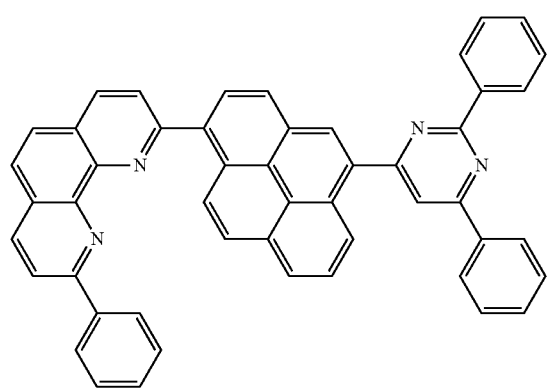
EN-174
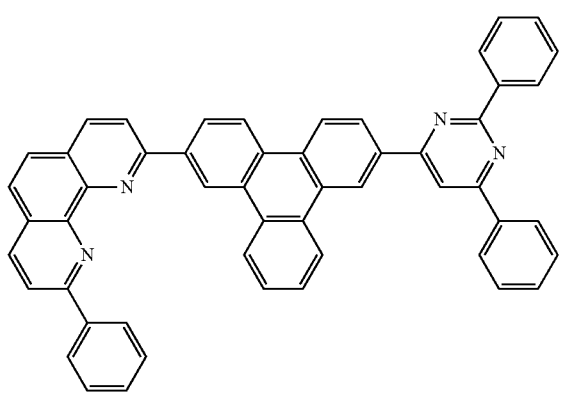

EN-175
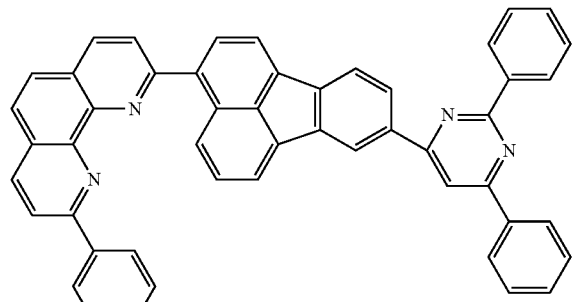
EN-176
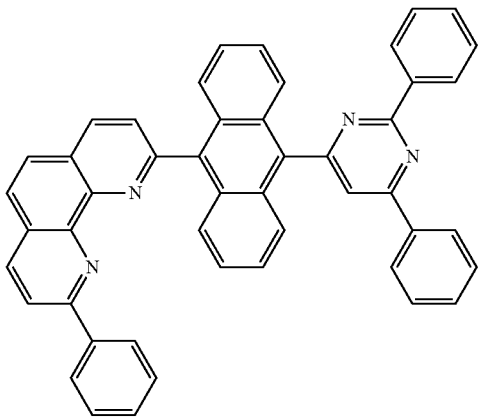
EN-177
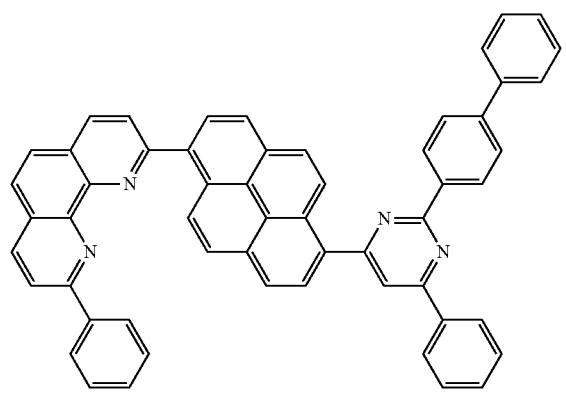
EN-178
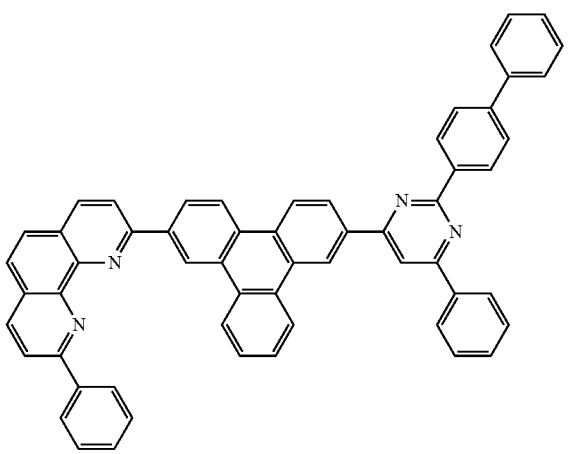
EN-179
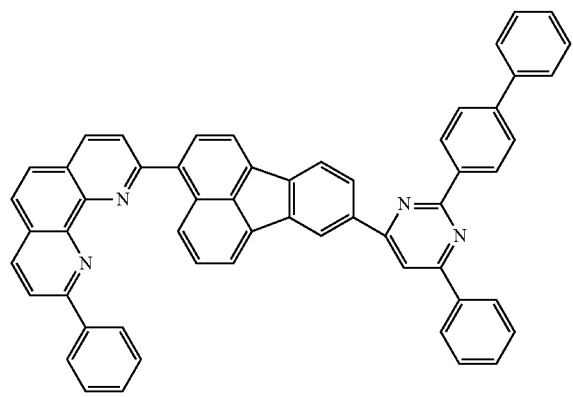
EN-180
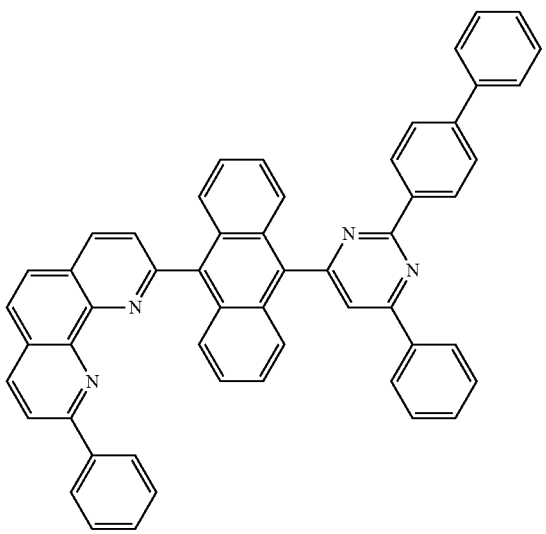

EN-181
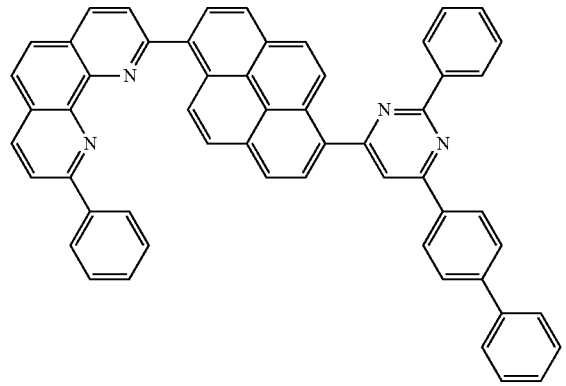
EN-182
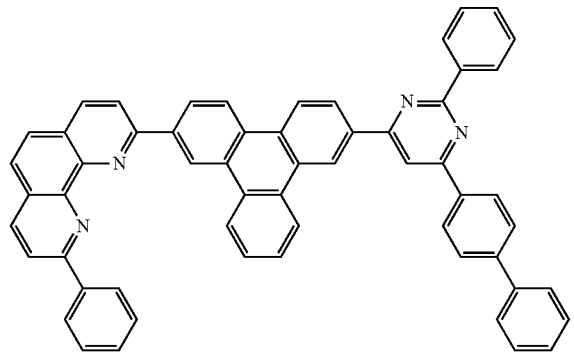
EN-183
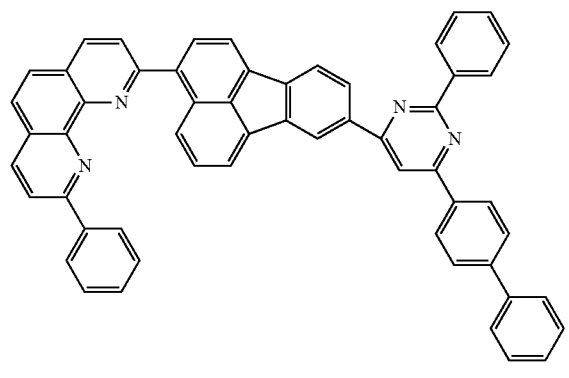
EN-184
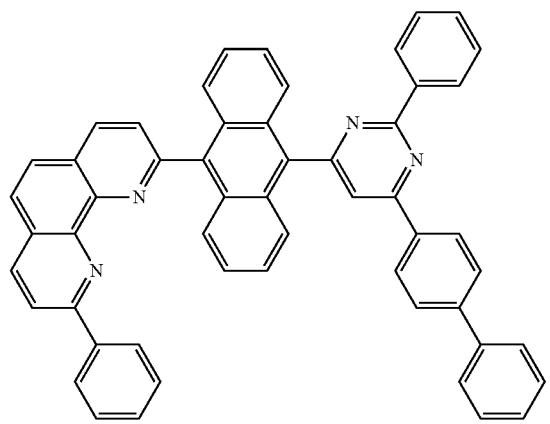
EN-185
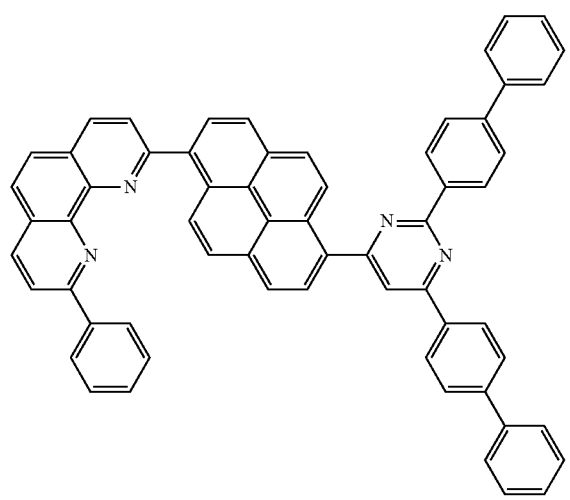
EN-186
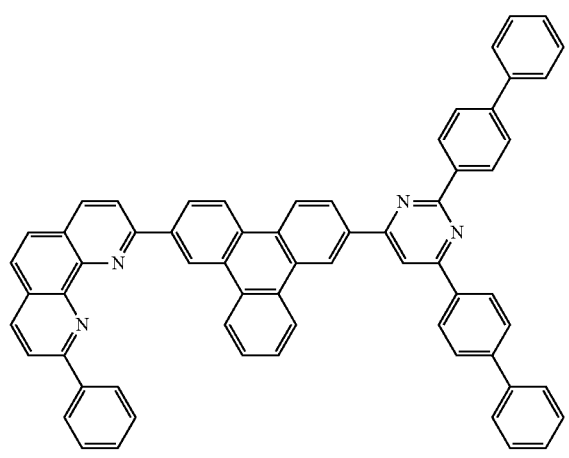

-continued
EN-187
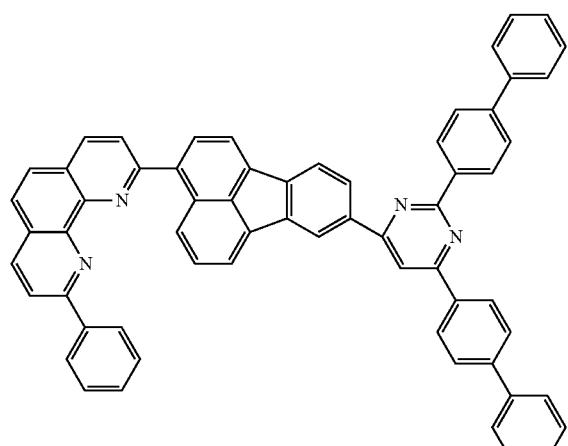
EN-188
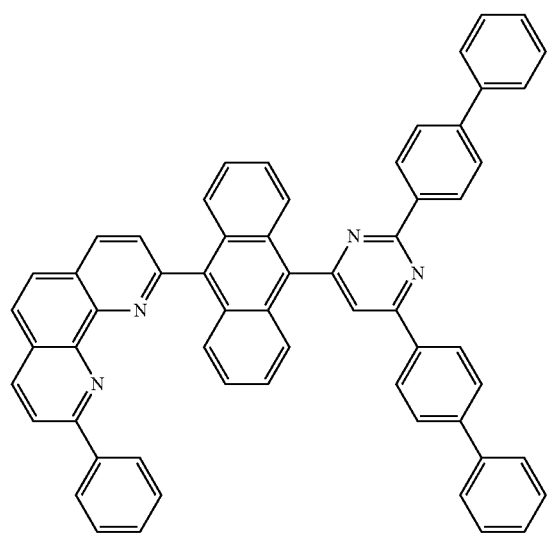
EN-189
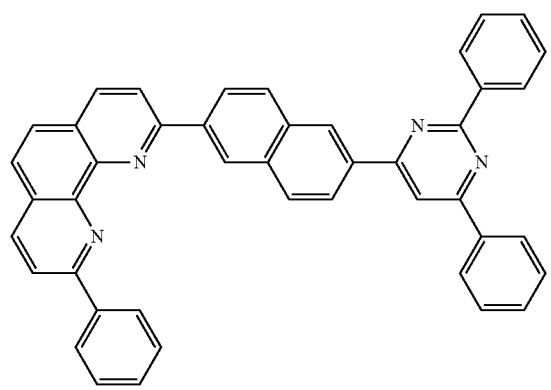
EN-190
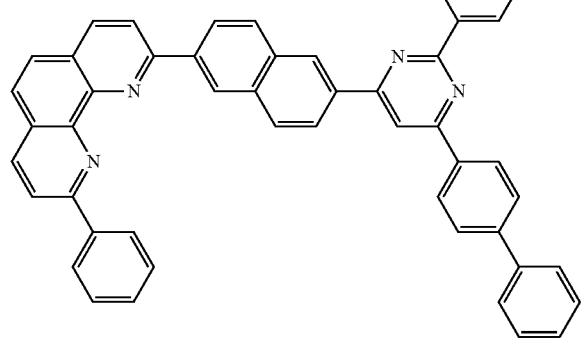
EN-191
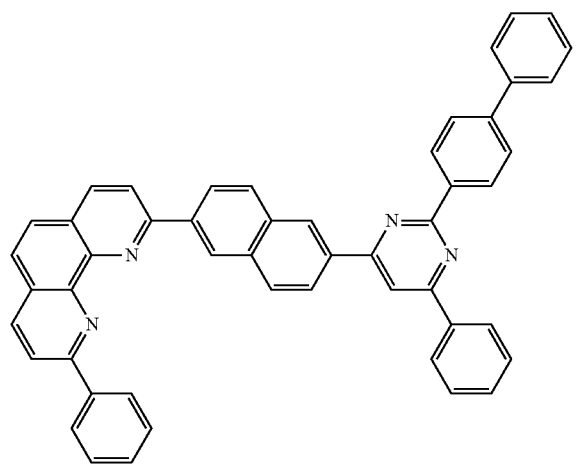
EN-192
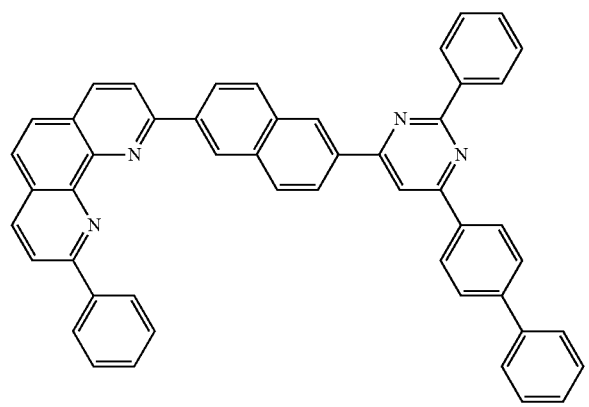

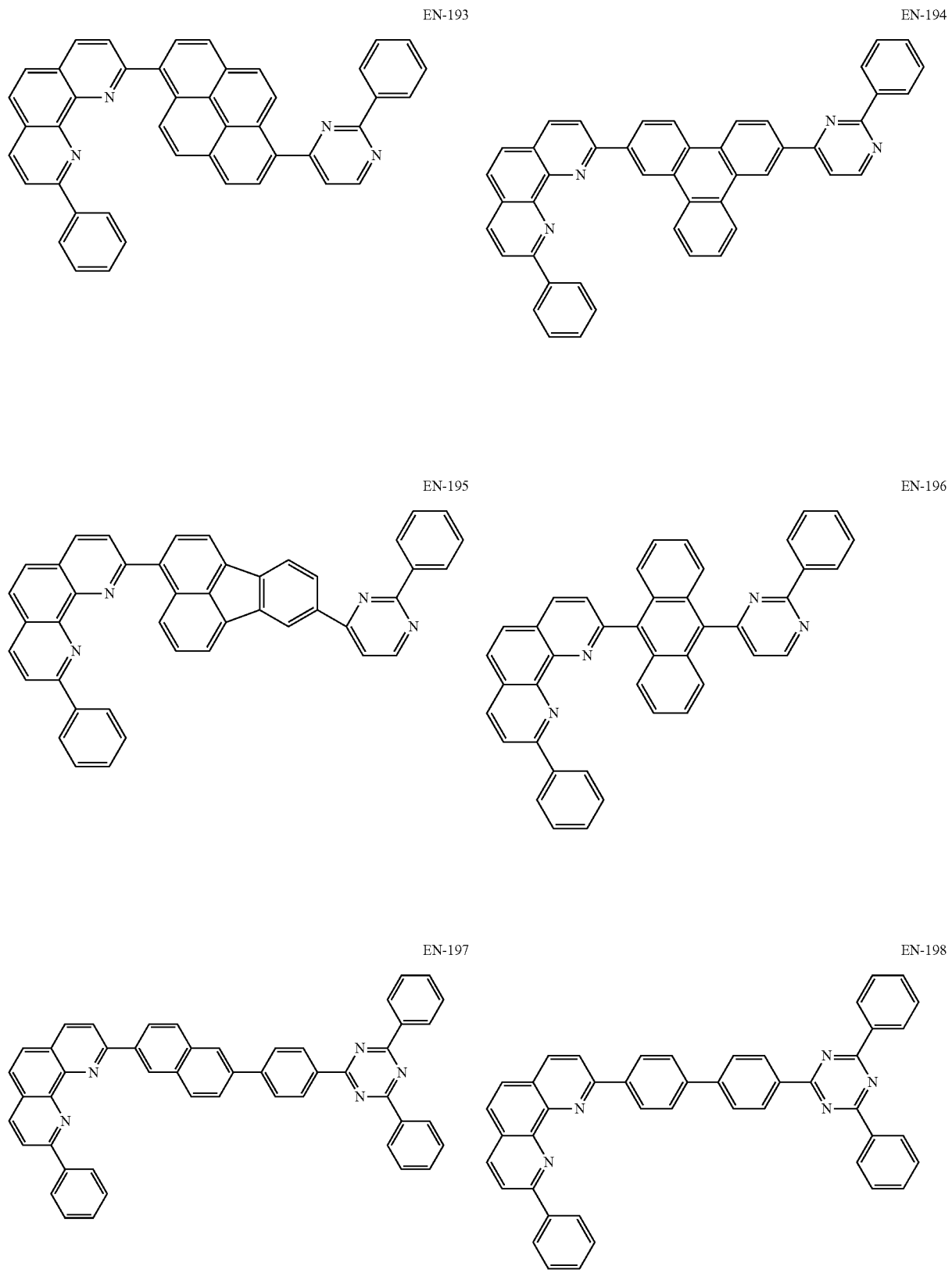

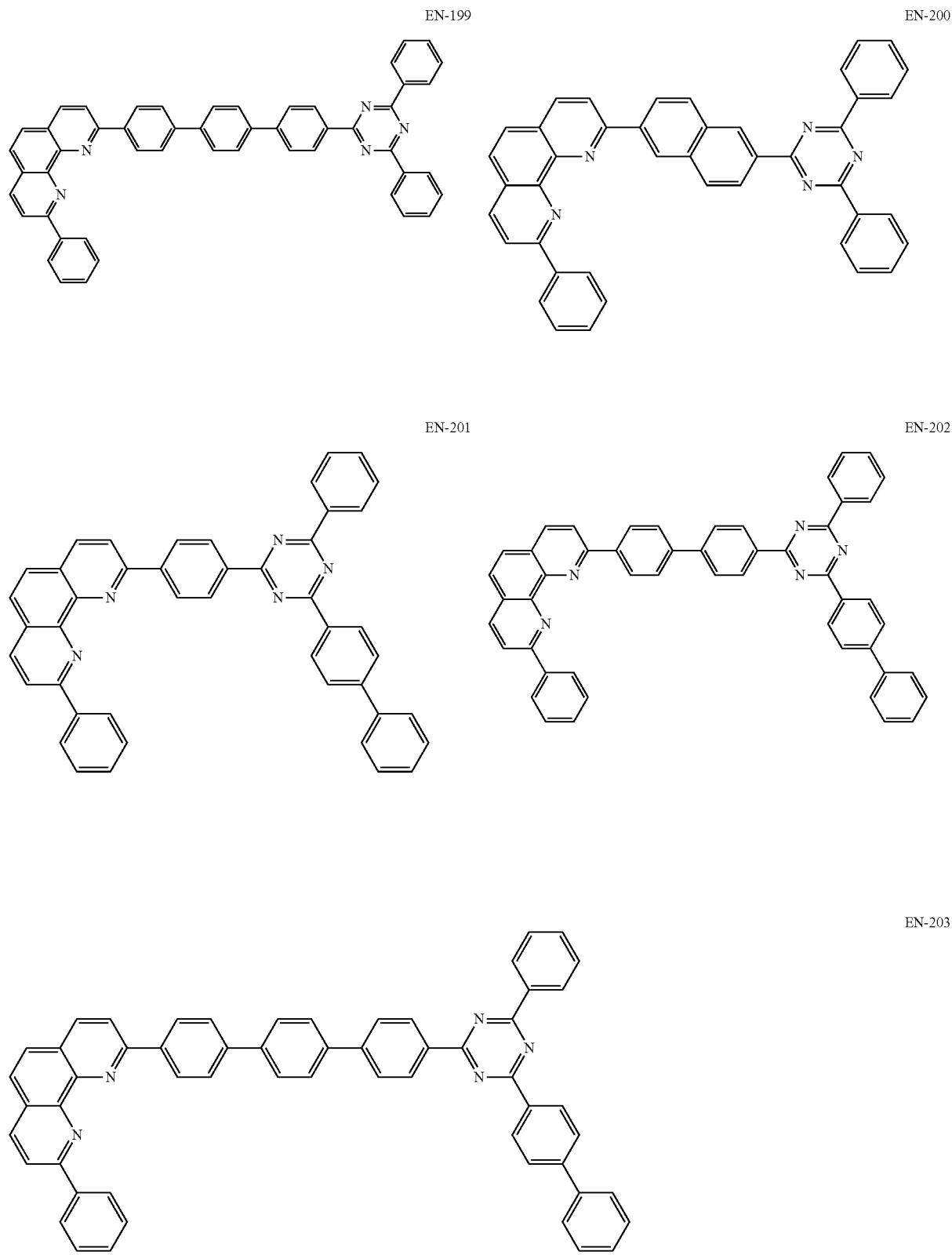

-continued
EN-204
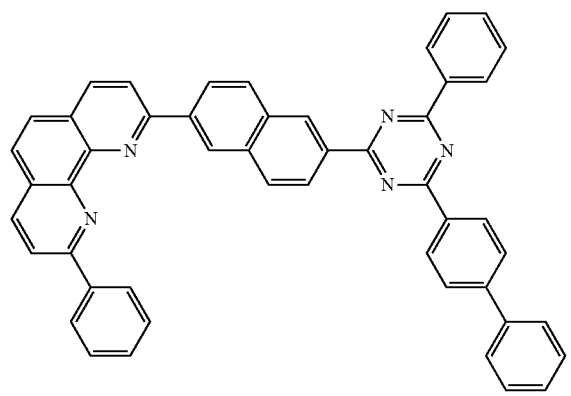
EN-205
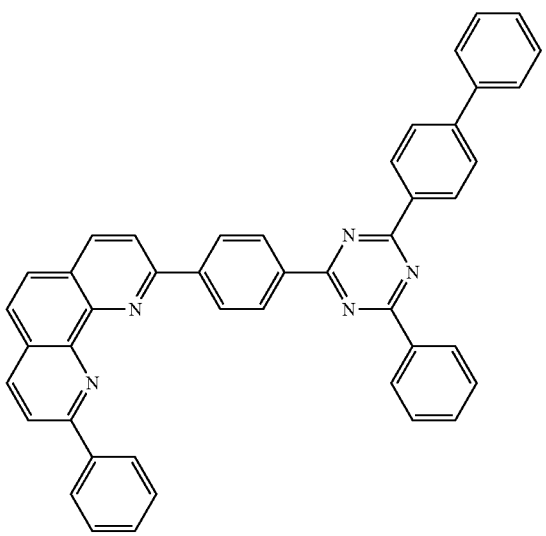
EN-206
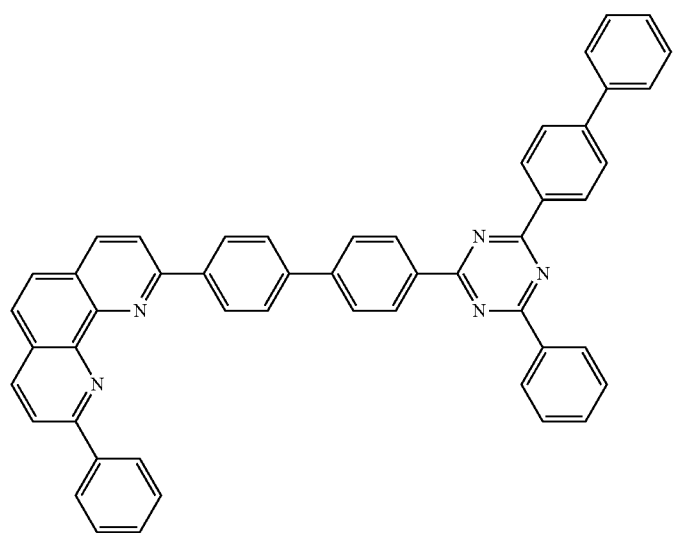
EN-207
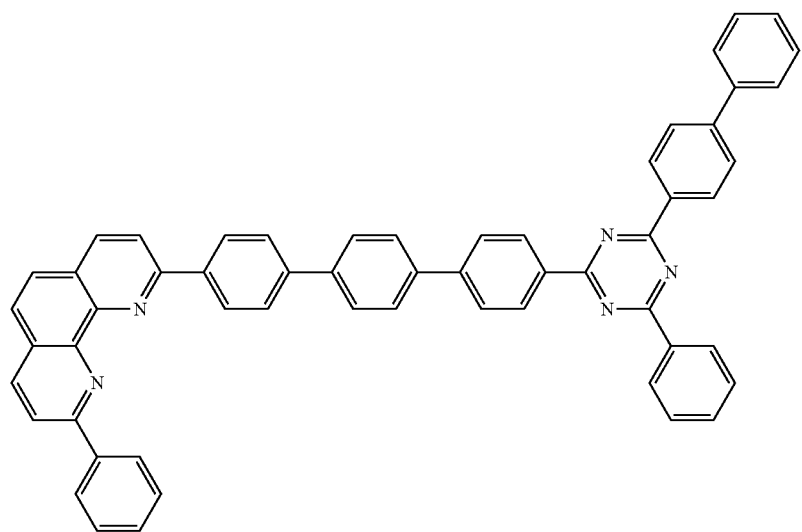

EN-208
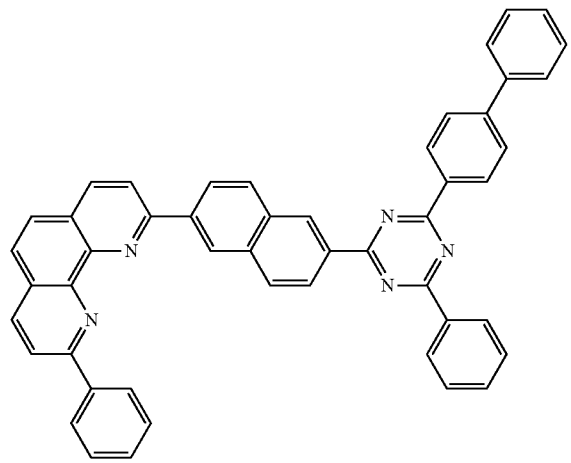
EN-209
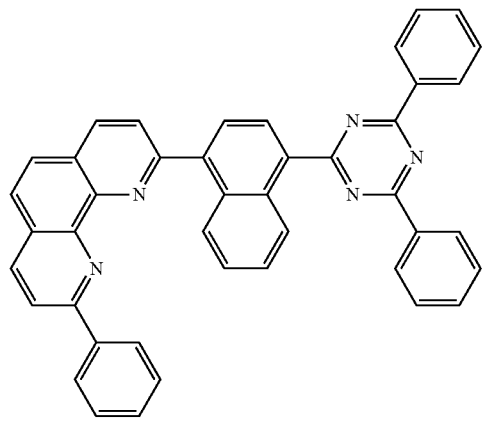
EN-210
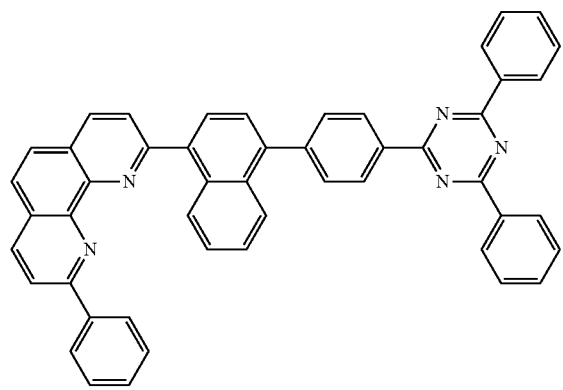
EN-211
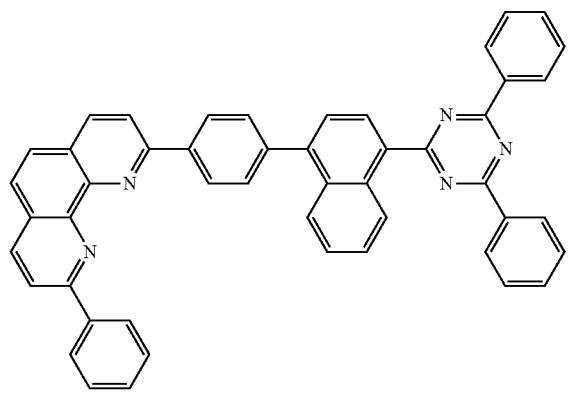
EN-212
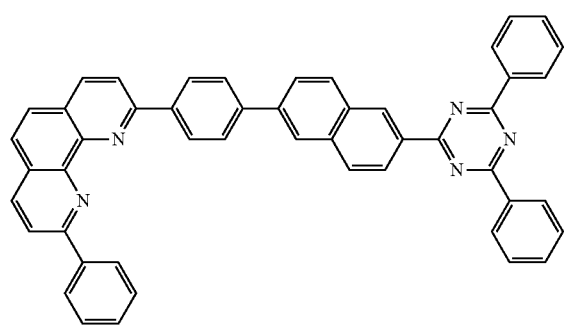
EN-213
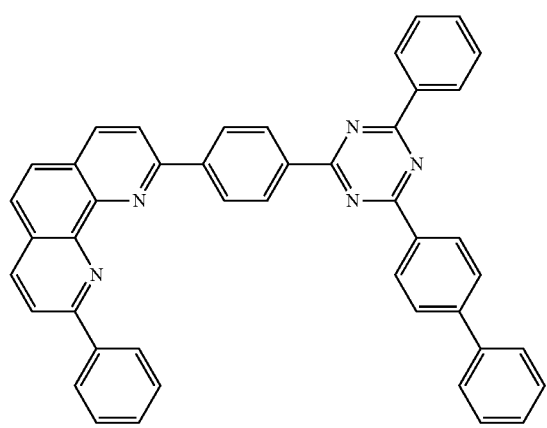

-continued
EN-214
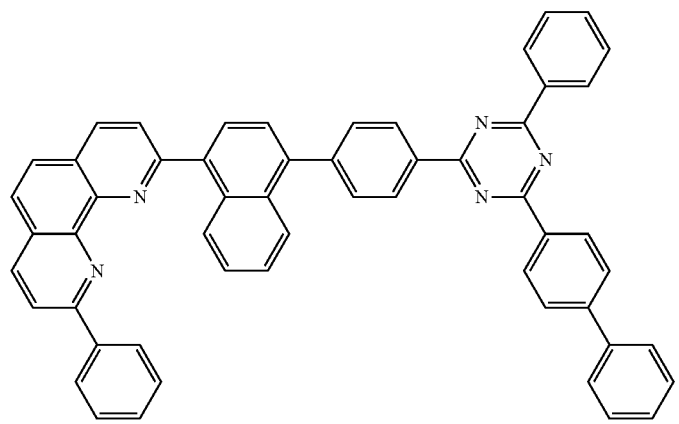
EN-215
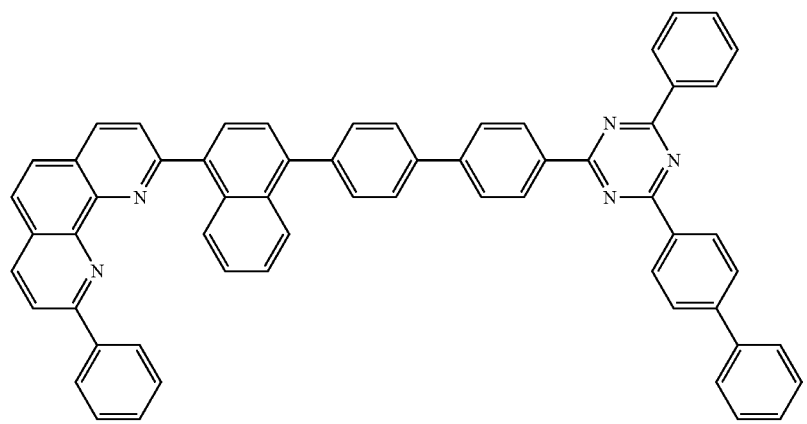
EN-216
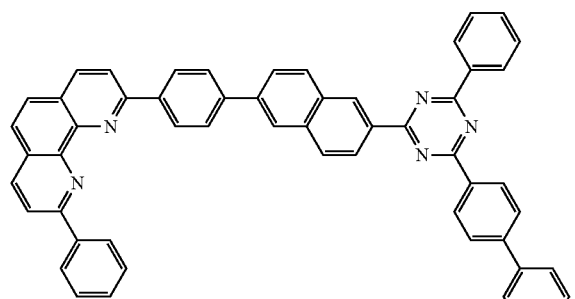
EN-217
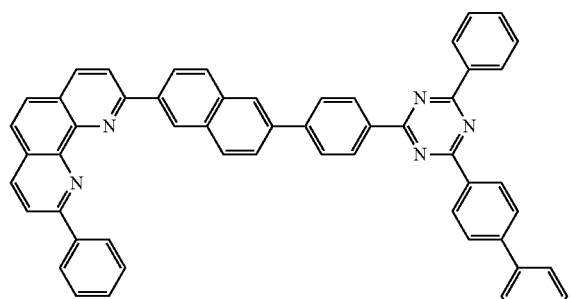
EN-218
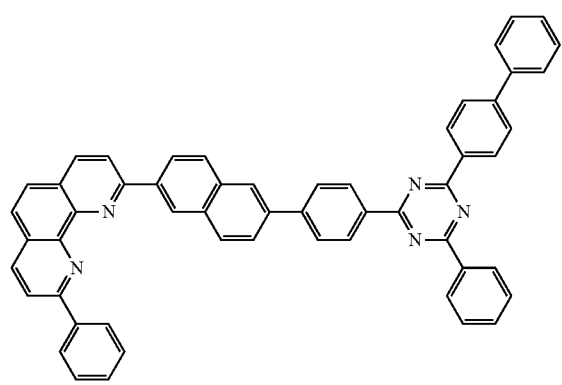
EN-219
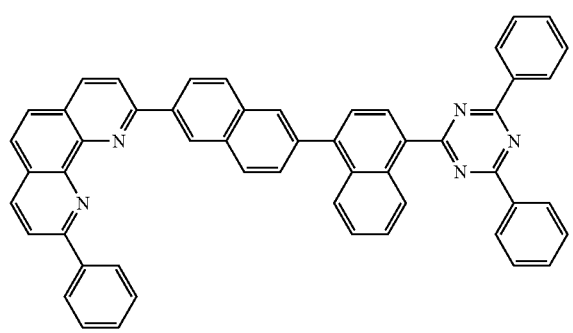

-continued
EN-220
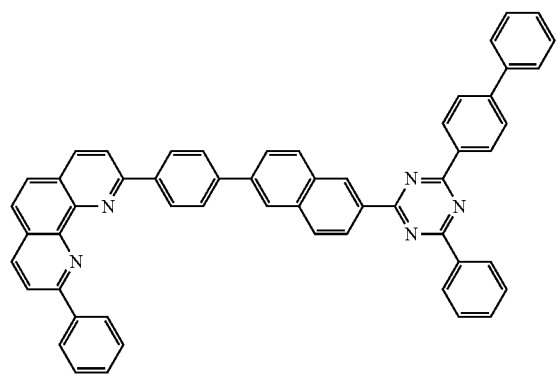
EN-222
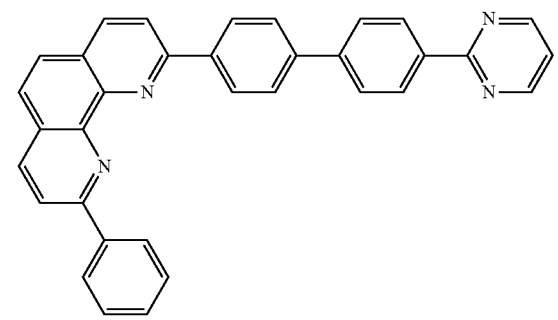
EN-223
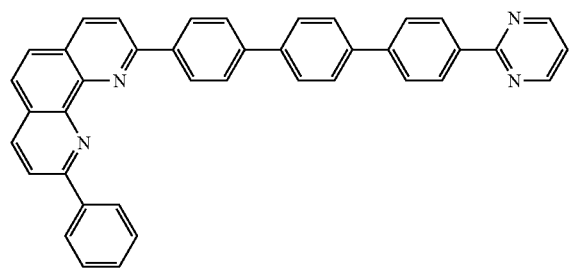
EN-224
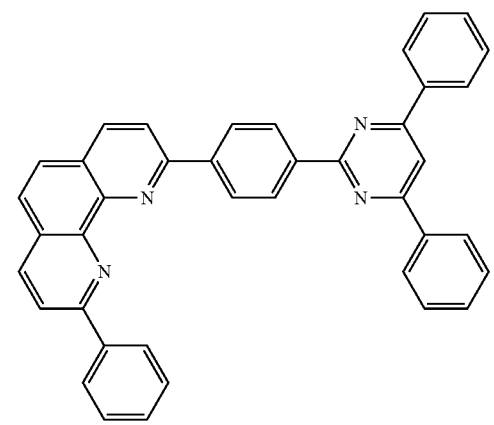
EN-226
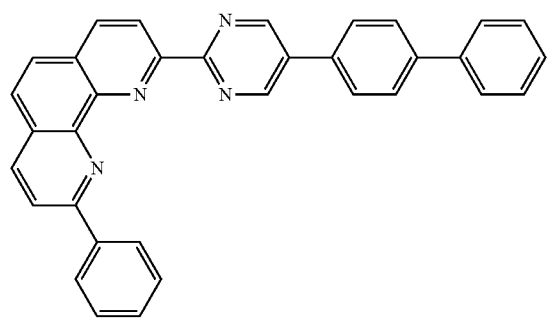
EN-227
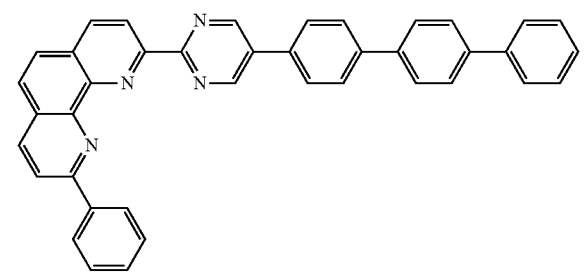
EN-228
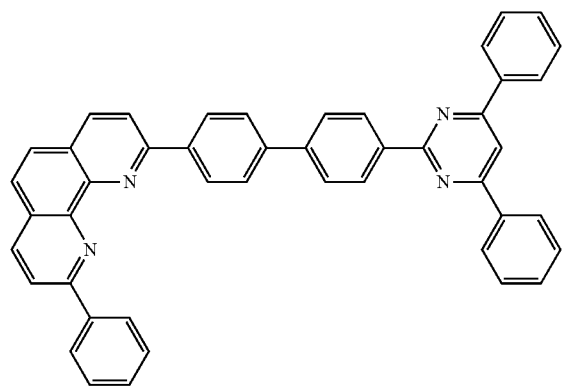
EN-230
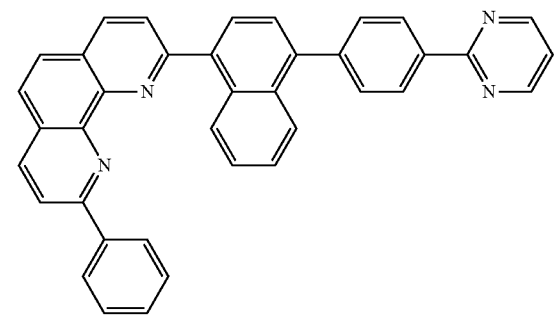

-continued
EN-231
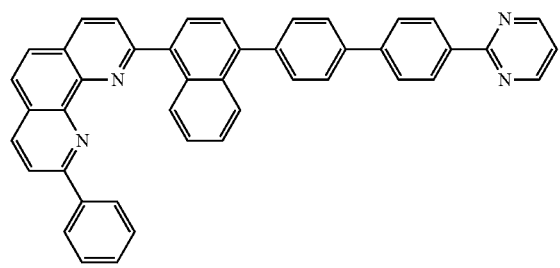
EN-232
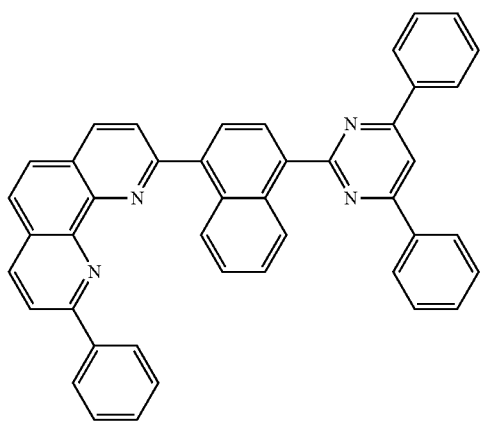
EN-234
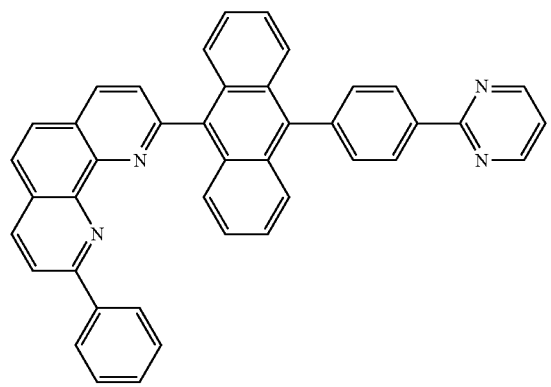
EN-235
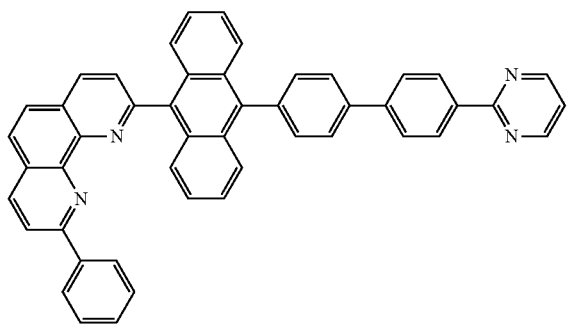
EN-236
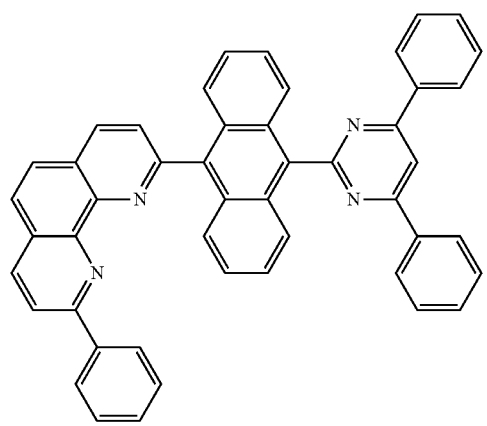
EN-237
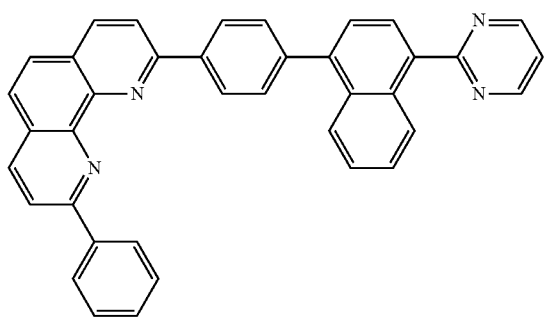
EN-238
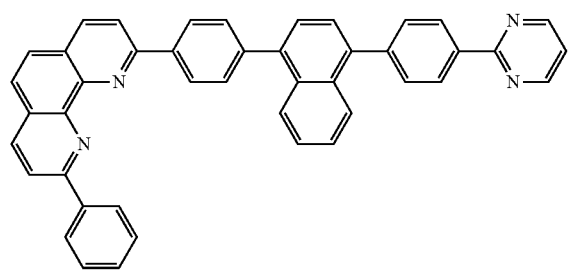
EN-239
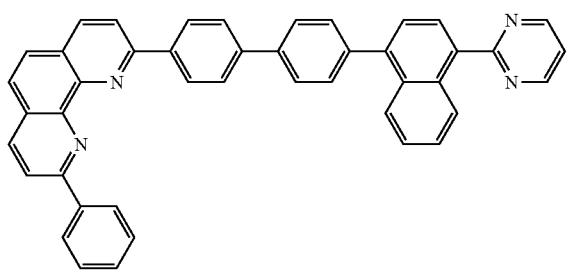

EN-240
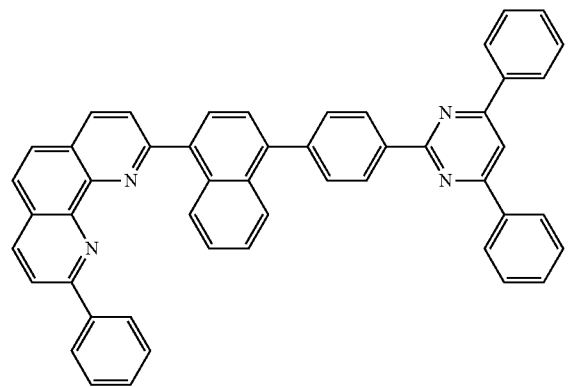
EN-241
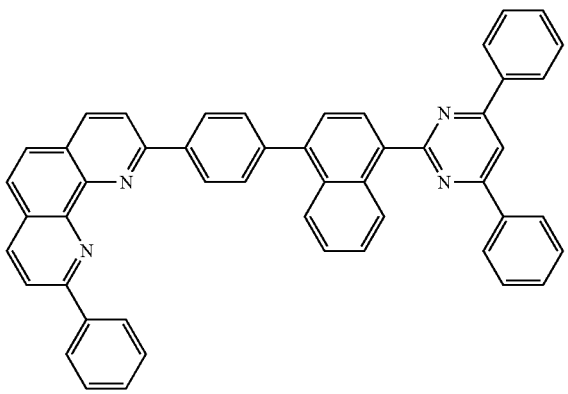
EN-242
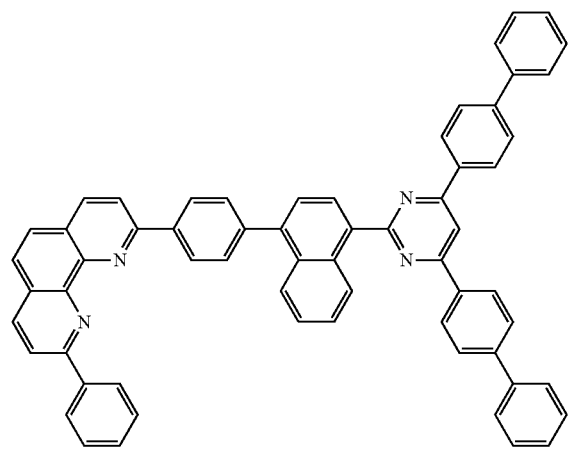
EN-243
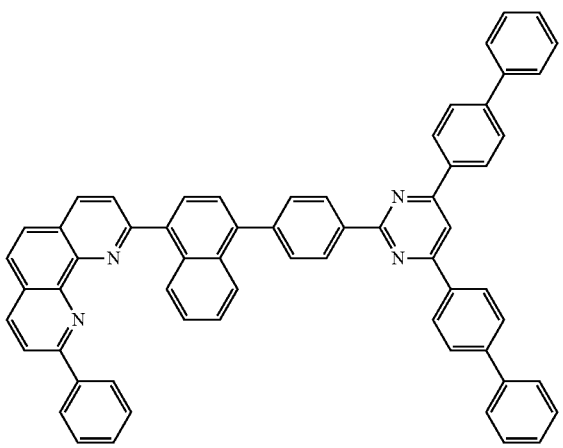
EN-244
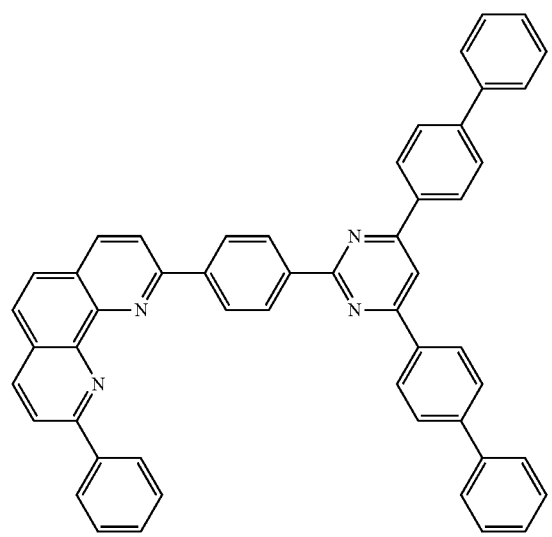
EN-245
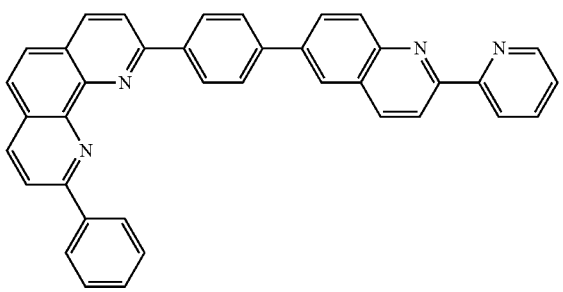

-continued
EN-246
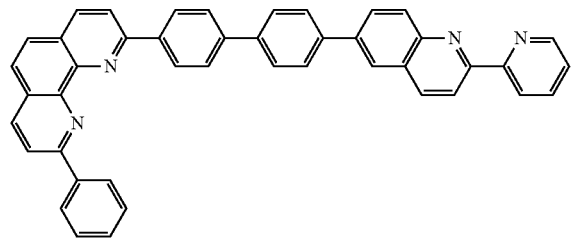
EN-247
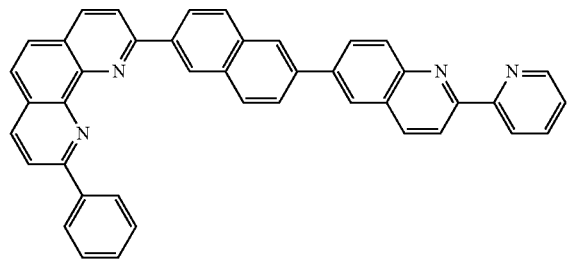
EN-248
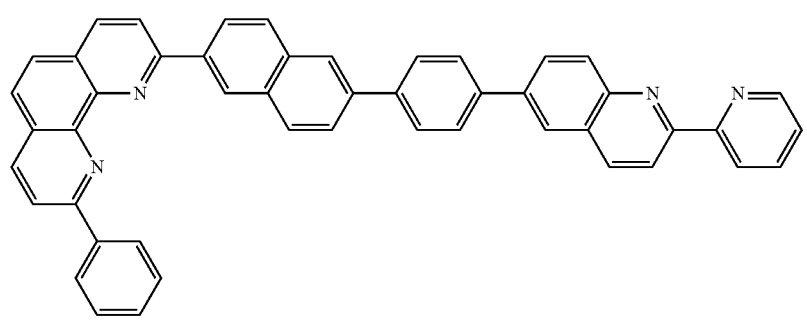
EN-249
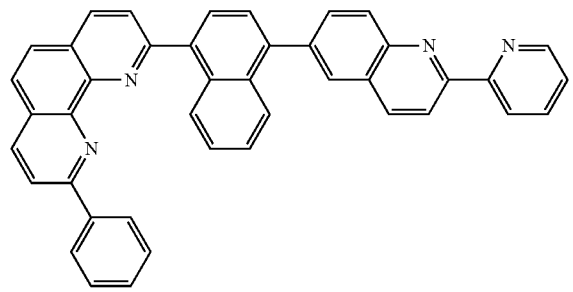
EN-250
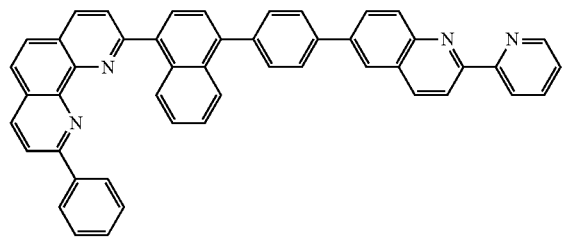
EN-251
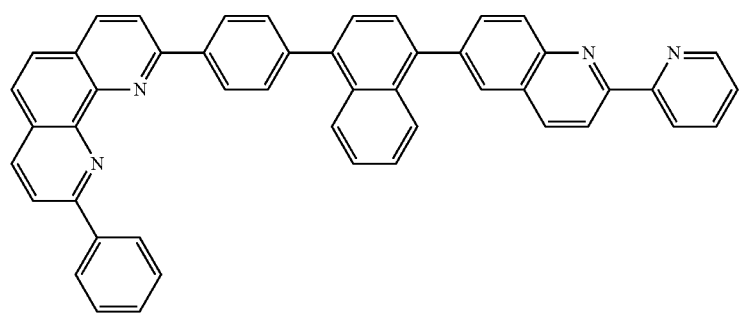
EN-252
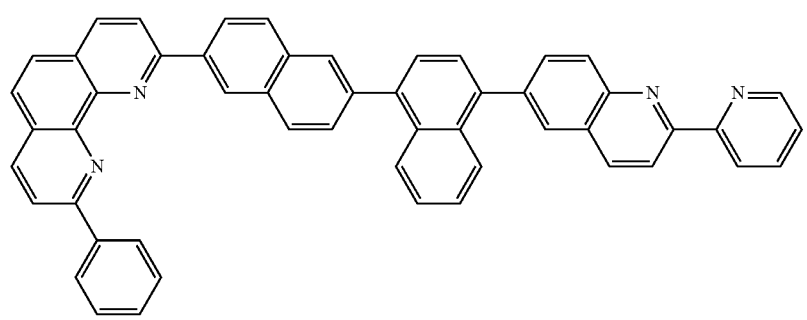

EN-254
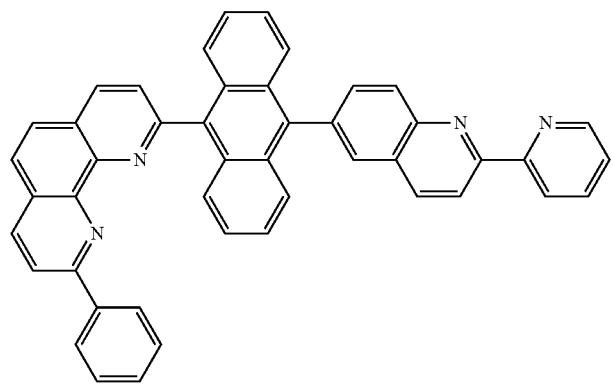
EN-255
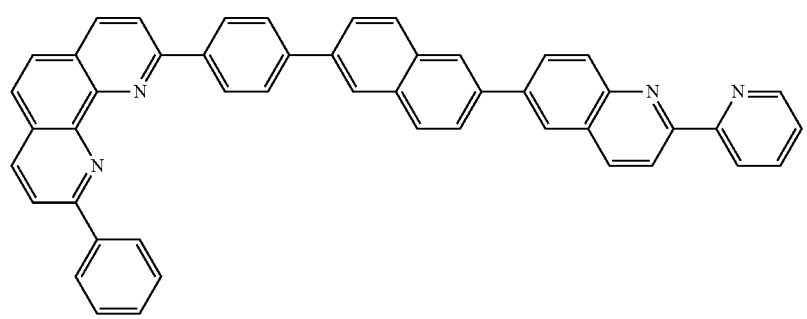
EN-256
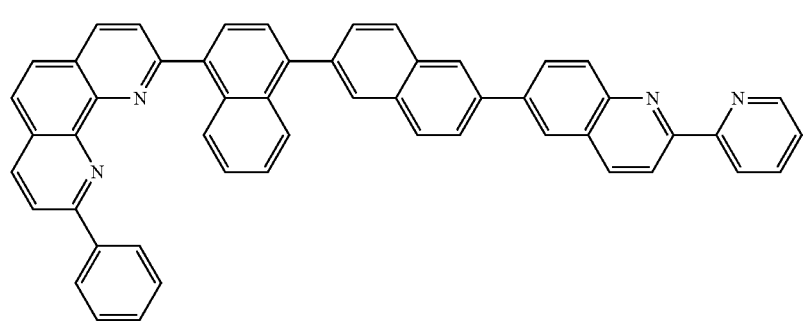
EN-258
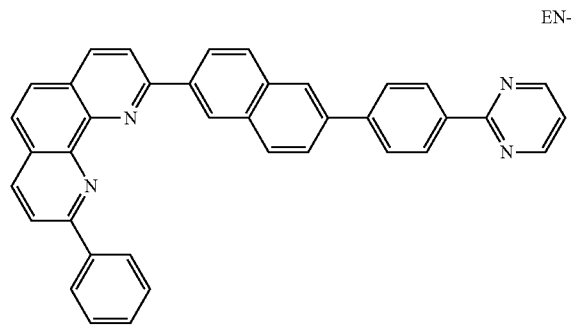
EN-259
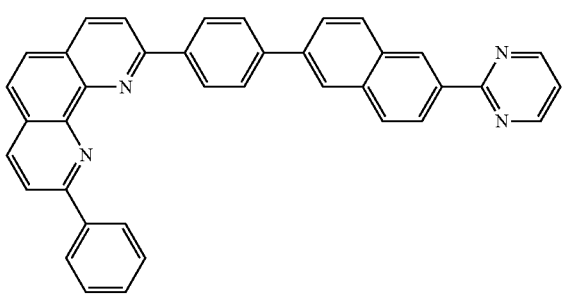

-continued
EN-260
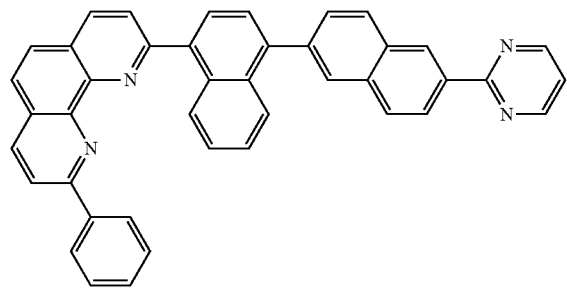
EN-261
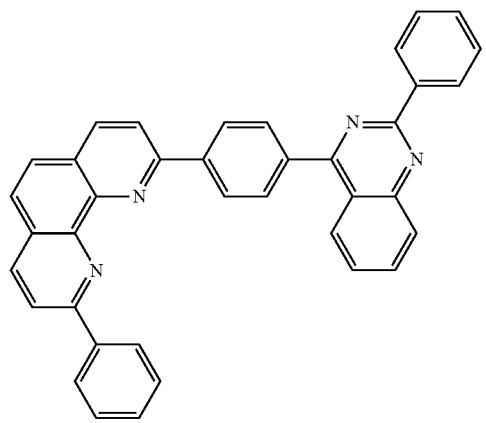
EN-262
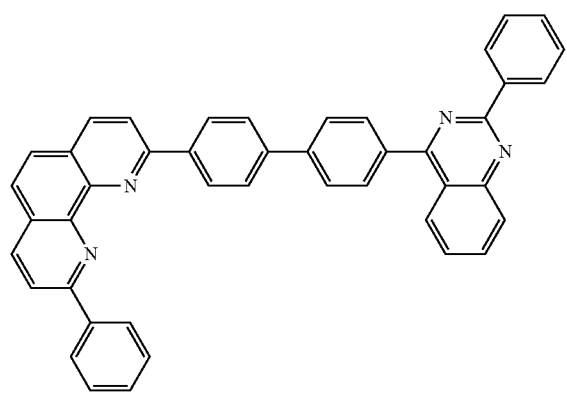
EN-263
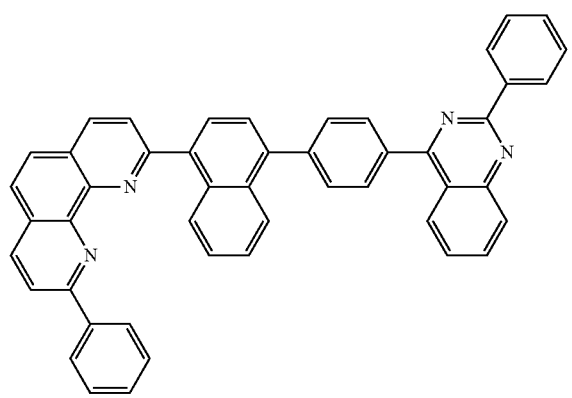
EN-264
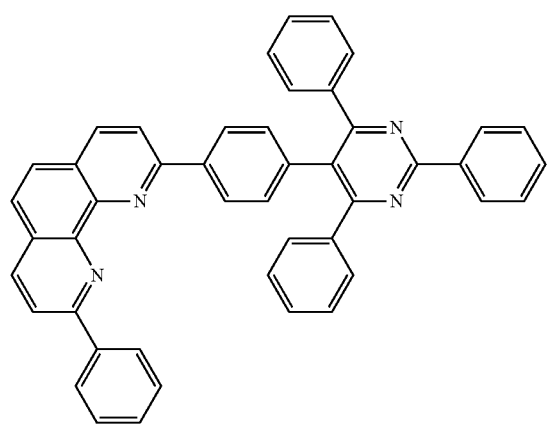
EN-265
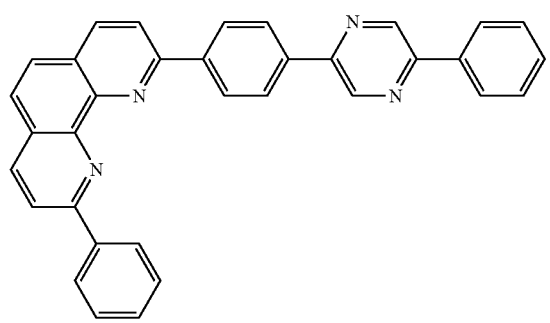
EN-266
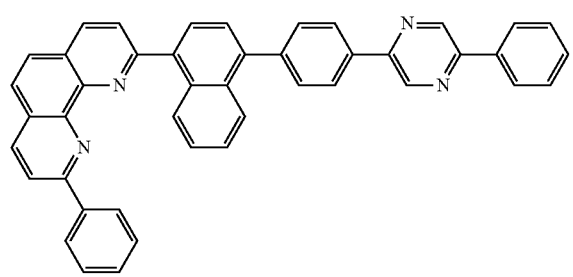
EN-267
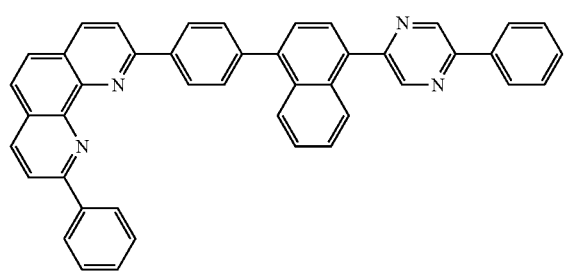

-continued
EN-268

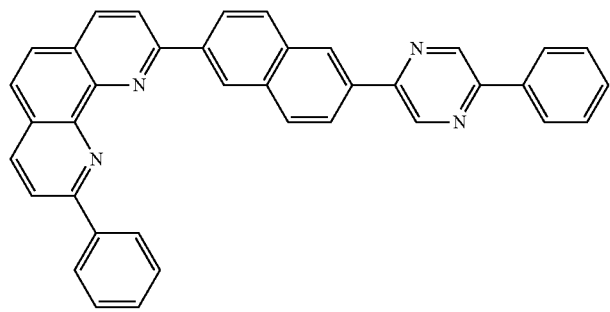

and wherein the driving element is connected to the first electrode.

6. The organic light emitting diode display device of claim 5, further comprising a color filter layer between the substrate and the first electrode.

7. The organic light emitting diode display device of claim 5, further comprising a color filter layer on the light emitting diode.

8. The light emitting diode of claim 2, wherein the organic compound is selected from:

EN-008

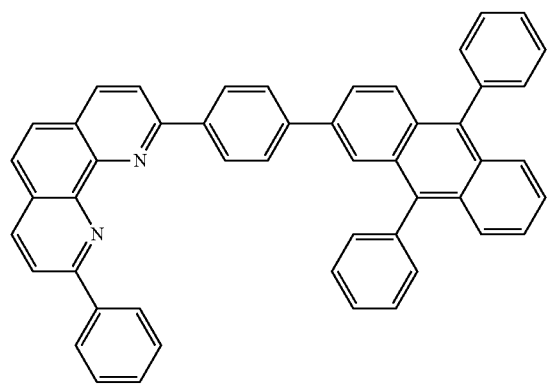

EN-012

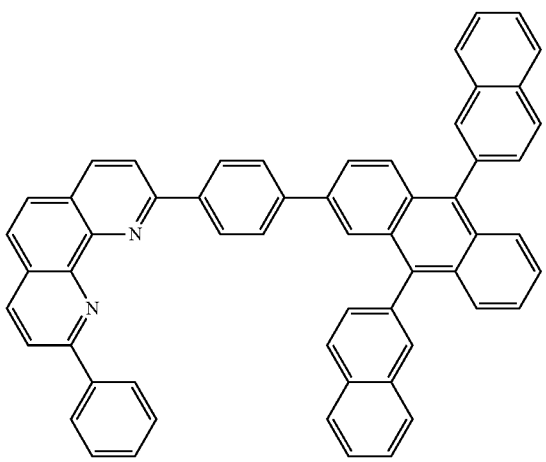

EN-020

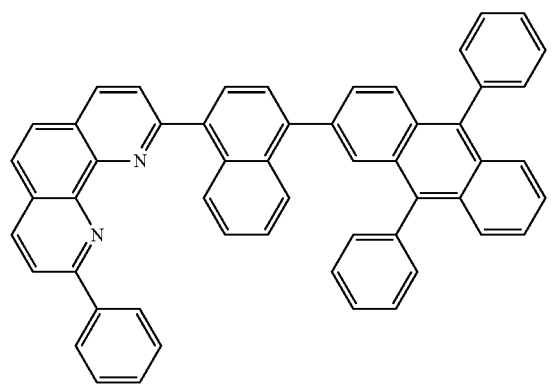

EN-024

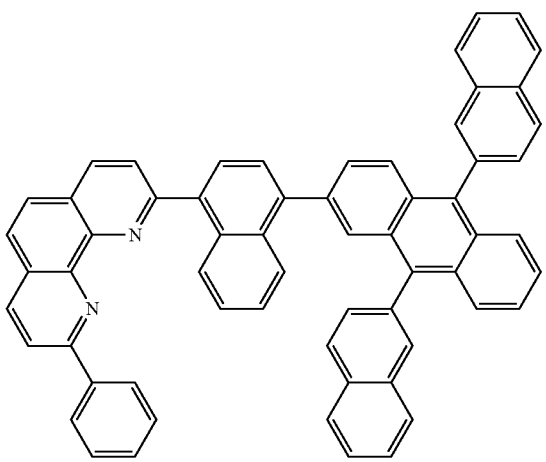

-continued
EN-025
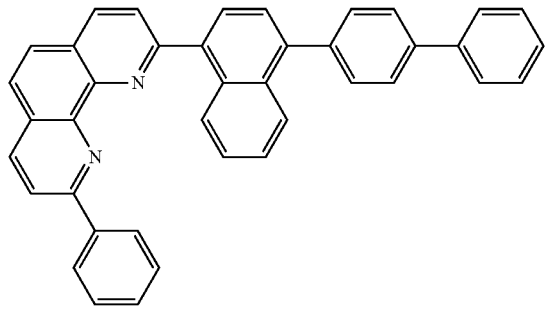
EN-026
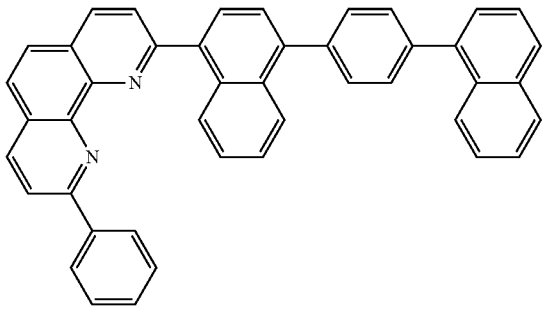
EN-027
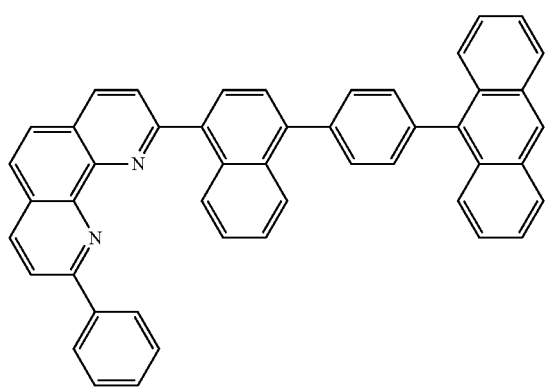
EN-028
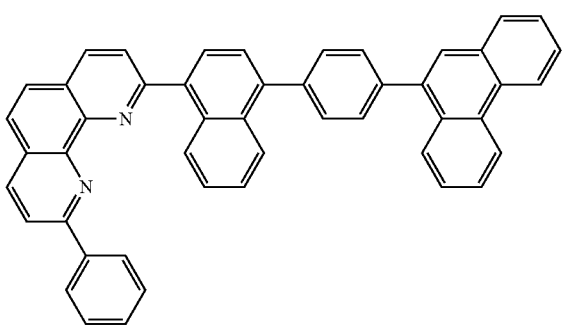
EN-029
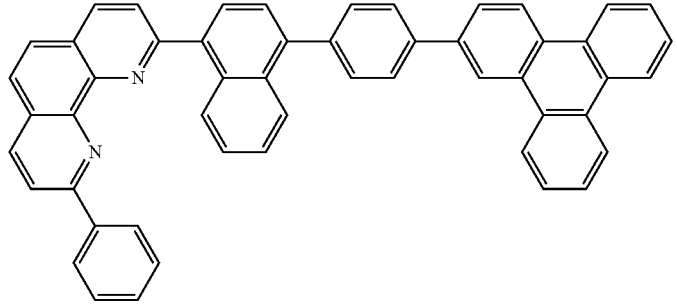
EN-030
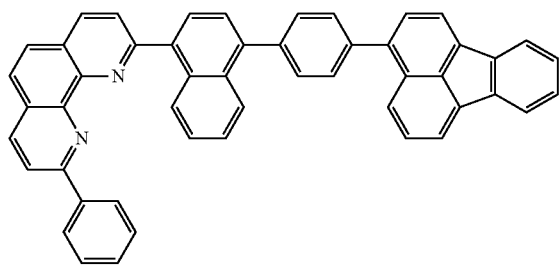
EN-031
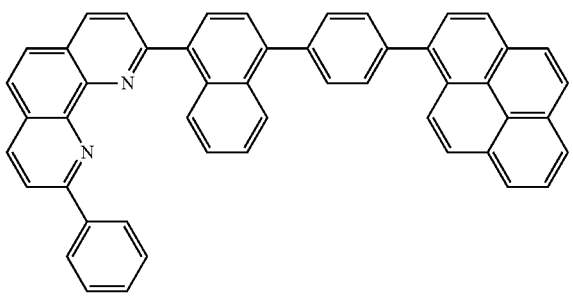

-continued
EN-032
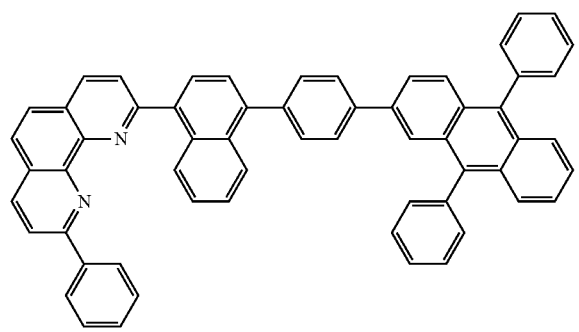
EN-033
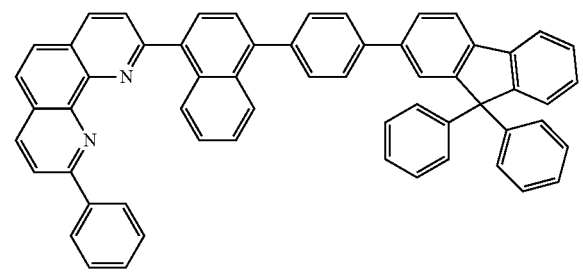
EN-034
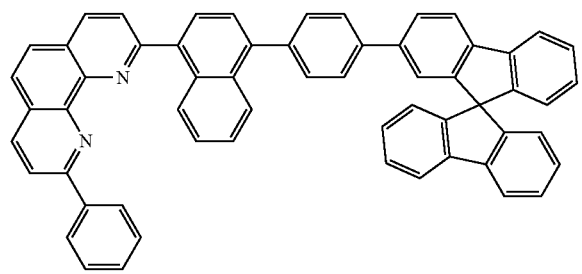
EN-035
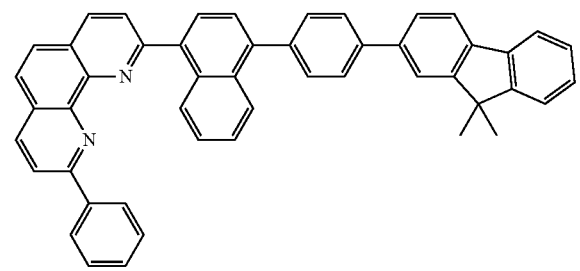
EN-036
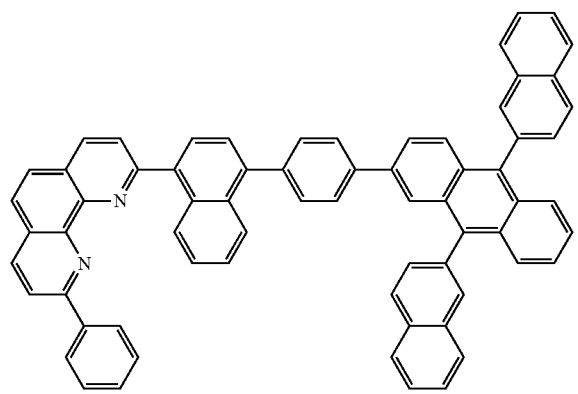
EN-037
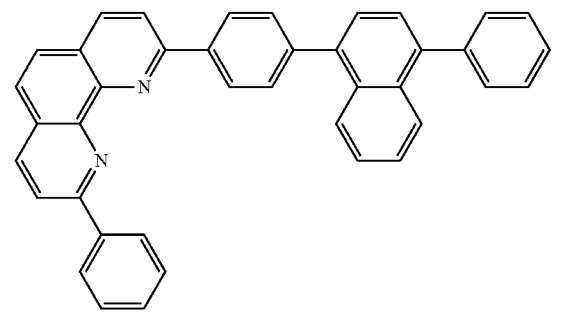
EN-038
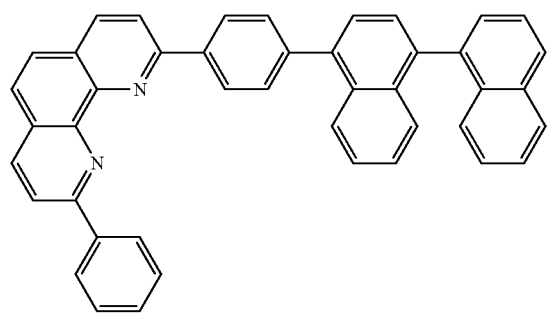
EN-039
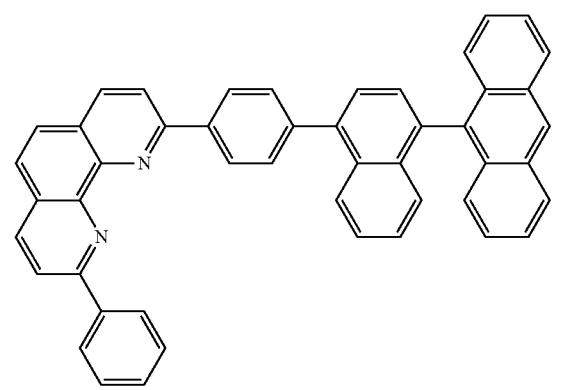

-continued
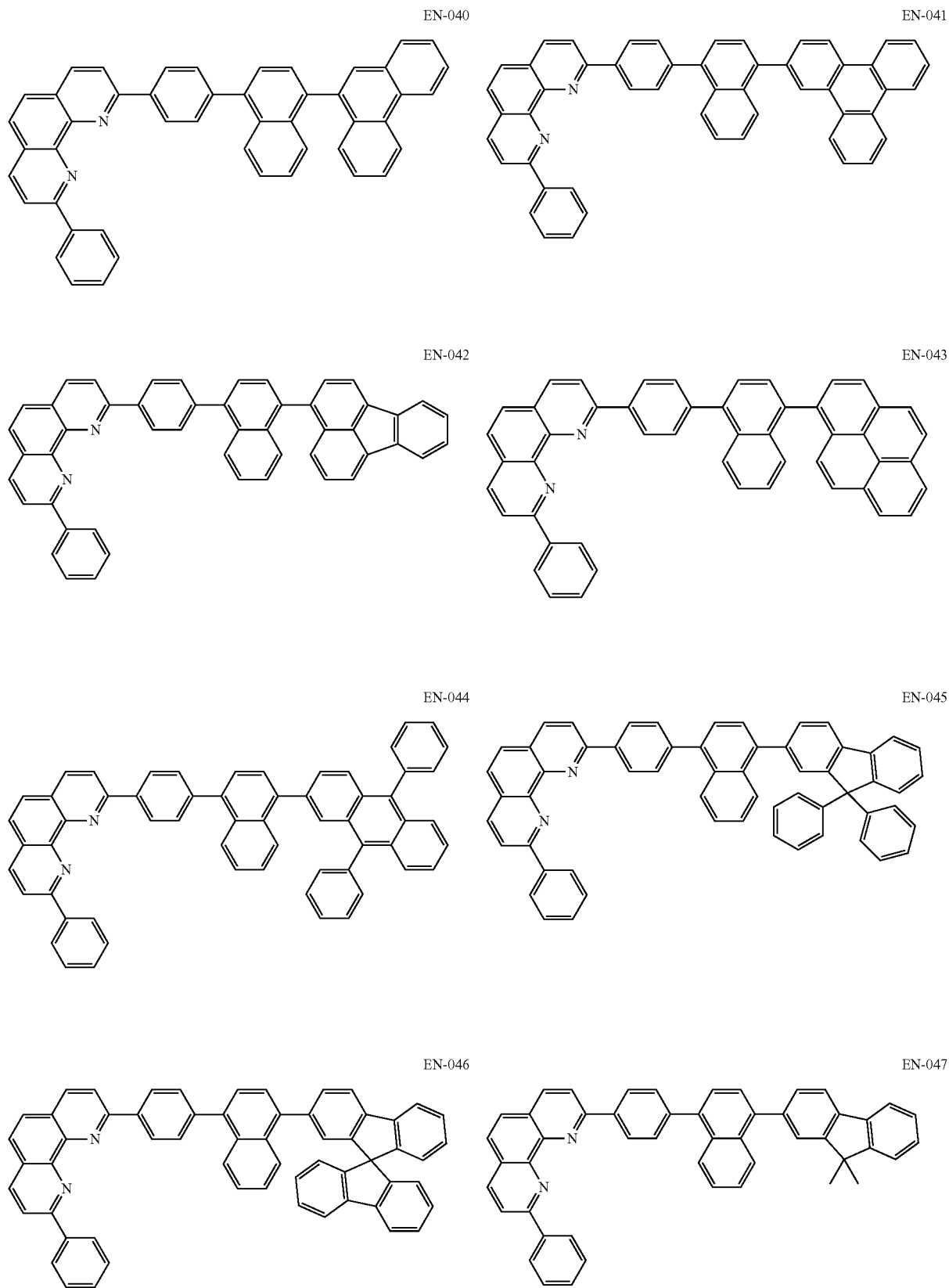

-continued
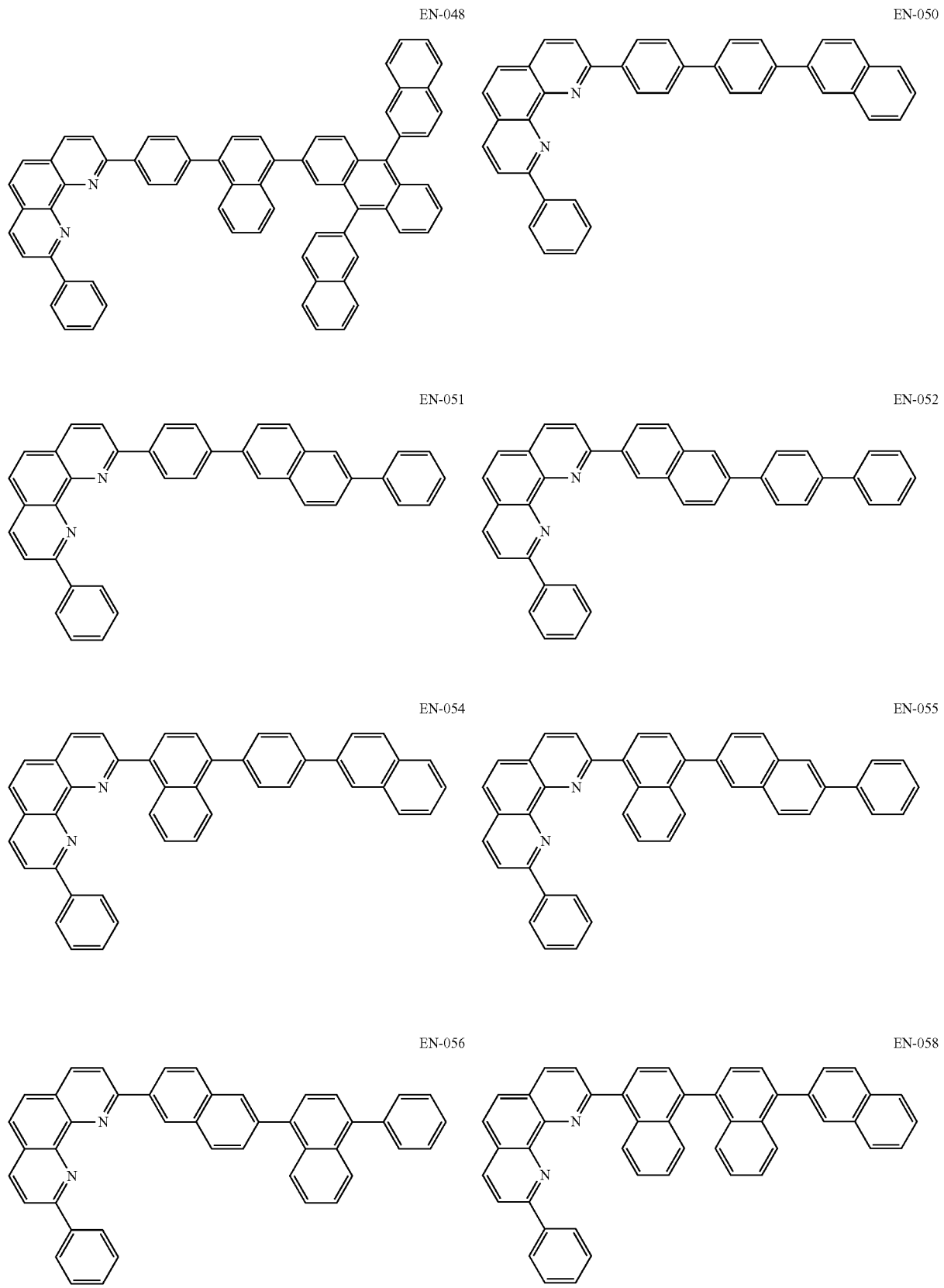

-continued
EN-059
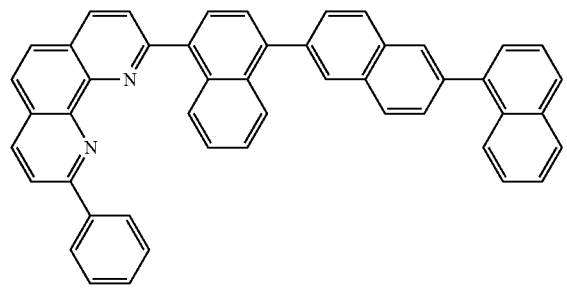
EN-060
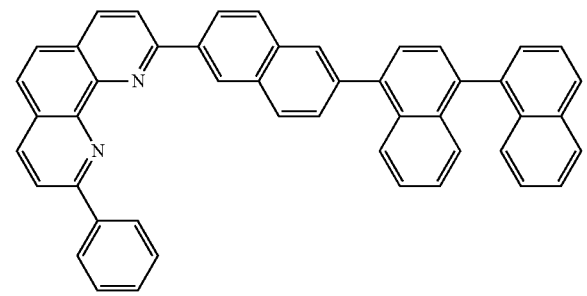
EN-061
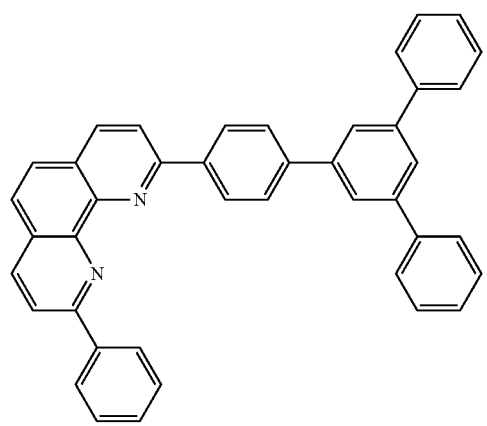
EN-062
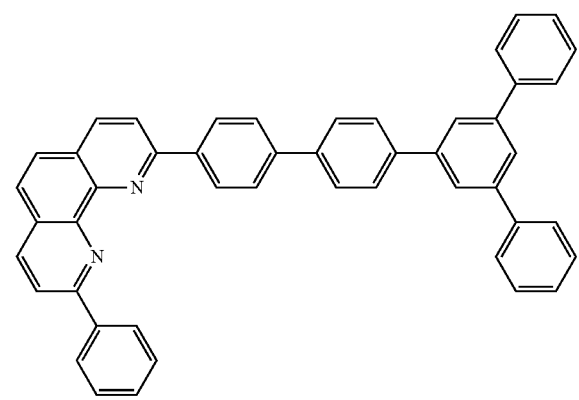
EN-063
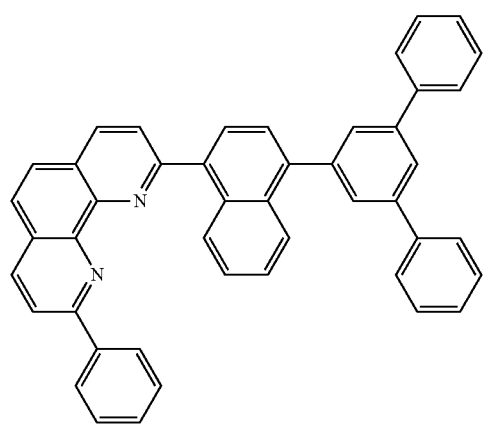
EN-064
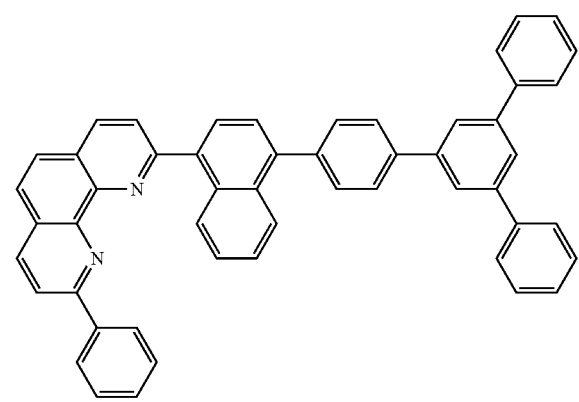
EN-065
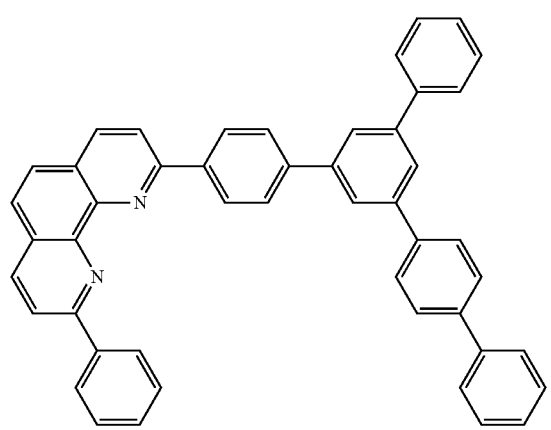
EN-066
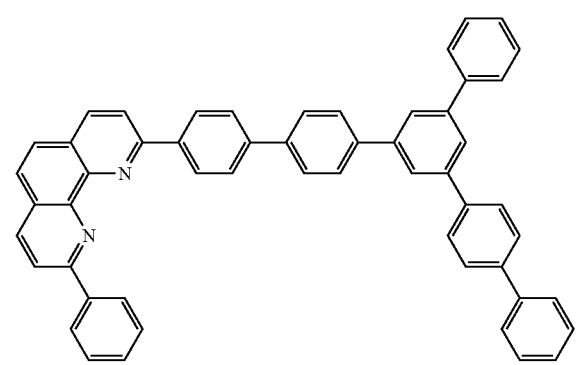

-continued
EN-067
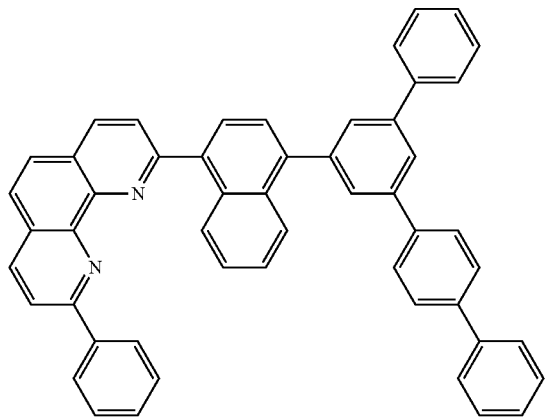
EN-068
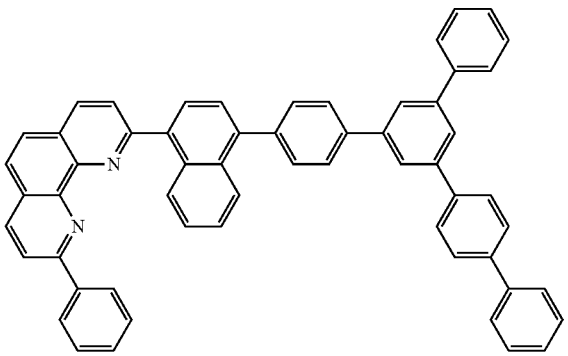
EN-069
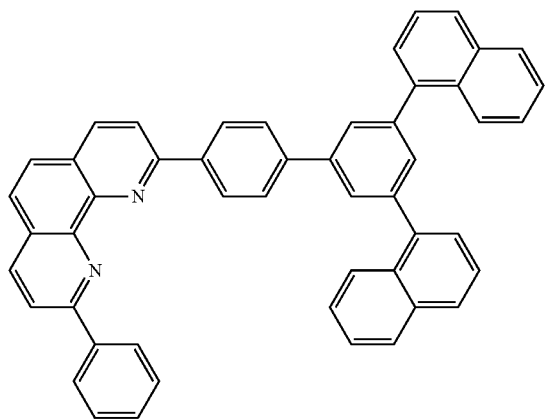
EN-070
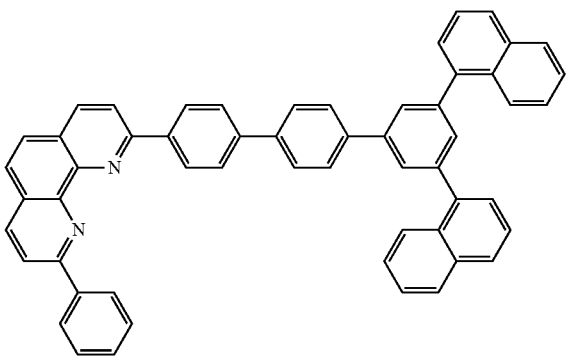
EN-071
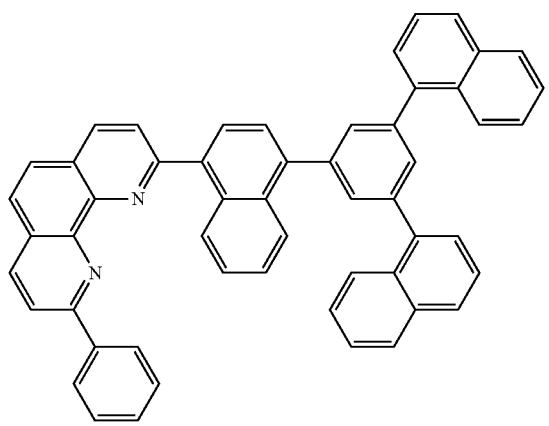
EN-072
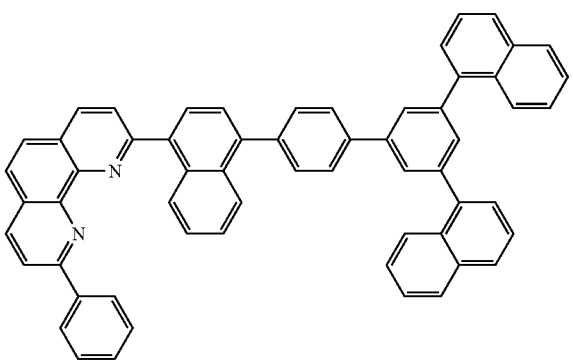

-continued
EN-080
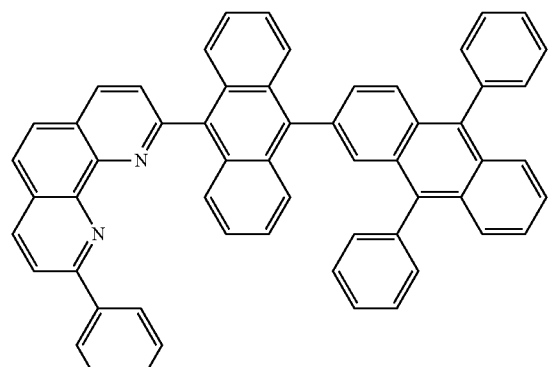
EN-084
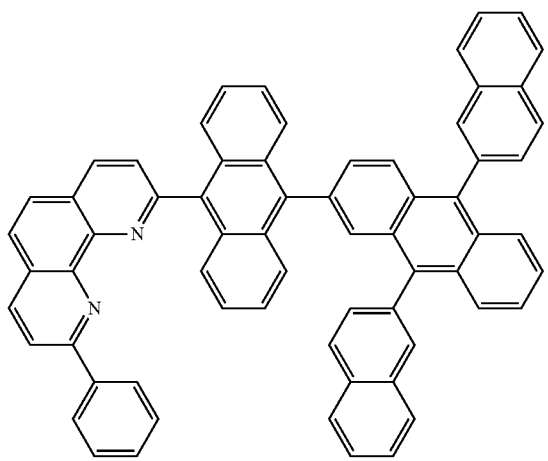
EN-085
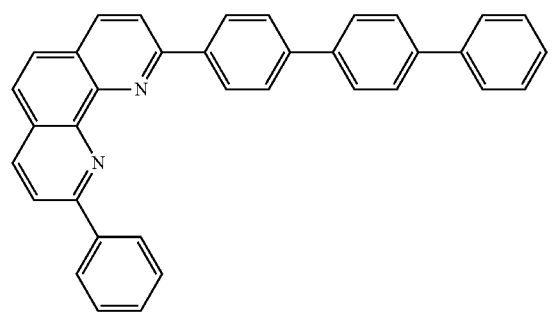
EN-086
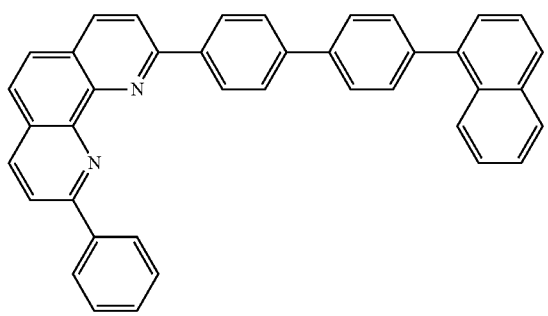
EN-087
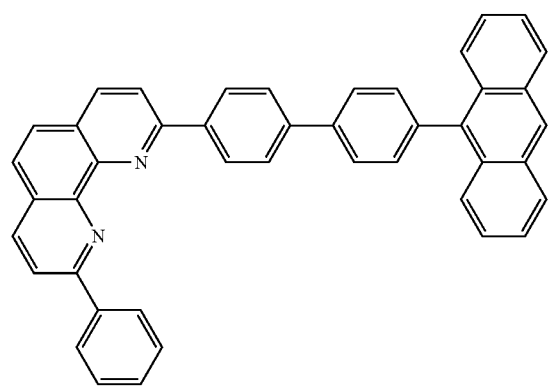
EN-088
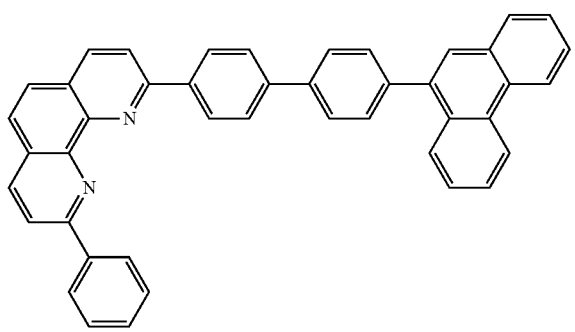
EN-089
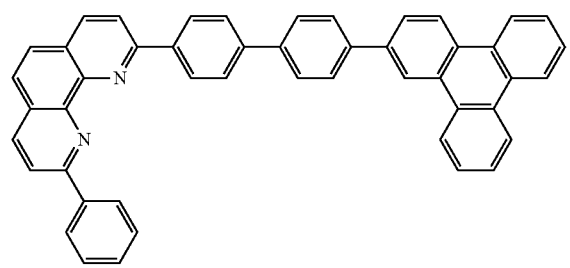
EN-090
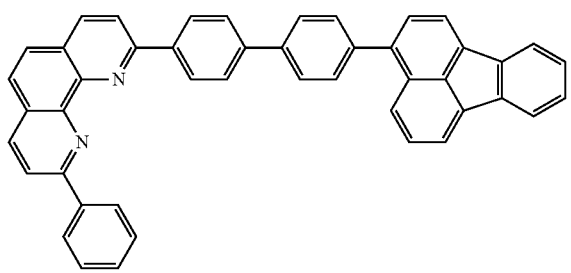

-continued
EN-091
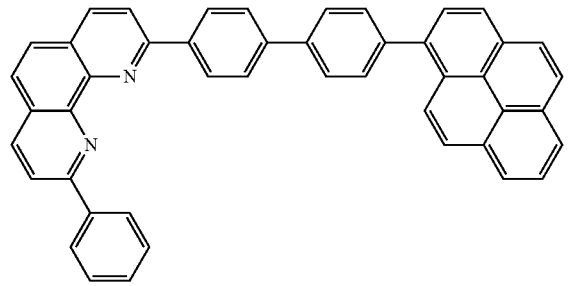
EN-092
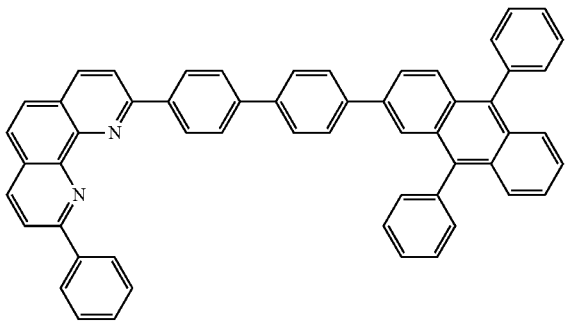
EN-093
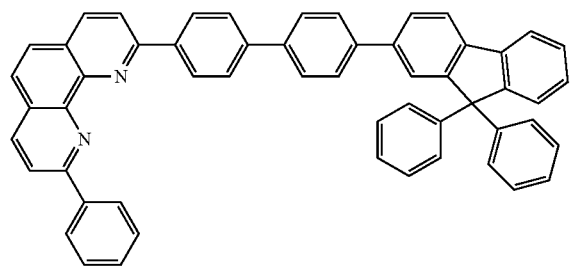
EN-094
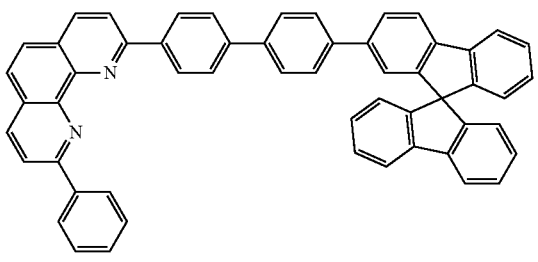
EN-095
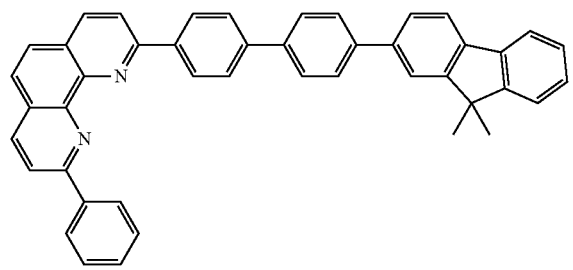
EN-096
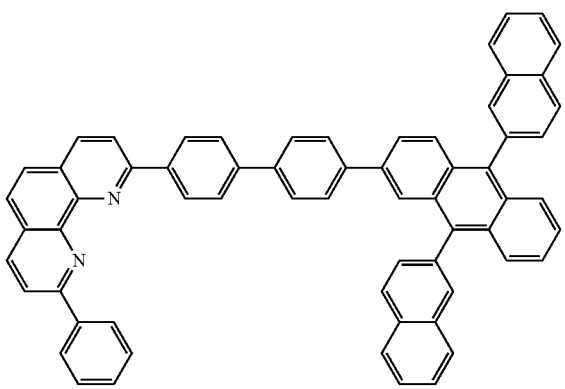
EN-097
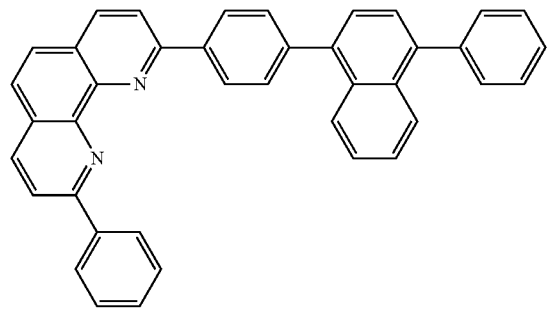
EN-098
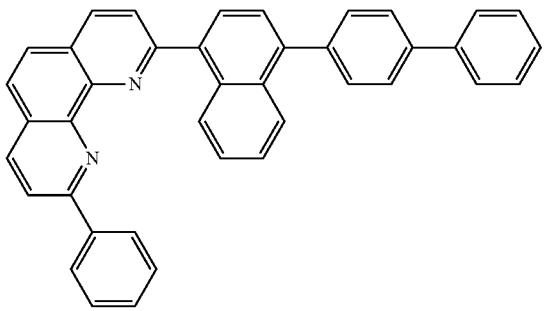

-continued
EN-099
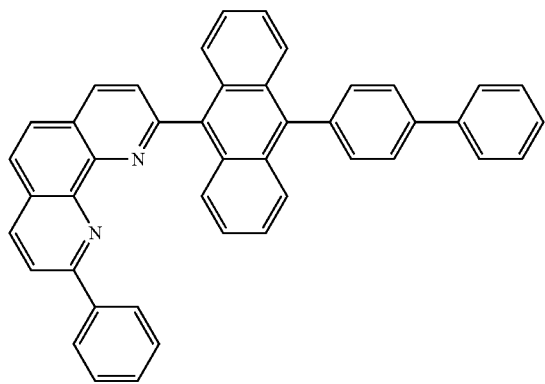
EN-100
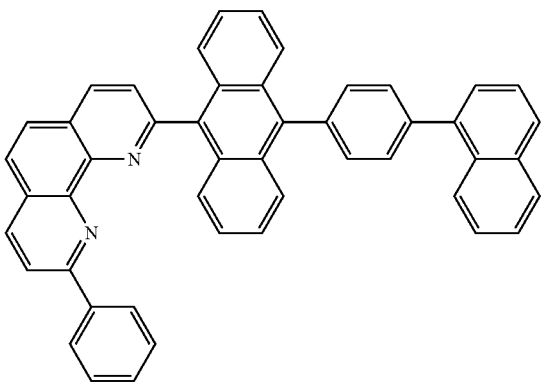
EN-109
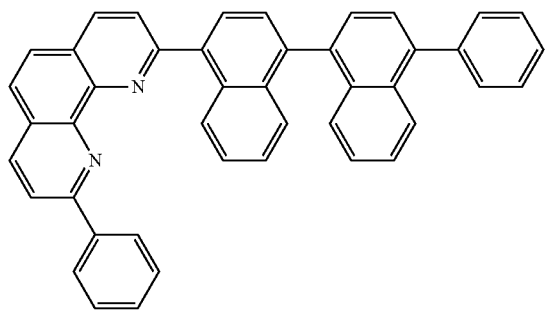
EN-110
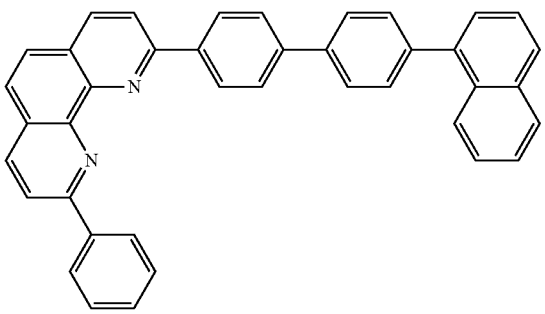
EN-111
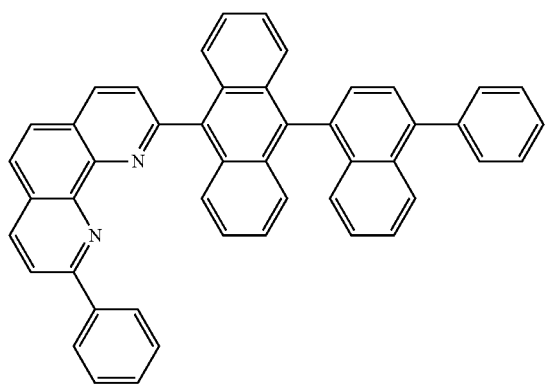
EN-112
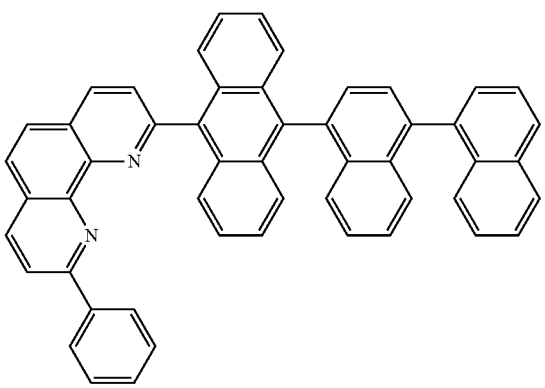
EN-121
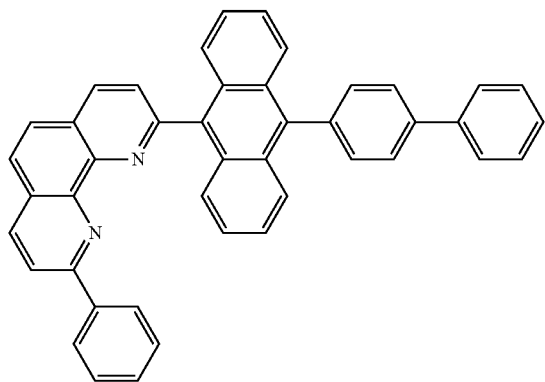
EN-122
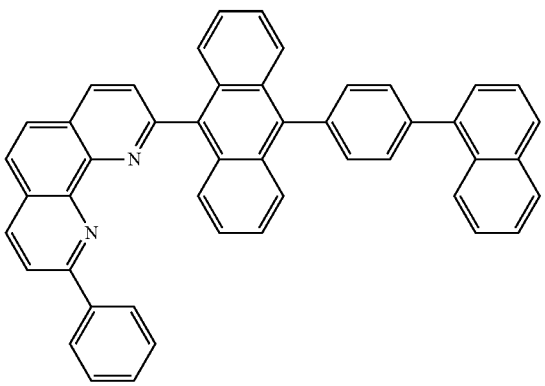

-continued
EN-123
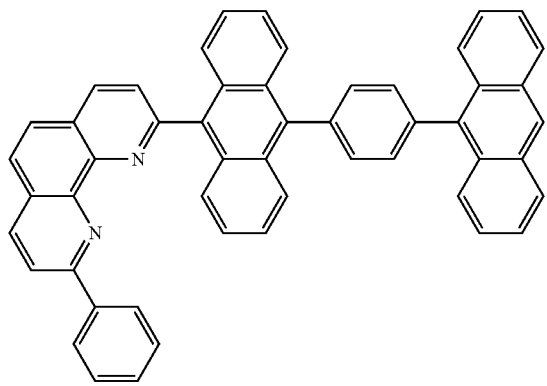
EN-124
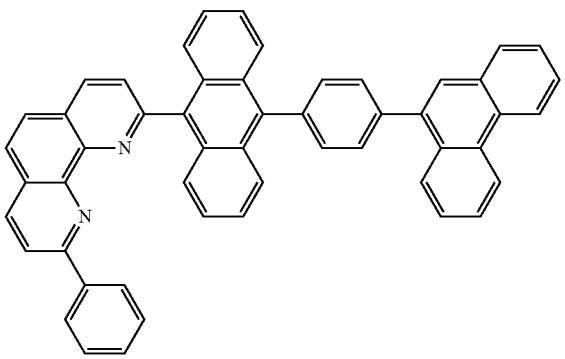
EN-125
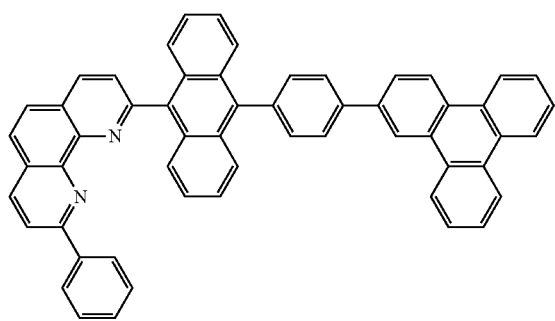
EN-126
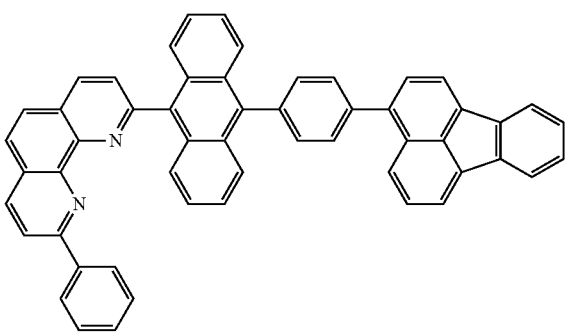
EN-127
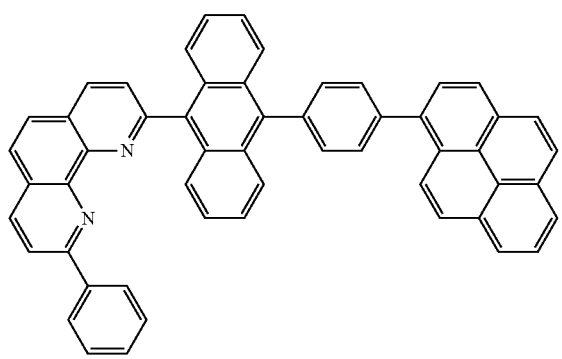
EN-128
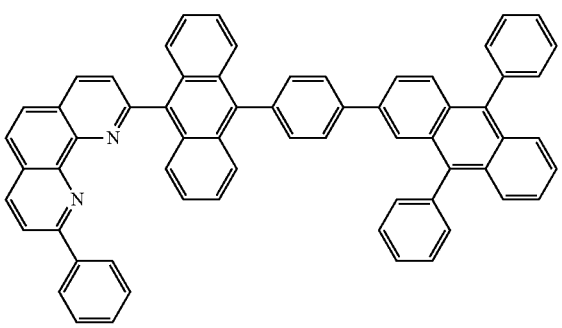
EN-129
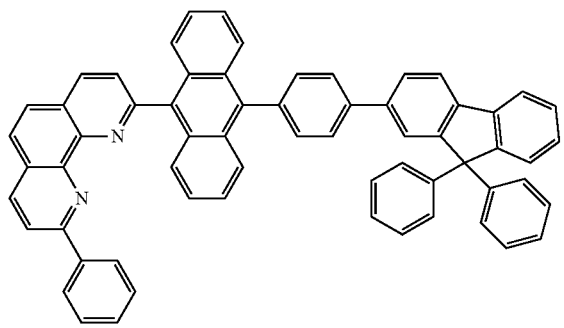
EN-130
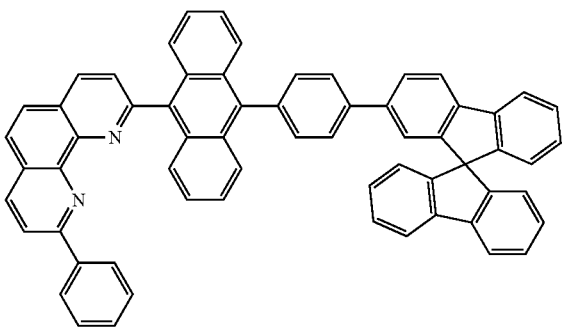

-continued
EN-131
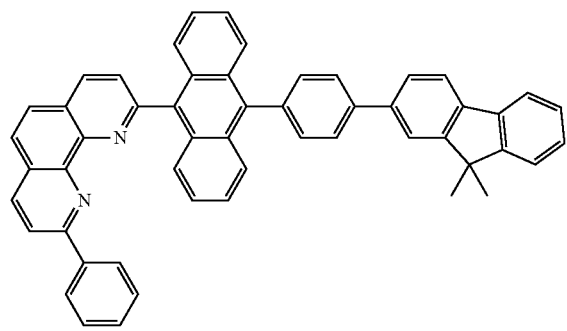
EN-132
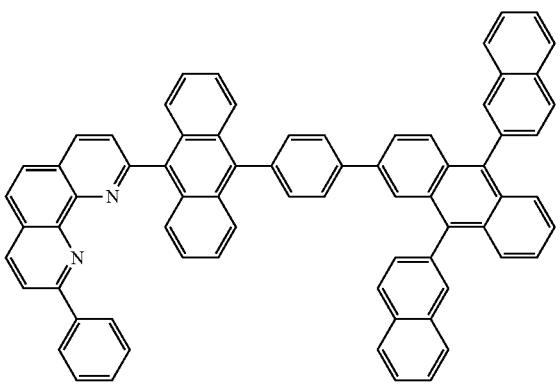
EN-133
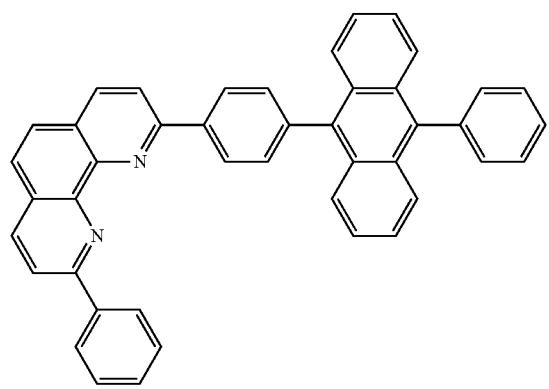
EN-135
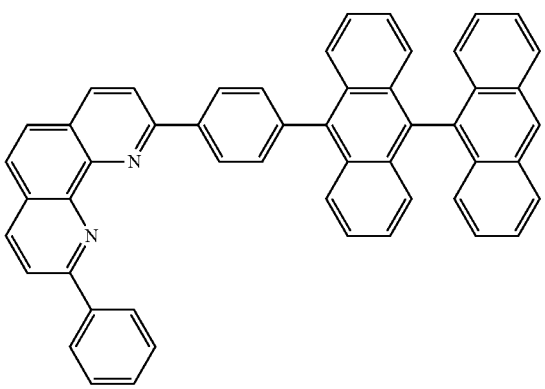
EN-136
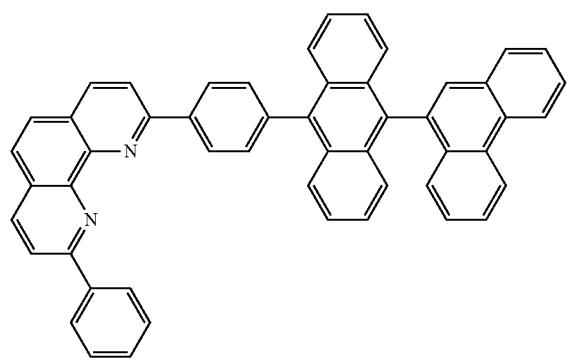
EN-137
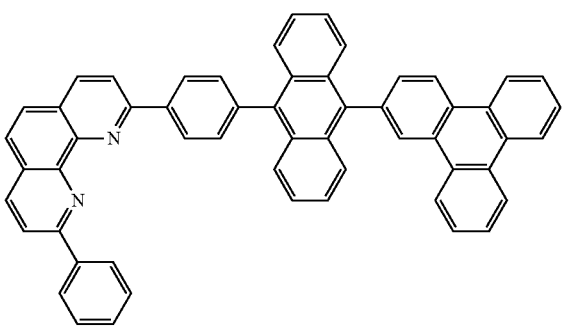
EN-138
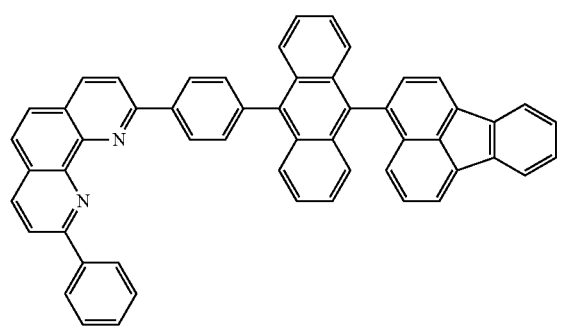
EN-139
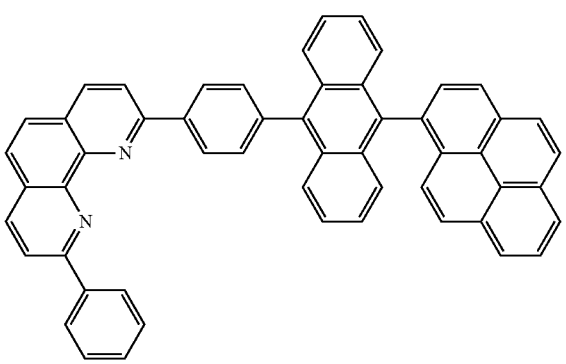

-continued
EN-140
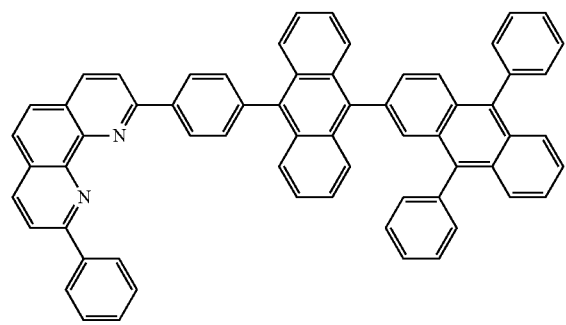
EN-141
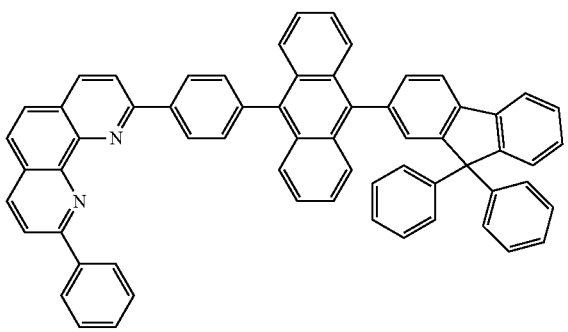
EN-142
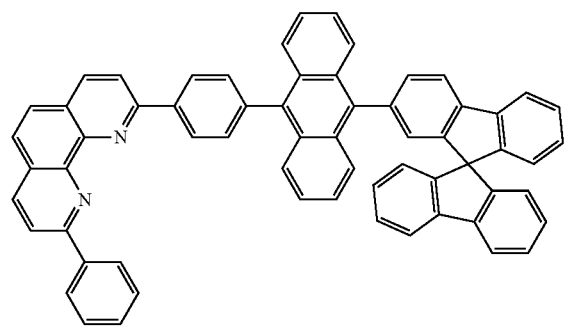
EN-143
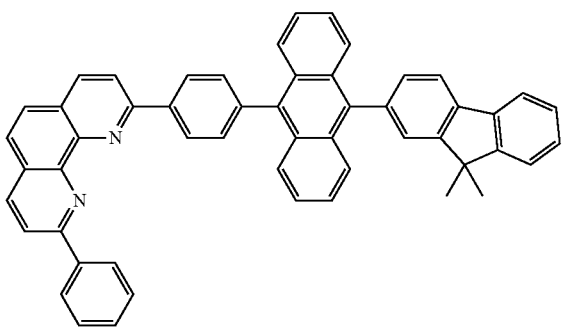
EN-144
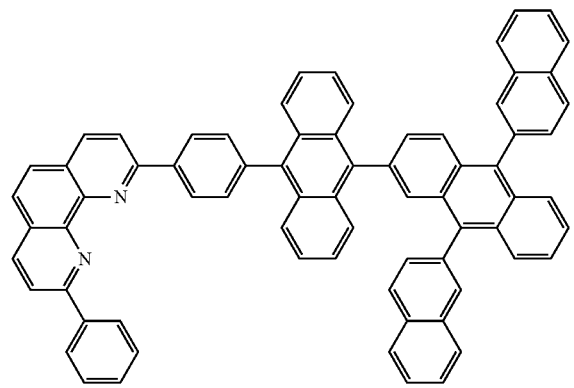
EN-145
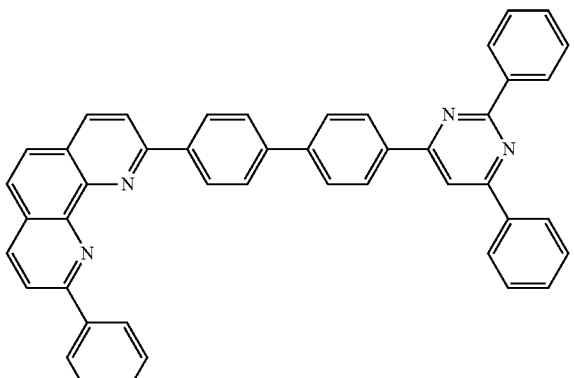
EN-146
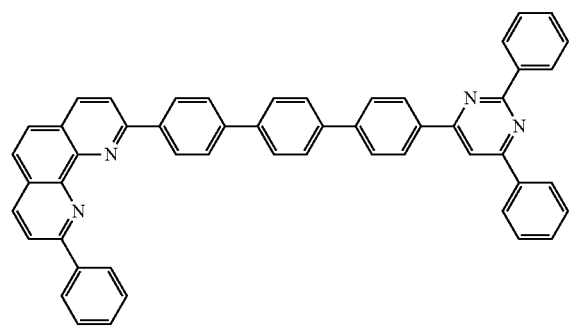
EN-147
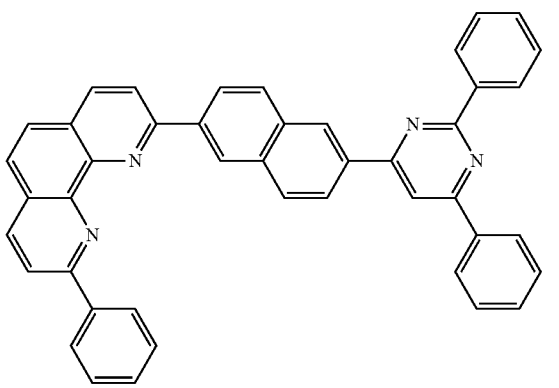

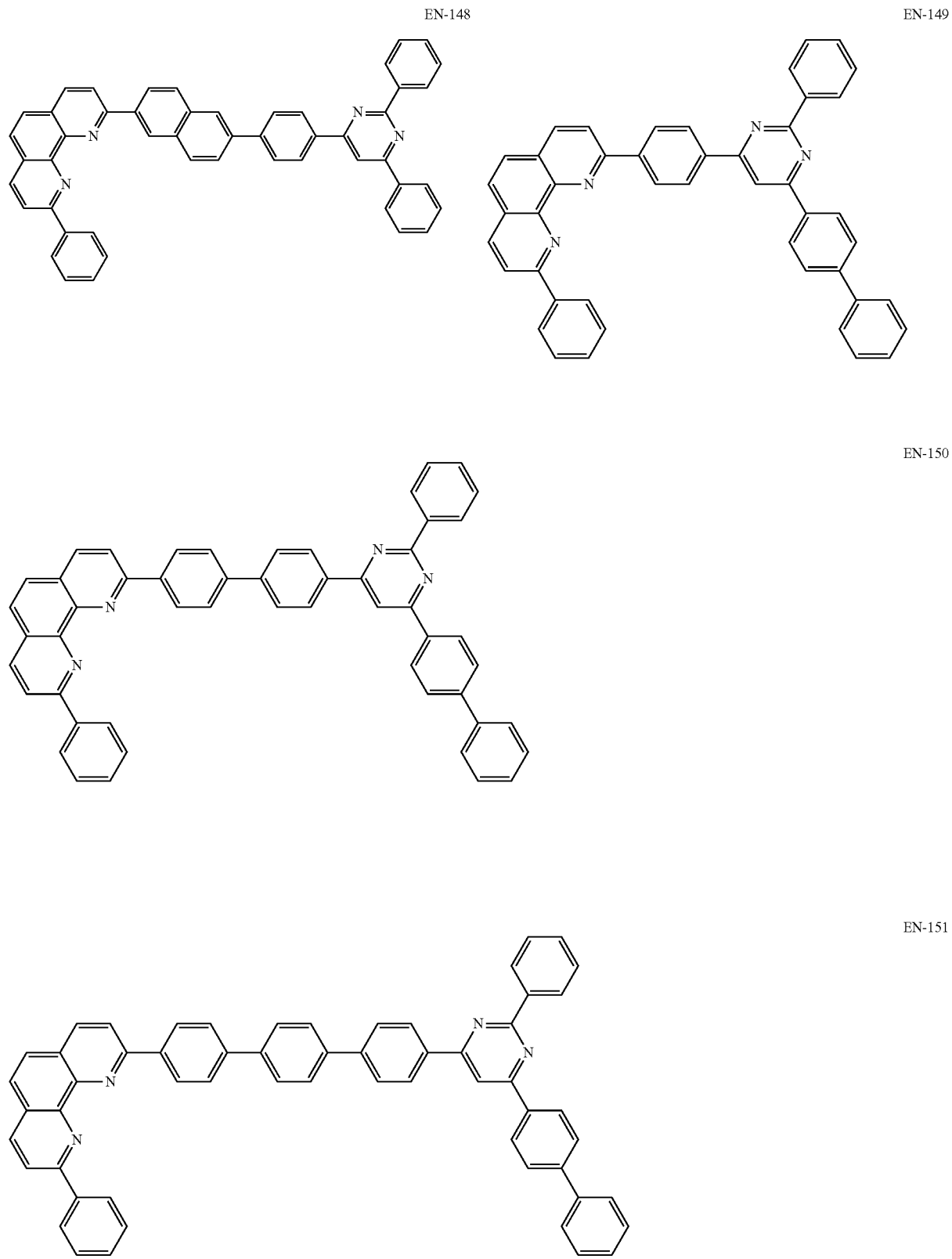
EN-148
EN-149
EN-150
EN-151

EN-152
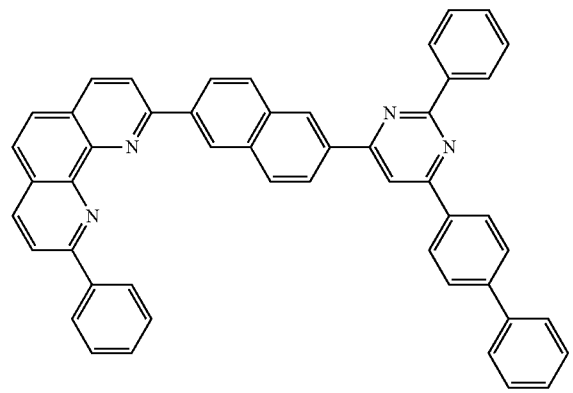
EN-153
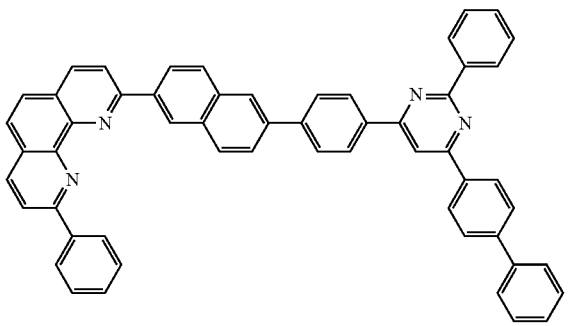
EN-154
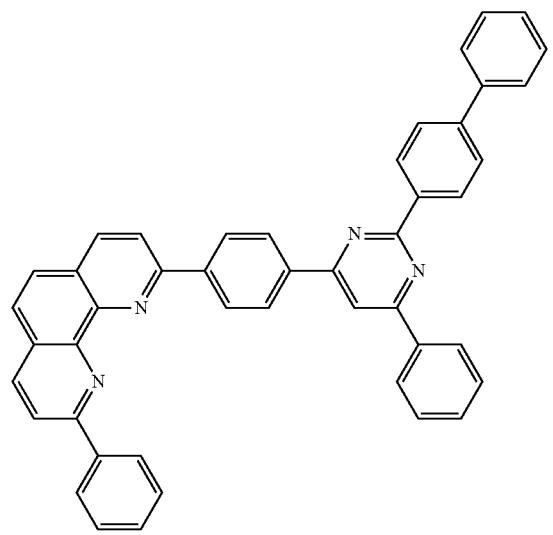
EN-155
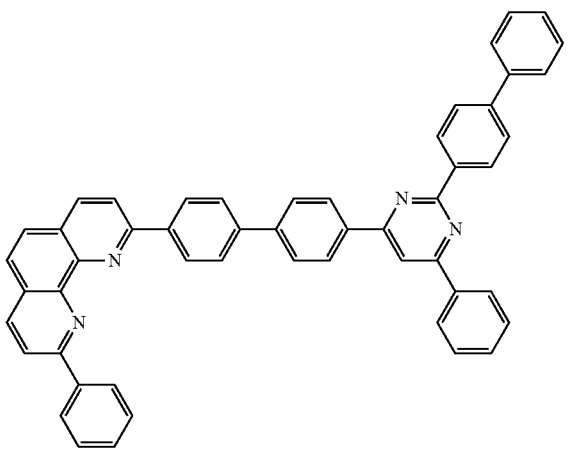
EN-156
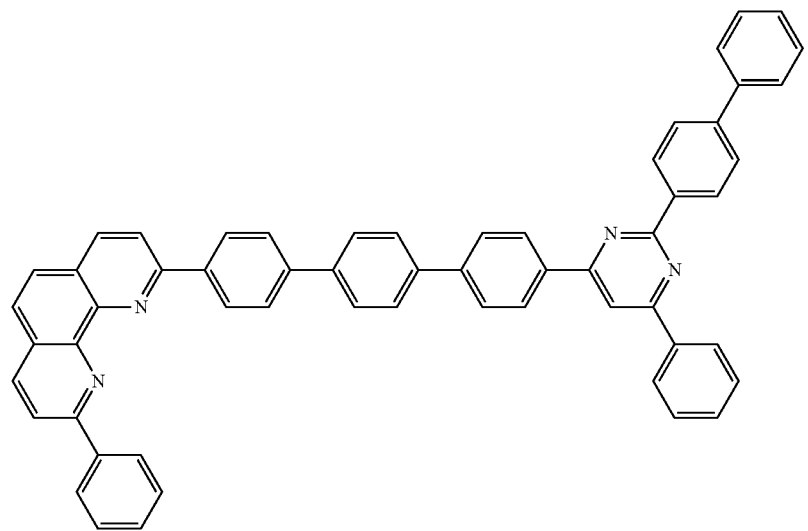

EN-157
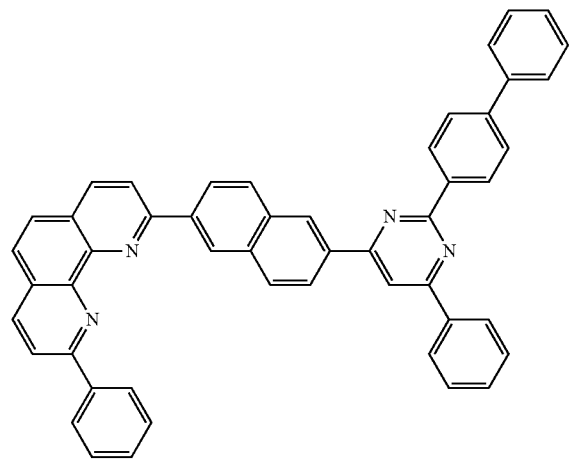
EN-158
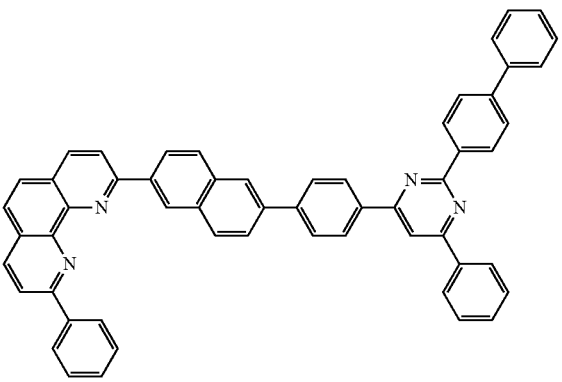
EN-159
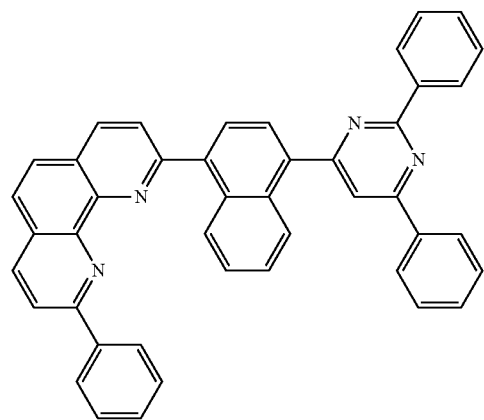
EN-160
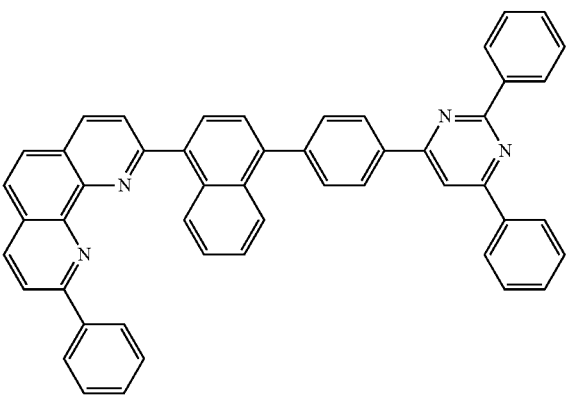
EN-161
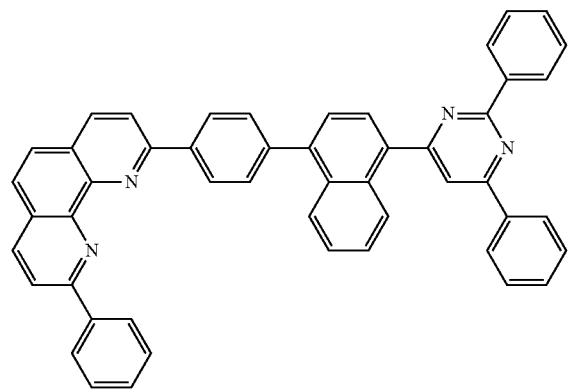
EN-162
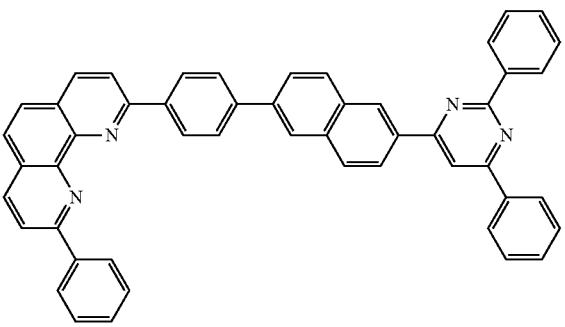

EN-163
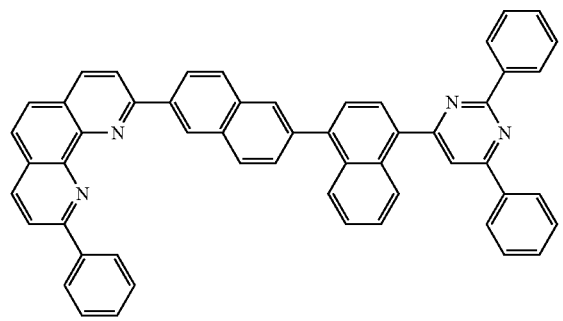
EN-164
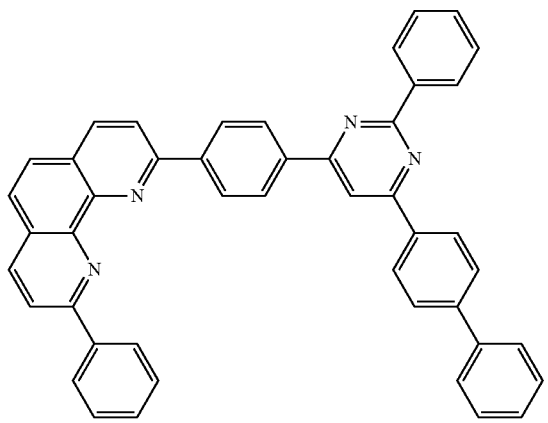
EN-165
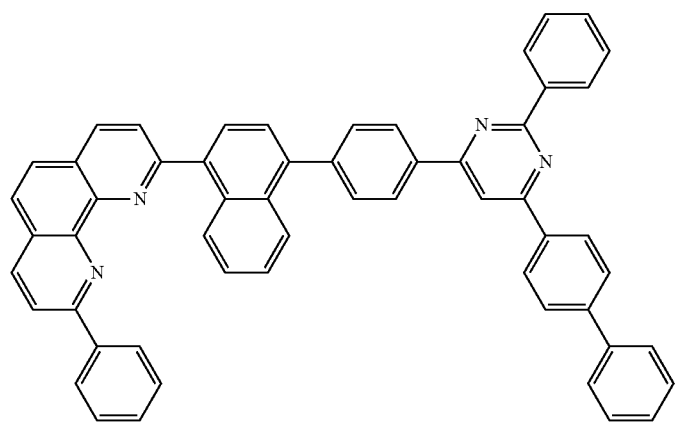
EN-166
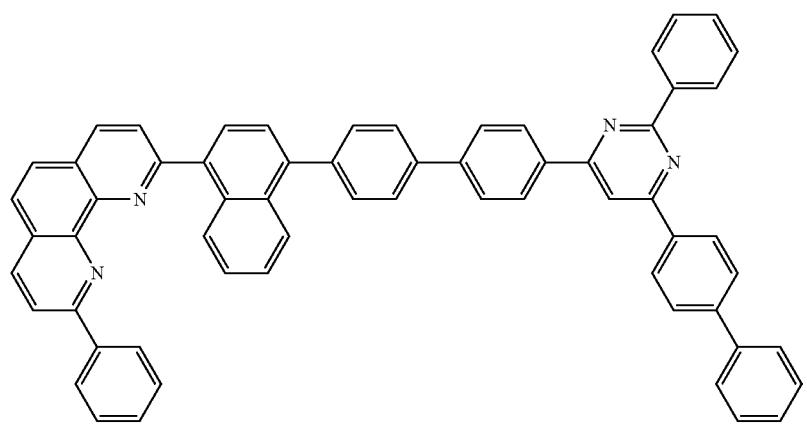

EN-167
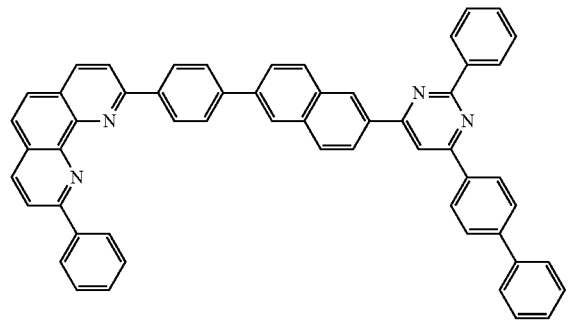
EN-168
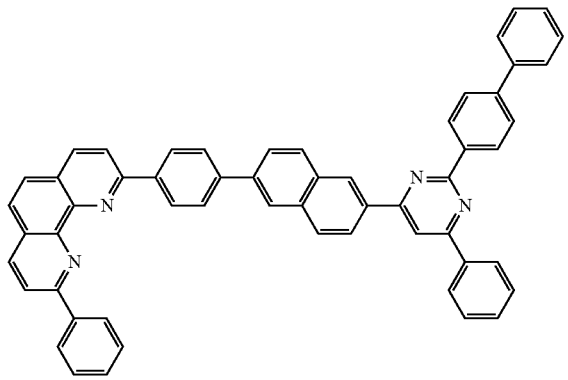
EN-173
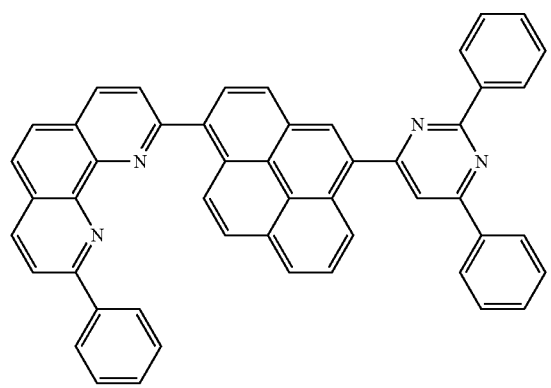
EN-174
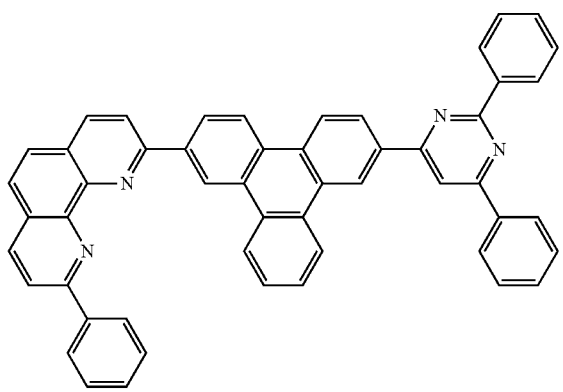
EN-175
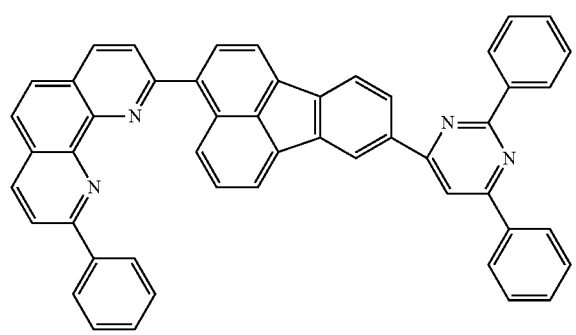
EN-176
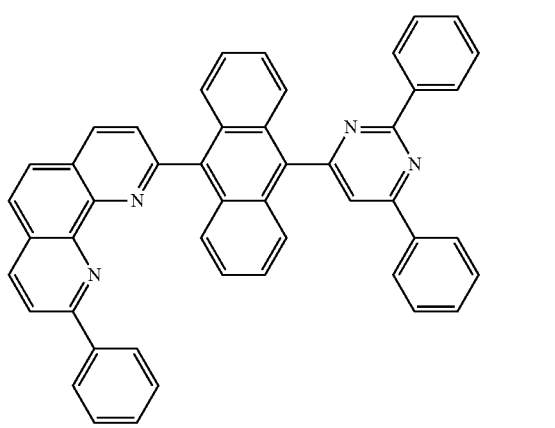

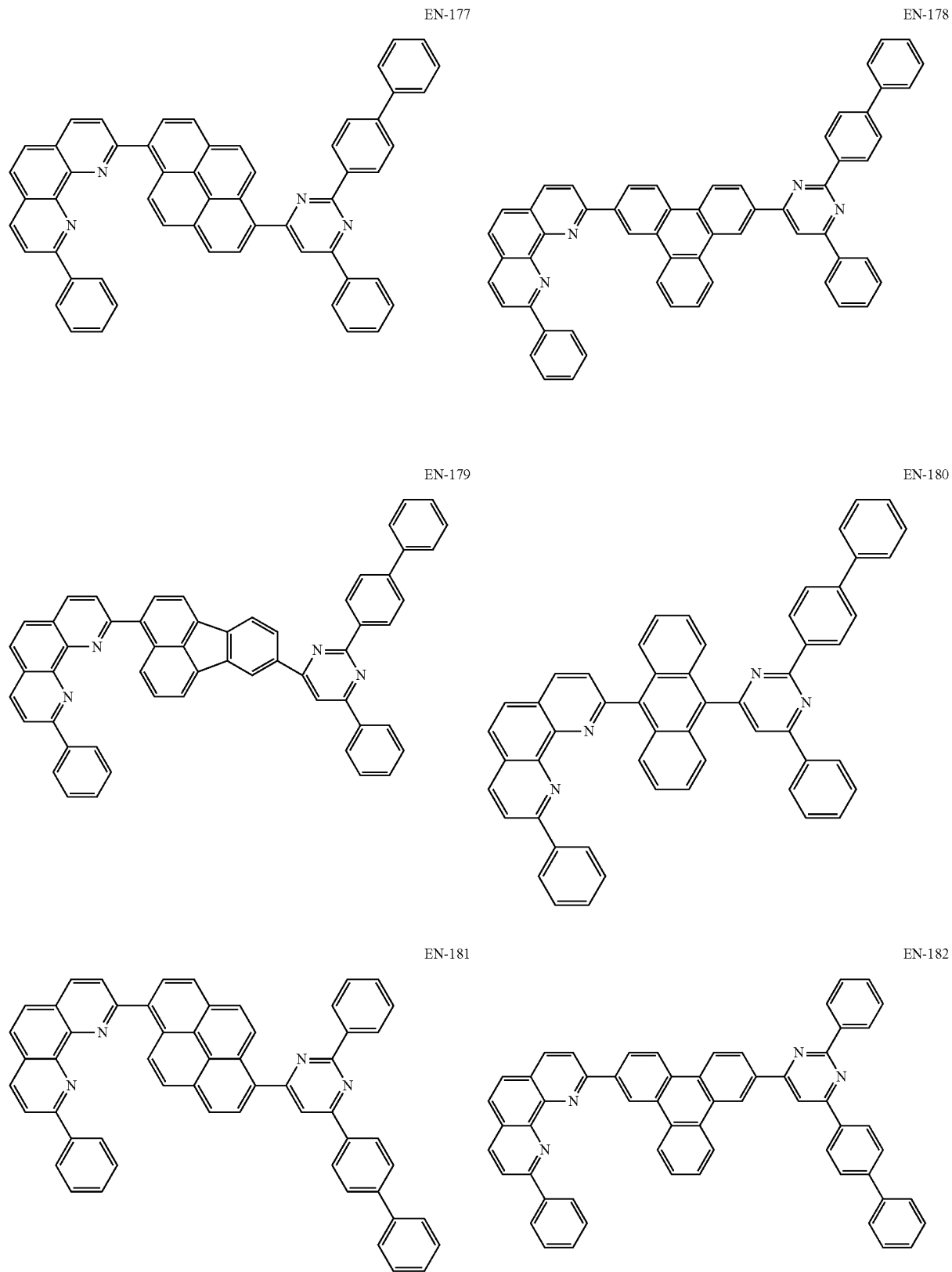

-continued
EN-183
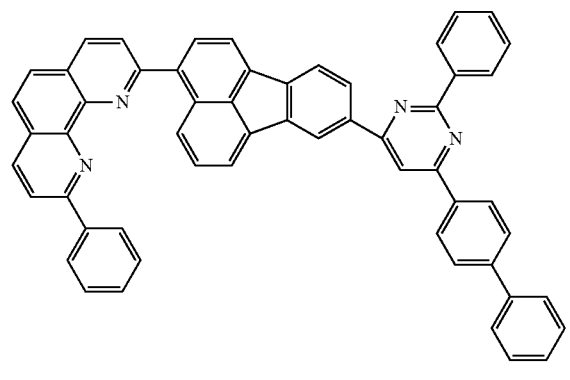
EN-184
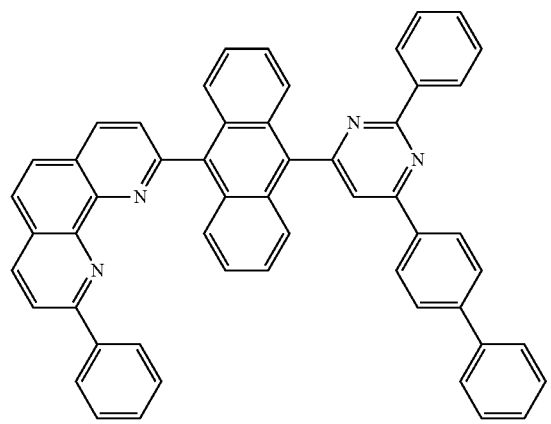
EN-185
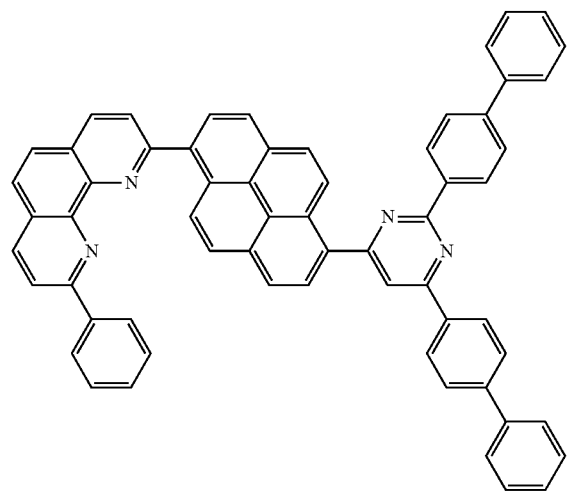
EN-186
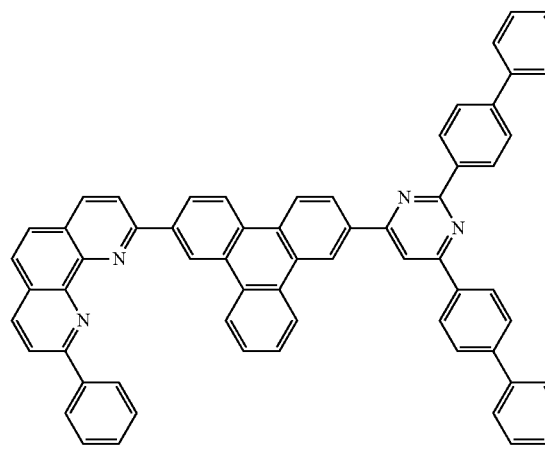
EN-187
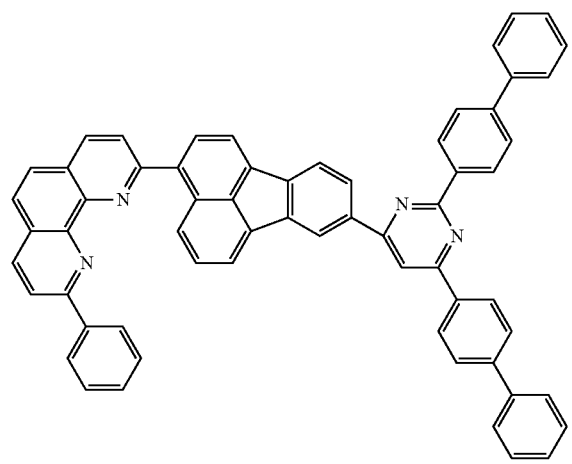
EN-188
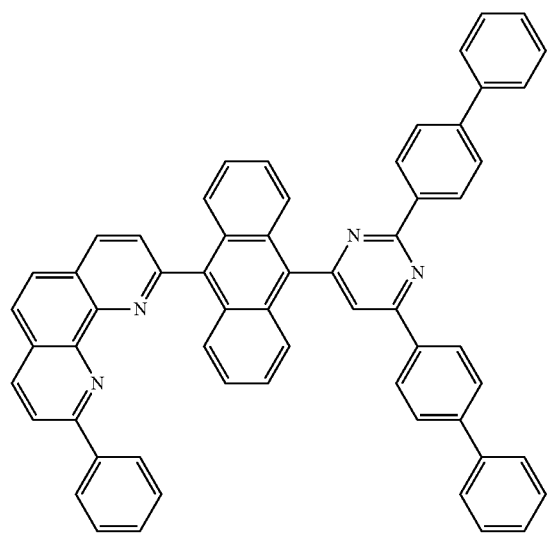

EN-189
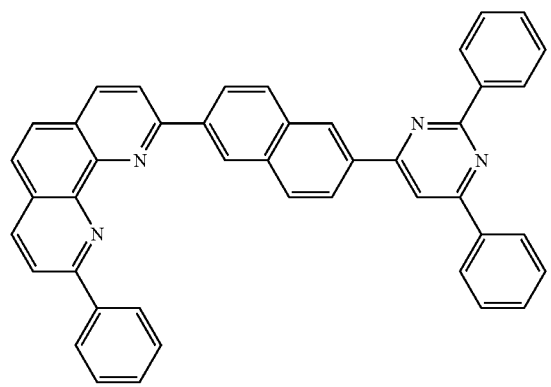
EN-190
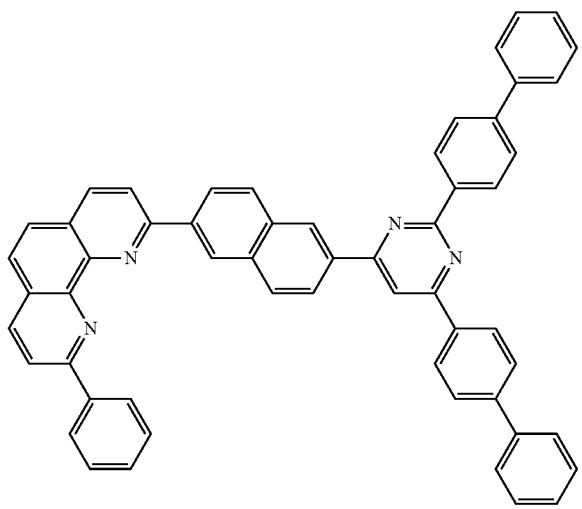
EN-191
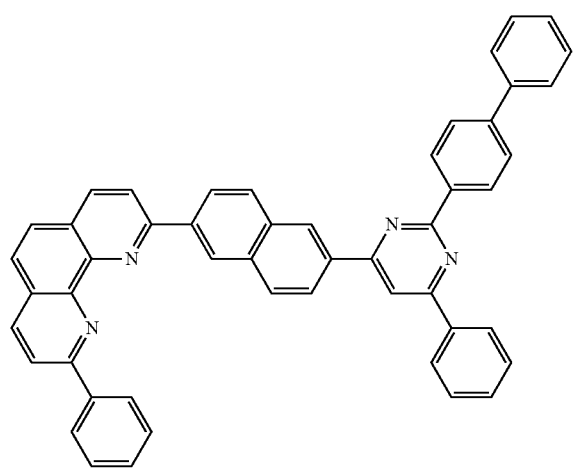
EN-192
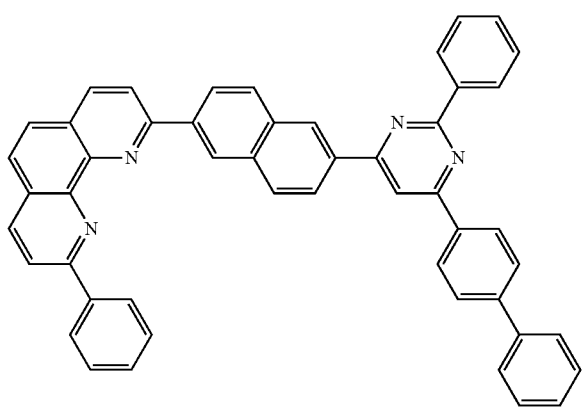
EN-193
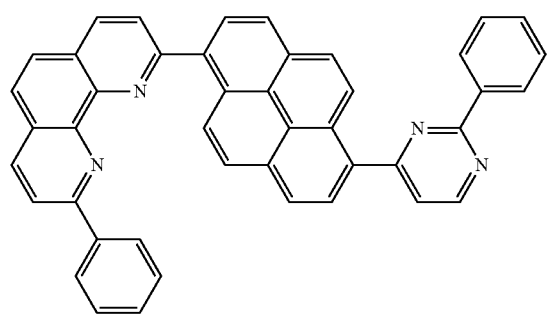
EN-194
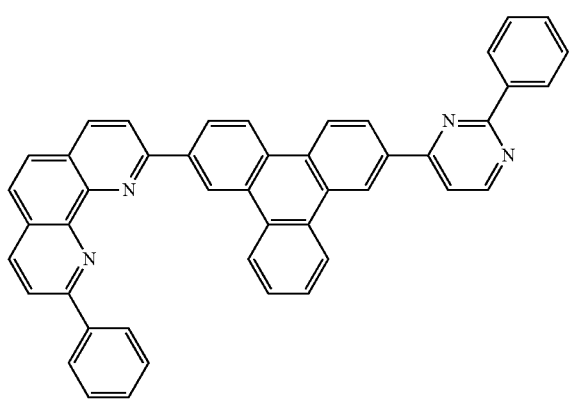

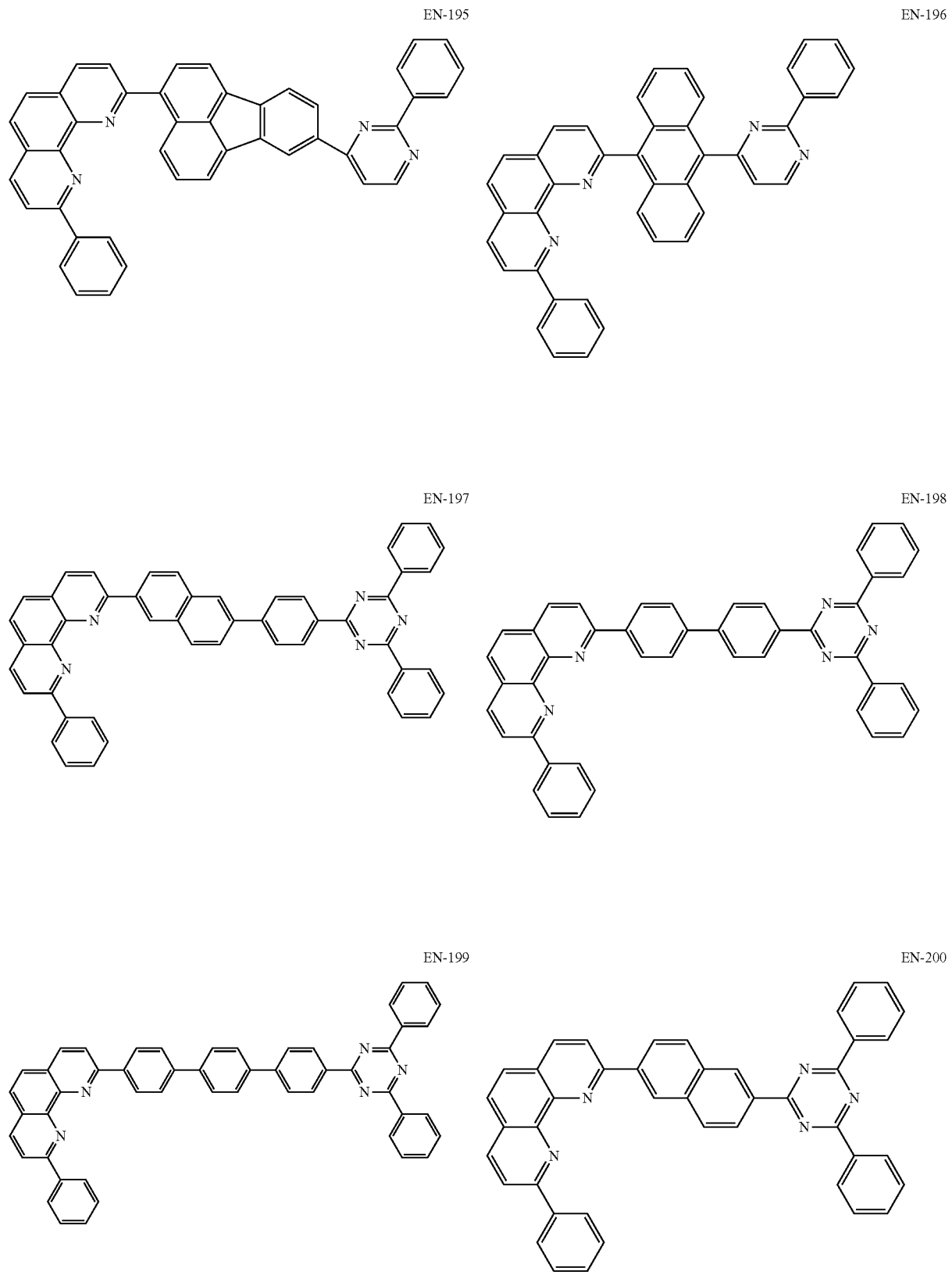

EN-201
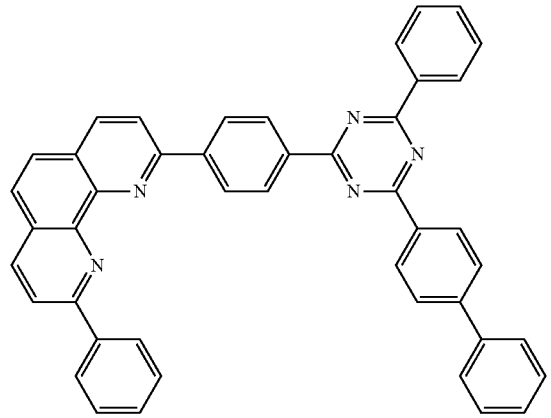
EN-202
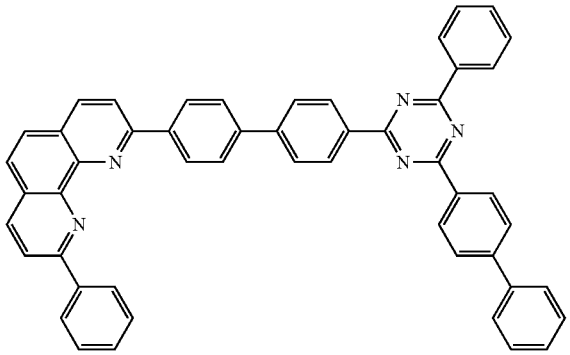
EN-203
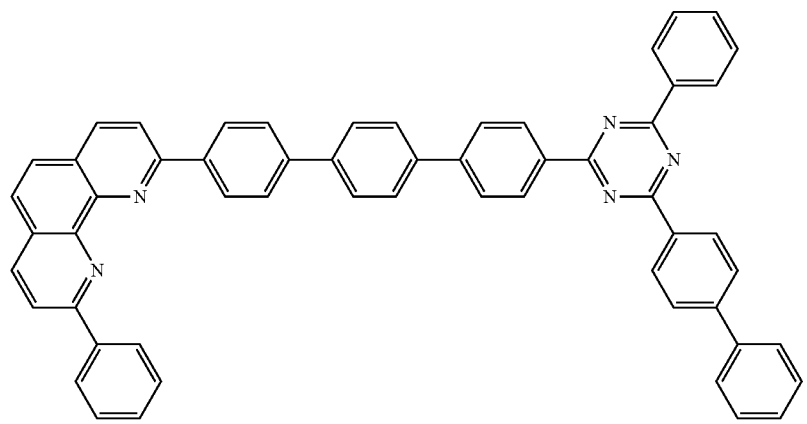
EN-204
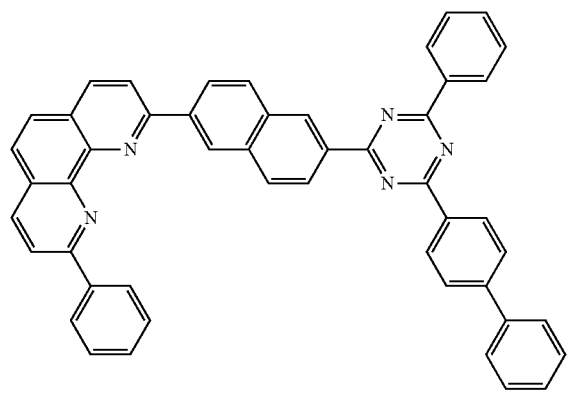
EN-205
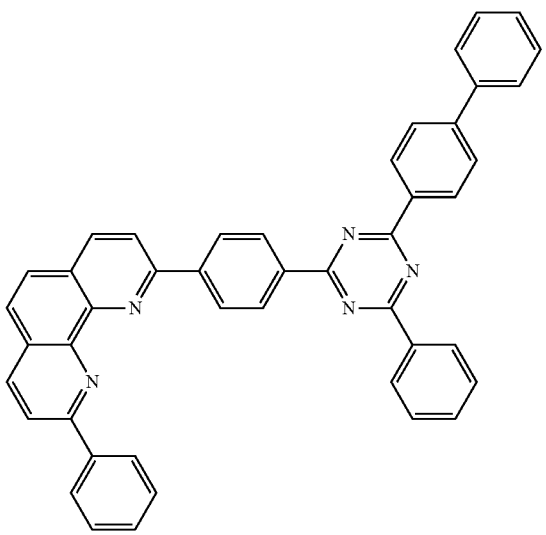

EN-206
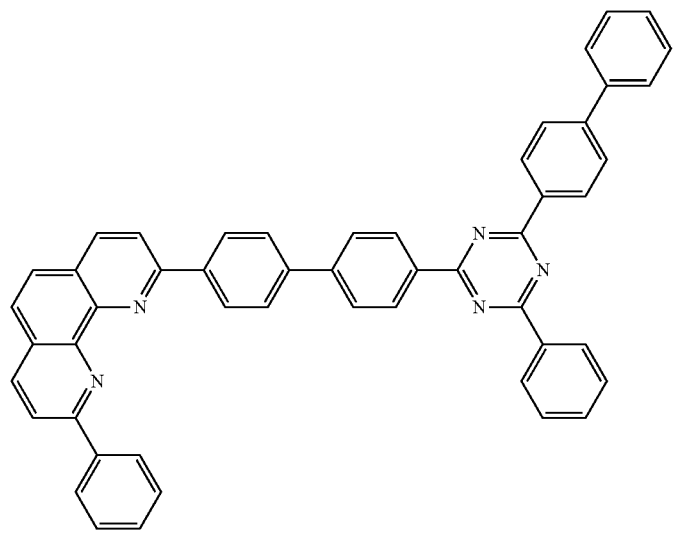
EN-207
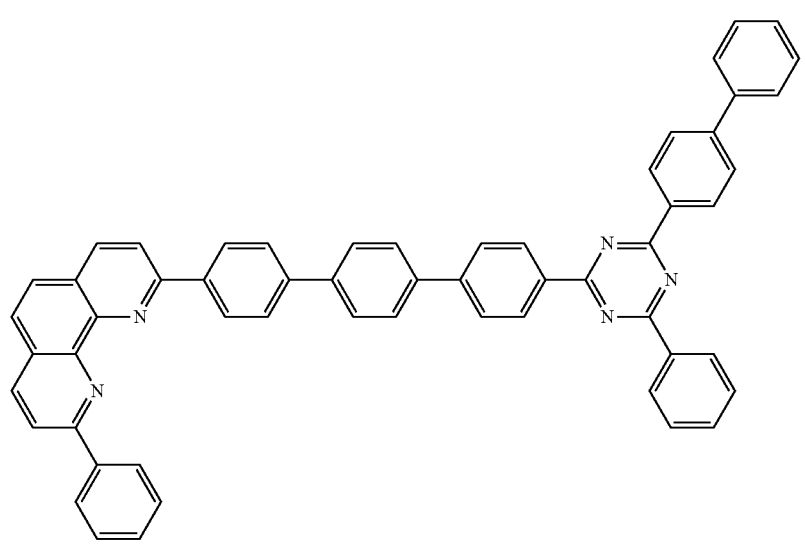
EN-208 EN-209
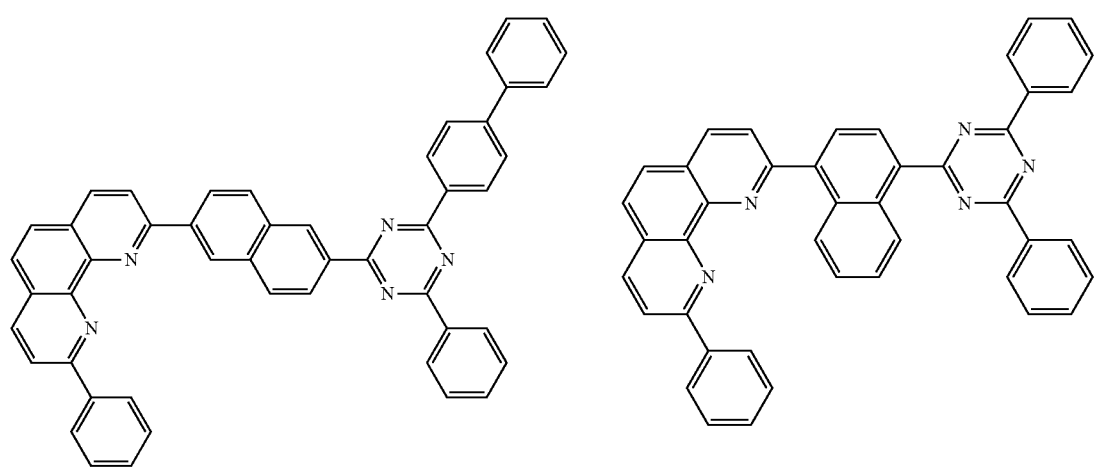

EN-210
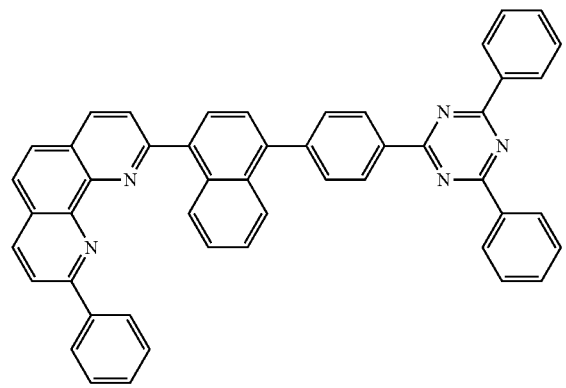
EN-211
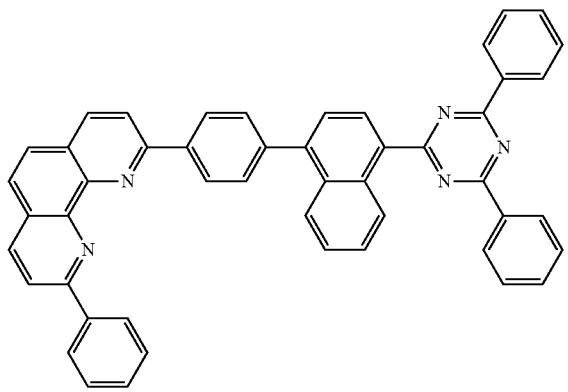
EN-212
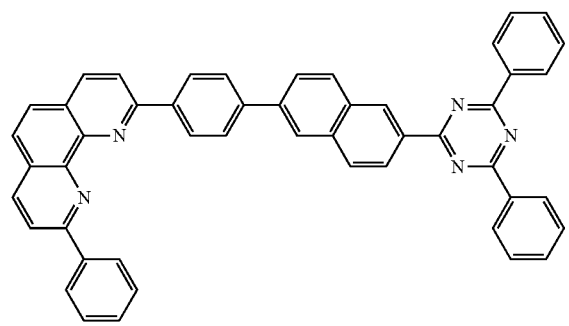
EN-213
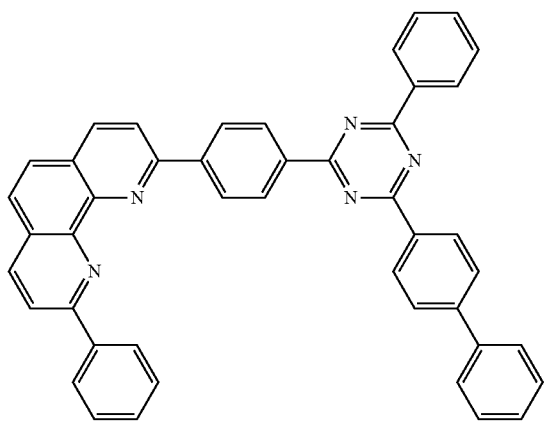
EN-214
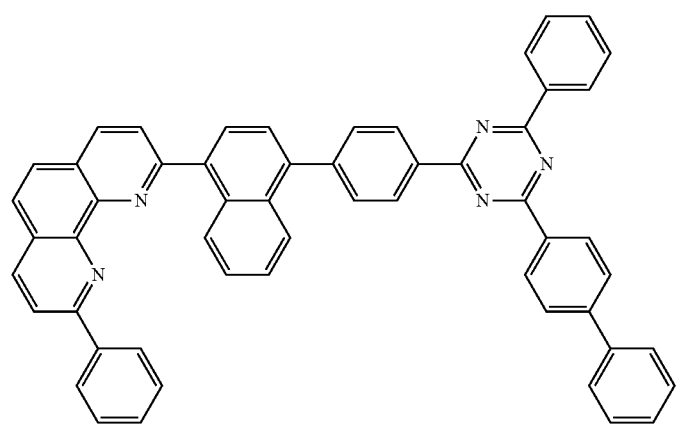

-continued
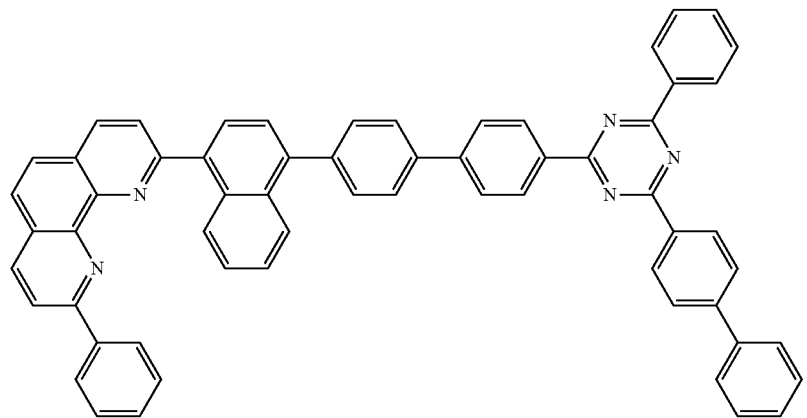
EN-215
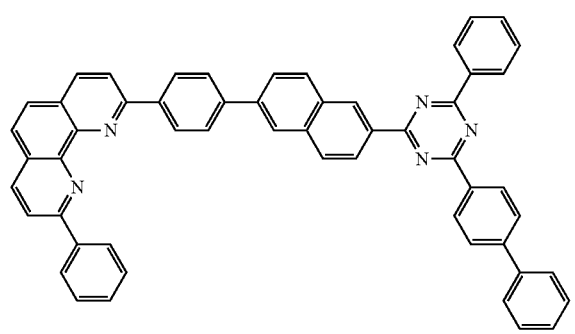
EN-216
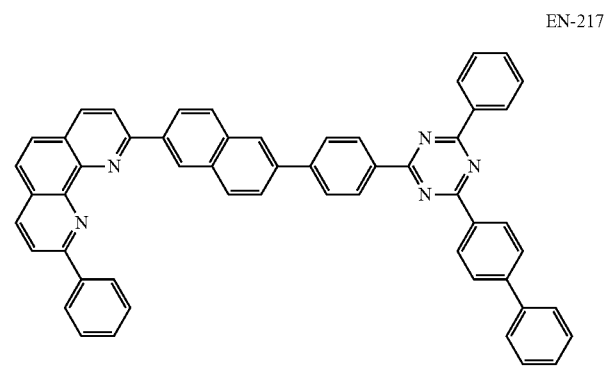
EN-217
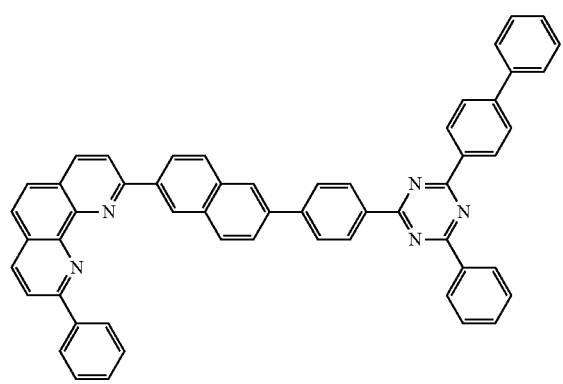
EN-218
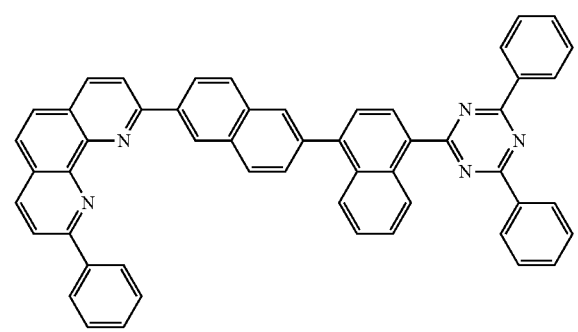
EN-219
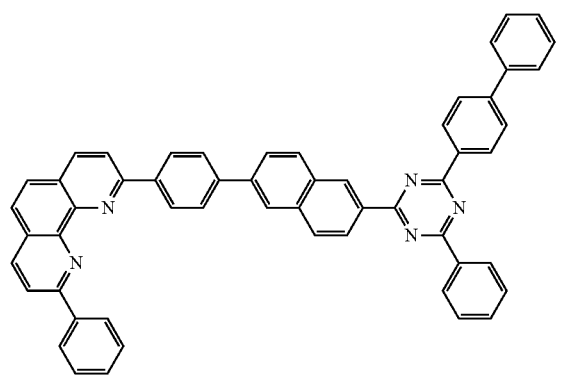
EN-220
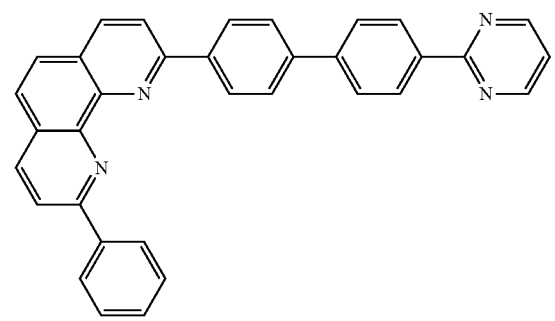
EN-222

-continued
EN-223
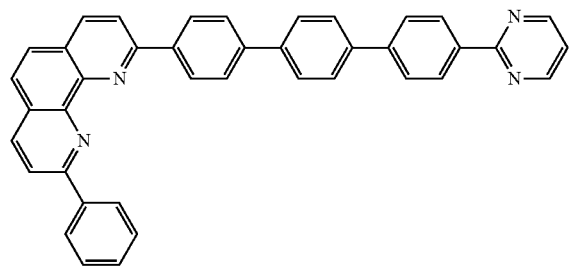
EN-224
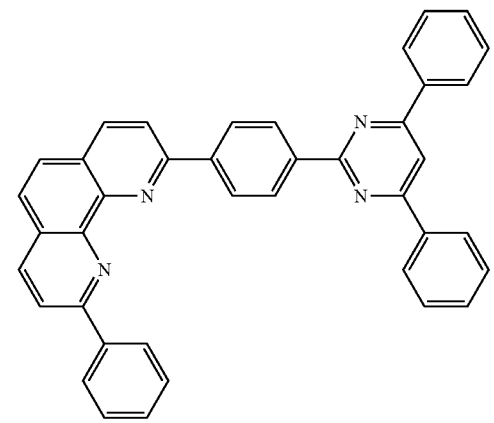
EN-226
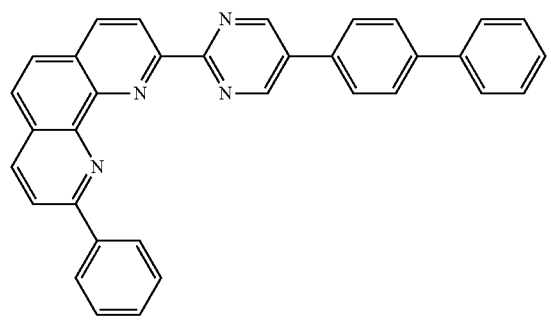
EN-227
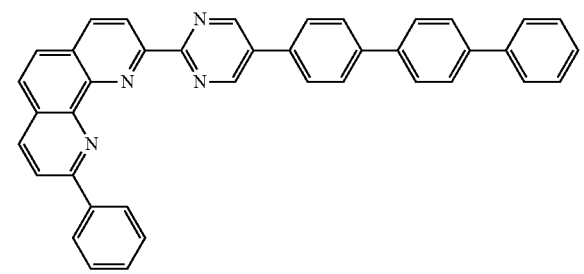
EN-228
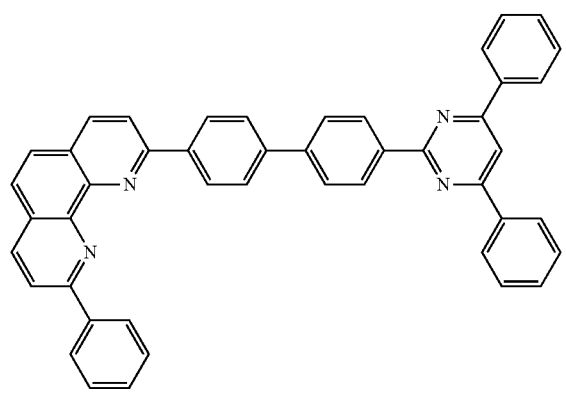
EN-230
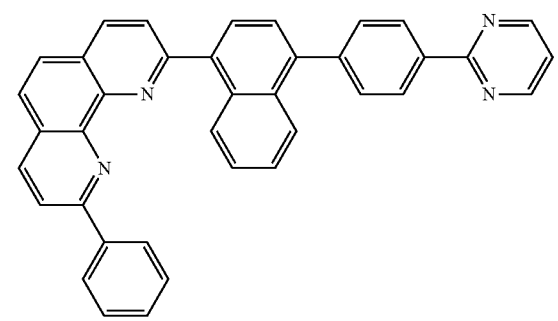
EN-231
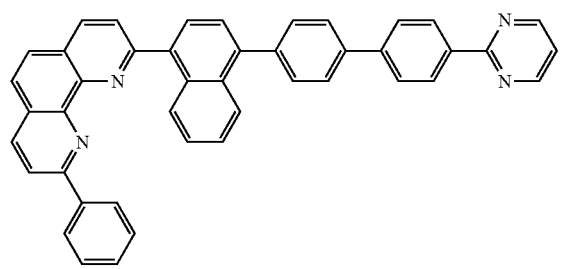
EN-232
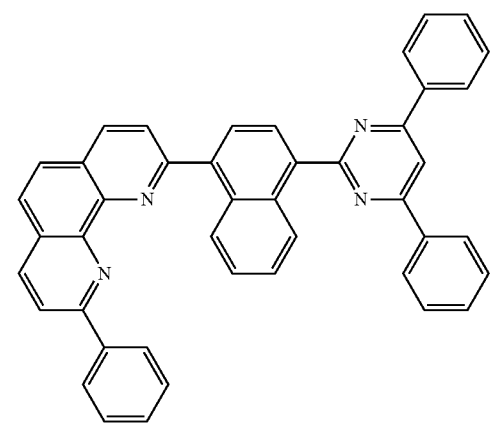

-continued
EN-234
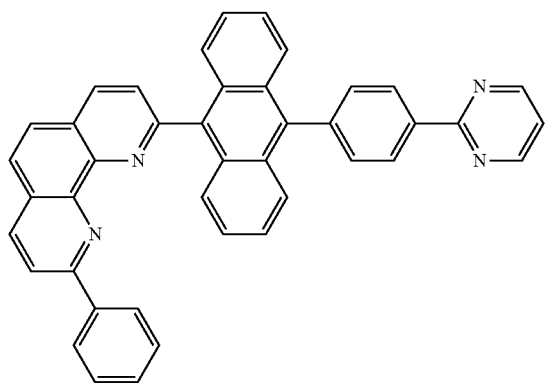
EN-235
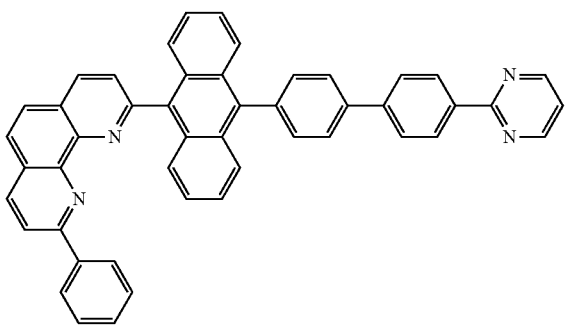
EN-236
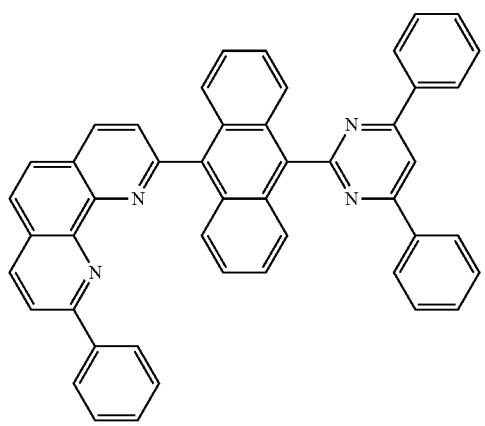
EN-237
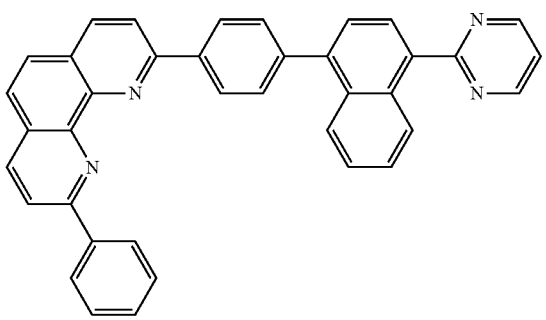
EN-238
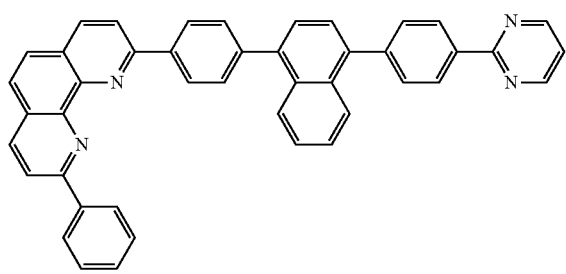
EN-239
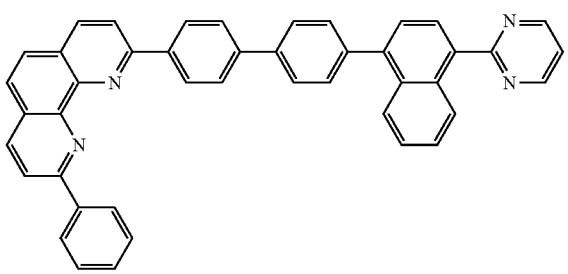
EN-240
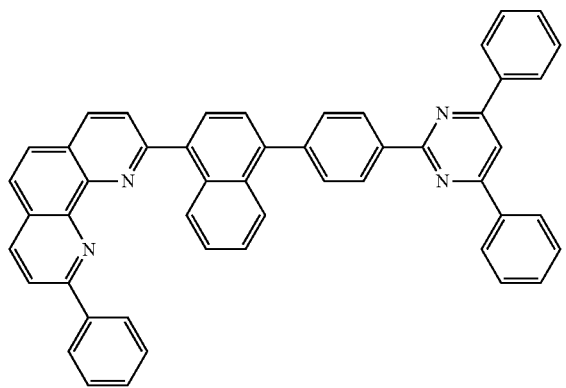
EN-241
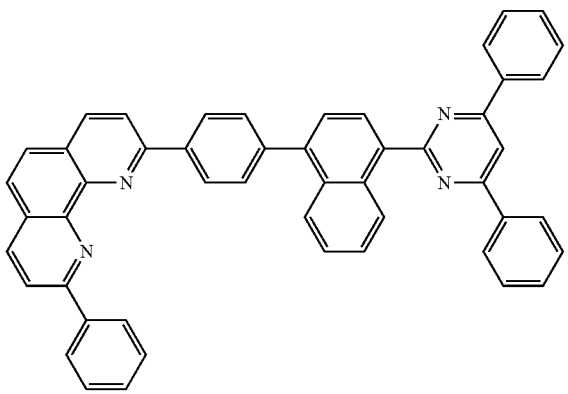

-continued
EN-242
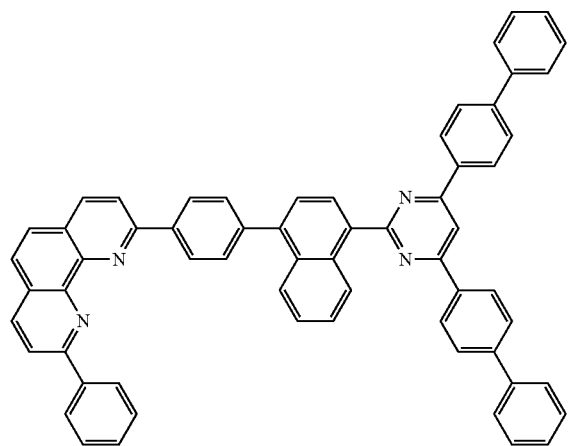
EN-243
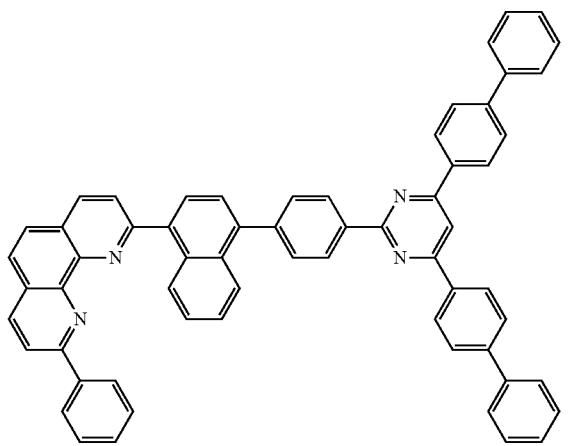
EN-244
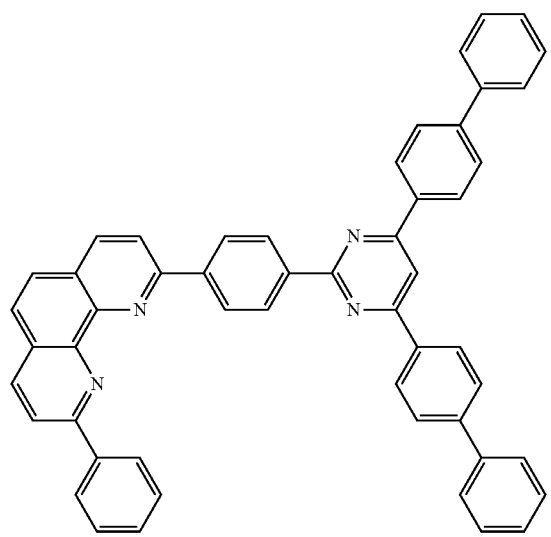
EN-245
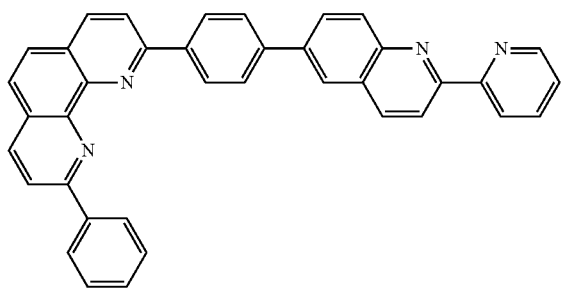
EN-246
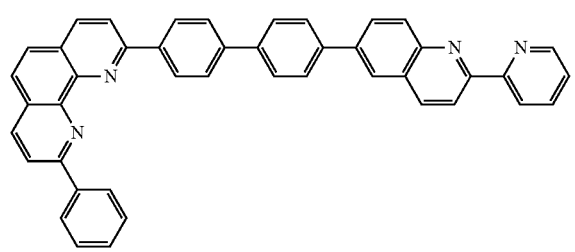
EN-247
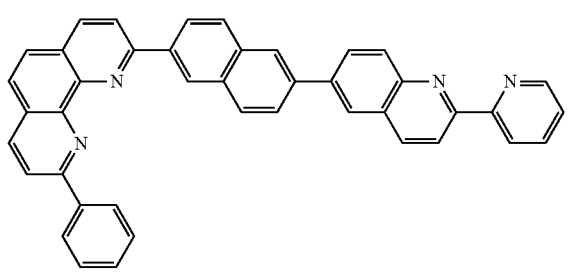
EN-248
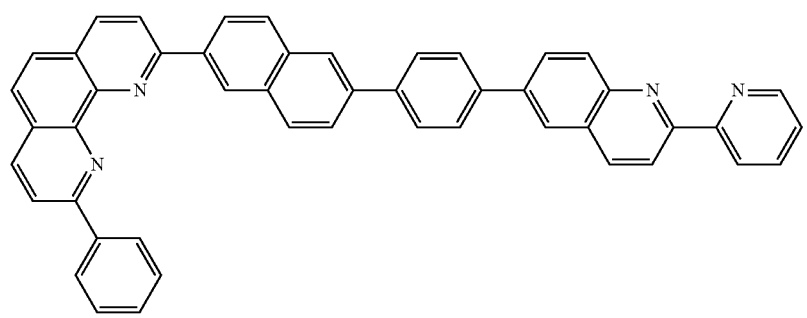

-continued
EN-249
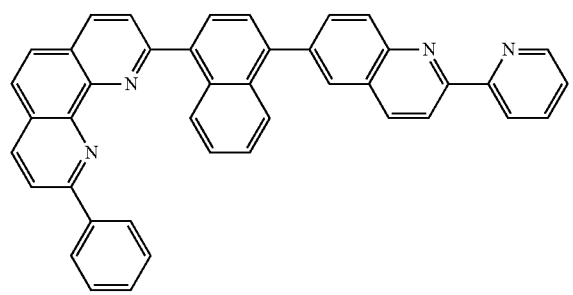
EN-250
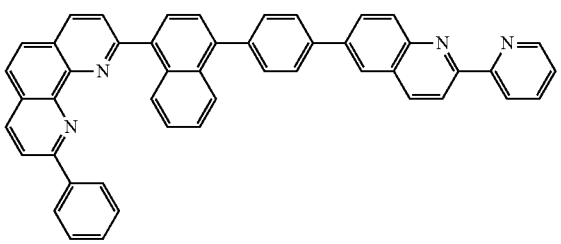
EN-251
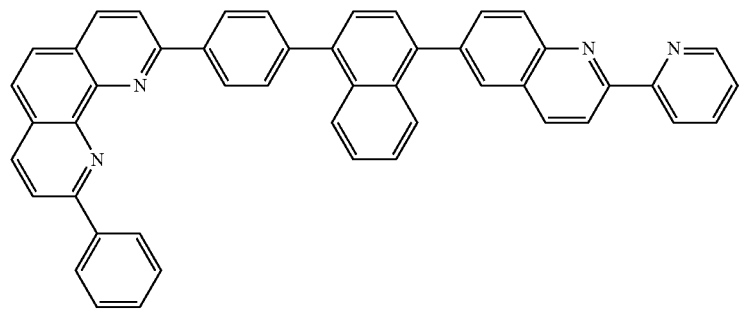
EN-252
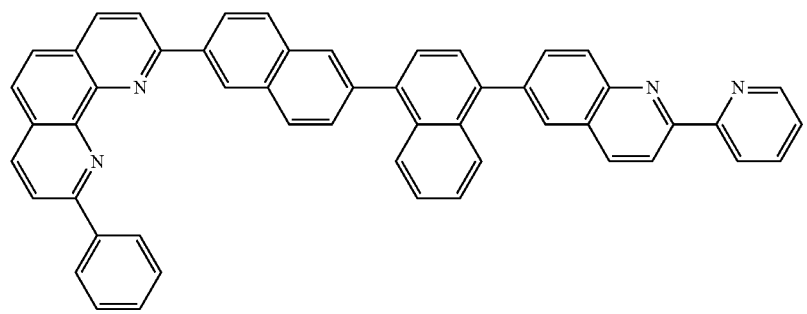
EN-254
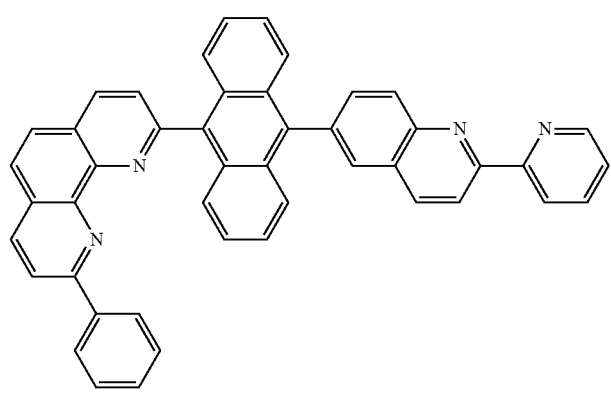
EN-255
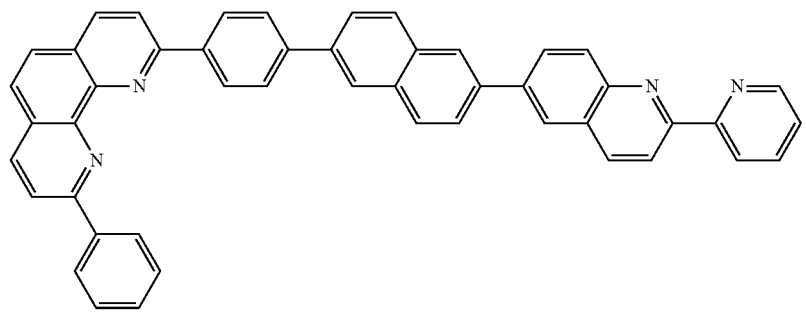

-continued
EN-256
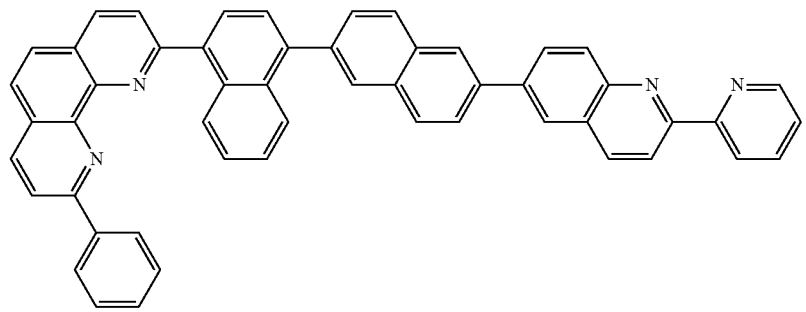
EN-258
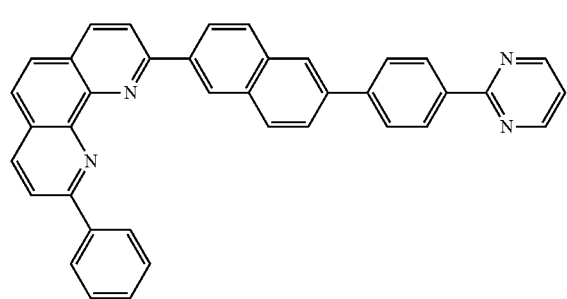
EN-259
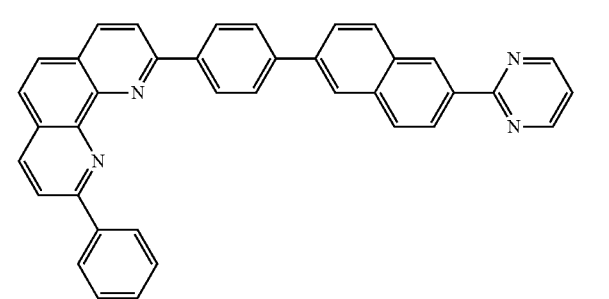
EN-260
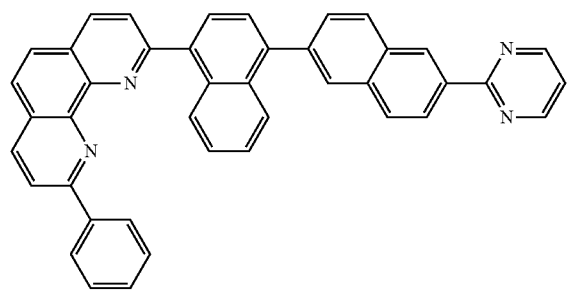
EN-261
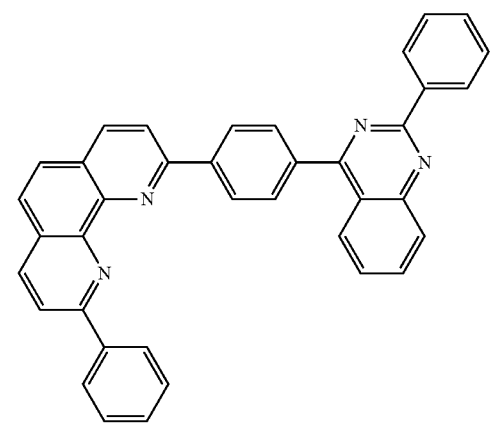
EN-262
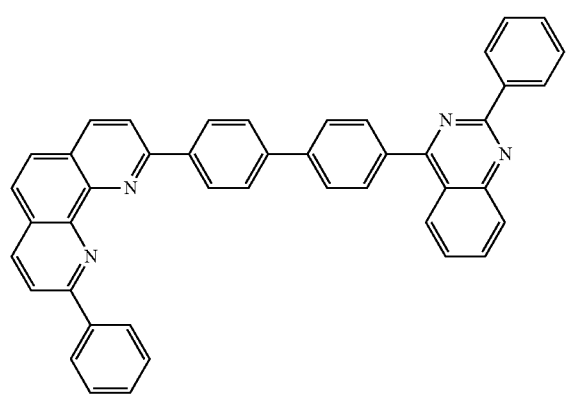
EN-263
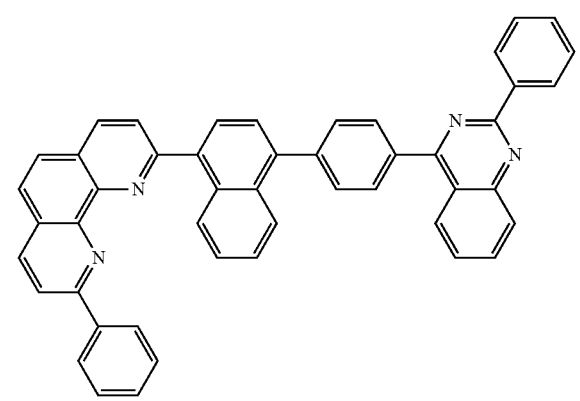

EN-264
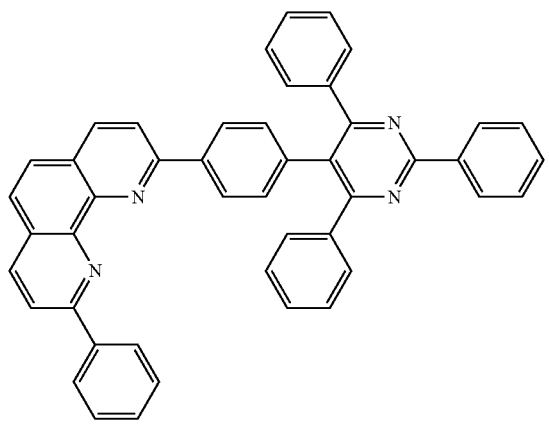

EN-265
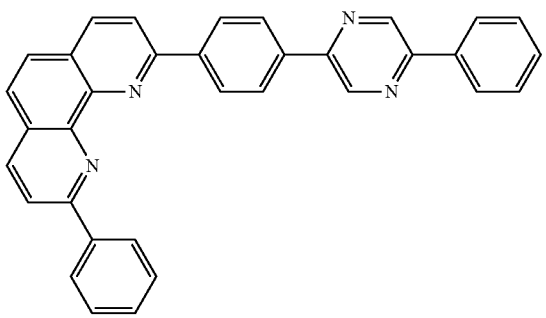

EN-266
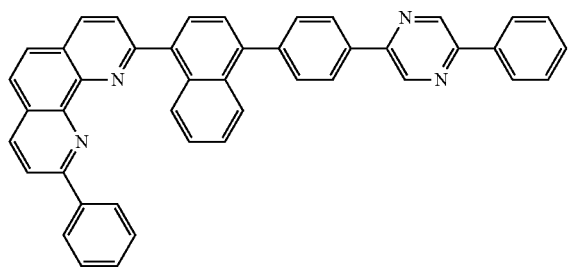

EN-267
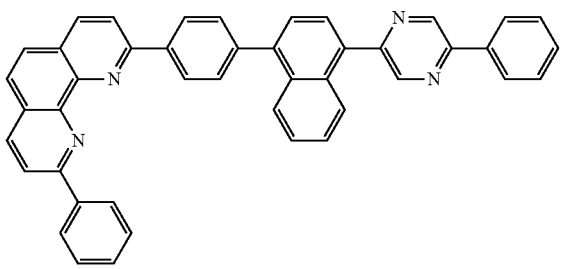

EN-268
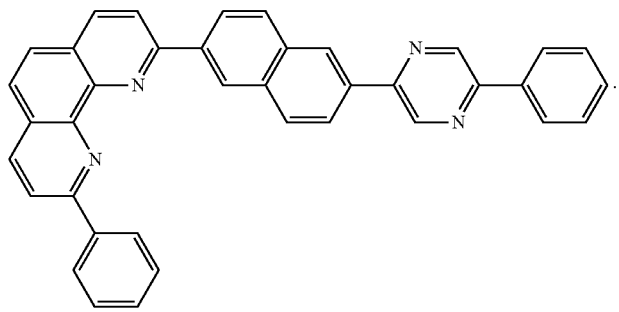

9. An organic light emitting diode display device comprising:
  a substrate;
  a light emitting diode on the substrate; and
  a driving element between the substrate and the light emitting diode,
  wherein the light emitting diode comprises:
    first and second electrodes facing each other;
    a first emitting part between the first and second electrodes and including a first emitting material layer and an electron transporting layer;
    a second emitting part between the first emitting part and the second electrode and including a second emitting material layer; and
    a first charge generation layer between the first and second emitting parts,
  wherein at least one of the electron transporting layer and the first charge generation layer includes an organic compound by a following chemical formula 1,
  wherein the first charge generation layer includes an N type charge generation layer and a P type charge generation layer, and the N type charge generation layer includes the organic compound:

Chemical Formula 1

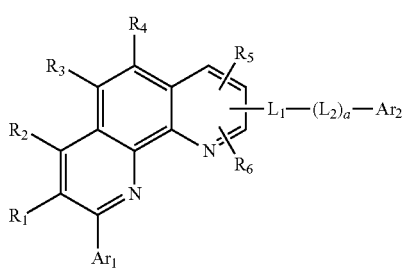

wherein, each of $R_1$ to $R_6$ is independently one of hydrogen, deuterium, tritium, a non-substituted or substituted alkyl group of C1 to C20, a non-substituted or substituted alkoxy group of C1 to C20, a non-substituted or substituted aryl group of C5 to C60 and a non-substituted or substituted hetero aryl group of C4 to C60;

each of $L_1$ and $L_2$ is independently one of a non-substituted or substituted arylene group of C5 to C60 and a non-substituted or substituted hetero arylene group of C5 to C60, a is 1, and each of $Ar_1$ and $Ar_2$ is independently one of a non-substituted aryl group of C5 to C60, a substituted aryl group of C5 to C60, a non-substituted hetero aryl group of C4 to C30, and a substituted hetero aryl group of C4 to C30, with the proviso that when $R_1$ to $R_6$ are each hydrogen, $L_1$ is phenylene, $L_2$ is anthracenylene, and $Ar_1$ is phenyl, then $Ar_2$ cannot be a naphthyl group, and wherein the driving element is connected to the first electrode.

10. The organic light emitting diode display device of claim 9, wherein the $Ar_2$ is the non-substituted hetero aryl group of C4 to C30 or the substituted hetero aryl group of C4 to C30.

* * * * *